United States Patent [19]
von Borstel et al.

[11] Patent Number: 6,054,441
[45] Date of Patent: Apr. 25, 2000

[54] OXYPURINE NUCLEOSIDES AND THEIR CONGENERS, AND ACYL DERIVATIVES THEREOF, FOR IMPROVEMENT OF HEMATOPOIESIS

[75] Inventors: Reid W. von Borstel; Michael K. Bamat, both of Potomac; Bradley M. Hiltbrand, Columbia; James C. Butler; Shyam Shirali, both of Gaithersburg, all of Md.

[73] Assignee: Pro-Neuron, Inc., Rockville, Md.

[21] Appl. No.: 08/463,790

[22] Filed: Jun. 5, 1995

Related U.S. Application Data

[60] Division of application No. 08/289,214, Aug. 12, 1994, which is a continuation-in-part of application No. 07/925,931, Aug. 7, 1992, abandoned, which is a continuation-in-part of application No. 07/653,882, Feb. 8, 1991, abandoned, which is a continuation-in-part of application No. 07/487,984, Feb. 5, 1990, abandoned, which is a continuation-in-part of application No. 07/115,923, Oct. 28, 1987, abandoned.

[51] Int. Cl.[7] .................. A61K 31/70; C07D 473/00; C07H 19/16

[52] U.S. Cl. ............................ 514/45; 514/261; 514/814

[58] Field of Search ................................ 514/45, 814, 261

[56] References Cited

U.S. PATENT DOCUMENTS

| | | |
|---|---|---|
| 4,022,963 | 5/1977 | Deutsch . |
| 4,539,205 | 9/1985 | Goodman et al. . |
| 4,643,992 | 2/1987 | Goodman et al. . |
| 4,849,411 | 7/1989 | Goodman et al. . |
| 5,093,318 | 3/1992 | Goodman et al. . |
| 5,116,615 | 5/1992 | Gokcen et al. . |
| 5,136,030 | 8/1992 | Chen . |
| 5,206,219 | 4/1993 | Desai . |
| 5,320,846 | 6/1994 | Bistrian et al. . |
| 5,441,942 | 8/1995 | Goodman et al. ................ 514/45 |
| 5,539,098 | 7/1996 | Kreitsky et al. ................ 536/27.81 |

FOREIGN PATENT DOCUMENTS

| | | |
|---|---|---|
| 0 233 629 | 8/1987 | European Pat. Off. . |
| 268110 | 5/1988 | European Pat. Off. . |
| WO80/03838 | 5/1989 | WIPO . |
| WO89/03837 | 5/1989 | WIPO . |
| WO 92/13561 | 8/1992 | WIPO . |

OTHER PUBLICATIONS

Martin et al, Journal of Pharmaceutical Sciences, vol. 76, No. 2, issued Feb. 1987, "Synthesis and Antiviral Activity of Various Esters of 9–[(1,3–Dihydroxy–2–propoxy)methyl] guanine;" p. 180–184.

Wright, G., Blood, vol. 69, No. 1, issued Jan. 1987, "A Role For Guanine Ribonucleotides in the Regulation of Myeloid Cell Maturation," p. 334–337.

Oshita et al, Blood, vol. 49, No. 4, Issued Apr. 1977, "cGMP Stimulation of Stem Cell Proliferation," p. 585–591.

Fleming, W.A., et al, J. Cell. Physiol., vol. 88, issued 1976, "Cellular Responsiveness to Stimulation in Vitro: Increased Responsiveness to Colony Stimulating Factor of Bone Marrow Colony–forming Cells Treated with Surface–Active Agents and Cyclic 3', 5' AMP," p. 323–330.

Sugahara et al, Brookhaven Symposium in Biology, issued 1968, "Studies on the Effect of Chemical Treatment on the Survival of Repeatedly Irradiated Mice," p. 284–302.

Bennett, D.W., and Drury, A.N., J. Physiol. 72:288 (1931), p. 303–306.

Beljanski et al, Cancer Treat., Rep. 67:611–619 (1983).

Sigma Chemical Company 1991 Catalog: 1702–1704.

Morikawa, K., et al, Cancer Research 47:37–41 (1987).

Huang, G., et al, Zhonghua Zueyexue Zazhi 11(2):66–68 (Abstract), 1978.

Chemical Abstracts, vol. 78, Abstract No. 92644, 1970, Markley et al, J. Trauma, 10: 598–607, 1970.

*Primary Examiner*—Gary L. Kunz
*Attorney, Agent, or Firm*—Nixon & Vanderhye

[57] ABSTRACT

The invention relates to certain oxypurine nucleosides, congeners of such oxypurine nucleosides, and acyl derivatives thereof, and compositions which contain at least one of these compounds. The invention also relates to methods of treating or preventing hematopoietic disorders and modifying hematopoiesis, and treating or preventing inflammatory diseases and bacterial infections by administering a compound or composition of the present invention to an animal.

21 Claims, 69 Drawing Sheets

Time (days) after cyclophosphamide

Time following 5-FU administration

Time following 5-FU administration

Time following CP (days)

Time (days) following CP administration

Time (days) following CP administration

Time (days) following CP administration

OXYPURINE NUCLEOSIDES AND THEIR CONGENERS, AND ACYL DERIVATIVES THEREOF, FOR IMPROVEMENT OF HEMATOPOIESIS

This is a Divisional of application Ser. No. 81/289,214, filed Aug. 12, 1994; which is a CIP of Ser. No. 07/925,931, filed Aug. 7, 1992 now abandoned; which is a CIP of Ser. No. 07/653,882, filed Feb. 8, 1991, abandoned; which is a CIP of Ser. No. 07/487,984 filed Feb. 5, 1990, abandoned; which is a CIP of Ser. No. 07/115,923 filed Oct. 28, 1987 now abandoned.

FIELD OF THE INVENTION

This invention relates generally to oxypurine nucleosides including guanosine, deoxyguanosine, inosine, xanthosine, deoxyxanthosine and deoxyinosine, congeners of these nucleosides, and acyl derivatives of these nucleosides and congeners, and to the prophylactic and therapeutic uses of these compounds. The invention also relates to the administration of these compounds, alone or in combinations, with or without nonionic surfactants or other agents, to animals. These compounds are capable of modifying hematopoiesis in intact, normal animals and in animals with damage to or deficiencies of the hematopoietic system caused by irradiation, chemotherapy, poisoning, disease, or the like. Compounds of the subject invention also improve host leukocyte-mediated defenses against infection.

BACKGROUND OF THE INVENTION

A major complication of cancer chemotherapy, of antiviral chemotherapy, or of exposure to ionizing radiation is damage to bone marrow cells or suppression of their function. Specifically, chemotherapy and exposure to ionizing radiation damage or destroy hematopoietic progenitor cells, primarily found in the bone marrow and spleen, impairing the production of new blood cells (granulocytes, lymphocytes, erythrocytes, monocytes, platelets, etc.). Treatment of cancer patients with cyclophosphamide or 5-fluorouracil, for example, destroys leukocytes (lymphocytes and/or granulocytes), and can result in enhanced susceptibility of the patients to infection. Many cancer patients die of infection or other consequences of hematopoietic failure subsequent to chemotherapy or radiation therapy. Chemotherapeutic agents can also result in subnormal formation of platelets which produces a propensity toward hemorrhage. Similarly, mustard gas poisoning results in damage to the hematopoietic system, leaving one more susceptible to infection. Inhibition of erythrocyte production can result in anemia. Failure of the surviving bone marrow stem cells to proliferate and differentiate rapidly enough to replenish leukocyte populations results in the inability of the body to resist pathogenic infectious organisms. Various disease states, such as neutropenia, including idiopathic forms, are also related to impairment of specific components of the hematopoietic system.

Compounds which improve or aid in the restoration of hematopoiesis after bone marrow damage or suppression caused by chemicals, radiation, disease, or other pathological conditions associated with deficient hematopoiesis, are useful as therapeutic and prophylactic agents.

Several polypeptide hematopoietic growth factors (produced primarily through recombinant DNA technology) are known. These hematopoietic growth factors, which include erythropoietin (EPO), the interleukins (especially Interleukin-1, Interleukin-3, and Interleukin-6) and the colony-stimulating factors (such as granulocyte colony-stimulating factor, granulocyte/macrophage colony-stimulating factor, or stem-cell colony-stimulating factor), have been reported to have some utility in improving hematopoiesis. Some agents broadly characterized as "biological response modifiers" (BRM's) can also enhance some indices of hematopoiesis. BRM's which modify hematopoiesis include agents like bacterial endotoxin, double-stranded RNA, azimexone, glucans and other yeast and bacterial polysaccharides, dextran sulfate, maleic acid divinyl ether polyanion (MVE2), and tumor necrosis factor.

D. W. Bennett and A. N. Drury, J. Physiol. 72:288 (1931) disclosed that the administration of 100 mg of guanosine to rabbits by intraperitoneal injection resulted in an intense decline in leukocyte counts. Initial levels of leukocyte counts were 7700 per $mm^3$, but after administration of guanosine, the leukocyte counts declined to only 500 to 1000 per $mm^3$. After 10 hours, and for 24 hours thereafter, there was leukocytosis (11,000 per $mm^3$).

D. G. Wright, Blood 69:334–337 (1987) reported the effect of guanosine and guanine on cultures of a specific human myeloid leukemia cell line (HL-60). The conversion of immature blast cells into mature granulocytes in vitro was reported to be induced by various chemical agents (including retinoic acid, dimethylformamide and tiazofurin). Incubation of HL-60 cells with guanine or guanosine prevented their induced maturation into functional neutrophils; incubation with inosine had no effect on induced maturation.

A. K. Oshita, et al., Blood 49:585–591 (1977) suggested that cyclic nucleotides (e.g., 3',5'-cylic adenosine monophosphate (cAMP) or 3',5'-cyclic guanosine monophosphate (cGMP)) may participate in the regulation of cell proliferation. In mouse bone marrow cells in culture, cGMP produced an increase in the number of colonies formed under stimulatory influence of serum taken from endotoxin-treated mice. cGMP had no effect in the absence of post-endotoxin serum. 5'-guanosine monophosphate and cAMP were inactive.

Beljanski et al., Cancer Treat. Rep. 67:611–619 (1983) disclosed that partial hydrolysis of E. coli ribosomal RNA yields short (approximately 40 bases) oligonucleotides that have some demonstrable leukopoietic activity in rabbits treated with cyclophosphamide. The authors proposed that the oligonucleotides were acting as replication primers for DNA synthesis in bone marrow cells. They also disclosed that the polyribonucleotides polyguanosine monophosphate, polyadenosine monophosphate, and a copolymer of adenine and guanine nucleotides failed to stimulate leukocyte formation.

T. Sugahara et al., Brookhaven Symposia in Biology:284–302 (1968) reported that yeast RNA hydrolysate, mixtures of adenosine, cytidine, guanosine, uridine, and their corresponding 3'-ribonucleoside monophosphates did not improve survival after acute lethal doses of ionizing radiation. The compounds improved survival of mice when administered periodically during repeated exposure to sublethal doses of gamma irradiation. The authors stated that the treatment agents were not improving proliferation or differentiation of surviving stem cells, but were apparently prolonging the survival of damaged mature cells. The hydrolysate, the ribonucleosides, and the ribonucleoside monophosphates all decreased the numbers of nucleated cells and hematopoietic cell colonies (colony-forming units) in spleen and bone marrow (the major sites of hematopoiesis) compared to irradiated untreated control mice.

Goodman et al. (U.S. Pat. Nos. 4539205, 4849411, and 4643992) disclose the use of aldosyl guanine derivatives having substituents having an electron-withdrawing effect greater than hydrogen in the 8 position of the guanine moiety, for modulating immune response.

Some acyl derivatives of oxypurine nucleosides have been synthesized for use as protected intermediates in the synthesis of oligonucleotides or analogs of nucleosides or nucleotides. See Sigma Chemical Company 1991 catalog, pages 1702–1704.

W. A. Fleming and T. A. McNeill, J. Cell. Physiol. 88:323–330 (1976) reported that the nonionic surfactant compounds Polysorbate 80 and Saponin increase the responsiveness of bone marrow cells in culture to the influence of sub-optimal amounts of colony stimulating factors. The surfactants were active over a very narrow concentration range, with maximum activity at 10 ng/ml, and minimal activity at concentrations ten-fold greater or ten-fold lower. The effect of surfactants on hematopoiesis in vivo was not examined.

OBJECTS OF THE INVENTION

It is a primary object of this invention to provide a family of compounds which effectively promote or otherwise modify hematopoiesis. Administration of these compounds to an animal before, during or after damage to the hematopoietic system, prevents or treats the hematopoietic disorders.

It is a further object of this invention to provide a family of compounds for the treatment of a variety of hematological disorders and other pathological conditions involving low blood cell counts.

It is a further object of this invention to provide a family of compounds to improve host leukocyte-mediated defenses against infection.

It is a further object of the invention to provide compounds which can modify hematopoiesis and which can be administered orally or parenterally.

SUMMARY OF THE INVENTION

These and other objects of the invention are achieved by oxypurine nucleosides such as guanosine, inosine, xanthosine, deoxyxanthosine, deoxyinosine, and deoxyguanosine, congeners of such oxypurine nucleosides, and acyl and alkyl derivatives of such oxypurine nucleosides and congeners, which can be administered to animals, including mammals such as humans. The administration of these compounds alone, or in combination, is useful in modifying hematopoiesis in an animal.

Thus, the compounds of the invention, alone or in combinations, are useful in the treatment of disorders of hematopoiesis induced by irradiation or chemical agents; are useful as adjuncts to cancer and anti-viral chemotherapy; are useful to improve host leukocyte-mediated defenses against infection; and are useful for the treatment of other pathological conditions.

An important aspect of this invention is the discovery that oxypurine nucleosides such as guanosine, deoxyguanosine, inosine, xanthosine, deoxyxanthosine and deoxyinosine, congeners of such nucleosides and acyl and alkyl derivatives of such nucleosides and congeners, have unexpected therapeutic properties.

The invention also encompasses the discovery that surfactant compounds administered in vivo can enhance the effect of hematopoietic stimulants, including, but not limited to the compounds of the invention, erythropoietin, colony stimulating factors, or interleukins.

The invention also includes a method for treating or preventing bacterial or fungal infection in an animal comprising administering to said animal a pharmaceutically effective amount of a compound or composition of the invention.

COMPOUNDS OF THE INVENTION

In all cases except where indicated, letters and letters with subscripts symbolizing variable substituents in the chemical structures of the compounds of the invention are applicable only to the structure immediately preceding the description of the symbol.

The compounds useful in modifying hematopoiesis have the following structure:

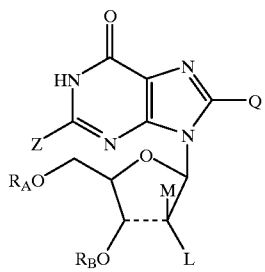

$R_A$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and $R_B$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and Z=H, OH, =O, or $NHR_C$ where $R_C$=H or an acyl radical of a carboxylic acid with 2 to 30 carbon atoms, or an alkyl radical with 2–30 carbon atoms, and L=H or $OR_D$, where $R_D$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and M=H or $OR_E$, where $R_E$=H or an acyl radical of a carboxylic, alkylphosphonic, or alkylsulfonic acid, a radical of an alkyl phosphate or alkyl sulfate, or an alkyl radical, with 2 to 30 carbon atoms, with the proviso that at least one of L and M is H, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, and the C—C bond between the 2' and 3' positions of the aldose moiety is optionally present,

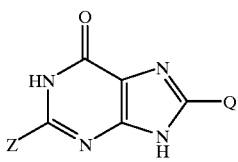

$Z=NHR_C$ where $R_C=H$ or an acyl radical of a carboxylic acid with 2 to 30 carbon atoms, or an alkyl radical with 2–30 carbon atoms, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms.

Novel compositions of the invention include the above-noted compounds (optionally as pharmaceutically acceptable salts) wherein at least one of $R_A$, $R_B$, $R_C$, $R_D$ or $R_E$ is not H, and in compounds where Z is $NH_2$ or $NHR_C$, Q is then H or $NHR_F$ where $R_F$ is H or an acyl or alkyl radical containing 1 to 10 carbon atoms, along with a pharmaceutically acceptable carrier.

Broadly, guanosine, its congeners, and acyl and alkyl derivatives thereof are represented by the formula (I):

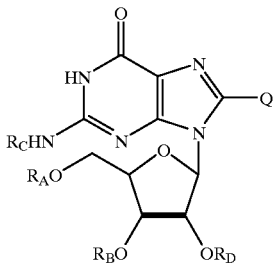

(I)

wherein $R_A$, $R_B$, $R_C$ and $R_D$ are the same, or different, and each is hydrogen (H), an acyl radical, or an alkyl radical, and Q=H, a halogen, $NHR_F$ where $R_F$ is H or an acyl or alkyl radical containing 1 to 10 carbon atoms, $SR_G$ where $R_G$ is H or an acyl or alkyl radical containing 1 to 10 carbon atoms, =O, or $OR_E$ where $R_H$ is H or an acyl or alkyl radical containing 1 to 10 carbon atoms, or a pharmaceutically acceptable salt thereof.

Broadly, inosine, its congeners, and acyl or alkyl derivatives thereof are represented by the formula (II):

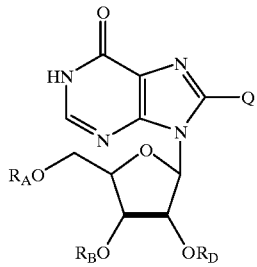

(II)

wherein $R_A$, $R_B$, and $R_D$ are the same, or different, and each is an acyl radical, or an alkyl radical, and Q=H, a halogen, $NHR_F$ where $R_F$ is H or an acyl or alkyl radical containing 1 to 10 carbon atoms, $SR_G$ where $R_G$ is H or an acyl or alkyl radical containing 1 to 10 carbon atoms, =O, or $OR_H$ where $R_H$ is H or an acyl or alkyl radical containing to 10 carbon atoms, or a pharmaceutically acceptable salt thereof.

Broadly, xanthosine, its congeners, and acyl or alkyl derivatives thereof are represented by the formula (III):

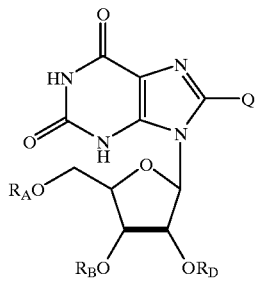

(III)

wherein $R_A$, $R_B$, and $R_D$ are the same, or different, and each is H, an acyl radical, or an alkyl radical, and Q=H, a halogen, $NHR_F$ where $R_F$ is H or an acyl or alkyl radical containing 1 to 10 carbon atoms, $SR_G$ where $R_G$ is H or an acyl or alkyl radical containing 1 to 10 carbon atoms, =O, or $OR_H$ where $R_H$ is H or an acyl or alkyl radical containing 1 to 10 carbon atoms, or a pharmaceutically acceptable salt thereof.

Broadly, deoxyinosine, its congeners, and acyl or alkyl, derivatives thereof are represented by the formula (IV):

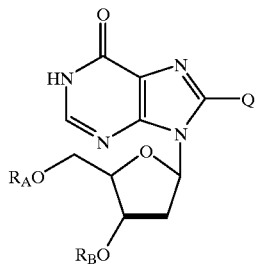

(IV)

wherein $R_A$ and $R_B$ are the same, or different, and each is H, an acyl radical, or an alkyl radical, and Q=H, a halogen, $NHR_F$ where $R_F$ is H or an acyl or alkyl radical containing 1 to 10 carbon atoms, $SR_G$ where $R_G$ is H or an acyl or alkyl radical containing 1 to 10 carbon atoms, =O, or $OR_H$ where $R_H$ is H or an acyl or alkyl radical containing 1 to 10 carbon atoms, or a pharmaceutically acceptable salt thereof.

Broadly, deoxyguanosine, its congeners, and acyl or alkyl derivatives thereof are represented by the formula (V):

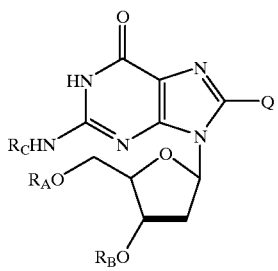

(V)

wherein $R_A$, $R_B$, and $R_C$ may be the same or different, and each is hydrogen (H), an acyl radical, or an alkyl radical, and Q=H, a halogen, $NHR_F$ where $R_F$ is H or an acyl or alkyl radical containing 1 to 10 carbon atoms, $SR_G$ where $R_G$ is H or an acyl or alkyl radical containing 1 to 10 carbon atoms, =O, or $OR_H$ where $R_H$ is H or an acyl or alkyl radical containing 1 to 10 carbon atoms, or a pharmaceutically acceptable salt thereof.

Broadly, deoxyxanthosine, its congeners, and acyl or alkyl derivatives thereof are represented by the formula (VI):

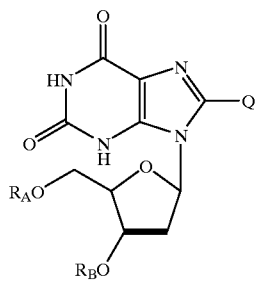

(VI)

wherein $R_A$ and $R_B$ are the same, or different, and each is H, an acyl radical, or an alkyl radical, and Q=H, a halogen, $NHR_F$ where $R_F$ is H or an acyl or alkyl radical containing 1 to 10 carbon atoms, $SR_G$ where $R_G$ is H or an acyl or alkyl radical containing 1 to 10 carbon atoms, =O, or $OR_H$ where $R_H$ is H or an acyl or alkyl radical containing 1 to 10 carbon atoms, or a pharmaceutically acceptable salt thereof.

Broadly, inosine 2',3'-acyclic dialcohol, its congeners, and acyl or alkyl derivatives thereof are represented by the formula (VII):

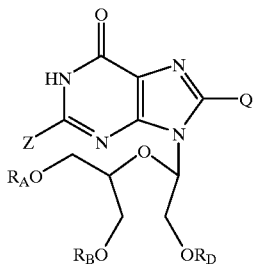

(VII)

wherein $R_A$, $R_B$, and $R_D$ are the same, or different, and each is H, an acyl radical, or an alkyl radical, and Z is H, OH, =O, or $NHR_C$ where $R_C$=H or an acyl radical of a carboxylic acid with 2 to 30 carbon atoms, and Q=H, a halogen, $NHR_F$ where $R_F$ is H or an acyl or alkyl radical containing 1 to 10 carbon atoms, $SR_G$ where $R_G$ is H or an acyl or alkyl radical containing 1 to 10 carbon atoms, =O, or $OR_H$ where $R_H$ is H or an acyl or alkyl radical containing 1 to 10 carbon atoms, or a pharmaceutically acceptable salt thereof.

Broadly, guanine, its congeners, and acyl and alkyl derivatives thereof are represented by the formula (I):

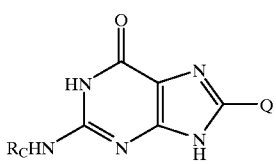

(I)

wherein $R_C$ is an acyl radical or an alkyl radical, and

Q=H, a halogen, $NHR_F$ where $R_F$ is H or an acyl or alkyl radical containing 1 to 10 carbon atoms, $SR_G$ where $R_G$ is H or an acyl or alkyl radical containing 1 to 10 carbon atoms, =O, or $OR_H$ where $R_H$ is H or an acyl or alkyl radical containing 1 to 10 carbon atoms, or a pharmaceutically acceptable salt thereof.

The classes of novel derivatives that are desirable in terms of both efficacy and safety when used in accordance with the invention are:

(1) acyl or alkyl derivatives of guanosine or its congeners having the formula:

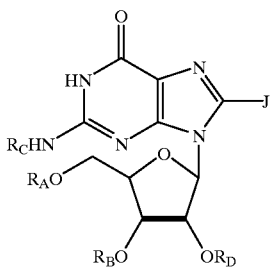

wherein $R_A$, $R_B$, and $R_D$ are the same, or different, and are hydrogen or
  I. an acyl group derived from
    a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
b. an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine and ornithine,
c. a dicarboxylic acid having 3–22 carbon atoms,
d. a cycloalkyl carboxylic acid containing 4 to 22 carbon atoms,
e. a carboxylic acid derived from
   i. a polymer of ethylene glycol with the structure $HOOC—(CH_2)_m—(CH_2CH_2O)_nH$ or $HOOC—(CH_2)_m—(CH_2CH_2O)_nCH_3$, or
   ii. a polymer of vinyl alcohol with the structure $HOOC—(CH_2)_m—(CH_2CHOH)_nH$ or $HOOC—(CH_2)_m—(CH_2CHOH)_nCH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
   a. an alkylphosphonic or alkylsulfonic acid, or
   b. an alkyl phosphate or alkyl sulfate, provided that not all of $R_A$, $R_B$, and $R_D$ are hydrogen; and $R_C$ is hydrogen or
I. an acyl group derived from
   a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
   c. a dicarboxylic acid having 3–22 carbon atoms,
   d. a cycloalkyl carboxylic acid containing 4 to 22 carbon atoms,
   e. a nicotinic acid, or
   f. a substituted or unsubstituted aromatic carboxylic acid with 7 to 22 carbon atoms,
   g. a carboxylic acid derived from
      i. a polymer of ethylene glycol with the structure $HOOC—(CH_2)_m—(CH_2CH_2O)_nH$ or $HOOC—(CH_2)_m—(CH_2CH_2O)_nCH_3$, or
      ii. a polymer of vinyl alcohol with the structure $HOOC—(CH_2)_m—(CH_2CHOH)_nH$ or $HOOC—(CH_2)_m—(CH_2CHOH)_nCH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, and
J=H or $NHR_r$ where $R_r$ is H or an acyl or alkyl radical containing 1 to 10 carbon atoms;
(2) acyl or alkyl derivatives of inosine or its congeners having the formula

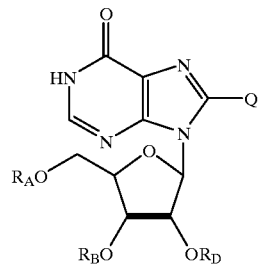

wherein $R_A$ is hydrogen or
I. an acyl group derived from
   a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. a dicarboxylic acid having 3–22 carbon atoms,
   c. nicotinic acid or
   d. a cycloalkyl carboxylic acid containing 4 to 22 carbon atoms; and
   e. a carboxylic acid derived from
      i. a polymer of ethylene glycol with the structure $HOOC—(CH_2)_m—(CH_2CH_2O)_nH$ or $HOOC—(CH_2)_m—(CH_2CH_2O)_nCH_3$, or
      ii. a polymer of vinyl alcohol with the structure $HOOC—(CH_2)_m—(CH_2CHOH)_nH$ or $HOOC—(CH_2)_m—(CH_2CHOH)_nCH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
   a. an alkylphosphonic or alkylsulfonic acid, or
   b. an alkyl phosphate or alkyl sulfate,
wherein $R_B$ and/or $R_D$ are hydrogen or
I. an acyl group derived from
   a. an unbranched fatty acid with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
   c. a dicarboxylic acid having 3–22 carbon atoms,
   d. nicotinic acid or
   e. a cycloalkyl carboxylic acid containing 4 to 22 carbon atoms,
   f. a carboxylic acid derived from
      i. a polymer of ethylene glycol with the structure $HOOC—(CH_2)_m—(CH_2CH_2O)_nH$ or $HOOC—(CH_2)_m—(CH_2CH_2O)_nCH_3$, or
      ii. a polymer of vinyl alcohol with the structure $HOOC—(CH_2)_m—(CH_2CHOH)_nH$ or $HOOC—(CH_2)_m—(CH_2CHOH)_nCH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or III. an acyl group derived from
  a. an alkylphosphonic or alkylsulfonic acid, or
  b. an alkyl phosphate or alkyl sulfate, provided that not all of $R_A$, $R_B$, and $R_D$ are hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

(3) acyl or alkyl derivatives of xanthosine or its congeners having the formula:

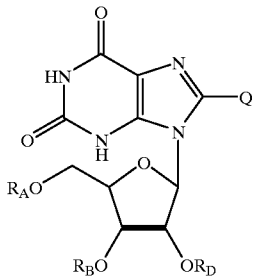

wherein $R_A$, $R_B$, and $R_D$ are the same, or different, and are hydrogen or

I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure $HOOC-(CH_2)_m-(CH_2CH_2O)_nH$ or $HOOC-(CH_2)_m-(CH_2CH_2O)_nCH_3$, or
    ii. a polymer of vinyl alcohol with the structure $HOOC-(CH_2)_m-(CH_2CHOH)_nH$ or $HOOC-(CH_2)_m-(CH_2CHOH)_nCH_3$, where m=0–3 and n=2–8, or II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or III. an acyl group derived from
  a. an alkylphosphonic or alkylsulfonic acid, or
  b. an alkyl phosphate or alkyl sulfate, provided that not all of $R_A$, $R_B$, and $R_D$ are hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

(4) acyl or alkyl derivatives of deoxyinosine or its congeners having the formula:

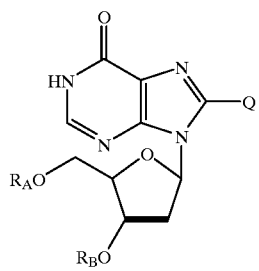

wherein $R_A$ and $R_B$ are the same, or different, and are hydrogen or

I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure $HOOC-(CH_2)_m-(CH_2CH_2O)_nH$ or $HOOC-(CH_2)_m-(CH_2CH_2O)_nCH_3$, or
    ii. a polymer of vinyl alcohol with the structure $HOOC-(CH_2)_m-(CH_2CHOH)_nH$ or $HOOC-(CH_2)_m-(CH_2CHOH)_nCH_3$, where m=0–3 and n=2–8, or II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or III. an acyl group derived from
  a. an alkylphosphonic or alkylsulfonic acid, or
  b. an alkyl phosphate or alkyl sulfate, provided that at least one of $R_A$ and $R_B$ is not hydrogen, and Q=H, a halogen, NHR$_F$ where R$_F$ is H or an acyl or alkyl radical containing 1 to 10 carbon atoms, S divalently bound to the carbon in which case the adjacent carbon-nitrogen double bond is a single bond and an H is then attached to that nitrogen, SR$_G$ where R$_G$ is H or an acyl or alkyl radical containing 1 to 10 carbon atoms, O divalently bound to the carbon, in which case the adjacent carbon-nitrogen double bond is a single bond and an H is then attached to that nitrogen, or OR$_H$ where R$_H$ is H or an acyl or alkyl radical containing 1 to 10 carbon atoms;

(5) acyl or alkyl derivatives of deoxyguanosine or its congeners having the formula:

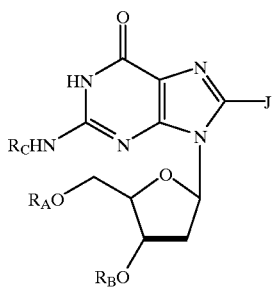

wherein R$_A$ and R$_B$ may be the same or different, and each is hydrogen or
I. an acyl group derived from
  a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
  b. an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, phenylalanine, and ornithine,
  c. a dicarboxylic acid having 3–22 carbon atoms,
  d. a cycloalkyl carboxylic acid containing 4 to 22 carbon atoms,
  e. nicotinic acid
  f. a carboxylic acid derived from
    i. a polymer of ethylene glycol with the structure HOOC—(CH$_2$)$_m$—(CH$_2$CH$_2$O)$_n$H or HOOC—(CH$_2$)$_m$—(CH$_2$CH$_2$O)$_n$CH$_3$, or
    ii. a polymer of vinyl alcohol with the structure HOOC—(CH$_2$)$_m$—(CH$_2$CHOH)$_n$H or HOOC—(CH$_2$)$_m$—(CH$_2$CHOH)$_n$CH$_3$, or
II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, or
III. an acyl group derived from
  a. an alkylphosphonic or alkylsulfonic acid, or
  b. an alkyl phosphate or alkyl sulfate,
provided that not both of R$_A$ and R$_B$ are hydrogen; and R$_C$ is hydrogen or
I. an acyl group derived from
  a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. a cycloalkyl carboxylic acid containing 4 to 22 carbon atoms,
  e. a nicotinic acid, or
  f. a substituted or unsubstituted aromatic carboxylic acid with 7 to 22 carbon atoms,
  g. a carboxylic acid derived from
    i. a polymer of ethylene glycol with the structure HOOC—(CH$_2$)$_m$—(CH$_2$CH$_2$O)$_n$H or HOOC—(CH$_2$)$_m$—(CH$_2$CH$_2$O)$_n$CH$_3$, or
    ii. a polymer of vinyl alcohol with the structure HOOC—(CH$_2$)$_m$—(CH$_2$CHOH)$_n$H or HOOC—(CH$_2$)$_m$—(CH$_2$CHOH)$_n$CH$_3$, where m=0–3 and n=2–8, or
II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, and where R$_C$ is not H, then R$_A$ and/or R$_B$ may also be acetyl, and
J=H or NHR$_r$ where R$_r$ is H or an acyl or alkyl radical containing 1 to 10 carbon atoms;

(6) acyl or alkyl derivatives of deoxyxanthosine or its congeners having the formula:

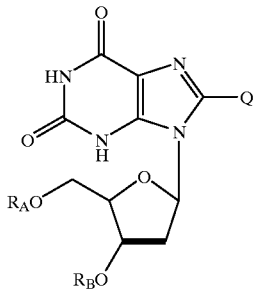

wherein R$_A$ and R$_B$ are the same, or different, and are hydrogen or
I. an acyl group derived from
  a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure HOOC—(CH$_2$)$_m$—(CH$_2$CH$_2$O)$_n$H or HOOC—(CH$_2$)$_m$—(CH$_2$CH$_2$O)$_n$CH$_3$, or ii. a polymer of vinyl alcohol with the structure $HOOC-(CH_2)_m-(CH_2CHOH)_nH$ or $HOOC-(CH_2)_m-(CH_2CHOH)_nCH_3$, where m=0–3 and n=2–8, or II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or III. an acyl group derived from
  a. an alkylphosphonic or alkylsulfonic acid, or
  b. an alkyl phosphate or alkyl sulfate, provided that at least one of $R_A$ and $R_B$ is not hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

(7) acyl or alkyl derivatives of inosine acyclic 2',3'-dialcohol or its congeners having the formula:

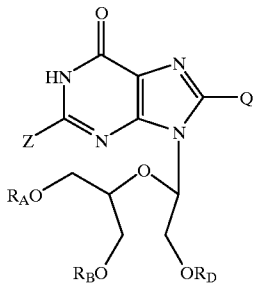

wherein $R_A$, $R_B$, and $R_D$ are the same, or different, and are hydrogen or

I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure $HOOC-(CH_2)_m-(CH_2CH_2O)_nH$ or $HOOC-(CH_2)_m-(CH_2CH_2O)_nCH_3$, or
    ii. a polymer of vinyl alcohol with the structure $HOOC-(CH_2)_m-(CH_2CHOH)_nH$ or $HOOC-(CH_2)_m-(CH_2CHOH)_nCH_3$, where m=0–3 and n=2–8, or II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or III. an acyl group derived from
  a. an alkylphosphonic or alkylsulfonic acid, or
  b. an alkyl phosphate or alkyl sulfate, provided that not all of $R_A$, $R_B$, and $R_D$ are hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, Z is H, OH, =O, or $NHR_C$ where $R_C$=H or an acyl radical of a carboxylic acid with 2 to 30 carbon atoms or an alkyl radical with 2 to 30 carbon atoms;

(8) acyl or alkyl derivatives of guanine or its congeners having the formula:

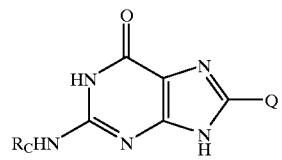

wherein RC is hydrogen or an acyl group derived from
i. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
ii. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
iii. a dicarboxylic acid having 3–22 carbon atoms,
iv. a cycloalkyl carboxylic acid containing 4 to 22 carbon atoms,
v. a nicotinic acid, or
vi. a substituted or unsubstituted aromatic carboxylic acid with 7 to 22 carbon atoms,
vii. a carboxylic acid derived from
  1. a polymer of ethylene glycol with the structure $HOOC-(CH_2)_m-(CH_2CH_2O)_nH$ or $HOOC-(CH_2)_m-(CH_2CH_2O)_nCH_3$, or
  2. a polymer of vinyl alcohol with the structure $HOOC-(CH_2)_m-(CH_2CHOH)_mH$ or $HOOC-(CH_2)_m-(CH_2CHOH)_nCH_3$, where m=0–3 and n=2–8, or
viii. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms.

For all of the above structures, where the substituent at the 2 position of the purine base (Z) or at the 8 position of the purine base (Q or L) is attached to the purine base with a double bond (e.g. =O or =S), the adjacent carbon-nitrogen double bond in the purine base becomes a single carbon-nitrogen bond and an additional hydrogen is then present on the nitrogen of that carbon-nitrogen single bond.

Also encompassed by the invention are the pharmaceutically acceptable salts of the above-noted compounds.

Figure 1:
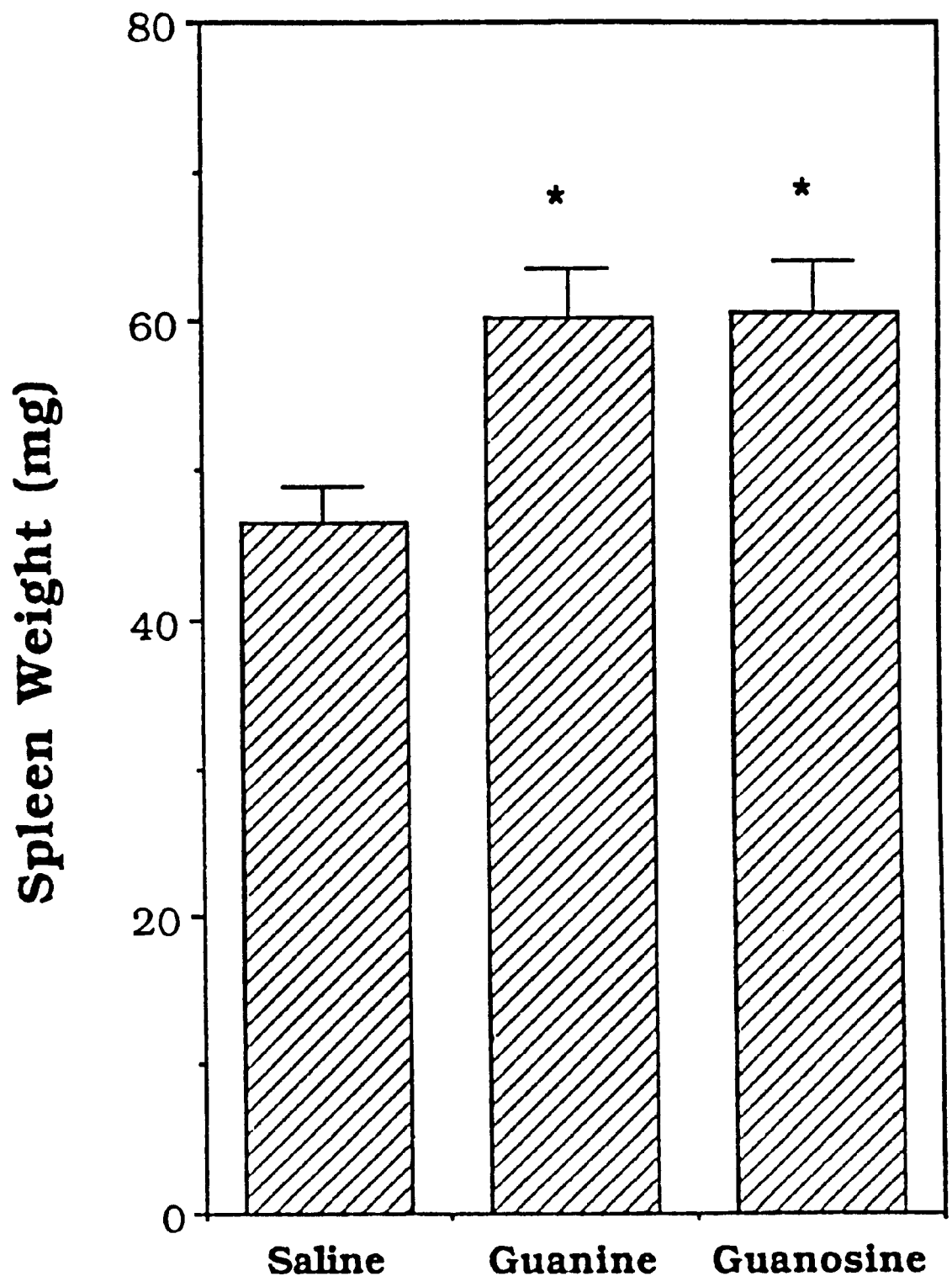
FIG. 1 is a graph comparing spleen weight of mice after treatment with saline, guanine and guanosine as described in Example 37. (In this figure and each figure hereafter an asterisk (*) indicates statistically significant differences.)

The invention, as well as other objects, features and advantages thereof, will be understood more clearly and fully from the following detailed description when read with reference to the accompanying figures which illustrate the results of the experiments discussed in the examples below.

DETAILED DESCRIPTION OF THE INVENTION

The subject invention relates to oxypurine nucleosides, congeners of these nucleosides, and acyl and alkyl derivatives of these nucleosides and their congeners, and the use of these compounds for the modification of hematopoiesis in animals including humans.

A. Definitions

The term "oxypurine base" as used herein means a purine base with an exocyclic oxygen or hydroxyl group at the 6 position and hydrogen, oxygen, an hydroxyl group or an amino group at the 2 position.

The term "oxypurine nucleoside" as used herein means an oxypurine base conjugated from the nitrogen at the 9 position to the 1' position of a 5-carbon aldose. The term oxypurine nucleoside includes but is not limited to the compounds guanosine, inosine, deoxyinosine, xanthosine, deoxyxanthosine, and deoxyguanosine.

The term "congener" as used herein means an oxypurine nucleoside with a substituent attached at the 7 or 8 position of the purine ring moiety, and/or an oxypurine nucleoside with a ring-cleaved aldose (e.g. guanosine 2',3'dialcohol).

The term "acyl derivative" as used herein means a derivative of an oxypurine nucleoside or congener in which a substantially nontoxic organic acyl substituent derived from a carboxylic acid is attached to one or more of the free hydroxyl groups of the ribose moiety of the oxypurine nucleoside with an ester linkage and/or where such a substituent is attached to the amine substituent on the purine ring of guanosine, with an amide linkage. Such acyl substituents are derived from carboxylic acids which include, but are not limited to, compounds selected from the group consisting of lactic acid, an amino acid, a fatty acid, nicotinic acid, dicarboxylic acids, p-aminobenzoic acid and orotic acid. Advantageous acyl substituents are compounds which are normally present in the body, either as dietary constituents or as intermediary metabolites.

The term "pharmaceutically acceptable salts" as used herein means salts with pharmaceutically acceptable acid addition salts of the derivatives, which include, but are not limited to, sulfuric, hydrochloric, or phosphoric acids.

The term "coadministered" means that at least two of the compounds of the invention are administered during a time frame wherein the respective periods of pharmacological activity overlap.

The term "amino acids" as used herein includes, but is not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, carnitine, and other naturally occurring amino acids.

The term "fatty acids" as used herein means aliphatic carboxylic acids having 2–22 carbon atoms. Such fatty acids may be saturated, partially saturated or polyunsaturated.

The term "dicarboxylic acids" as used herein means fatty acids with a second carboxylic acid substituent.

The term "therapeutically effective amount" as used herein refers to that amount which provides therapeutic effects for a given condition and administration regime.

B. Compounds of the Invention

The compounds of the invention useful in modifying matopoiesis have the following structure:

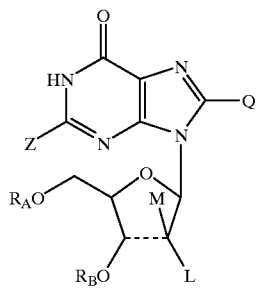

$R_A$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and $R_B$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and Z=H, OH, =O, or $NHR_C$ where $R_C$=H or an acyl radical of a carboxylic acid with 2 to 30 carbon atoms, or an alkyl radical with 2–30 carbon atoms, and L=H or $OR_D$, where $R_D$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and M=H or $OR_E$, where $R_E$=H or an acyl radical of a carboxylic, alkylphosphonic, or alkylsulfonic acid, a radical of an alkyl phosphate or alkyl sulfate, or an alkyl radical, with 2 to 30 carbon atoms, with the proviso that at least one of L and M is H, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, and the C—C bond between the 2' and 3' positions of the aldose moiety is optionally present, or,

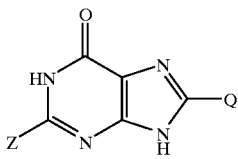

Z=NHR_C where $R_C$=H or an acyl radical of a carboxylic acid with 2 to 30 carbon atoms, or an alkyl radical with 2–30 carbon atoms, and Q=H, a halogen, NHR_F where $R_F$ is H or an acyl or alkyl radical containing 1 to 10 carbon atoms, S divalently bound to the carbon in which case the adjacent carbon-nitrogen double bond is a single bond and an H is then attached to that nitrogen, SR_G where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or OR_H where $R_H$ is H or an acyl or alkyl radical containing 1 to 10 carbon atoms.

Novel compositions of the invention include the above-noted compounds wherein at least one of $R_A$, $R_B$, $R_C$, $R_D$ or $R_E$ is not H, and in compounds where Z is $NH_2$ or NHR_C, Q is then H or NHR_F where $R_F$ is H or an acyl or alkyl radical containing 1 to 10 carbon atoms, along with a pharmaceutically acceptable carrier.

Specifically, novel compounds of the invention include but are not limited to:

(1) acyl or alkyl derivatives of guanosine or its congeners having the formula:

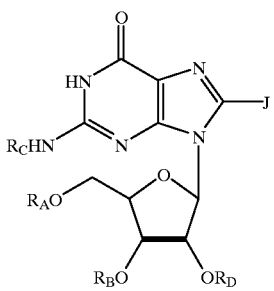

wherein $R_A$, $R_B$, and $R_D$ are the same, or different, and are hydrogen or

I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. a cycloalkyl carboxylic acid containing 4 to 22 carbon atoms,
  e. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n CH_3$, or
    ii. a polymer of vinyl alcohol with the structure HOOC—$(CH_2)_m$—$(CH_2CHOH)_n$H or HOOC—$(CH_2)_m$—$(CH_2CHOH)_n CH_3$, where m=0–3 and n=2–8, or II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or III. an acyl group derived from
  a. an alkylphosphonic or alkylsulfonic acid, or
  b. an alkyl phosphate or alkyl sulfate, provided that not all of $R_A$, $R_B$, and $R_D$ are hydrogen; and $R_C$ is hydrogen or I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. a cycloalkyl carboxylic acid containing 4 to 22 carbon atoms,
  e. a nicotinic acid, or
  f. a substituted or unsubstituted aromatic carboxylic acid with 7 to 22 carbon atoms,
  g. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n CH_3$, or
    ii. a polymer of vinyl alcohol with the structure HOOC—$(CH_2)_m$—$(CH_2CHOH)_n$H or HOOC—$(CH_2)_m$—$(CH_2CHOH)_n CH_3$, where m=0–3 and n=2–8, or II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, and J=H or NHR_r where $R_r$ is H or an acyl or alkyl radical containing 1 to 10 carbon atoms;

(2) acyl or alkyl derivatives of inosine or its congeners having the formula

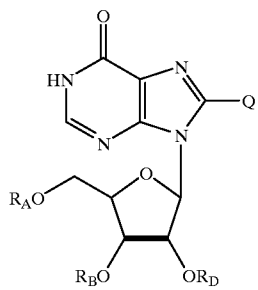

wherein $R_A$ is hydrogen or
I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, b. a dicarboxylic acid having 3–22 carbon atoms,
c. nicotinic acid or
d. a cycloalkyl carboxylic acid containing 4 to 22 carbon atoms; and
e. a carboxylic acid derived from
  i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
  ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
  a. an alkylphosphonic or alkylsulfonic acid, or
  b. an alkyl phosphate or alkyl sulfate,
wherein $R_B$ and/or $R_D$ are hydrogen or
I. an acyl group derived from
  a. an unbranched fatty acid with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
    ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
  a. an alkylphosphonic or alkylsulfonic acid, or
  b. an alkyl phosphate or alkyl sulfate,
provided that not all of $R_A$, $R_B$, and $R_D$ are hydrogen, and
Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

(3) acyl or alkyl derivatives of xanthosine or its congeners having the formula:

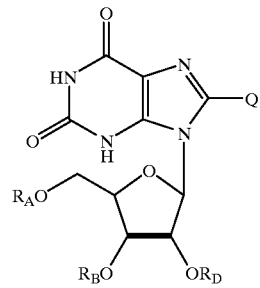

wherein $R_A$, $R_B$, and $R_D$ are the same, or different, and are hydrogen or
I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
    ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
  a. an alkylphosphonic or alkylsulfonic acid, or
  b. an alkyl phosphate or alkyl sulfate, provided that not all of $R_A$, $R_B$, and $R_D$ are hydrogen, and
Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

(4) acyl or alkyl derivatives of deoxyinosine or its congeners having the formula:

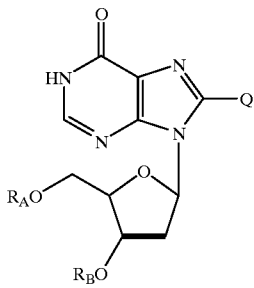

wherein $R_A$ and $R_B$ are the same, or different, and are hydrogen or
I. an acyl group derived from
   a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
   c. a dicarboxylic acid having 3–22 carbon atoms,
   d. nicotinic acid or
   e. a cycloalkyl carboxylic acid containing 4 to 22 carbon atoms,
   f. a carboxylic acid derived from
      i. a polymer of ethylene glycol with the structure $HOOC-(CH_2)_m-(CH_2CH_2O)_nH$ or $HOOC-(CH_2)_m-(CH_2CH_2O)_nCH_3$, or
      ii. a polymer of vinyl alcohol with the structure $HOOC-(CH_2)_m-(CH_2CHOH)_nH$ or $HOOC-(CH_2)_m-(CH_2CHOH)_nCH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
   a. an alkylphosphonic or alkylsulfonic acid, or
   b. an alkyl phosphate or alkyl sulfate,
provided that at least one of $R_A$ and $R_B$ is not hydrogen, and
Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

(5) acyl or alkyl derivatives of deoxyguanosine or its congeners having the formula:

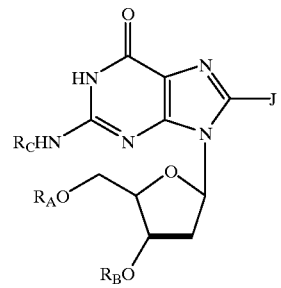

wherein $R_A$ and $R_B$ may be the same or different, and each is hydrogen or
I. an acyl group derived from
   a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. an amino acid selected from the group consisting of glycine, the L forms of alanine, valine, leucine, isoleucine, tyrosine, proline, hydroxyproline, serine, threonine, cysteine, aspartic acid, arginine, lysine, histidine, phenylalanine, and ornithine,
   c. a dicarboxylic acid having 3–22 carbon atoms,
   d. a cycloalkyl carboxylic acid containing 4 to 22 carbon atoms,
   e. nicotinic acid
   f. a carboxylic acid derived from
      i. a polymer of ethylene glycol with the structure $HOOC-(CH_2)_m-(CH_2CH_2O)_nH$ or $HOOC-(CH_2)_m-(CH_2CH_2O)_nCH_3$, or
      ii. a polymer of vinyl alcohol with the structure $HOOC-(CH_2)_m-(CH_2CHOH)_nH$ or $HOOC-(CH_2)_m-(CH_2CHOH)_nCH_3$, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
   a. an alkylphosphonic or alkylsulfonic acid, or
   b. an alkyl phosphate or alkyl sulfate, provided that not both of $R_A$ and $R_B$ are hydrogen; and $R_C$ is hydrogen or
I. an acyl group derived from
a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
c. a dicarboxylic acid having 3–22 carbon atoms,
d. a cycloalkyl carboxylic acid containing 4 to 22 carbon atoms,
e. a nicotinic acid, or
f. a substituted or unsubstituted aromatic carboxylic acid with 7 to 22 carbon atoms,
g. a carboxylic acid derived from i. a polymer of ethylene glycol with the structure HOOC—(CH$_2$)$_m$—(CH$_2$CH$_2$O)$_n$H or HOOC—(CH$_2$)$_m$—(CH$_2$CH$_2$O)$_n$CH$_3$, or
ii. a polymer of vinyl alcohol with the structure HOOC—(CH$_2$)$_m$—(CH$_2$CHOH)$_n$H or HOOC—(CH$_2$)$_m$—(CH$_2$CHOH)$_n$CH$_3$, where m=0–3 and n=2–8, or II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, and where R$_C$ is not H, then R$_A$ and/or R$_B$ may also be acetyl, and J=H or NHR$_r$ where R$_r$ is H or an acyl or alkyl radical containing 1 to 10 carbon atoms;

(6) acyl or alkyl derivatives of deoxyxanthosine or its congeners having the formula:

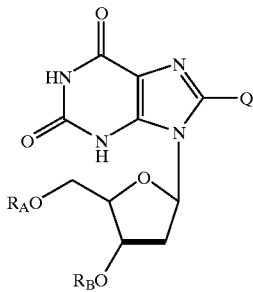

wherein R$_A$ and R$_B$ are the same, or different, and are hydrogen or
I. an acyl group derived from
   a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
   b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
   c. a dicarboxylic acid having 3–22 carbon atoms,
   d. nicotinic acid or
   e. a cycloalkyl carboxylic acid containing 4 to 22 carbon atoms,
   f. a carboxylic acid derived from
      i. a polymer of ethylene glycol with the structure HOOC—(CH$_2$)$_m$—(CH$_2$CH$_2$O )$_n$H or HOOC—(CH$_2$)$_m$—(CH$_2$CH$_2$O )$_n$CH$_3$, or
      ii. a polymer of vinyl alcohol with the structure HOOC—(CH$_2$)$_m$—(CH$_2$CHOH)$_n$H or HOOC—(CH$_2$)$_m$—(CH$_2$CHOH)$_n$CH$_3$, where m=0–3 and n=2–8, or
II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, or
III. an acyl group derived from
   a. an alkylphosphonic or alkylsulfonic acid, or
   b. an alkyl phosphate or alkyl sulfate,
provided that at least one of R$_A$ and R$_B$ is not hydrogen, and Q=H, a halogen, NHR$_F$ where R$_F$ is H or an acyl or alkyl radical containing 1 to 10 carbon atoms, S divalently bound to the carbon in which case the adjacent carbon-nitrogen double bond is a single bond and an H is then attached to that nitrogen, SR$_G$ where R$_G$ is H or an acyl or alkyl radical containing 1 to 10 carbon atoms, O divalently bound to the carbon, in which case the adjacent carbon-nitrogen double bond is a single bond and an H is then attached to that nitrogen, or OR$_H$ where R$_H$ is H or an acyl or alkyl radical containing 1 to 10 carbon atoms;

(7) acyl or alkyl derivatives of inosine acyclic 2',3'-dialcohol or its congeners having the formula:

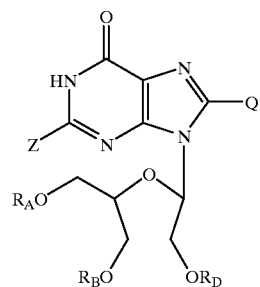

wherein R$_A$, R$_B$, and R$_D$ are the same, or different, and are hydrogen or
I. an acyl group derived from
   a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
   b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
   c. a dicarboxylic acid having 3–22 carbon atoms,
   d. nicotinic acid or
   e. a cycloalkyl carboxylic acid containing 4 to 22 carbon atoms,
   f. a carboxylic acid derived from
      i. a polymer of ethylene glycol with the structure HOOC—(CH$_2$)$_m$—(CH$_2$CH$_2$O)$_n$H or HOOC—(CH$_2$)$_m$—(CH$_2$CH$_2$O)$_n$CH$_3$, or
      ii. a polymer of vinyl alcohol with the structure HOOC—(CH$_2$)$_m$—(CH$_2$CHOH)$_n$H or HOOC—(CH$_2$)$_m$—(CH$_2$CHOH)$_n$CH$_3$, where m=0–3 and n=2–8, or
II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, or
III. an acyl group derived from
   a. an alkylphosphonic or alkylsulfonic acid, or
   b. an alkyl phosphate or alkyl sulfate, provided that not all of R$_A$, R$_B$ and R$_D$ are hydrogen, and Q=H, a halogen, NHR$_F$ where R$_F$ is H or an acyl or alkyl radical containing 1 to 10 carbon atoms, S divalently bound to the carbon in which case the adjacent carbon-nitrogen double bond is a single bond and an H is then attached to that nitrogen, SR$_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, and Z is H, OH, =O, or $NHR_C$ where $R_C$=H or an acyl radical of a carboxylic acid with 2 to 30 carbon atoms or an alkyl radical with 2 to 30 carbon atoms;

(8) acyl or alkyl derivatives of guanine or its congeners having the formula:

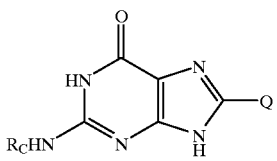

wherein $R_C$ is hydrogen or an acyl group derived from
i. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
ii. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
iii. a dicarboxylic acid having 3–22 carbon atoms,
iv. a cycloalkyl carboxylic acid containing 4 to 22 carbon atoms,
v. a nicotinic acid, or
vi. a substituted or unsubstituted aromatic carboxylic acid with 7 to 22 carbon atoms,
vii. a carboxylic acid derived from
 1. a polymer of ethylene glycol with the structure $HOOC-(CH_2)_m-(CH_2CH_2O)_nH$ or $HOOC-(CH_2)_m-(CH_2CH_2O)_nCH_3$, or
 2. a polymer of vinyl alcohol with the structure $HOOC-(CH_2)_m-(CH_2CHOH)_nH$ or $HOOC-(CH_2)_m-(CH_2CHOH)_nCH_3$, where m=0–3 and n=2–8, or
viii. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms.

Also encompassed by the invention are the pharmaceutically acceptable salts of the above-noted compounds.

Advantageous compounds of the invention are fatty acid esters of deoxyguanosine, deoxyinosine, guanosine, inosine, deoxyxanthosine and xanthosine, especially those with 8 or more carbon atoms in the acyl substituent(s). Particularly advantageous compounds are fatty acid esters of deoxyguanosine or deoxyinosine with 12 to 18 carbon atoms in the acyl substituent. 3',5'-O-$N^2$-tripalmitoyl-2'-deoxyguanosine is particularly active. Compounds with a polar amino acid substituent, e.g. lysine or arginine, conjugated to either a hydroxyl group on the aldose moiety or to the exocyclic amino group of guanosine or deoxyguanosine, and optionally with a fatty acid esterified to a hydroxyl group on the aldose moiety, are particularly suited for formulation in aqueous pharmaceutical carriers.

In one embodiment of the invention, derivatives of the compounds of the invention with enhanced water solubility are prepared by attaching phosphate or sulfate moieties to a free hydroxy group on the aldose moiety of the purine nucleoside.

In another embodiment, substituents, such as short chain alkyl or substituted alkyl radicals, e.g. methyl, ethyl or propyl, are attached at the 1,3, and/or 7 position of the oxypurine moiety of the above-described compounds.

In another embodiment of the invention, the exocyclic amino group of guanosine, deoxyguanosine or their congeners may have two acyl substituents, which may be the same or different. In such cases, the acyl substituents are selected from the groups of acyl radicals designated as $R_C$ in the descriptions for guanosine, deoxyguanosine and their congeners.

Nonionic Surfactants

It has been found that a variety of nonionic surfactants including but not limited to polyoxyethylene sorbitan acylates e.g. Tween 80 [polyoxyethylene sorbitan mono-oleate], Tween 60 [polyoxyethylene sorbitan monostearate], etc.; polyoxyethylene ethers, e.g. Brij 96 [polyoxyethylene-10-oleyl ether] and Triton X-100; or ethylene oxide condensates, e.g. Nonidet 40-P [octylphenol-ethylene oxide condensate]) enhance the effect of compounds of the invention on hematopoiesis in vivo. Further, these surfactants alone accelerate hematopoietic recovery after bone marrow damage caused by cytoreductive agents such as cyclophosphamide (see Example 52). Novel compositions of the invention include one or more of the above-noted nonionic surfactants and erythropoietin, an interleukin, a colony-stimulating factor, or another compound capable of stimulating hematopoiesis.

Compositions of the Invention

In one embodiment of the invention, novel pharmaceutical compositions comprise as an active agent one or more oxypurine nucleosides selected from guanosine, inosine, xanthosine, deoxyxanthosine, deoxyinosine, deoxyguanosine, congeners of these oxypurine nucleosides, and acyl and alkyl derivatives of these oxypurine nucleosides and congeners, together with a pharmaceutically acceptable carrier.

In another embodiment, the compounds of the invention include in addition to one or more compounds of the invention and at least one of the following compounds which affect hematopoiesis: a nonionic surfactant, an interleukin such as IL-1,-2,-3,-4,-5,-6,-7,-8 (advantageously IL-1, 3, and 6), a colony-stimulating factor, for example granulocyte colony-stimulating factor (G-CSF), granulocyte/macrophage colony-stimulating factor (GM-CSF), erythropoietin (EPO), glucan, polyinosine-polycytidine, or any other agent having beneficial effects on hematopoiesis. The compositions, depending on the intended use, are manufactured in the form of a liquid, a suspension, a tablet, a capsule, a dragee, an injectable solution, a topical solution, or a suppository (see discussion of formulation below).

In another embodiment of the invention, the composition comprises at least one compound of the invention and a radioprotective compound.

In another embodiment of the invention, the composition comprises at least one compound of the invention and an antiviral or anti-neoplastic agent, or other pharmaceutical agent which decreases blood cell counts.

Therapeutic Uses of the Compounds and Compositions of the Invention

The therapeutic activities of the compounds of the invention fall into at least three main classifications of disease states: cytopenias or impaired hematopoiesis, bacterial infection, and inflammatory disease. The biological activities indicating therapeutic utility of the compounds of the invention in these disease states are demonstrated in the Examples.

The compounds of the invention are useful to modify, improve, or aid in the process of hematopoiesis and immune system function in animals. The compounds restore hematopoiesis or blood cell counts after bone marrow damage or suppression caused by chemicals, radiation, or disease; protect against damage due to chemicals, radiation, or disease; and modify blood cell (e.g. leukocyte and platelet) counts or activity in animals. The compounds of the invention are useful in treating humans; however, the invention is not intended to be so limited, it being within the contemplation of the invention to treat all animals that experience a beneficial effect from the administration of the active compounds of the invention.

Substantial amelioration of effects of ionizing radiation is obtained, where the compounds of the invention are used in conjunction with a radioprotective compound.

The invention is furthermore embodied in the systemic administration of a pharmaceutical compound or composition containing guanosine, deoxyguanosine, inosine, xanthosine, deoxyxanthosine, deoxyinosine, congeners of such nucleosides or acyl and alkyl derivatives of such nucleosides or congeners, or in combinations, for the purpose of improving hematopoiesis in patients with depressed blood cell counts, impaired bone marrow function or who are otherwise in need of increased hematopoietic activity.

Specific conditions where advantages are achieved using the compounds, compositions, and methods of the invention include situations where improvement of hematopoiesis is desired. Such conditions include treating animals, e.g. human patients, subjected to cytoreductive cancer chemotherapy, antiviral chemotherapy, therapeutic or accidental exposure to ionizing radiation, animals in need of improved host leukocyte-mediated defense against infection, and animals with anemia or bone marrow hypoplasia caused by disease or accidental poisoning. Advantages are also achieved using the compounds, compositions, and methods of the invention in the following ways: increasing leukocyte counts in animals with normal cell counts, e.g. for improving host resistance to infection, increasing thrombocyte counts in animals with normal cell counts, for example for improving blood-clotting potential (e.g., before surgery), pretreatment of animals scheduled to undergo anticancer or antiviral chemotherapy (or therapeutic irradiation), pretreatment of bone marrow transplant donors, accelerating or improving recovery after bone marrow transplants, treatment of bone marrow cells in culture prior to transplant, treatment of bone marrow cells in culture (for either research purposes or prior to transplant). Specifically included are veterinary applications requiring modulation of blood cell counts.

In addition to restore blood cell counts in cytopenic animals, compounds of the invention display activity in fighting bacterial infections and in attenuating inflammatory responses. As demonstrated in Example XX, Cytopenias The compounds and compositions of the invention are useful in the treatment of cytopenias as enumerated and discussed below:

A. Neutropenia

Neutropenia due to cancer or cancer chemotherapy; neutropenia due to antiviral chemotherapy; neutropenia due to exposure to ionizing radiation (accidental or therapeutic exposure); neutropenia due to immunosuppressive chemotherapy (e.g. treatment of autoimmune disorders like rheumatoid arthritis with cytotoxic drugs); neutropenia in burn patients (neutropenia is common in patients with severe burns); neutropenia due to viral infections (e.g. pancytopenia often found in AIDS patients, which is exaggerated by treatment with myelosuppressive drugs such as AZT); neutropenia secondary to aplastic anemia or myelodysplastic syndrome; neutropenia due to poisoning (e.g. benzene; also, a number of ethical pharmaceutical agents list agranulocytosis as a side effect); idiopathic neutropenia; chronic neutropenia; neutropenia due to hairy cell leukemias or other lymphocytic leukemias; neutropenia from any other causes; neutropenia in non-human animals (veterinary conditions).

B. Thrombocytopenia

Low thrombocyte (platelet) counts due to cancer chemotherapy; thrombocytopenia due to antiviral chemotherapy; thrombocytopenia due to exposure to ionizing radiation (accidental or therapeutic exposure); low thrombocyte counts due to immunosuppressive chemotherapy (e.g. treatment of autoimmune disorders like rheumatoid arthritis with cytoxic drugs); thrombocytopenia due to viral infections (e.g. pancytopenia often found in AIDS patients, which is exaggerated by treatment with myelosuppressive drugs such as AZT); thrombocytopenia secondary to aplastic anemia, myelodysplastic syndrome or hypoplastic bone marrow syndromes; thrombocytopenia from any other cause.

C. Lymphocytopenia

Low lymphocyte counts due to cancer chemotherapy; lymphocytopenia due to antiviral chemotherapy; Low lymphocyte counts due to exposure to ionizing radiation (accidental or therapeutic exposure); low lymphocyte counts due to immunosuppressive chemotherapy (e.g. treatment of autoimmune disorders like rheumatoid arthritis with cytotoxic drugs); lymphocytopenia due to viral infection, such as AIDS; lymphocytopenia from any other cause.

D. Anemia

Low erythrocyte counts due to kidney dialysis; low erythrocyte counts due to kidney damage; aplastic anemia; anemia due to viral infections or myelosuppressive chemotherapy agents; anemia due to infection or disease (e.g. malaria); anemia due to hemorrhage; anemia from any other cause.

Treatment of Complications Associated with Radiation Exposure

Three situations wherein active compounds of the invention may be clinically useful in treating radiation damage are 1) accidental exposure to ionizing radiation, as in a nuclear accident; 2) diagnostic exposure to radiation during radiography; and 3) therapeutic exposure to radiation, such as in radiotherapy of cancer.

In the first case, in one embodiment, the active compounds are administered in a formulation suitable for parenteral injection, followed by oral or parenteral administration once to several times per day of doses sufficient to enhance hematopoiesis, e.g. 0.01 to 3 grams per day according to the effect achieved.

In the second case, X-ray exposure during diagnostic radiography, in one embodiment, active compounds are given orally before and after exposure.

In the third case, during cancer radiotherapy, the active compounds are particularly useful in restoring bone marrow function after its undesirable but unavoidable suppression during irradiation.

The compounds of the invention are administered before, during, and/or after exposure to radiation.

The compounds of the invention are useful for prevention or amelioration of the effects of ionizing radiation when coadministered with other radioprotective compounds such as WR-2721, NAC, DDC, cysteamine, 2-mercaptoethanol, mercaptoethylamine, dithiothreitol, glutathione, 2-mercaptoethanesulfonic acid, WR-1065, nicotinamide, 5-hydroxytryptamine, 2-beta-aminoethyl-isothiouronium-Br-Hbr, glucans, GLP/BO4, GLP/BO5, OK-432, Biostim, PSK, Lentinan, Schizophyllan, Rhodexman, Levan, Mannozym, MVE-3, MNR, MMZ, IL-1, IL-2, TNF, thymic factor TF-5, glutathione peroxidase, superoxide dismutase, catalase, glutathione reductase, glutathione transferase, selenium, CdCl2, MnCl2, Zn acetate, vitamin A, beta carotene, prostaglandins, tocopherol and methylene blue and PABA. The administration of these protective compounds along with the compounds of the invention provides protection greater than if the compounds or the other radioprotective agents are given alone.

Treatment of Complications Associated with Cancer Chemotherapy

The white blood cell counts, and particularly the neutrophil counts, of patients treated with standard anti-neoplastic chemotherapy agents (e.g., 5-fluorouracil, fluorodeoxyuridine, vinca alkaloids, cyclophosphamide and other alkylating agents such as busulfan, hexalen or melphalan, daunorubicin, doxorubicin, methotrexate, cytosine arabinoside, 6-mercaptopurine, 6-methylmercaptopurine riboside, thioguanosine, podophyllotoxins, cisplatin, combinations of such cytoreductive agents, or cytoreductive agents plus modulators like leucovorin, PALA, or WR-2721) are often greatly diminished. Daily oral administration (or parenteral injection) of an effective dose, (for example, 0.01–3.0 grams) of a compound of the invention such as palmitoyl-(or other acyl derivatives of) deoxyguanosine for a number of days diminishes or abolishes the neutrophil nadir, which would otherwise occur several days after chemotherapy is initiated. Treatment of recipients of chemotherapeutic agents with the acylated deoxyguanosine also greatly increases the total white blood cell count, including neutrophils and lymphocytes, on subsequent days compared to patients receiving only the chemotherapeutic regimen. This reduces the likelihood of infection throughout the course of treatment, and makes it possible for the patient to receive larger doses of the chemotherapeutic agents and/or to receive repeated doses sooner than comparable patients not treated with the deoxyguanosine derivative(s).

The compounds of the invention are administered before, during, and/or after administration of the anti-neoplastic agents.

Treatment of Complications Associated with Antiviral Chemotherapy

Treatment of patients with AIDS or AIDS-Related Complex with azidothymidine (AZT) and other antiviral agents is complicated by anemia, neutropenia, and thrombocytopenia. Administration of appropriate doses of a compound of the invention such as palmitoylguanosine (or other acylated forms of guanosine) for a number of days (or, depending on the protocol of antiviral treatment, throughout the course of treatment) greatly diminishes the AZT- and/or ddc-induced neutropenia, anemia, thrombocytopenia, and other side effects. This reduces the probability of septic complications and allows the patients to receive larger doses of the antiviral compounds over a shorter time period than patients not also treated with a compound of the invention.

The compounds of the invention are administered before, during, and/or after administration of antiviral agents.

Treatment of Complications Associated with Poisoning and Side Effects of Various Drugs Benzene poisoning or side effects of a variety of substances including numerous prescription drugs, such as anti-thyroid drugs, sulfonamide, phenylthiazines, phenylbutazones, and aminopyrines result in agranulocytosis/neutropenia. Cytopenia is also caused by benzene poisoning and by mustard gas and related alkylating agents. Administration of the compounds of the invention to the victims of such poisoning or the recipients of such drugs, improves recovery by stimulating the production of blood cells such as neutrophils.

Treatment of Cytopenias Associated with Various Diseases

Numerous diseases are associated with various forms of cytopenia. For example, hairy cell leukemia is associated with neutropenia. Thrombocytopenic purpura and aplastic anemia are associated with reduced levels of platelets. Administration of the compounds of the invention increases levels of neutrophils, lymphocytes, and platelets in those afflicted with such diseases.

Treatment of Complications Associated with HIV Infection

HIV-infected patients, especially those afflicted with AIDS, suffer from a variety of symptoms and diseases which result from and, in some cases, further exacerbate a severely compromised immune system. Many of these patients are given antiviral chemotherapeutic agents, such as AZT, which also have detrimental effects on the body's immune function, further lowering resistance to infections of all kinds. Administration of the compounds of the invention—orally, intravenously, or by parenteral injection—raises the low blood cell counts due to viral infections, countering the pancytopenia seen in AIDS patients. Such treatment elevates neutrophil, lymphocyte, and thrombocyte levels and thereby helps to restore immunocompetence. Because greater susceptibility to infections is a dose- and rate-limiting factor in chemotherapeutic treatment of AIDS patients, treatment of the patients with these compounds reduces chemotherapeutic side effects (and thus improves the quality of life) and permits a more intensive chemotherapeutic regimen to be employed.

In patients infected with HIV, inflammatory cytokines also play a role in the pathology associated with AIDS. Tumor necrosis factor (TNF), an inflammatory cytokine, stimulates replication of the virus. As shown in Example 75, compounds of the invention attenuate production fo TNF in response to inflammatory stimuli. Moreover, other inflammatory cytokines, e.g. interferon gamma, are involved in complications associated with AIDS. Interferon-gamma contributes to cachexia and neurological problems in AIDS patients (Brown et al., *Adv. Exp. Med. Biol.* 294:425–35, 1991). Compounds of the invention also attenuate interferon-gamma production (see Example 75).

Regulation of Apoptosis

Programmed Cell Death (apoptosis) is involved in many pathological and physiological aspects of hematopoiesis, lymphopoiesis, and antigen-specific selection of lymphocytes. Drugs such as corticosteroids or cytotoxic cancer chemotherapy agents induce apoptosis. Cell death after exposure to ionizing radiation is in part due to apoptosis. The pathogenesis of AIDS involves excessive apoptosis of lymphocytes. The compounds of the invention, advantageously long-chain fatty acid acyl derivatives of deoxyguanosine such as 3',5'-di-O-palmitoyldeoxyguanosine or $N^2$,3',5'-tripalmitoyldeoxyguanosine, regulate apoptosis of blood cells. The capacity to regulate apoptosis permits therapeutic modification of the production and survival of blood cells (including leukocytes and platelets), function and activity of the immune system as well as other cells and organ systems.

Treatment of Complications Associated with Cancer

Several varieties of cancer are associated with hematological cytopenias independent of those produced by cytoreductive chemotherapy. Hairy cell leukemia is often associated with neutropenia. Neoplastic bone marrow infiltration often impairs hematopoiesis. Administration of the compounds of the invention increases levels of neutrophils and other cell types in those afflicted with such diseases. Some types of granulocytic leukemias are characterized by overproduction of immature, non-differentiating granulocyte precursors. As demonstrated in Examples 41 through 65 below, compounds of the subject invention elicit enhanced terminal differentiation of neutrophil precursors, indicating utility in treatment of leukemias, such as granulocytic leukemia.

A common complication of cancer is cachexia, characterized by weight loss and an inability to utilize nutrients. Cachexia is generally associated with elevated levels of inflammatory cytokines like TNF and interferon-gamma (Brown et al., *Adv. Exp. Med. Biol.* 294:425–35, 1991). As shown in Example 75, compounds of the invention attenuate production of these inflammatory cytokines. Compounds of the invention are useful for treatment of cachexia and other complications of cancer related to such cytokines.

Use of the Compounds of the Invention in Bone Marrow Transplants

Transplantation of the bone marrow is used to treat those suffering the effects of accidental or therapeutic radiation exposure and of cytoreductive chemotherapy (anti-viral and/or anti-neoplastic). The compounds of the invention are used in a variety of ways to support bone marrow transplantation. Administration of the compounds to bone marrow transplant donors elevates levels of various blood cell types, such a neutrophils, lymphocytes, megakaryocytes, and thrombocytes (platelets) in peripheral blood and especially their progenitors in the bone marrow itself. Administration of the compounds to bone marrow recipients following, prior to, or during transplantation, accelerates hematopoietic recovery. In addition, incubation of bone marrow cells in culture with the compounds of the invention prior to transplantation improves the quality of the transplant.

Use of the Compounds for Autologous Blood Transfusion

Autologous blood transfusion, or the intentional storage of quantities of a patient's own blood for subsequent transfusion, e.g. prior to elective surgery or as a precaution for unanticipated situations requiring transfusion, is important in view of the possibility of contamination of blood from other donors with viruses such as HIV or hepatitis viruses. The compounds of the subject invention are useful in restoring blood counts when administered after removal of a patient's blood for storage. Alternatively, these compounds may be administered prior to removal of blood in order to boost cell counts. As shown in Example 76, compounds of the invention mobilize hematopoietic stem cells from the bone marrow into the peripheral circulation. This facilitates collection of adequate numbers of hematopoietic progenitors from peripheral blood, avoiding the need for painful and inconvenient aspiration of stem cells from a patient's bone marrow.

Prophylactic Use of the Compounds of the Subject Invention

There are numerous clinical and veterinary situations in which it is desireable to boost or otherwise modify aspects of the hematopoietic system in anticipation of various challenges.

For example, there are many circumstances in which it is beneficial to improve resistance to infection, for example in anticipation of surgical procedures or exposure to viral or bacterial infections. Administration of the compounds of the invention to an animal with normal cell counts increases leukocyte counts and improves host resistance to infection.

There are situations in which it is useful to improve an animal's blood-clotting potential, for example before surgery. Administration of the compounds of the invention prior to surgery increases thrombocyte counts and thereby improves the blood-clotting potential.

In situations where damage to the bone marrow and/or hematopoietic system is anticipated, such as in anticancer or antiviral chemotherapy or in therapeutic irradiation it is beneficial to improve or enhance hematopoietic function. Pretreatment of an animal scheduled to undergo such therapy with the compounds of the invention accelerates the production of white blood cells and platelets, and/or attenuates damage to blood cell precursors. The compounds positively modify the hematopoietic system prophylactically.

Administration of the compounds to bone marrow transplant donors prior to donation elevates levels of various blood cell types, such a neutrophils, lymphocytes, megakaryocytes, and thrombocytes (platelets) in peripheral blood and elevates hematopoietic progenitor cells in the bone marrow itself.

Treatment or Prevention of Infection

As shown in Example 73, compounds of the invention strongly improve survival in severe polymicrobial infection caused by intestinal bacteria. Both gram-negative and gram-positive bacteria are present in this infection model. Compounds of the invention are useful in combating bacterial infection when used in a variety of ways. Prophylactic treatment is administered prior to high-risk surgery, or in patients at risk for infections due to exposure to pathogens or impaired immune function. This treatment prevents (attenuates bacterial proliferation and thereby eliminates full clinical manifestation of the infectious process) infection. Compounds of the invention are also useful when administered to patients with established infections, and are optionally used in conjunction with antibiotic drugs such as penicillin, erythromycin, cephalosporins, gentamycin, or metronidazole. Compounds of the invention improve endogenous mechanisms for clearing bacteria and also attenuate deleterious responses to bacterial inflammatory components (see Example 74). Compounds of the invention are also useful for treating or preventing fungal infection.

For treatment of infection, whether prophylactic or after infection is already present, effective doses of compounds of the invention are administered orally or parenterally in appropriate formulations. Doses ranging from one milligram up to one gram are chosen according to therapeutic effect. Doses are administered between once per week and several times per day according to severity of the disease and response of the patient.

Treatment or Attenuation of Inflammatory Disease

Compounds of the invention also have therapeutic activity in inflammatory disease. As demonstrated in Example 74, compounds of the invention allow animals to survive otherwise lethal doses of bacterial endotoxin. Endotoxin, a lipopolysaccharide component of bacterial cell walls, is a potent inflammatory stimulus which elicits secretion of inflammatory cytokines and other mediators. These mediators, which include tumor necrosis factor (TNF), interleukin-1, interleukin-6, gamma-interferon, leukotrienes and other agents, account for the inflammatory activity of endotoxin. Such mediators, which are released from macrophages, lymphocytes and other cell types, also participate in pathogenesis of a variety of inflammatory disease states, even when endotoxin is not involved as a primary stimulus.

Compounds of the invention modulate cytokine release in response to inflammatory stimuli including but not restricted to endotoxin. Other inflammatory stimuli include bacterial, fungal, or viral components. As shown in Example 75, compounds of the invention reduce serum cytokine levels in response to an endotoxin challenge. This anti-inflammatory activity coincides with a marked improvement in survival of a lethal dose of endotoxin (see Example 74).

Compounds of the invention are useful in disease conditions in which either endotoxin or inflammatory cytokines contribute to pathogenesis. Such conditions include autoimmune conditions, inflammation secondary to infection, or idiopathic inflammatory conditions. Autoimmune disease conditions in which cytokines modulated by compounds of the invention include but are not limited to psoriasis, multiple sclerosis, rheumatoid arthritis, autoimmune hepatitis, and lupus. Inflammatory conditions in which such cytokines participate include but are not limited to inflammatory responses to viral, bacterial or fungal infection, including systemic inflammatory response syndrome (sepsis), as well as localized tissue inflammation and injury in diseases like viral hepatitis, AIDS (e.g. cachexia and neuropathy) and poliomyelitis. Similarly, inflammatory cytokines are implicated in cachexia in cancer patients and in rejection of allogeneic organ or tissue transplants.

For treatment of inflammatory skin conditions, compounds of the invention are formulated for topical administration, and are applied at at frequency of once per week to several times per day. Concentrations in a topical formulation range from 0.01 to 50 mg/ml.

For treatment of systemic inflammatory disease, effective doses of compounds of the invention are administered orally or parenterally in appropriate formulations. Doses ranging from one milligram up to one gram are chosen according to therapeutic effect. Doses are administered between once per week and several times per day according to severity of the disease. Similar doses and regimens are appropriate for treatment of infectious disease.

D. Administration and Formulation of Compounds and Compositions of the Invention The compounds and compositions of the invention are administered orally, by parenteral injection, intravenously, topically, or by other means, depending on the condition being treated.

The compounds and compositions of the invention are administered chronically or intermittently. The compounds and compositions are administered prior to, during, or after an event (e.g. irradiation or exposure to cytoreductive chemotherapy agents) which causes damage to the hematopoietic system. In the case of after an event, the compounds and compositions are administered before and/or after the nadir in blood cell or bone marrow cell counts is reached.

The compounds of the invention are formulated in biodegradable, bioerodible, or other gradual-release matrices for sustained release of the compounds after oral administration or subcutaneous implantation. In the case of intravenous or intramuscular injection, the compounds are optionally formulated in liposomes.

The pharmacologically active compounds optionally are combined with suitable pharmaceutically acceptable carriers comprising excipients and auxiliaries which facilitate processing of the active compounds. These are administered as tablets, dragees, capsules, and suppositories. The compositions are administered for example orally, rectally, vaginally, or released through the buccal pouch of the mouth, and may be applied in solution form by injection, orally or by topical administration. The compositions may contain from about 0.1 to 99 percent, preferably from about 50 to 90 percent of the active compound(s), together with the excipient(s).

For parenteral administration by injection or intravenous infusion, the active compounds are suspended or dissolved in aqueous medium such as sterile water or saline solution. Injectable solutions or suspensions optionally contain a surfactant agent such as polyoxyethylenesorbitan esters, sorbitan esters, polyoxyethylene ethers, or phospholipids, or solubilizing agents like propylene glycol or ethanol. One suitable formulation is prepared by dissolving a compound of the invention in ethanol and then adding it to physiological saline while sonicating or stirring vigorously, with a final ethanol concentration ranging from 0.5 to about 20 percent. A surfactant such as Tween 80 or phosphatidylcholine is optionally included. The compounds of the invention may are optionally suspended or dissolved in injectable fat emulsions for parenteral administration. Compounds of the invention are also optionally formulated in phospholipid complexes. The solution or suspension typically contains 0.01 to 5% of the active compounds. The active compounds optionally are dissolved in pharmaceutical grade vegetable oil for intramuscular injection. Such preparations contain about 1% to 50% of the active compound(s) in oil.

Suitable excipients include fillers such as sugars, for example lactose, sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch or potato starch, gelatin, tragacanth, methyl cellulose, hydroxypropylmethyl cellulose, sodium carboxymethyl cellulose and/or polyvinyl pyrrolidone.

Auxiliaries include flow-regulating agents and lubricants, for example, silica, talc, stearic acid or salts thereof, such as magnesium stearate or calcium stearate and/or polyethylene glycol. Dragee cores are provided with suitable coatings which, if desired, are resistant to gastric juices. For this purpose, concentrated sugar solutions are used, which optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate are used. Dyestuffs or pigments are optionally added to the tablets or dragee coatings, for example, for identification or in order to characterize different compound doses.

The pharmaceutical preparations of the present invention are manufactured in a manner which is itself known, for example, by means of conventional mixing, granulating, dragee- making, dissolving, or lyophilizing processes. Thus, pharmaceutical preparations for oral use are obtained by combining the active compound(s) with solid excipients, optionally grinding the resulting mixture and processing the mixture of granules, after adding suitable auxiliaries, if desired or necessary, to obtain tablets or dragee cores.

Other pharmaceutical preparations which are useful for oral delivery include push-fit capsules made of gelatin, as well as soft-sealed capsules made of gelatin and a plasticizer such as glycerol or sorbitol. The push-fit capsules contain the active compound(s) in the form of granules which optionally are mixed with fillers such as lactose, binders such as starches and/or lubricants such as talc or magnesium stearate, and, optionally stabilizers. In soft capsules, the active compounds are preferably dissolved or suspended in suitable liquids such as fatty oils, liquid paraffin, or polyethylene glycols. In addition, stabilizers optionally are added.

In another embodiment, compounds of the invention are formulated for oral administration as phospholipid complexes, liposomes, or mixed lipid-surfactant micelles. Components of micelles include but are not limited to triglycerides, fatty acids (unsaturated or saturated), phospholipids including phosphatidylcholine and phosphatidylserine, bile salts, and synthetic nonionic surfactants. Lipid-surfactant micelles improve delivery of compounds of the invention into the intestinal lymphatic system after oral administration.

Pharmaceutical preparations which are used rectally include, for example, suppositories which consist of a combination of active compounds with a suppository base. Suitable suppository bases are, for example, natural or synthetic triglycerides, paraffin hydrocarbons, polyethylene glycols or higher alkanols. In addition, gelatin rectal capsules which consist of a combination of the active compounds with a base are useful. Base materials include, for example, liquid triglycerides, polyethylene glycols, or paraffin hydrocarbons.

Suitable formulations for parenteral administration include aqueous solutions of the active compounds in water soluble form, for example, water soluble salts. In addition, suspensions or solutions of the appropriate active compounds in oily injection vehicles, solvents such as propylene glycol, or lipid-aqueous emulsions are administered. Suitable lipophilic solvents or vehicles include fatty oils, for example, sesame oil, or synthetic fatty acid esters, for example, ethyl oleate or triglycerides. Aqueous injection suspensions optionally include substances which increase the viscosity of the suspension which include, for example, sodium carboxymethylcellulose, sorbitol and/or dextran. The suspension optionally contains stabilizers.

In another embodiment, the active compounds are formulated as part of a skin lotion for topical administration. Suitable lipophilic solvents or vehicles include fatty oils, for example sesame oil or coconut oil, or synthetic fatty acid esters, for example ethyl oleate or triglycerides.

E. Synthesis of the Compounds of the Invention

Acylated derivatives of oxypurine nucleosides are synthesized by reacting an oxypurine nucleoside or congener with an activated carboxylic acid. An activated carboxylic acid is one that has been treated with appropriate reagents to render its carboxylate carbon more susceptible to nucleophilic attack than is the case in the original carboxylic acid. Examples of useful activated carboxylic acids for synthesis of the compounds of the invention are acid chlorides, acid anhydrides, n-hydroxysuccinimide esters, or carboxylic acids activated with BOP-DC. Carboxylic acids may also be linked to oxypurine nucleosides or congeners with coupling reagents like dicyclohexylcarbodiimide (DCC).

During preparation of the acyl compounds of the invention, when the acid source of the desired acyl derivative has groups which interfere with the acylation reactions, e.g., hydroxyl or amino groups, these groups are blocked with protecting groups, e.g., t-butyldimethylsilyl ethers or t-BOC groups, respectively, before preparation of the anhydride. For example, lactic acid is converted to 2-t-butyldimethylsiloxypropionic acid with t-butyldimethylchlorosilane, followed by hydrolysis of the resulting silyl ester with aqueous base. The anhydride is formed by reacting the protected acid with DCC. With amino acids, the N-t-BOC derivative is prepared, using standard techniques, which is then converted to the anhydride with DCC. With acids containing more than one carboxylate group (e.g., succinic, fumaric, or adipic acid) the acid anhydride of the desired dicarboxylic acid is reacted with an oxypurine nucleoside or congener in pyridine or pyridine plus dimethylformamide or dimethylacetamide.

Amino acids are coupled to the exocyclic amino groups of guanosine and deoxyguanosine, and to hydroxyl groups on the aldose moiety of oxypurine nucleosides or their congeners, by standard methods using DCC in a suitable solvent, particularly a mixture of (i) methylene chloride and (ii) dimethylacetamide or dimethylformamide.

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

THE EXAMPLES

The following examples relate to methods for preparing the compounds of the subject invention.

Example 1

Preparation of Octanoylguanosine

To a 100 mL flask was added guanosine (2.0 g, 7.06 mmol) and N,N-dimethyl-4-aminopyridine (0.017 g, 0.14 mmol). N,N-dimethylformamide (25 mL) was added via cannula with stirring, the flask was purged with argon gas and pyridine (14 mL) was added via cannula. The slurry was allowed to cool 10 min. in an ice/NaCl bath and octanoyl chloride (1.6 mL, 9.2 mmol) was added dropwise. The mixture was allowed to stir while it slowly warmed to 25° C. After 18 h, the mixture was poured into 300 mL of ice-cold 0.1 M sodium bicarbonate solution giving a white solid which was isolated by suction filtration, washed with 3×100 mL hot water, air dried, and recrystallized from hot methanol.

Example 2

Preparation of Lauroylguanosine

To a 100 mL flask was added guanosine (2.0 g, 7.06 mmol) and N,N-dimethyl-4-aminopyridine (0.017 g, 0.14 mmol). N,N-dimethylformamide (25 mL) was added via cannula with stirring, the flask was purged with argon gas and pyridine (14 mL) was added via cannula. The slurry was allowed to cool 10 min. in an ice/NaCl bath and lauroyl chloride (2.12 mL, 9.2 mmol) was added dropwise. The mixture was allowed to stir while it slowly warmed to 25° C. After 18 h, the mixture was poured into 300 mL of ice-cold 0.1 M sodium bicarbonate solution giving a white solid which was isolated by suction filtration, washed with 3×100 mL hot water, air dried, and recrystallized from hot methanol.

Example 3

Preparation of Palmitoylguanosine

To a 100 mL flask was added guanosine (2.0 g, 7.06 mmol) and N,N-dimethyl-4-aminopyridine (0.017 g, 0.14 mmol). N,N-dimethylformamide (25 mL) was added via cannula with stirring, the flask was purged with argon gas and pyridine (14 mL) was added via cannula. The slurry was allowed to cool 10 min. in an ice/NaCl bath and palmitoyl chloride (2.8 mL, 9.2 mmol) was added dropwise. The mixture was allowed to stir while it slowly warmed to 25° C. After 18 h, the mixture was poured into 300 mL of ice-cold 0.1 M sodium bicarbonate solution giving a white solid which was isolated by suction filtration, washed with 3×100 mL hot water, air dried, and recrystallized from hot 2-methoxyethanol.

Example 4

Preparation of Benzoylguanosine

To a 100 mL flask was added guanosine (2.0 g, 7.06 mmol) and N,N-dimethyl-4-aminopyridine (0.017 g, 0.14 mmol). N,N-dimethylformamide (30 mL) was added via cannula with stirring, the flask was purged with argon gas and pyridine (16 mL) was added via cannula. The slurry was allowed to cool 10 min. in an ice/NaCl bath and benzoyl chloride (1.2 mL, 8.5 mmol) was added dropwise. The mixture was allowed to stir while it slowly warmed to 25° C. After 72 h, the mixture was poured into 300 mL of 0.1 M sodium bicarbonate solution (warmed to 60° C.) giving a white solid which was isolated by suction filtration (using a medium glass frit), washed with 3×100 mL cold water, and air dried.

Example 5

Preparation of Palmitoylxanthosine

To a 50 mL flask was added xanthosine dihydrate (1.0 g, 3.52 mmol) and N,N-dimethyl-4-aminopyridine (0.0086 g, 0.07 mmol). N,N-dimethylformamide (16 mL) was added via cannula with stirring, the flask was purged with argon gas and pyridine (8 mL) was added via cannula. The slurry was allowed to cool 10 min. in an ice/NaCl bath and palmitoyl chloride (1.6 mL, 9.2 mmol) was added dropwise. The mixture was allowed to stir while it slowly warmed to 25° C. After 18 h, the mixture was poured into 300 mL of ice-cold 0.1 M sodium bicarbonate solution giving a white solid which was isolated by suction filtration, washed with 3×100 mL hot water, air dried, and recrystallized from hot methanol.

Example 6

Preparation of Palmitoylinosine

To a 50 mL flask was added inosine (1.0 g, 3.73 mmol) and N,N-dimethyl-4-aminopyridine (0.017 g, 0.074 mmol). N,N-dimethylformamide (16 mL) was added via cannula with stirring, the flask was purged with argon gas and pyridine (8 mL) was added via cannula. The slurry was allowed to cool 10 min. in an ice/NaCl bath and palmitoyl chloride (1.3 mL, 4.1 mmol) was added dropwise. The mixture was allowed to stir while it slowly warmed to 25° C. After 18 h, the mixture was quenched with a small chunk of ice and the solvents were evaporated leaving a white gum. Toluene (20 mL) was evaporated from the gum, which was then thoroughly triturated with 1:1 ethyl acetate-diethyl ether. The supernatant was isolated by suction filtration and the solvents evaporated leaving a syrup which turned into a soft, amorphous solid after 24 h in a vacuum desiccator.

Example 7

Preparation of Palmitoyldeoxyinosine

To a 100 mL flask was added deoxyinosine (1.5 g, 5.95 mmol) and N,N-dimethyl-4-aminopyridine (0.036 g, 0.297 mmol). N,N-dimethylformamide (35 mL) was added via cannula with stirring, the flask was purged with argon gas and pyridine (15 mL) was added via cannula. The slurry was allowed to cool 10 min. in an ice/NaCl bath and palmitoyl chloride (2.0 mL, 6.54 mmol) was added dropwise. The mixture was allowed to stir while it slowly warmed to 25° C. After 18 h, the mixture was poured into 300 mL of ice-cold 0.1 M sodium bicarbonate solution giving a white solid which was isolated by suction filtration, washed with 100 mL water, and dried overnight in a vacuum desiccator giving 2.72 g (93%) of palmitoyldeoxyinosine.

Example 8

Preparation of (5-carboxypentanoyl)guanosine

To 500 mg of guanosine in anhydrous pyridine was added adipic acid (5 mol eq) and bis(2-oxo-3-oxazolidinyl)-phosphinic chloride (BOPDC) (1.0 mol eq.). The mixture was allowed to stir at room temperature for 18 h, then the solvent was removed in vacuo. The residue was added to 100 mL of ice-cooled water and the aqueous layer adjusted to pH 3.0 and then extracted three times with 60 mL of ethyl acetate. The combined extracts are dried over anhydrous magnesium sulfate and evaporated in vacuo. The residue was chromatographed on a silica gel column and eluted with a mixture of chloroformethanol, whereupon the eluate was evaporated in vacuo.

Examples 9–11

Preparation of (5-carboxyhexanoyl)guanosine, (5-carboxyheptanoyl)guanosine, and (5-carboxynonanoyl)guanosine (5-carboxyhexanoyl)guanosine, (5-carboxyheptanoyl) guanosine, and (5-carboxynonanoyl)guanosine were prepared from guanosine with pimelic acid, suberic acid, and sebacic acid, respectively, in a manner similar to that used for (5-carboxypentanoyl)guanosine.

Example 12

Preparation of 3',5'-O,O-Bis-(5-carboxypentanoyl) guanosine

To 500 mg of guanosine in anhydrous pyridine was added adipic acid (10 mol eq) and bis(2-oxo-3-oxazolidinyl) phosphinic chloride (BOPDC) (2.0 mol eq.). The mixture was allowed to stir at room temperature for 18 h, then the solvent was removed in vacuo. The residue was added to 100 mL of ice-cooled water and the aqueous layer adjusted to pH 3.0 and then extracted three times with 60 mL of ethyl acetate. The combined extracts were dried over anhydrous magnesium sulfate and evaporated in vacuo. The residue was chromatographed on a silica gel column and eluted with a mixture of chloroformethanol, whereupon the eluate was evaporated in vacuo.

Examples 13–15

Preparation of 3',5'-O,O-Bis-(5-carboxyhexanoyl) guanosine, 3',5'-O,O-Bis-(5-carboxyheptanoyl) guanosine, and 3',5'-O,O-Bis-(5-carboxynonanoyl) guanosine 3',5'-O,O-Bis-(5-carboxyhexanoyl)guanosine, 3',5'-O,O-Bis-(5-carboxyheptanoyl)guanosine, and 3',5'-O-Bis-(5- carboxynonanoyl)guanosine were prepared from guanosine with pimelic acid, suberic acid, and sebacic acid, respectively, in a manner similar to that used for (5-carboxypentanoyl)guanosine.

Example 16

Preparation of (Nα-FMOC-Nε-CBZ-lysyl)guanosine

To 500 mg of guanosine in anhydrous pyridine was added Nα-FMOC-Nε-CBZ-lysine (2 mol eq, from Sigma) and dicyclohexylcarbodiimide (DCC) (1.0 mol eq.) The mixture was allowed to stir at room temperature for 18 h, then the solvent was removed in vacuo. The residue was added to 100 mL of ice-cooled water and the aqueous layer adjusted to pH 3.0 and then extracted three times with 60 mL of ethyl acetate. The combined extracts were dried over anhydrous magnesium sulfate and evaporated in vacuo. The residue was chromatographed on a silica gel column and eluted with a mixture of chloroformethanol, whereupon the eluate was evaporated in vacuo.

Example 17

Preparation of (Nα-FMOC-Nε-CBZ-lysyl)-2',3'-O-isopropylideneguanosine

To 2.0 g of 2',3'-o-isopropylideneguanosine (from Sigma) in anhydrous pyridine was added Nα-FMOC-Nε-CBZ-lysine (2 mol eq, from Sigma) and dicyclohexylcarbodiimide (DCC) (1.0 mol eq.). The mixture was allowed to stir at room temperature for 18 h, then the solvent was removed in vacuo. The residue was added to 100 ml of ice-cooled water and the aqueous layer adjusted to pH 3.0 and then extracted three times with 60 mL of ethyl acetate. The combined extracts were dried over anhydrous magnesium sulfate and evaporated in vacuo. The residue was chromatographed on a silica gel column and eluted with a mixture of chloroform-ethanol, whereupon the eluate was evaporated in vacuo.

Example 18

Preparation of (Nα-FMOC-Nε-CBZ-lysyl) guanosine

A solution of 1.5 g of (Nα-FMOC-Nε-CBZ-lysyl)-2',3'-O-isopropylideneguanosine in 18 mL of 50% aqueous HCO2H was allowed to stand for 20 hr at room temperature. The solution was evaporated to dryness giving a residue which was recrystallized from MeOH-EtOAc.

Example 19

Preparation of (Nα-FMOC-lysyl)guanosine

A solution of 1.0 g of (Nα-FMOC-Nε-CBZ-lysyl) guanosine in 150 mL of DMF was hydrogenated for 3.5 hr at 48 psi in the presence of 0.7 g of 10% Pd/C. The mixture was filtered and the filtrate evaporated and then treated with 30 mL of EtOH followed by 20 mL of H2O. The resulting solid was recrystallized from MeOH-EtOAc.

Example 20

Preparation of lysylguanosine

To a stirred solution of 800 mg of (Nα-FMOC-lysyl) guanosine in anhydrous pyridine was added anhydrous piperidine (4 mol eq.). The mixture was allowed to stir for 5 hr at 0° C. and then was evaporated to dryness. The residue was dissolved in DMF and purified by slow addition of the DMF solution to a rapidly stirred solution of EtOH-Et2O, yielding a precipitate.

Example 21

Preparation of Palmitoyl-2'-deoxyguanosine

To a 250 mL flask was added 2'-deoxyguanosine monohydrate (5.0 g, 17.5 mmol), triethylamine (3.13 ml, 22.4 mmol) and N,N-dimethyl-4-aminopyridine (0.046 g, 0.37 mmol). N,N-dimethylformamide (130 mL) was added via cannula with stirring and the flask was purged with argon gas. The slurry was allowed to cool 10 minutes in an ice/NaCl bath and palmitoyl chloride (6.3 mL, 20.6 mmol) was added dropwise. The mixture was allowed to stir while it slowly warmed to 25 degrees C. After 72 h, the mixture was poured with stirring into 400 mL of a 1:1 mixture of water and saturated aqueous sodium bicarbonate solution, which mixture had been warmed to about 60 degrees C. The resulting white solid was isolated by suction filtration, washed with water, and dried.

Example 22

Preparation of 3'-O-Palmitoyl-2'-deoxyguanosine

This compound was prepared using the procedure for Palmitoyl-2'-deoxyguanosine, substituting the appropriate amount of 5'-O-dimethoxytrityl-deoxyguanosine for 2'-deoxyguanosine monohydrate and deprotecting the 5'hydroxyl group as follows: removing the dimethoxytrityl group by stirring in 80% aqueous acetic acid at 25 degrees C. for 1 hour, isolating the crude product by filtration, triturating the crude product for 1 hour in methanol, recovering the product by filtration and drying.

Example 23

Preparation of 3,5'-O,O-Dipalmitoyl-2'-deoxyguanosine

This compound was obtained as side product from 5'-O-palmitoyl-2'-deoxyguanosine, as prepared above, and isolated as follows: suspending the crude product in toluene with silica gel, evaporating the toluene, applying the resulting solid to a column of silica gel capped with a short layer of alumina, eluting the column with chloroform-methanol, and evaporating the appropriate fractions.

Example 24

Preparation of Octanoyl-2'-deoxyguanosine

This compound was prepared using the procedure for palmitoyl-2'-deoxyguanosine, substituting the appropriate amount of octanoyl chloride for palmitoyl chloride.

Example 25

Preparation of Lauroyl-2'-deoxyguanosine

This compound was prepared using the procedure for palmitoyl-2'-deoxyguanosine, substituting the appropriate amount of octanoyl chloride for palmitoyl chloride.

Example 26

Preparation of Benzoyl-2'-deoxyguanosine

This compound was prepared using the procedure for palmitoyl-2'-deoxyguanosine, substituting the appropriate amount of benzoyl chloride for palmitoyl chloride, and substituting a 1:1 mixture of ice water and saturated aqueous sodium bicarbonate solution in the workup.

Example 27

Preparation of Butyryl-2'-deoxyguanosine

This compound was prepared using the procedure for palmitoyl-2'-deoxyguanosine, substituting the appropriate amount of butyryl chloride for palmitoyl chloride, and isolating as follows: evaporating the solvent after 72 hours, triturating the resulting material in 1:1 diethyl ether-ethyl acetate, and recovering the product by filtration.

Example 28

Preparation of Palmitoyl-8-bromo-2'-deoxyguanosine

This compound was prepared using the procedure for Palmitoyl-2'-deoxyguanosine, substituting the appropriate amount of 8-bromoguanosine for 2'-deoxyguanosine monohydrate.

Example 29

Preparation of Palmitoyl-8-mercapto-2'-deoxyguanosine

This compound was prepared using the procedure for palmitoyl-2'-deoxyguanosine, substituting the appropriate amount of 8-mercaptoguanosine for 2'-deoxyguanosine monohydrate.

Example 30

Preparation of Palmitoylguanosine 2,3'-acyclic dialcohol

This compound was prepared using the procedure for palmitoyl-2'-deoxyguanosine, substituting the appropriate amount of guanosine 2',3'-acylic dialcohol for 2'-deoxyguanosine monohydrate.

Example 31

Synthesis of 3', 5'-O-$N^2$-tripalmitoyl-2'-deoxyguanosine

To an oven-dried 500 mL round-bottomed flask was added 2'-deoxyguanosine monohydrate (1.0 g, 1 eq.). Dry N,N-dimethylformamide (DMF, 100 mL) was added via cannula with swirling and the mixture was swirled with heating (using a heat gun) until all of the solid material dissolved. The DMF was then stripped off via rotary evaporation in order to remove the water of hydration. A magnetic stir bar was added to the flask, the flask was fitted with a septum, and dry dimethylacetamide (DMA, 120 mL) and dry pyridine (60 mL) were added via cannula, with swirling and stirring. The flask was purged with argon gas, the slurry was allowed to cool 10 min. in an ice bath, and palmitoyl chloride (3.1 eq.) was added dropwise over 15 min. The mixture was allowed to stir while it slowly warmed to 25° C. After 18 h, the mixture was poured into 800 mL of 0.5 M sodium bicarbonate solution giving a white solid which was isolated by suction filtration, washed with 3×100 mL $H_2O$, air dried, and finally dried under high vacuum giving a white, somewhat waxy powder. This crude product was twice purified by flash chromatography (silica gel bed, eluted with chloroform-methanol) giving a clear glass, m.p. 59° C. $^1$H-NMR and elemental analysis data were consistent with the assigned structure.

Example 32

Alternative Synthesis of 3',5'-O-$N^2$-tripalmitoyl-2'-deoxyguanosine 1 g of 2'-deoxyguanosine and 15 ml of dry N'N'-dimethyl formamide were added to a 100 ml dry round bottom flask. Diethylformamide was removed by two successive evaporations using a rotovap apparatus to obtain dry 2'-deoxyguanosine. 0.56 g (2 mM) of the dry 2'-deoxyguanosine was added to a 100 ml round bottom flask fitted with a reflux condenser and 10 ml of dry dimethylformamide was added. 3 ml of dry pyridine and 2.9 g. (6 mM) palmitic anhydride were then added and the the reaction mixture was refluxed in an oil bath for 6 hr. The mixture was then allowed to cool at room temperature, and the dimethylformamide and pyridine were removed by rotary evaporation. Ice water was added and the resulting mixture was stirred for 15 minutes. The residue was filtered using a Buchner funnel and washed three times with water (30 ml portions). The residue was then transferred to a 100 ml beaker containing 40 to 50 ml dry ether, stirred for 5 to 7 minutes, isolated by filtration, and washed three times with ether (25 ml portions). The resulting compound was purified by column chromatography on silica gel (230–240 mesh) with chloroform : methanol (98:2) as solvent (1.5 liters).

Fractions containing material with identical Rf values were pooled and concentrated, and the resulting material further purified by preparative TLC (silica gel, 0.5 mm, fluorescent) in chloroform-methanol (9:1). Material with an Rf value of 0.689 was isolated; m.p 59° C. $^1$H-NMR and elemental analysis data agreed with the assigned structure.

Example 33

Synthesis of 5'-O-$N^2$-tripalmitoyl-2'-deoxyguanosine

To an oven-dried 100 mL round-bottomed flask containing a stir bar was added $N^2$-palmitoyl-2'-deoxyguanosine (0.75 g, 1 eq.). The flask was fitted with a septum and dry dimethylacetamide (DMA, 32 mL) and dry pyridine (16 mL) were added via cannula, with swirling and stirring. The flask was purged with argon gas, the slurry was allowed to cool 10 min. in an ice bath, and palmitoyl chloride (1.1 eq.) was added dropwise over 5 min. The mixture was allowed to stir while it slowly warmed to 25° C. After 88 h, the mixture was again cooled and 0.8 eq. more of palmitoyl chloride was added; the mixture was again allowed to stir while it slowly warmed to 25° C. After 5 h, the mixture was poured into 200 mL of 0.5 M potassium bicarbonate solution giving a white solid which was isolated by suction filtration, washed with 3×30 mL $H_2O$, air dried, and finally dried under high vacuum giving a white powder. This crude product was purified by flash chromatography (silica gel bed, eluted with chloroformmethanol) giving a white powder. $^1$H-NMR and elemental analysis data were consistent with the assigned structure.

Example 34

Synthesis of 5'-O-palmitoyl-$N^2$-isobutyryl-2'-deoxyguanosine

To an oven-dried 100 mL round-bottomed flask containing a stir bar was added $N^2$-isobutyryl-2'-deoxyguanosine (0.75 g, 1 eq.). The flask was fitted with a septum and dry dimethylacetamide (DMA, 32 mL) and dry pyridine (16 mL) were added via cannula, with swirling and stirring. The flask was purged with argon gas, the slurry was allowed to cool 10 min. in an ice bath, and palmitoyl chloride (2.5 eq.) was added dropwise over 5 min. The mixture was allowed to stir while it slowly warmed to 25° C. After 24 h, the mixture was poured into 200 mL of 0.5 M potassium bicarbonate solution giving a white solid which was isolated by suction filtration, washed with 3×30 mL $H_2O$, air dried, and finally dried under high vacuum giving a white powder. This crude product was purified by flash chromatography (silica gel bed, eluted with chloroform-methanol) giving a white powder. $^1$H-NMR and elemental analysis data were consistent with the assigned structure.

Example 35

Synthesis of 3', 5'-O-$N^2$-trioleyl-2'-deoxyguanosine 1 g of 2'-deoxyguanosine and 15 ml of dry N'N'-dimethyl formamide were added to a 100 ml dry round bottom flask. Diethylformamide was removed by two successive evaporations using a rotovap apparatus to obtain dry 2'-deoxyguanosine. 0.56 g (2 mM) of the dry 2'-deoxyguanosine was added to a 100 ml round bottom flask fitted with a reflux condenser and 10 ml of dry dimethylformamide was added. 3 ml of dry pyridine and 3.27 g. (6 mM) palmitic anhydride were then added and the the reaction mixture was refluxed in an oil bath for 6 hr. The mixture was then allowed to cool at room temperature, and the dimethylformamide and pyridine were removed by rotary evaporation. Ice water was added and the resulting mixture was stirred for 15 minutes. The reaction mixture was extracted twice with 30 ml chloroform, after which the chloroform extracts were washed twice with (saturated) $NaHCO_3$ and water (25 ml). The chloroform extract was then dried with anhydrous sodium sulfate, filtered, and evaporated. The resulting residue was purified by column chromatography on silica gel (230–240 mesh) with chloroform : methanol (98:2) as solvent (1.5 liters).

Fractions containing material with identical Rf values were pooled and concentrated, and the resulting material further purified by preparative TLC (silica gel, 0.5 mm, fluorescent) in chloroform-methanol (9:1). Material with an Rf value of 0.689 was isolated. $^1$H-NMR and elemental analysis data agreed with the assigned structure.

Example 36

Synthesis of 3',5'-O-$N^2$-tristearoyl-2'-deoxyguanosine 1 g of 2'-deoxyguanosine and 15 ml of dry N'N'-dimethyl formamide were added to a 100 ml dry round bottom flask. Diethylformamide was removed by two successive evaporations using a rotovap apparatus to obtain dry 2'-deoxyguanosine. 0.56 g (2 mM) of the dry 2'-deoxyguanosine was added to a 100 ml round bottom flask fitted with a reflux condenser and 10 ml of dry dimethylformamide was added. 3 ml of dry pyridine and 3.3 g. (6 mM) palmitic anhydride were then added and the the reaction mixture was refluxed in an oil bath for 6 hr. The mixture was then allowed to cool at room temperature, and the dimethylformamide and pyridine were removed by rotary evaporation. Ice water was added and the resulting mixture was stirred for 15 minutes. The residue was filtered using a Buchner funnel and washed three times with water (30 ml portions). The residue was then transferred to a 100 ml beaker containing 40 to 50 ml dry ether, stirred for 5 to 7 minutes, isolated by filtration, and washed three times with ether (25 ml portions). The resulting compound was purified by column chromatography on silica gel (230–240 mesh) with chloroform : methanol (98:2) as solvent (1.5 liters).

Fractions containing material with identical Rf values were pooled and concentrated, and the resulting material further purified by preparative TLC (silica gel, 0.5 mm, fluorescent) in chloroform-methanol (9:1). Material with an Rf value of 0.689 was isolated. $^1$H-NMR and elemental analysis data agreed with the assigned structure.

The following examples demonstrate the benefits of the compounds of the invention in vivo.

Example 37

Guanosine and Guanine Improve Hematopoietic Recovery After Cyclophosphamide

Cyclophosphamide (CP) (275 mg/kg, i.p.) was administered to 30 Balb/C female mice weighing approximately 20 grams each. Twenty-four hours later and each day thereafter for a total of 6 days, mice were given a 0.4 ml i.p. injection of either physiological saline (controls), guanine (5 μmoles/ mouse/day), or guanosine (5 μmoles/mouse/day). On day 7 all 10 mice in each of the three groups were bled, and then sacrificed by cervical dislocation. Spleens were removed and weighed, and complete blood cell counts performed.

Figure 2:
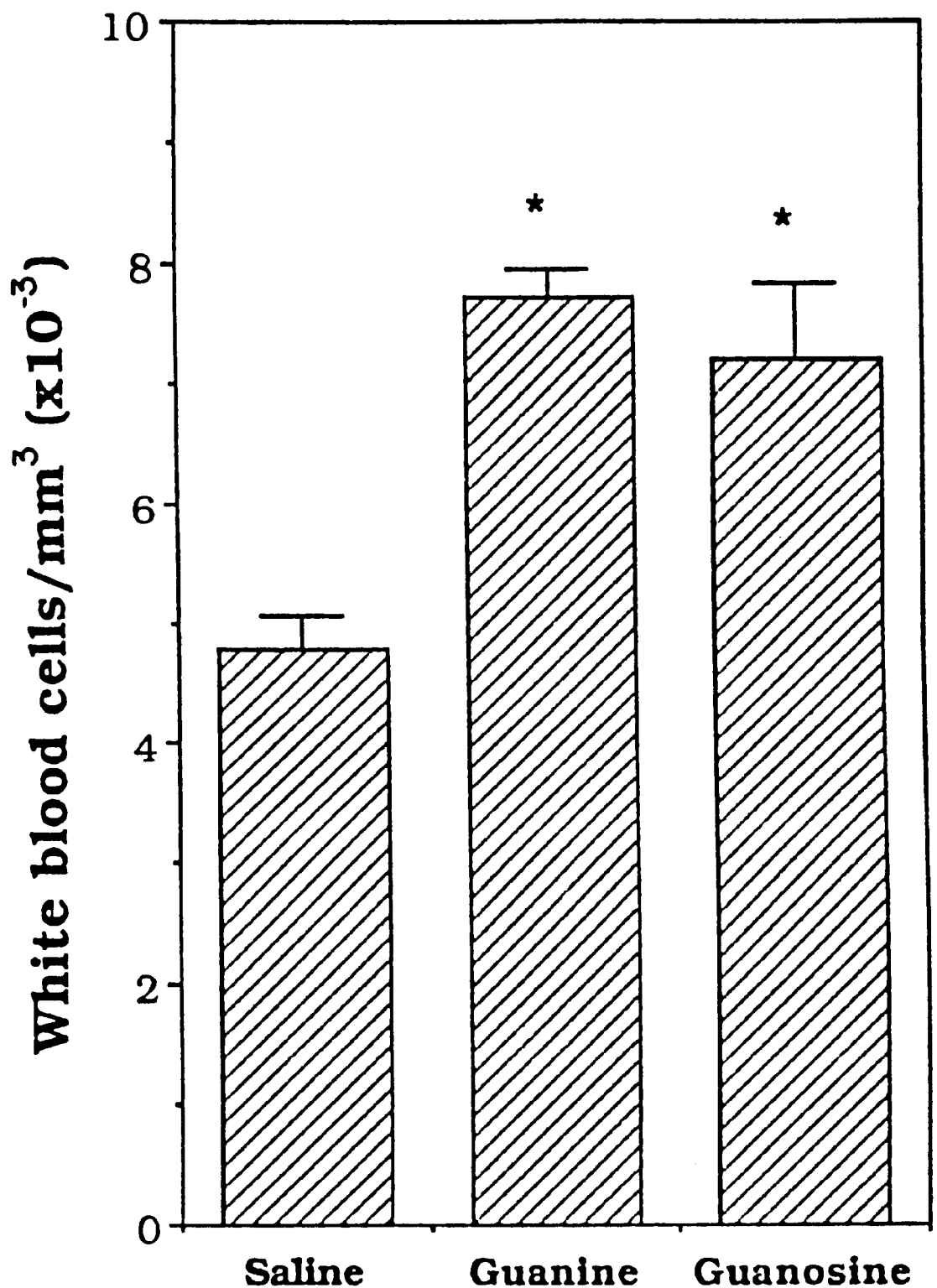
FIG. 2 is a graph comparing white blood cell count in mice after treatment with saline, guanine and guanosine as described in Example 37.
Figure 3:
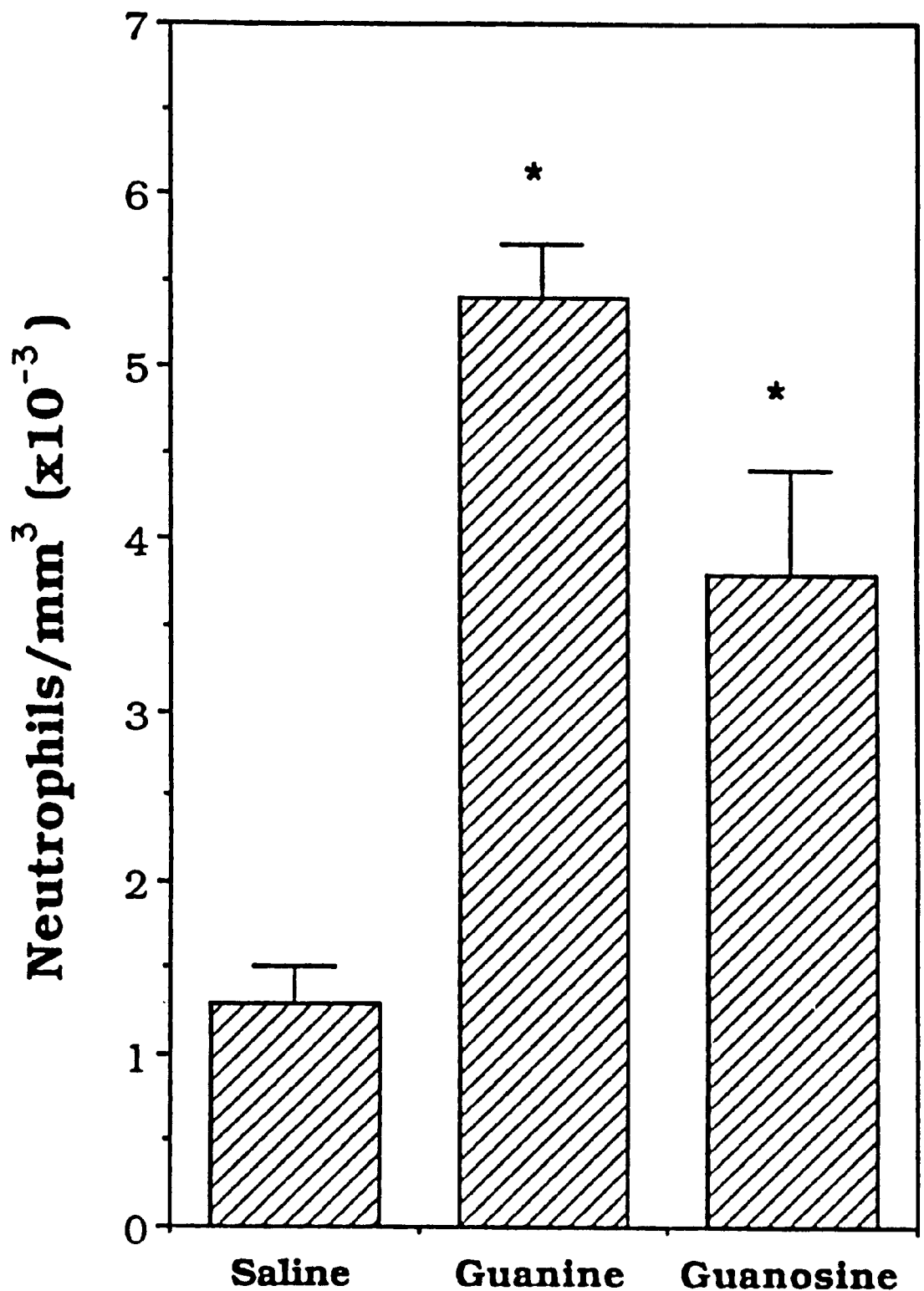
FIG. 3 is a graph comparing neutrophils in mice after treatment with saline, guanine and guanosine as described in Example 37.

Treatment with either guanine or guanosine resulted in significantly heavier spleens than in saline-treated controls (FIG. 1). Likewise, treatment with guanine or guanosine also resulted in significantly more peripheral total white blood cells and neutrophils (FIGS. 2 and 3, respectively). Thus, treatment of mice with guanine or guanosine following CP damage clearly accelerates the regeneration of myelopoiesis.

Example 38

Effect of Guanosine Acyl Substituent Chain Length on Hematopoietic Recovery after Cyclophosphamide Cyclophosphamide (CP) (275 mg/kg, i.p.) was administered to 70 Balb/C female mice weighing approximately 20 grams each. Twenty-four hours later and each day thereafter for a total of 6 days, mice were given a 0.4 ml i.p injection of either physiological saline (controls), Tween 80 (0.2%), guanosine (5 μmoles/mouse/day in 0.2% Tween 80), or 2.5 μmoles per mouse per day of one of the following acylated derivatives of guanosine in 0.2% Tween 80: triacetylguanosine, octanoylguanosine, lauroylguanosine, or palmitoylguanosine. On day 7 following CP administration all 10 animals from each of the 7 groups were bled, and then sacrificed by cervical dislocation. Spleens were removed and weighed, and complete blood counts performed.

Figure 4:
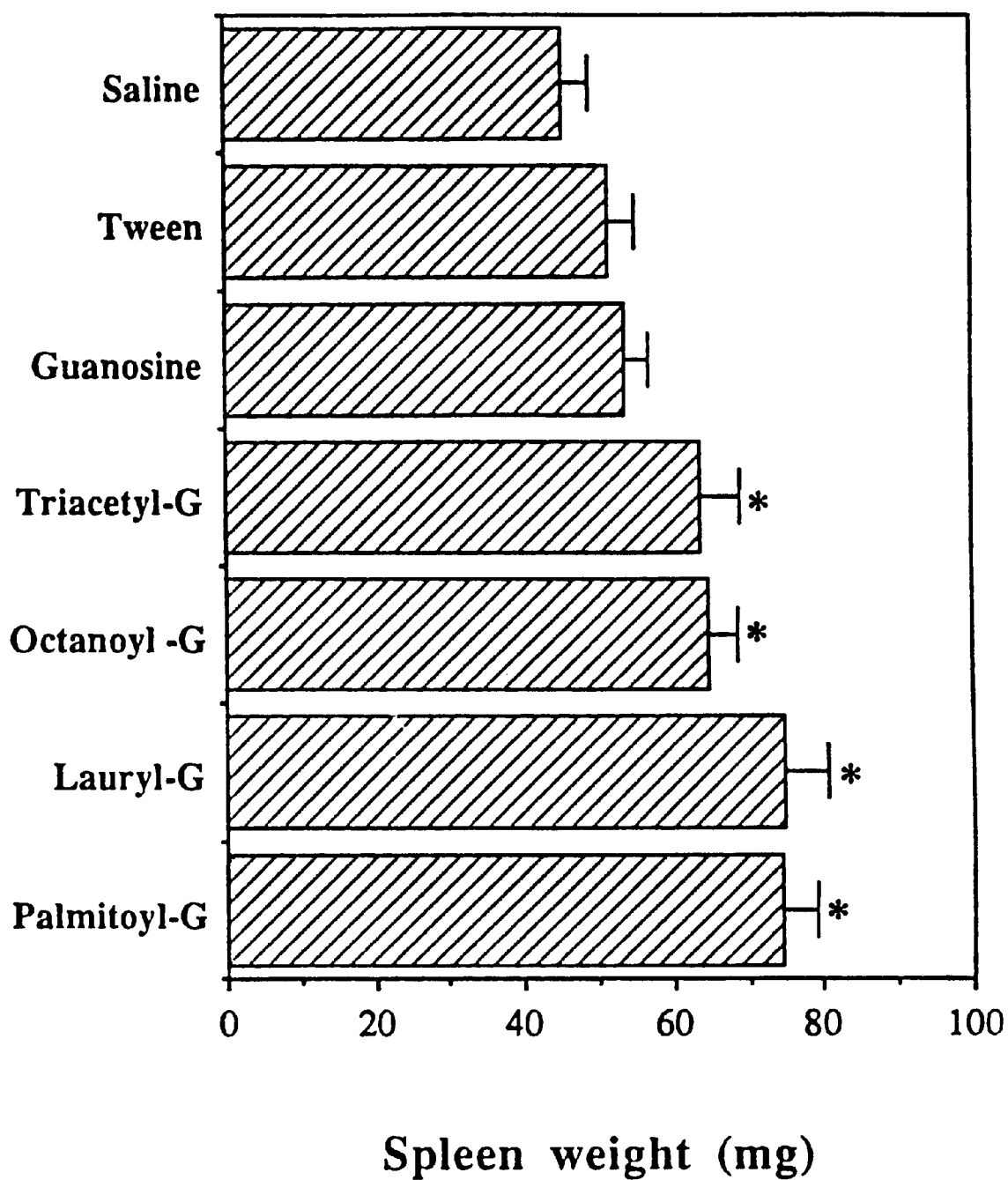
FIG. 4 is a graph comparing spleen weight of mice after treatment with saline, Tween-80, guanosine, triacetylguanosine, octanoylguanosine, laurylguanosine and palmitoylguanosine as described in Example 38.
Figure 5:
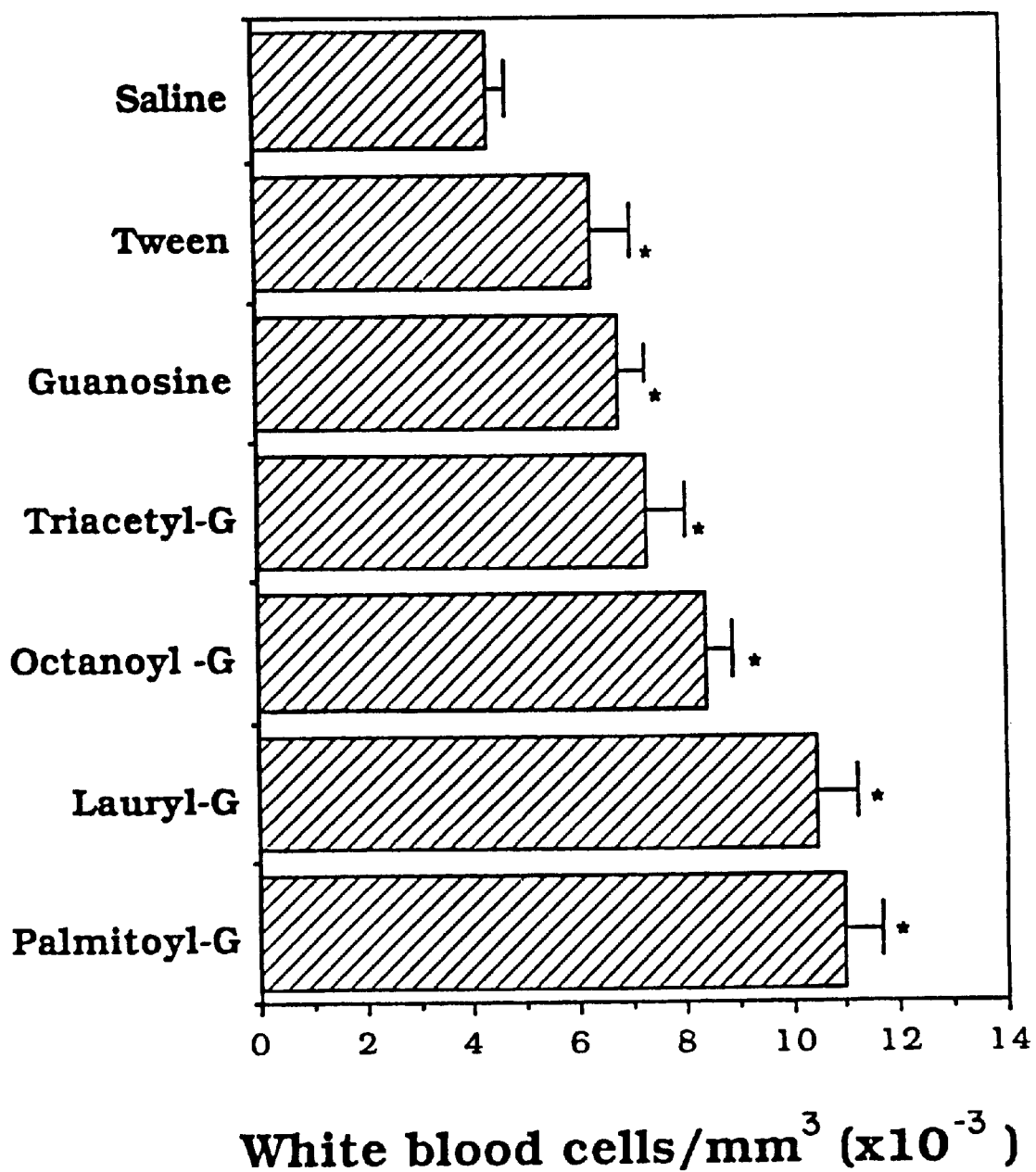
FIG. 5 is a graph comparing white blood cell count in mice after treatment with saline, Tween-80, guanosine, triacetylguanosine, octanoylguanosine, laurylguanosine and palmitoylguanosine as described in Example 38.
Figure 6:
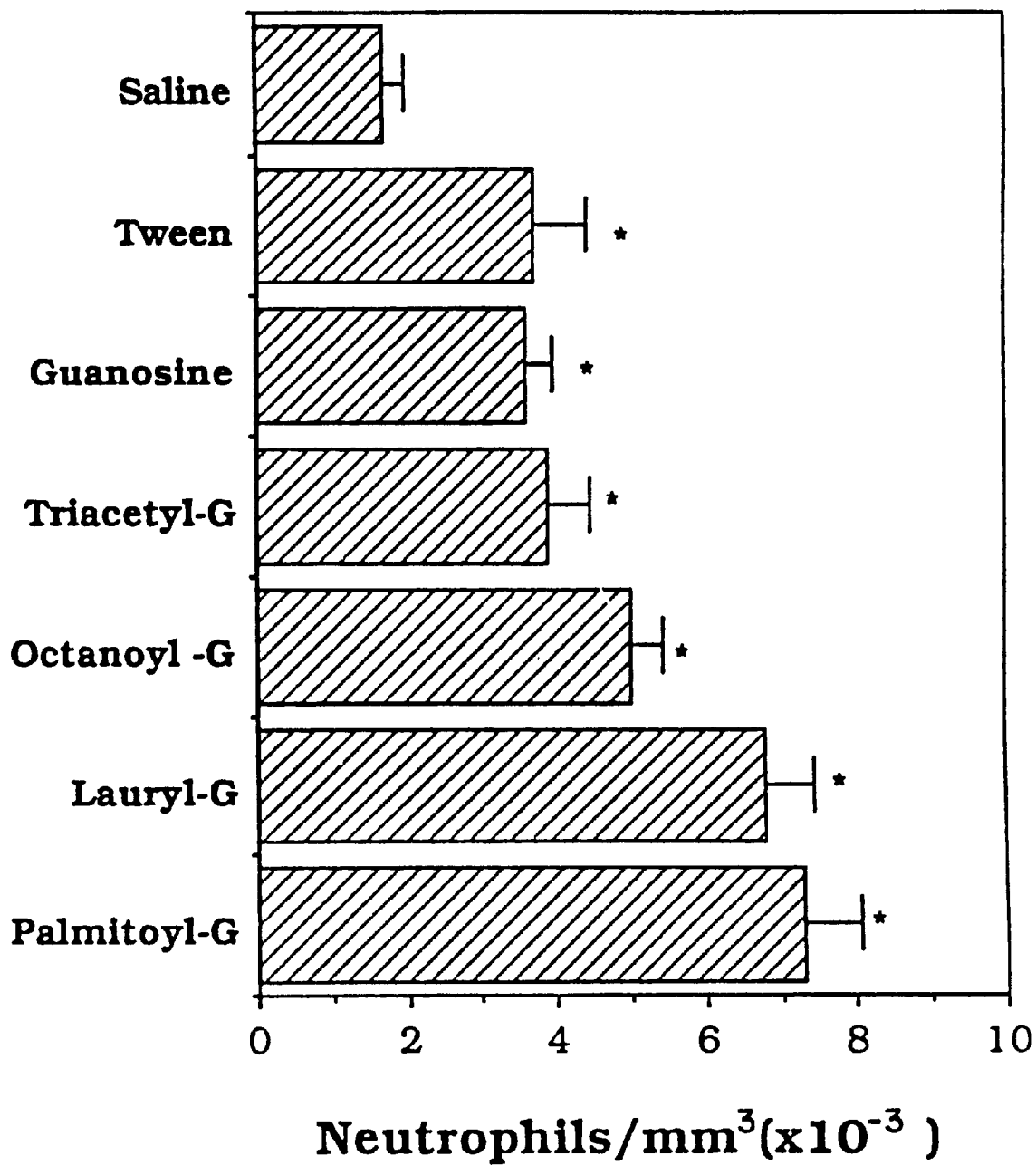
FIG. 6 is a graph comparing neutrophils in mice after treatment with saline, Tween-80, guanosine, triacetylguanosine, octanoylguanosine, laurylguanosine and palmitoylguanosine as described in Example 38.

No significant difference in spleen weight was seen between the groups treated with saline, Tween 80, or non-acylated guanosine. However, treatment of mice with acetylguanosine, octanoylguanosine, laurolyguanosine, or palmitoylguanosine resulted in significantly larger spleens on day 7 compared to the controls (FIG. 4). In this and subsequent examples, treatment with acylated oxypurine nucleosides or their congeners occasionally produced a transient reduction (approximately 10%) in erythrocyte counts. Treatment with any and all of these compounds resulted in significantly elevated white blood cell (WBC)

counts. However, the greater the chain length of the acyl group, the greater the effect on WBC count within the selection of compounds tested in this experiment. In this experiment, treatment with palmitoylguanosine had the greatest effect on total WBC counts (FIG. 5); a similar relationship between acyl radical chain length and amplitude of hematopoietic response was also observed with total neutrophil counts (FIG. 6).

Example 39

Palmitoylguanosine Improves Survival of Irradiated Mice

Thirty female Balb/C mice weighing 20 grams each were irradiated with Cobalt 60 gamma radiation at a dose rate of 7.3 Rads per minute. The total dose was either 700, 725, or 750 Rads. Twenty-four hours later and each day thereafter for a total of 6 days, these mice received an i.p. injection of either physiological saline (controls) or 50 mg/kg of palmitoylguanosine. The number of animals surviving in each group was observed over a 30 day period.

As is shown in Table 1, all of the irradiated mice treated with saline died during the 30 day observation period, even at the lowest radiation dose. In marked contrast, all of the mice treated with palmitoylguanosine survived. (Mice treated with palmitoylguanosine were only tested at the 2 higher doses of radiation.)

Therefore, treatment of mice with palmitoylguanosine following irradiation dramatically increases survival.

Pretreatment of mice with palmitoylguanosine prior to irradiation also improved survival.

TABLE 1

| Treatment | Radiation Dose | | |
| --- | --- | --- | --- |
|  | 700 R | 725 R | 750 R |
| Saline (control) | 0/10 | 0/5 | 0/5 |
| Palmitoylguanosine | — | 5/5 | 5/5 |

Values indicate number of mice surviving 30 days after irradiation over number of mice irradiated.

Example 40

Palmitoylguanosine Increases Colony Forming Units in Bone Marrow of Mice Recovering from Cyclophosphamide Treatment Seventy-two Balb/C female mice weighing approximately 20 grams each were given cyclophosphamide (275 mg/kg) by intraperitoneal (i.p.) injection. Twenty-four hours later and each day thereafter, mice received a 0.4 ml i.p. injection of either physiological saline (control) or palmitoylguanosine (2.5 μmoles/mouse/day in 0.2% Tween 80). On days 3, 5, 7, and 10 following CP administration 6 animals from each group were sacrificed by cervical dislocation, and the left femur of each animal obtained by sterile means. The bone marrow cells were then flushed from the femurs with McCoy's 5a Modified medium using a 23-gauge needle. Cells from femurs in the same group were pooled, dispersed by briefly vortexing, and counted using a hemocytometer. Cell suspensions were added to McCoy's Modified 5a medium containing 15% bovine calf serum, 1x Kanamycin, 0.3% agar, and 3% endotoxin-stimulated serum. The suspensions were then plated at a density of $1.2 \times 10^5$ cells/ml, except on day 3 when, due to lower cell counts at that time point, the plating density was $1.0 \times 10^5$. Each group was plated in quintuplicate. After 7 days in culture (at 37° in 5% $CO_2$ and humidified air) aggregates of 50 cells or more ("colonies") were counted using a dissecting microscope at 25x.

Figure 7:
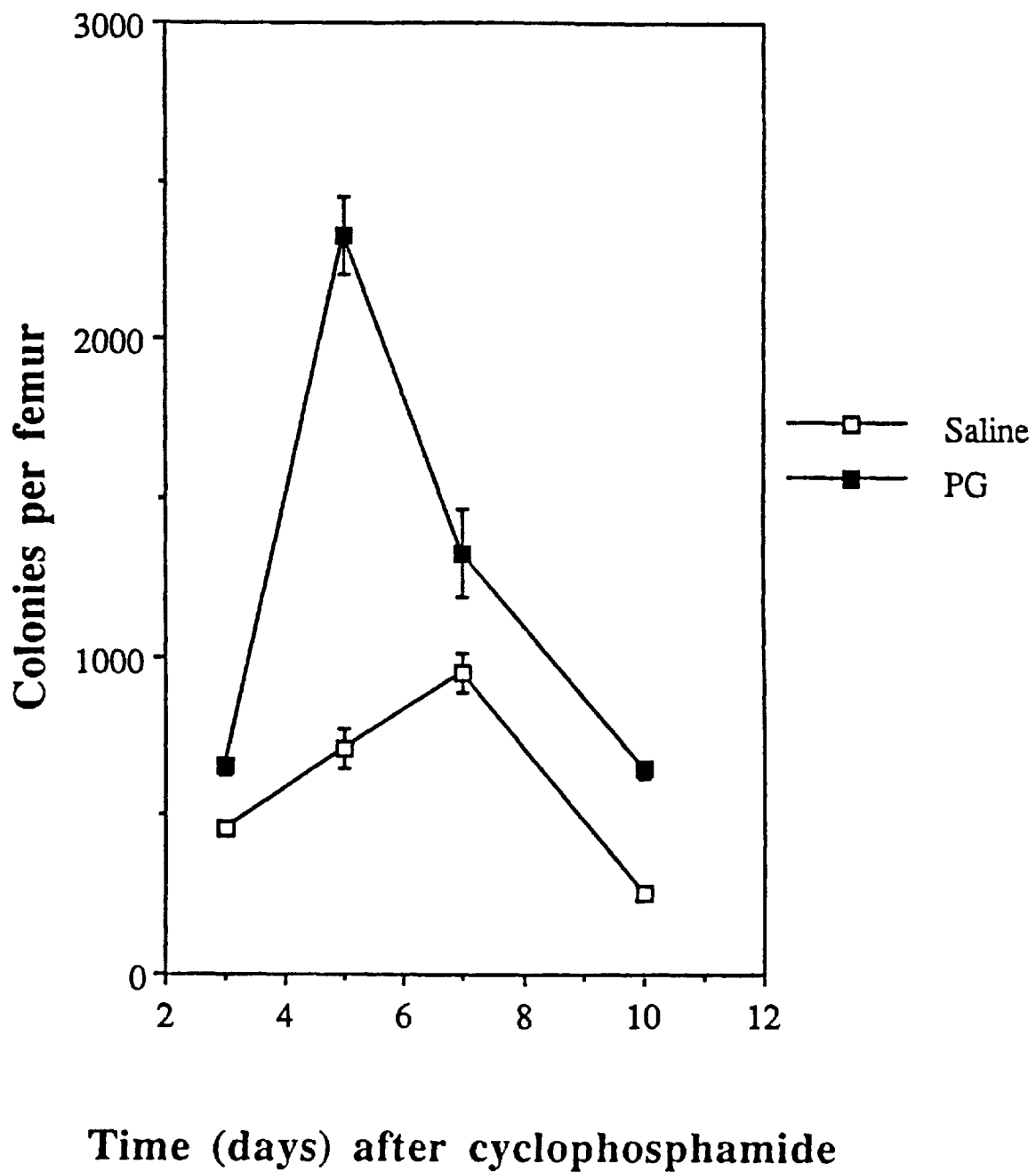
FIG. 7 is a graph showing colonies per femur after cyclophosphamide treatment as described in Example 40.

At each time point the number of colonies observed per femur from the palmitoylguanosine-treated mice was significantly greater than the number from the saline-treated group (FIG. 7 and Table 2. The greatest difference between the groups was seen on day 5.

TABLE 2

|  | Day 3 | Day 5 | Day 7 | Day 10 |
| --- | --- | --- | --- | --- |
| Saline (control) | 460 ± 22 | 714 ± 63 | 949 ± 61 | 253 ± 18 |
| Palmitoylguanosine | 645 ± 26 | 2327 ± 121 | 1328 ± 140 | 647 ± 25 |

Values indicate number of colony-forming units per femur in mice at various times after administration of cyclophosphamide Example 41

Effect of Timing of Palmitoylguanosine Administration on Hematopoietic Recovery after Cyclophosphamide Cyclophosphamide (CP) (275 mg/kg, i.p.) was administered to 81 Balb/C female mice weighing approximately 20 grams each. Twenty-four hours later treatment was begun. Mice were given a 0.4 ml i.p. injection of either physiological saline (controls), Tween 80 (0.2%), or palmitoylguanosine (5 μmoles/mouse/day in 0.2% Tween 80). The timing of the treatments was varied within the groups. The control group was given saline on days 1–6. The mice receiving Tween 80 were treated either on days 1–4, 4–6 or 1–6. Palmitoylguanosine-treated mice were treated either on days 1–2, 1–4, 3–5, 4–6 or 1–6. If a group of mice received no Tween 80 or palmitoylguanosine on a given day, saline was administered by i.p. injection. Thus, there were 9 groups of 9 animals in all. On day 7 following CP administration all of the animals were bled and then sacrificed by cervical dislocation. Spleens were removed and weighed, and complete blood cell counts performed.

Figure 8:
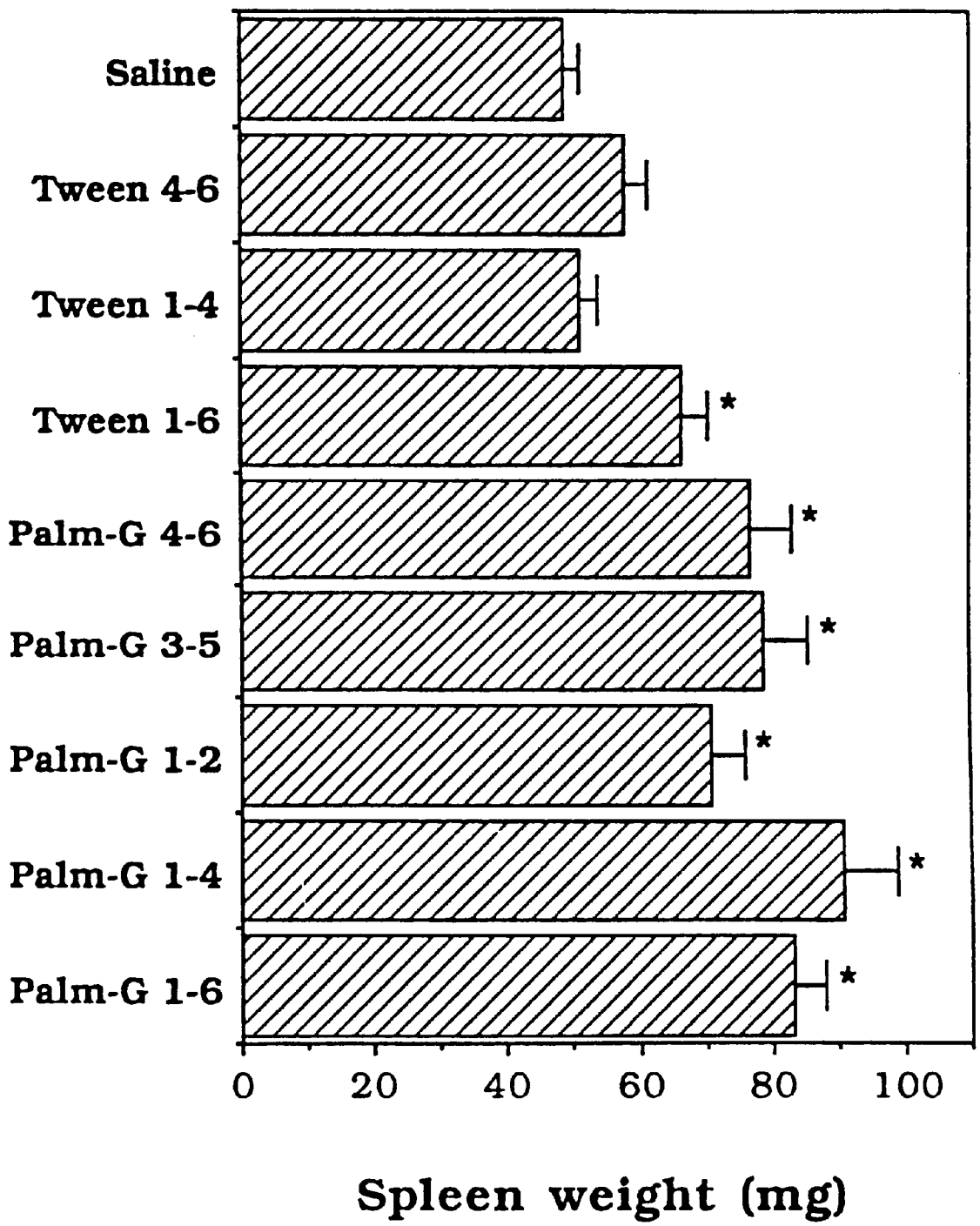
FIG. 8 is a graph comparing spleen weight of mice after treatment with saline, Tween-80 and palmitoylguanosine for various periods as described in Example 41.

Spleen weight was elevated compared to saline controls in all of the treatment groups except those receiving Tween 80 on days 1–4 only (FIG. 8). Administration of palmitoylguanosine for any of the time periods tested, including only treating on days 1 and 2, resulted in significantly greater spleen weight compared to the controls (also FIG. 8). In addition, treatment with palmitoylguanosine (for any period of time) resulted in larger spleens than in mice treated only with Tween 80. Treatment with palmitoylguanosine on days 1–4 or 1–6 had the greatest effect on spleen weight.

Figure 9:
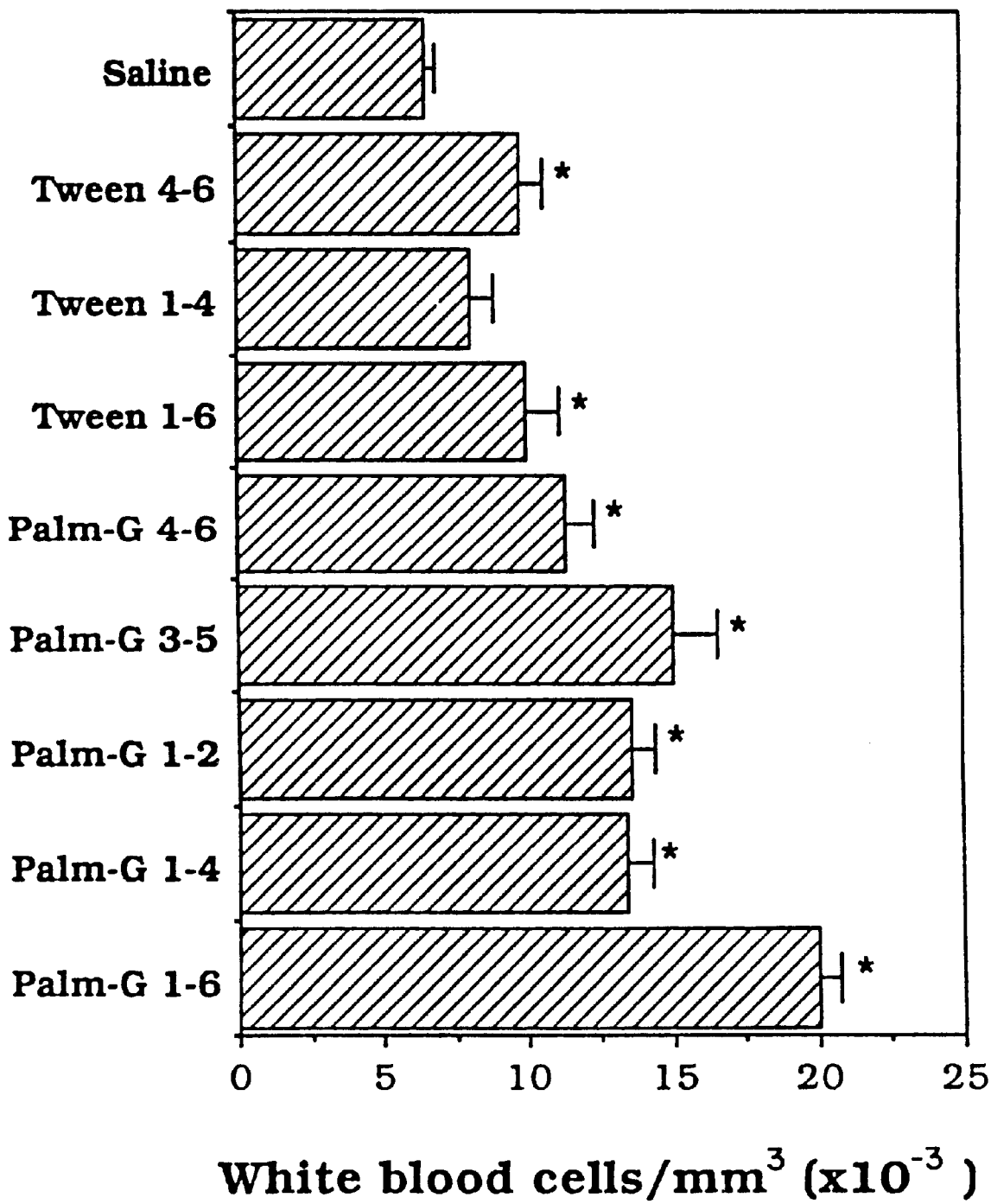
FIG. 9 is a graph comparing white blood cell count in mice after treatment with saline, Tween-80 and palmitoylguanosine as described in Example 41.
Figure 10:
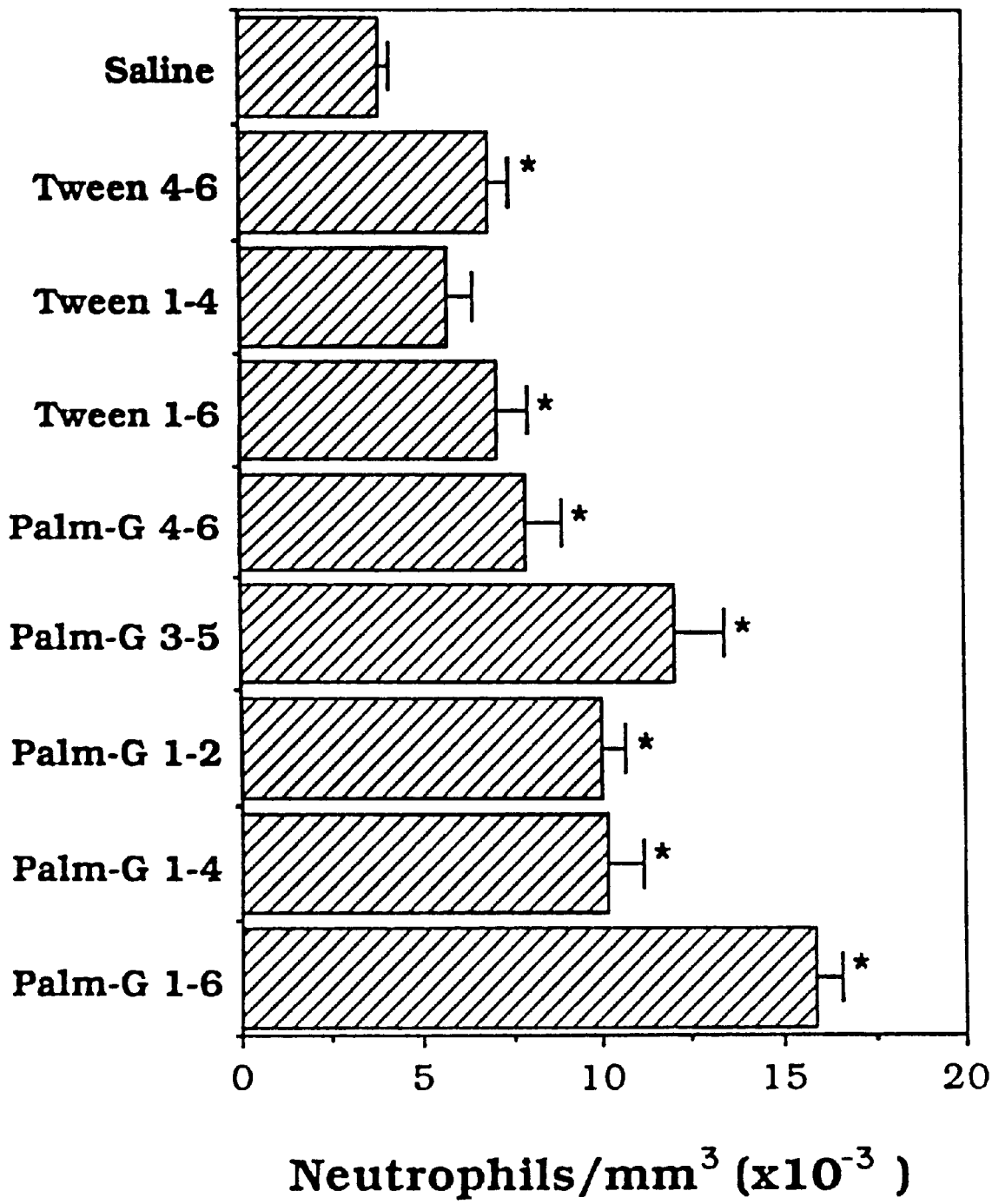
FIG. 10 is a graph comparing neutrophils in mice after treatment with saline, Tween-80 and palmitoylguanosine as described in Example 41.

Total white blood cell (WBC) counts were significantly greater in each of the groups receiving palmitoylyguanosine than in saline controls (FIG. 9). Further, WBC counts from all of the palmitoylguanosine-treated mice, except those treated only on days 4–6, were significantly greater than in mice treated with Tween 80 for any period of time. The greatest effect was seen in mice treated on days 1–6 with palmitoylguanosine. The number of WBC counts in this group was also significantly greater than any of the other palmitoylguanosine-treated groups. The pattern of results relative to WBC's was mirrored by the neutrophil data (FIG. 10), in which treatment with palmitoylguanosine on days 1–6 resulted in the greatest increase in total neutrophil counts. Treatment with palmitoylguanosine on only days 1 and 2 caused a significant increase in total neutrophils compared to either saline controls or Tween 80-treated mice.

Figure 11:
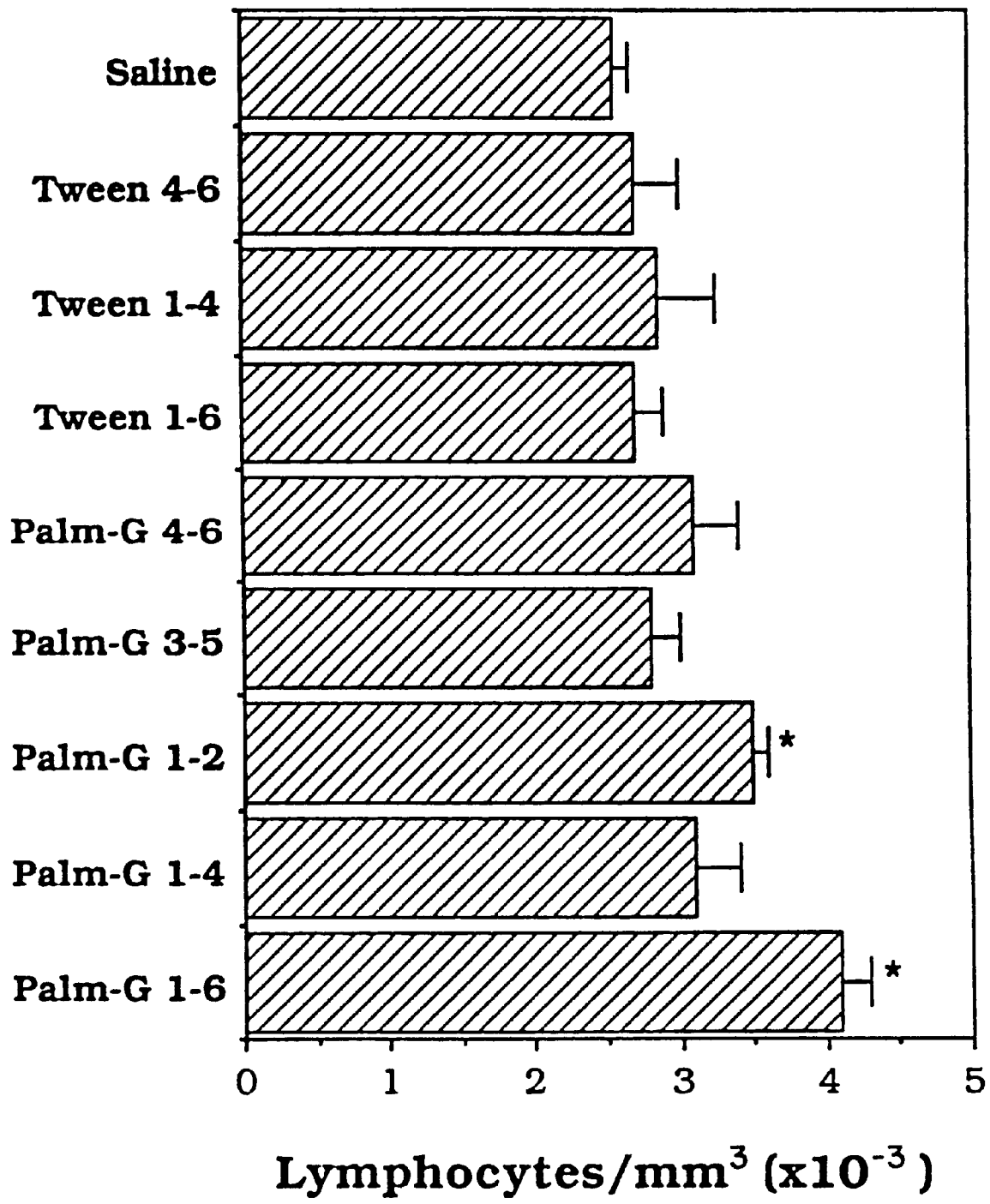
FIG. 11 is a graph comparing lymphocytes in mice after treatment with saline, Tween-80 and palmitoylguanosine as described in Example 41.

Lymphocyte counts were not affected by treatment with Tween 80 (or saline) for any period of time. Only treatment with palmitoylguanosine on days 1–2 or 1–6 (again the greatest effect) resulted in elevated lymphocyte counts (FIG. 11).

Example 42

Palmitoylguanosine Improves Hematopoietic Recovery after 5-fluorouracil

5-fluorouracil (5-FU) (150 mg/kg, i.p.) was administered to forty Balb/C female mice weighing approximately 20 grams each. Twenty-four hours later and each day thereafter for a total of 8 days, mice were given a 0.4 ml i.p. injection of either physiological saline (controls) or 5'-O-palmitoylguanosine (2.5 $\mu$moles/mouse/day in 0.2% Tween 80). On days 7 and 14 following 5-FU administration half of the animals from each group were bled and then were sacrificed by cervical dislocation. Spleens were removed and weighed, and complete blood cells counts performed.

Figure 12:
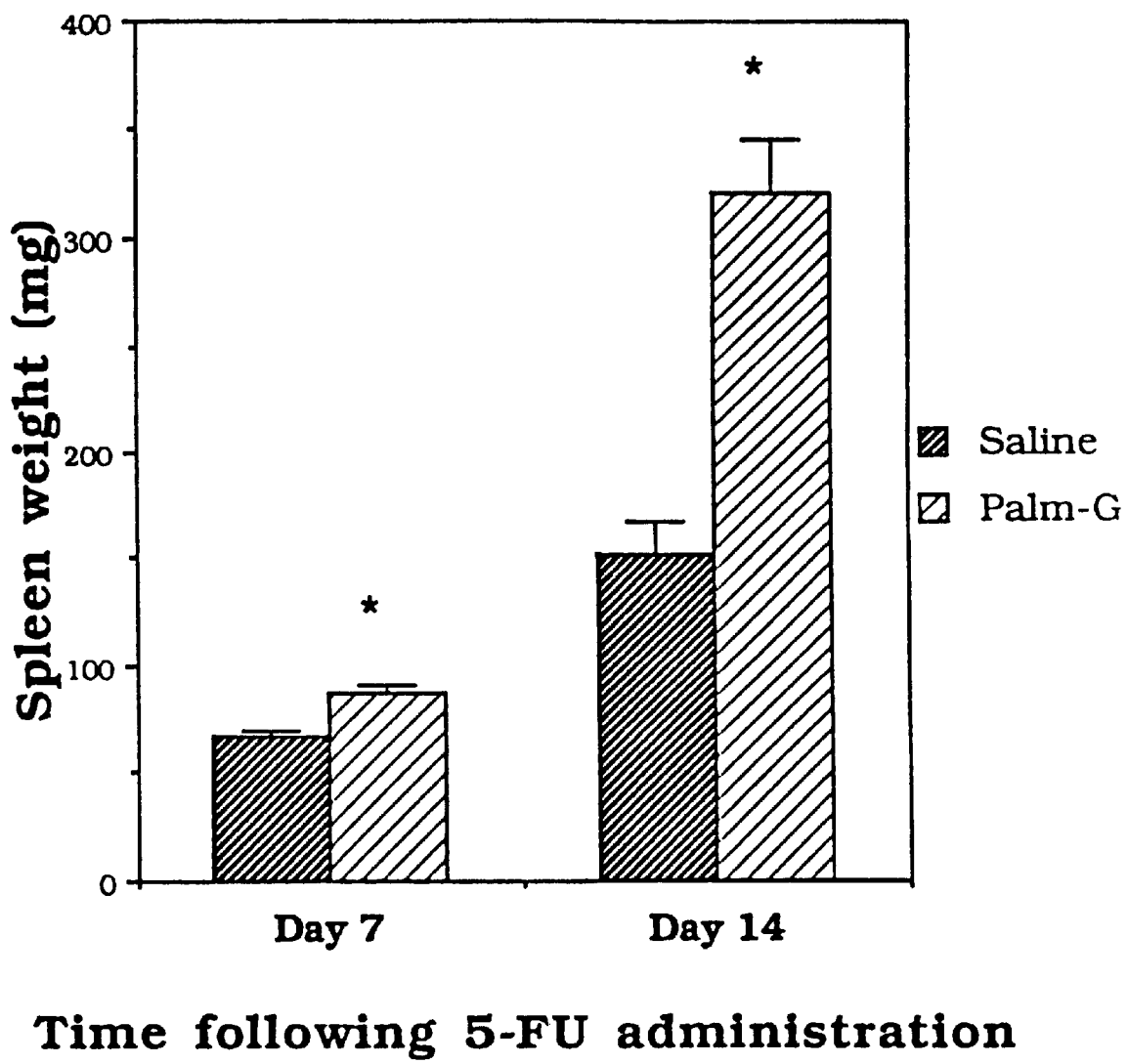
FIG. 12 is graph comparing spleen weight of mice after treatment with saline and palmitoylguanosine as described in Example 42. "5FU" is 5-fluorouracil.
Figure 13:
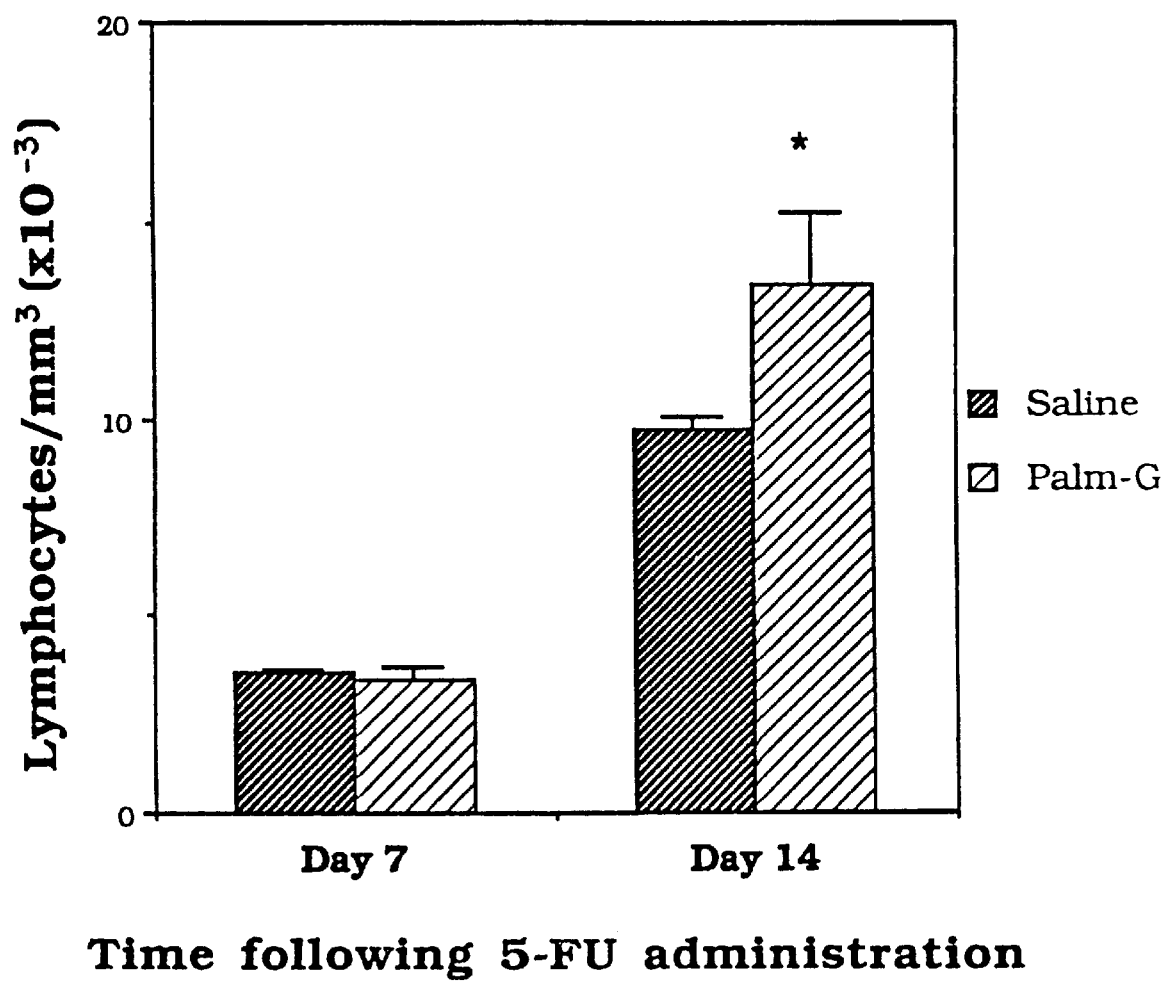
FIG. 13 is a graph comparing lymphocytes in mice after treatment with saline and palmitoylguanosine as described in Example 42.
Figure 14:
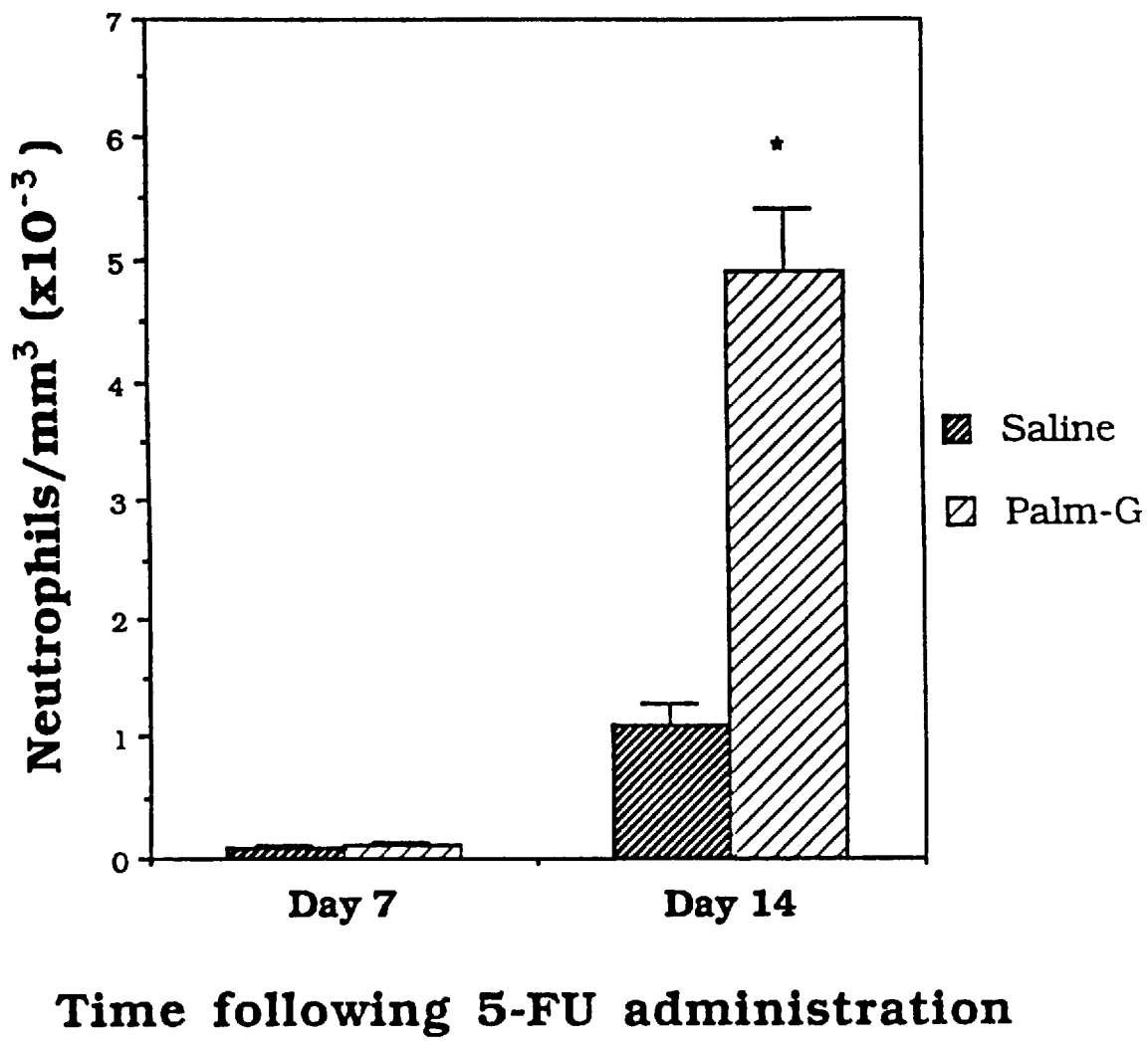
FIG. 14 is a graph comparing neutrophils in mice after treatment with saline and palmitoylguanosine as described in Example 42.
Figure 15:
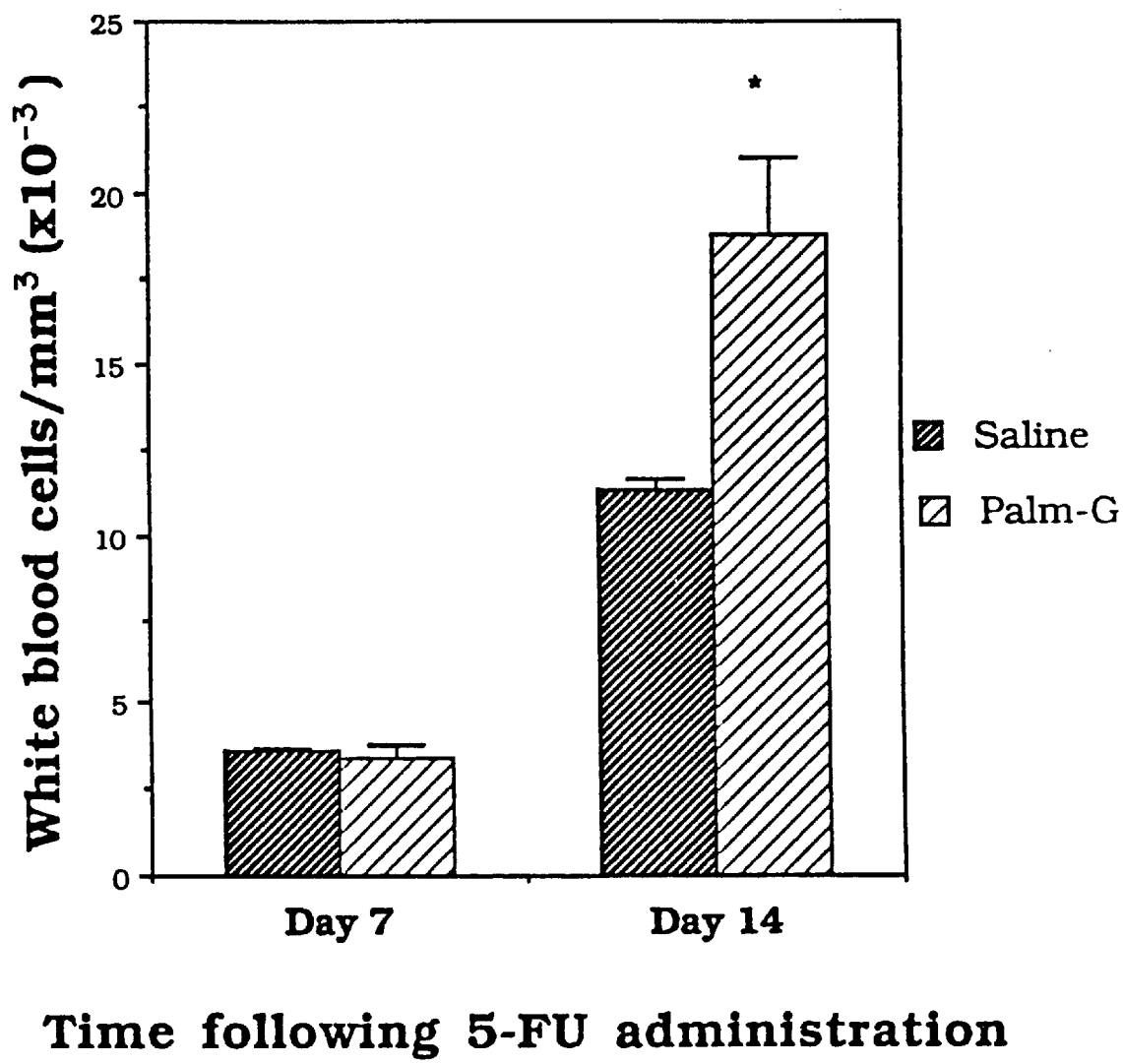
FIG. 15 is a graph comparing white blood cell count in mice after treatment with saline and palmitoylguanosine as described in Example 42.

On day 7 a slight, but statistically significant, increase in spleen weight was observed in the group treated with palmitoylguanosine (FIG. 12). No other differences were seen between control and treated animals on day 7. On day 14, however, those animals that received palmitoylguanosine had significantly higher numbers of total leukocytes, lymphocytes, neutrophils, and platelets, in addition to having significantly heavier spleens (FIGS. 13–15).

Example 43

Palmitoylguanosine Improves Hematopoietic Recovery after 5-fluorouracil

5-fluorouracil (5-FU) (150 mg/kg,i.p.) was administered to fifty-four Balb/C female mice weighing approximately 20 grams each. Twenty-four hours later and each day thereafter for a total of 7 days, mice were given a 0.4 ml i.p. injection of either physiological saline (controls) or palmitoylguanosine (2.5 $\mu$moles/mouse/day in 0.2% Tween 80). On days 8, 10 and 12 following administration of 5-FU nine animals from each group were bled and then sacrificed by cervical dislocation. Spleens were removed and weighed, and complete blood cell counts performed.

Figure 16:
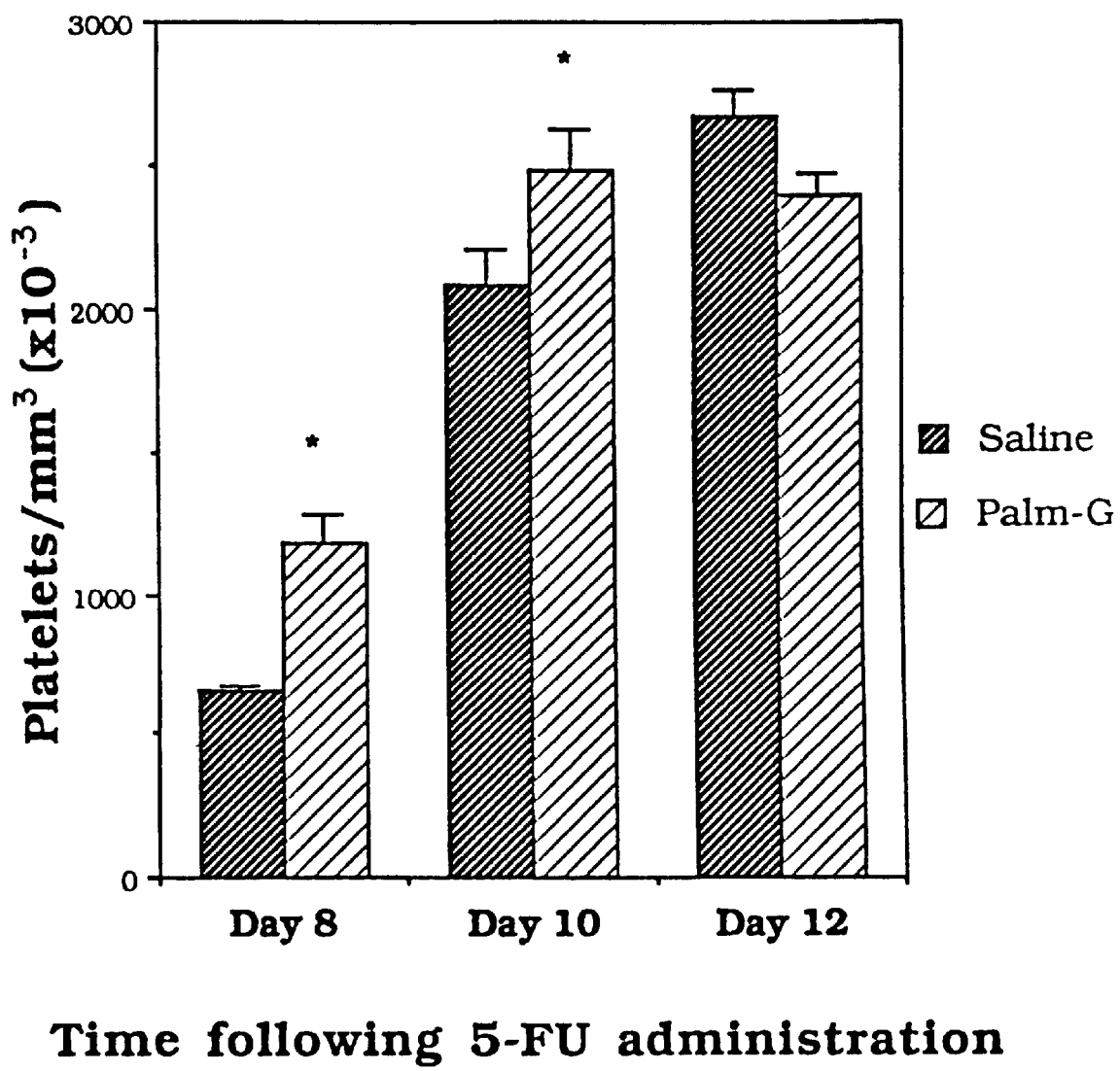
FIG. 16 is a graph showing platelets in mice after treatment with saline and palmitoylguanosine as described in Example 43.
Figure 17:
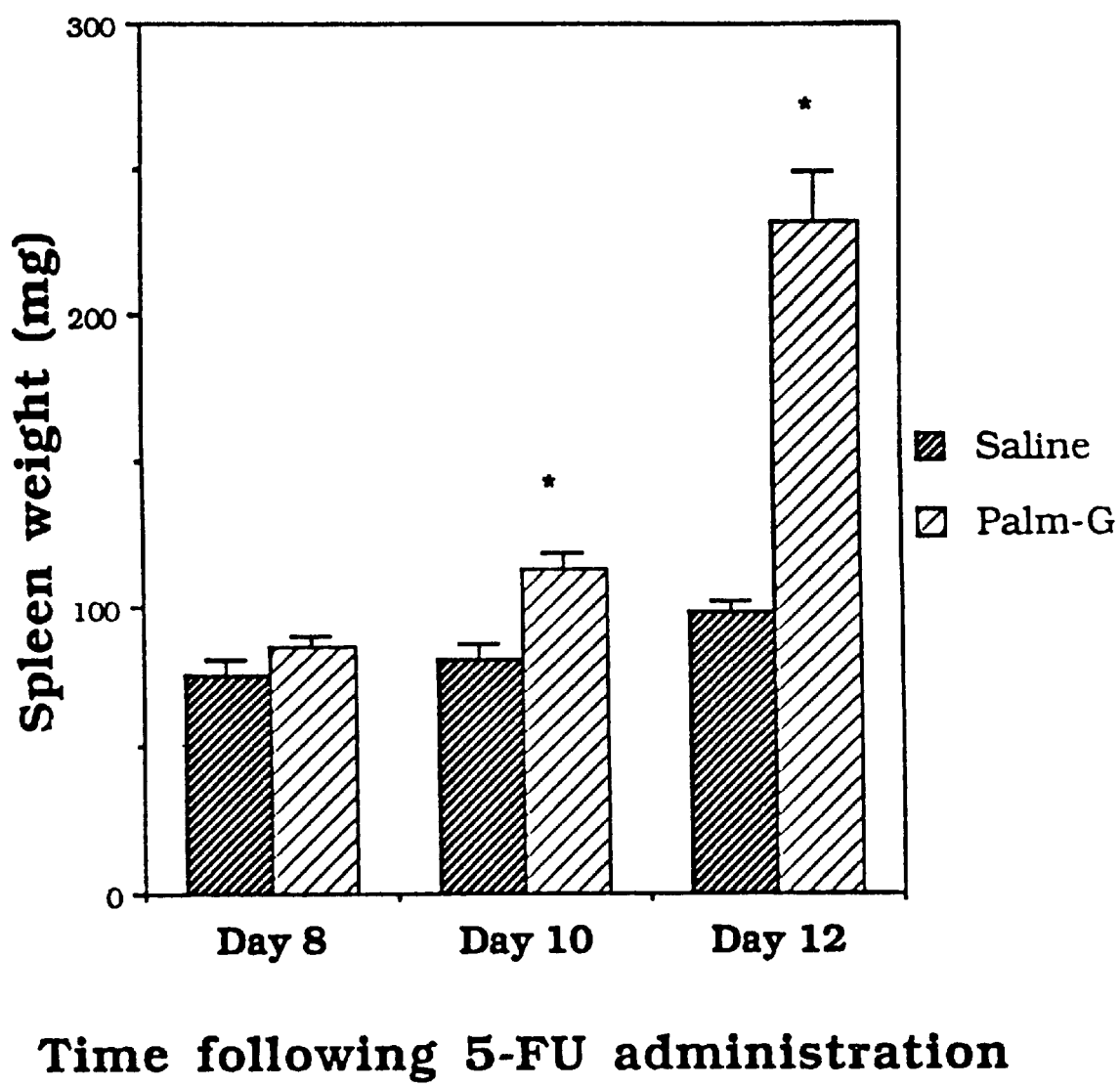
FIG. 17 is a graph comparing spleen weight of mice after treatment with saline and palmitoylguanosine as described in Example 43.
Figure 18:
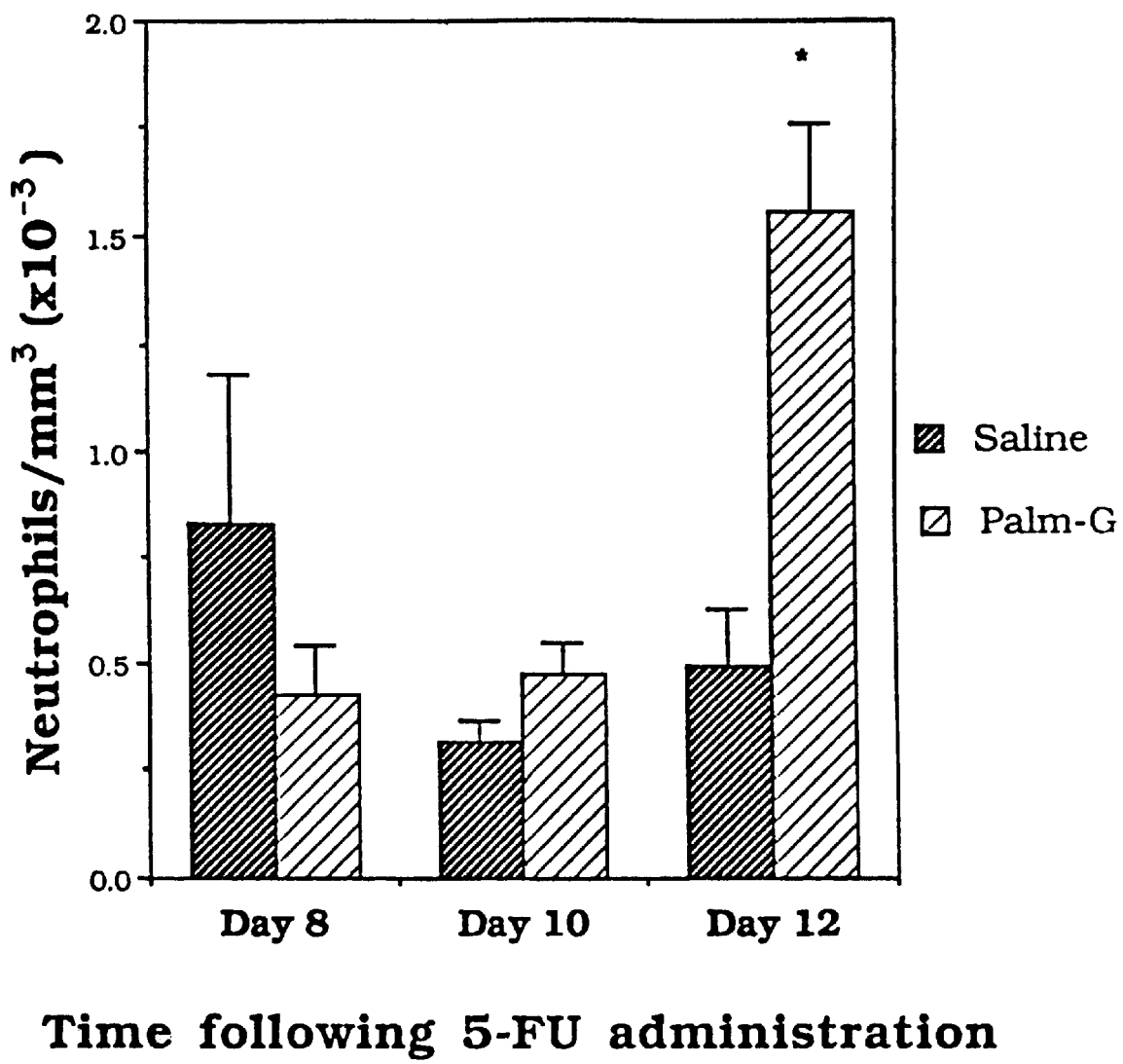
FIG. 18 is a graph showing neutrophils in mice after treatment with saline and palmitoylguanosine as described in Example 43.
Figure 19:
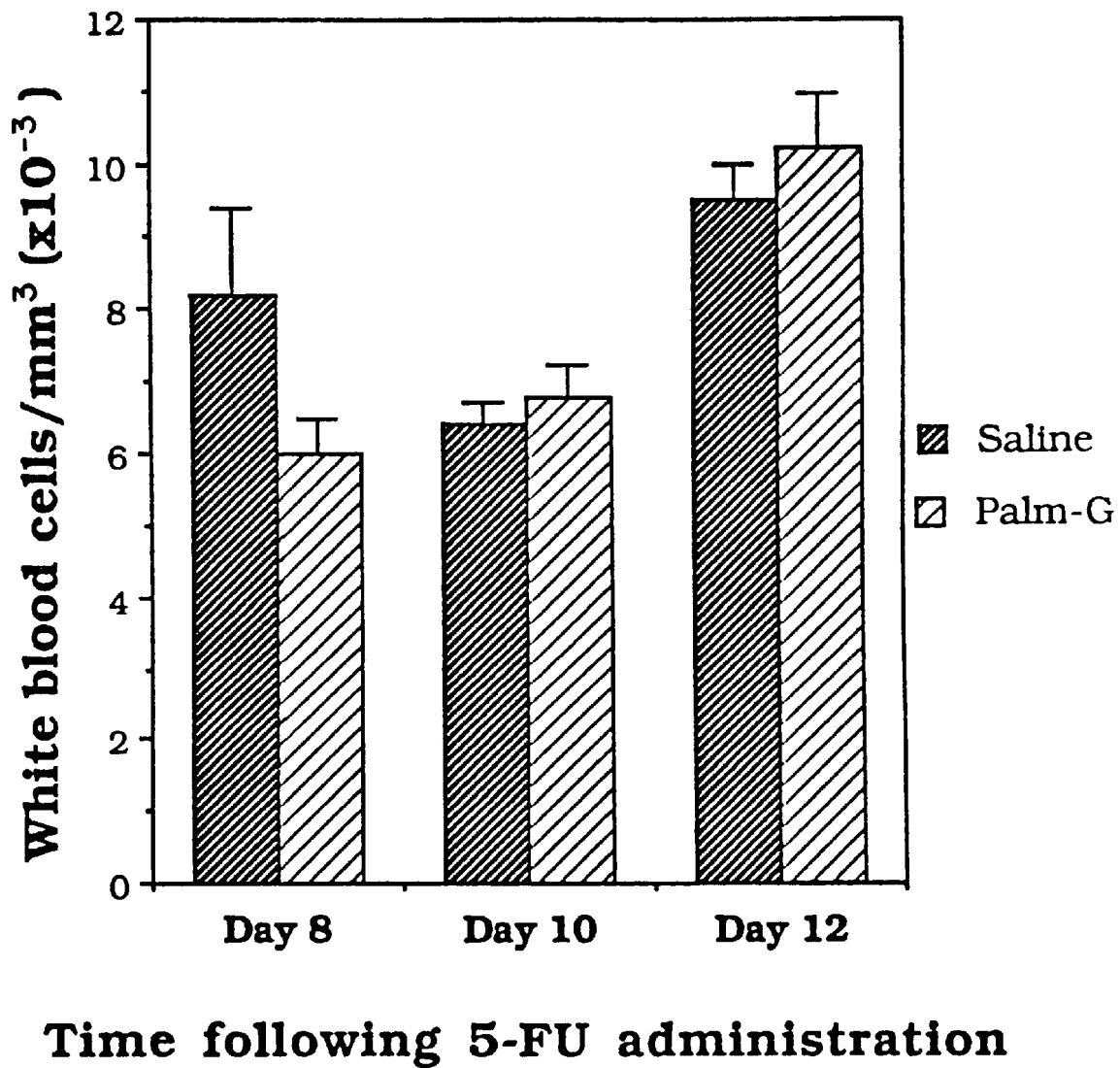
FIG. 19 is a graph showing white blood cell count in mice after treatment with saline and palmitoylguanosine as described in Example 43.

On day 8 the number of platelets in the blood samples from the mice treated with palmitoylguanosine was significantly greater than the number in the control group (FIG. 16). No other statistically significant differences between the groups were seen on day 8. On day 10, in addition to greater numbers of platelets in the treated group, the spleens from the mice receiving palmitoylguanosine were also significantly larger than those receiving only saline (FIG. 17). On day 12, the spleen weight of the animals in the treated group was more than double that of the control mice, and the number of neutrophils in the blood of the treated group was 3-fold greater than in the control samples (FIGS. 17 and 18). The white blood cell count is also shown (FIG. 19).

Example 44

Palmitoyldeoxyinosine and Palmitoylguanosine Enhance Hematopoiesis in Normal Mice

Normal, otherwise untreated, female Balb/C mice weighing approximately 20 grams each received a total of 4 or 9 0.4 ml intraperitoneal injections (one per day) of either Tween-80 (0.2%) (controls), palmitoylguanosine (2.5 $\mu$moles/mouse/day), or palmitoyldeoxyinosine (2.5 $\mu$moles/mouse/day). Twenty-four hours after the 4th or 9th treatment, groups of 5 or 6 animals from each of the 3 groups were bled and then sacrificed by cervical dislocation. Spleens were removed and weighed, and complete blood cell counts performed.

Figure 20:
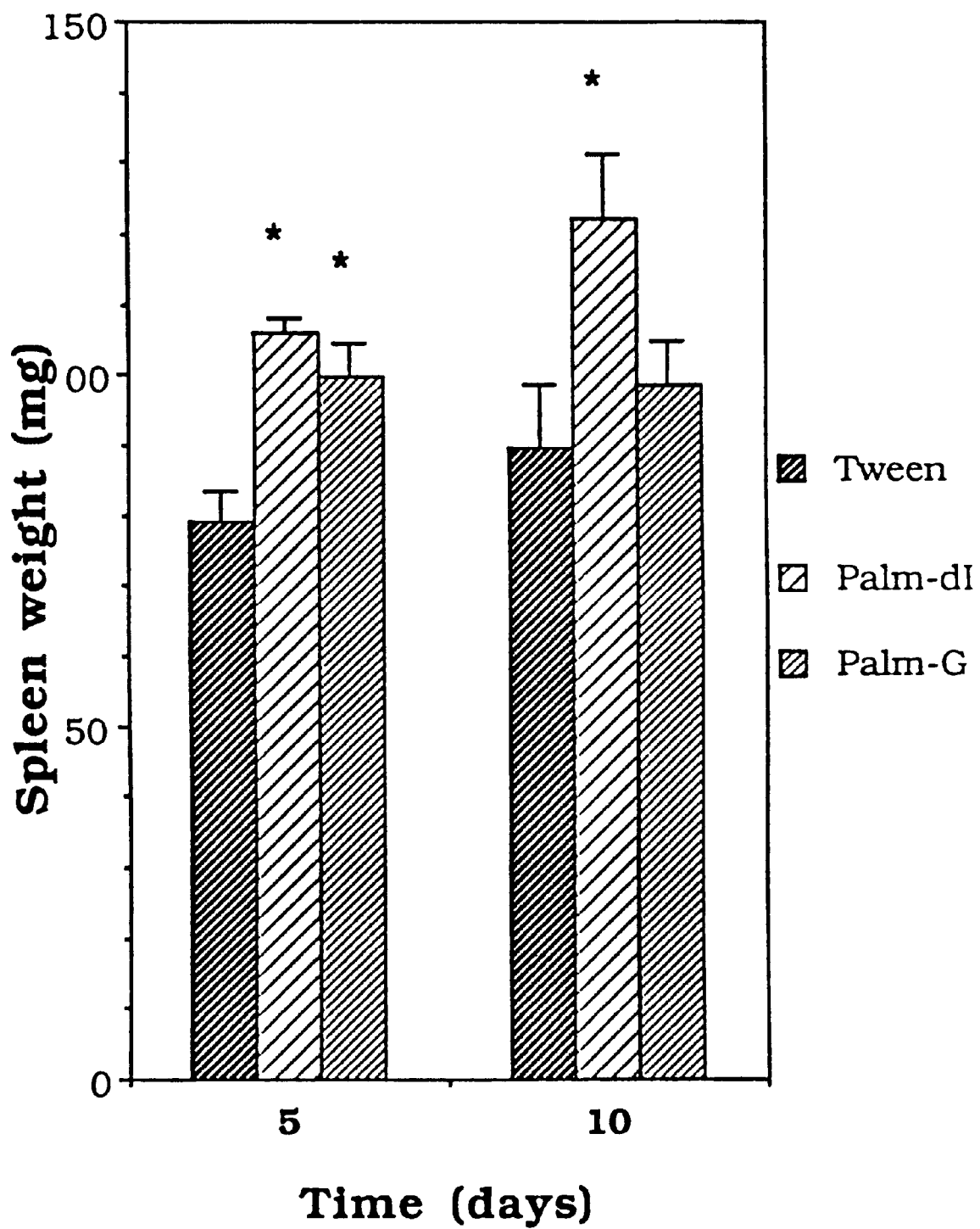
FIG. 20 is a graph comparing spleen weight of mice after treatment with Tween-80, palmitoylguanosine and palmitoyldeoxyinosine as described in Example 44.
Figure 21:
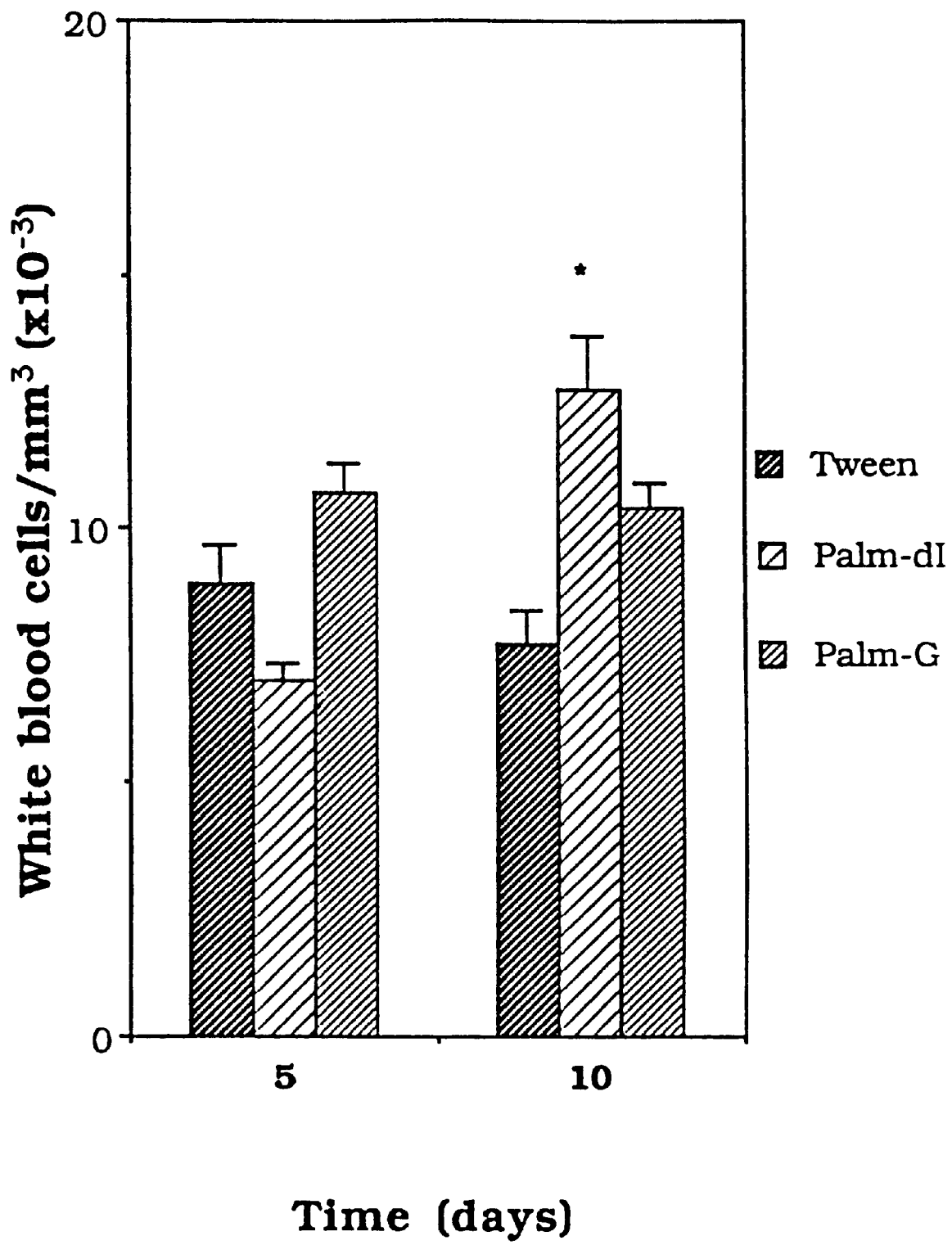
FIG. 21 is a graph comparing white blood cell count in mice after treatment with Tween-80, palmitoylguanosine and palmitoyldeoxyinosine as described in Example 44.
Figure 22:
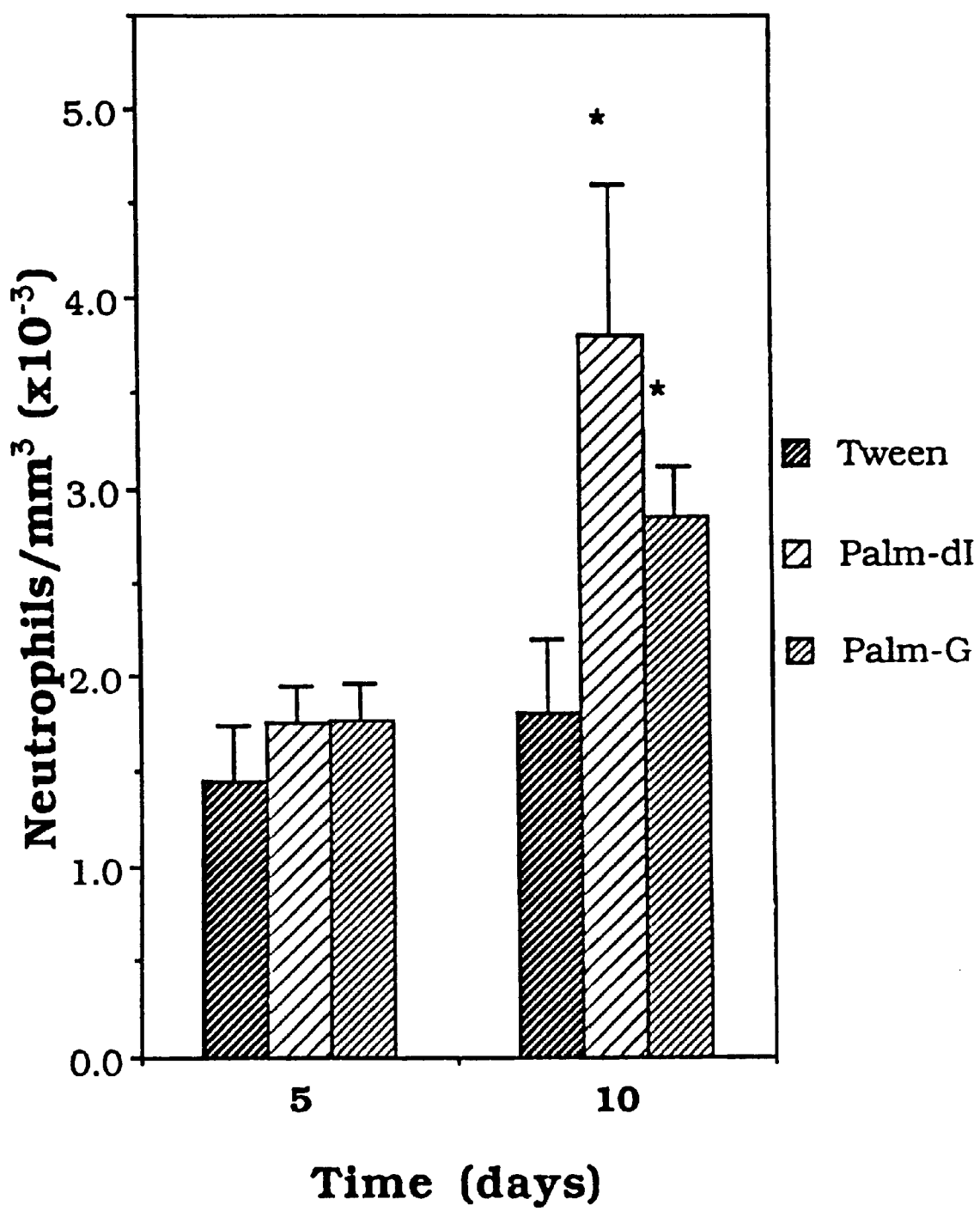
FIG. 22 is a graph comparing neutrophils in mice after treatment with Tween-80, palmitoylguanosine and palmitoyldeoxyinosine as described in Example 44.

Spleen weights on day 5 were significantly greater in the mice treated with palmitoylguanosine and palmitoyldeoxyinosine than in those treated with saline (FIG. 20). On day 10, spleen weights, total leukocyte counts, and neutrophil counts were all significantly greater in the mice treated with palmitoyldeoxyinosine than in the Tween 80 controls (FIGS. 20–22). Total leukocyte counts were also significantly elevated compared to controls in the mice treated with palmitoylguanosine.

Example 45

Dose-response for Octanoylguanosine in Improving Hematopoietic Recovery after Cyclophosphamide

Cyclophosphamide (CP) (275 mg/kg, i.p.) was administered to 45 Balb/C female mice weighing approximately 20 grams each. Twenty-four hours later and each day thereafter for a total of 6 days, mice were given a 0.4 ml i.p. injection of either physiological saline (controls), Tween 80 (0.5%), or one of three different doses of octanoylguanosine (0.5, 2.5, or 5 $\mu$moles/mouse/day in 0.5% Tween 80). On day 7 following CP administration all 9 animals from each of the 5 groups were bled and then sacrificed by cervical dislocation. Spleens were removed and weighed, and complete blood cell counts performed.

Figure 23:
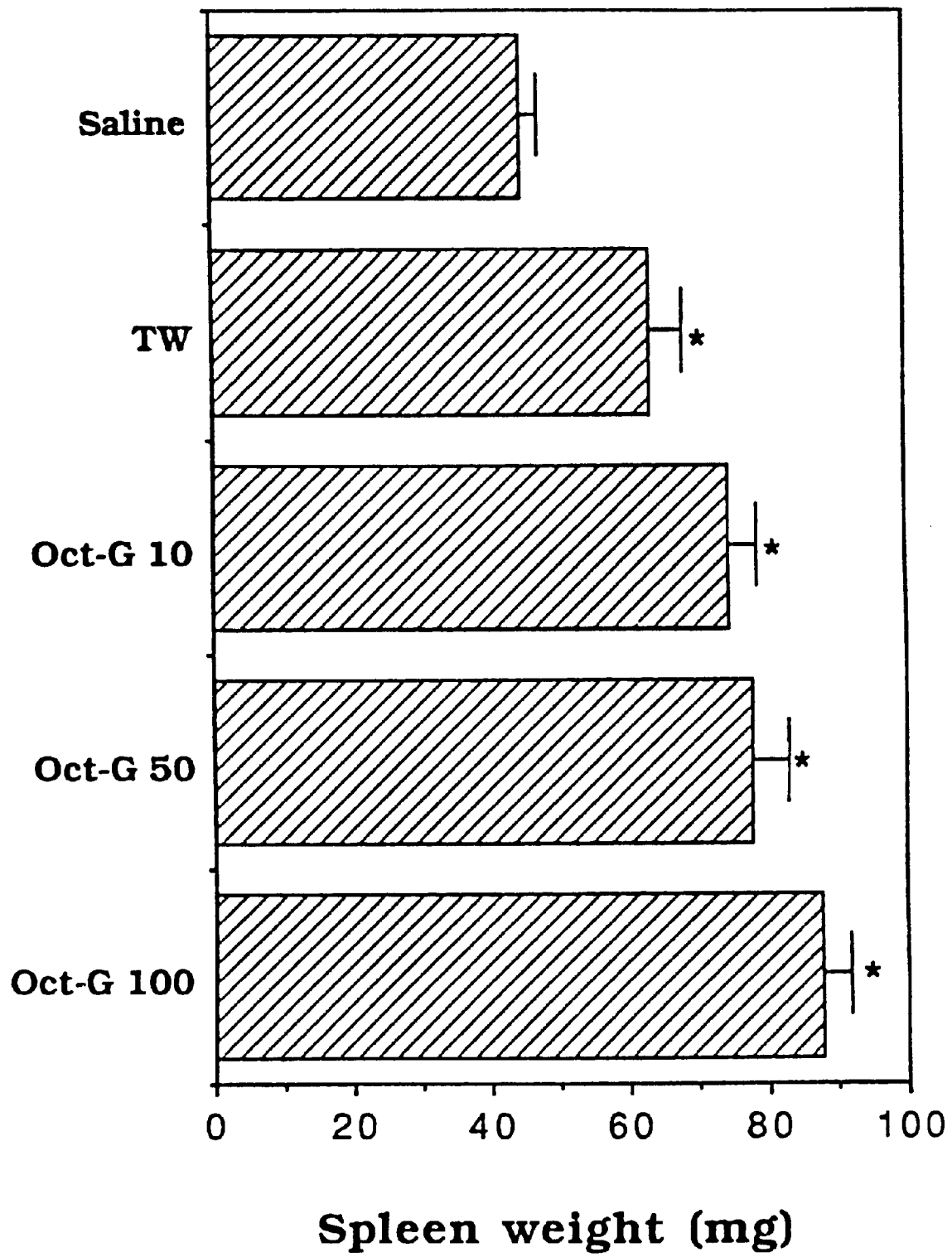
FIG. 23 is a graph comparing spleen weight of mice after treatment with saline, Tween-80 and octanoylguanosine at various concentrations as described in Example 44.
Figure 24:
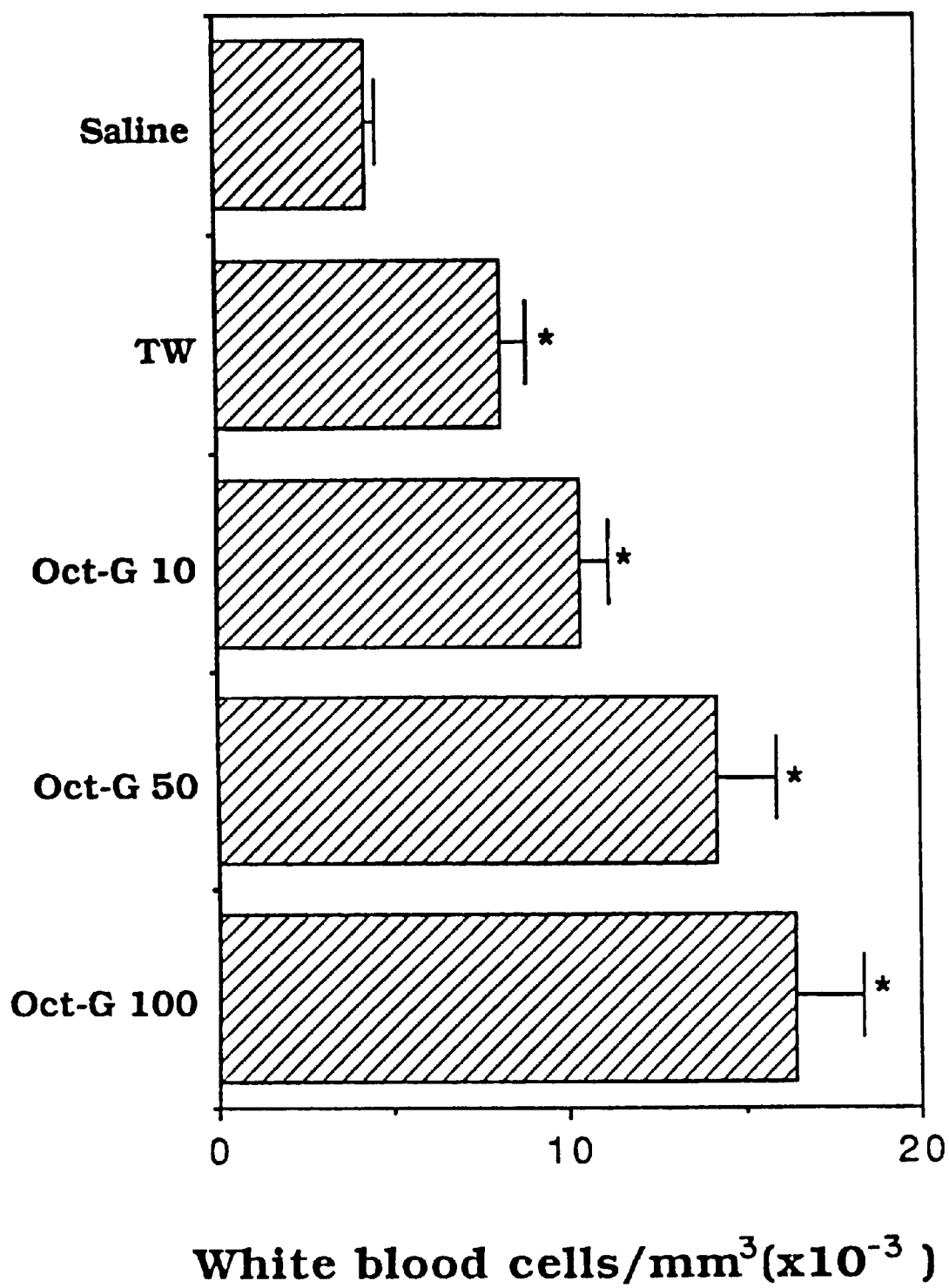
FIG. 24 is a graph comparing white blood cell count in mice after treatment with saline, Tween-80 and octanoylguanosine at various concentrations as described in Example 44.
Figure 25:
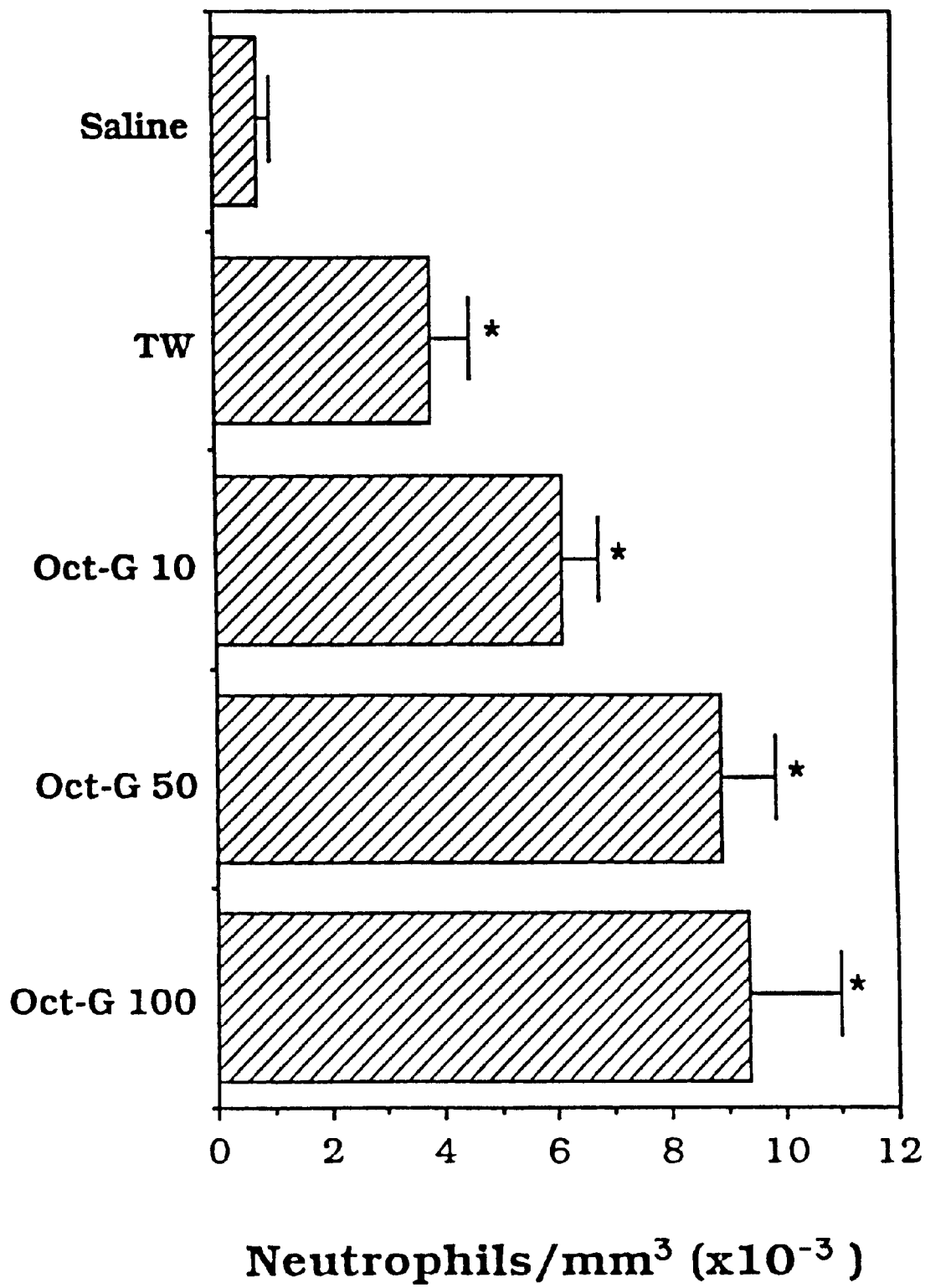
FIG. 25 is a graph comparing neutrophils in mice after treatment with saline, Tween-80 and octanoylguanosine as described in Example 45.
Figure 26:
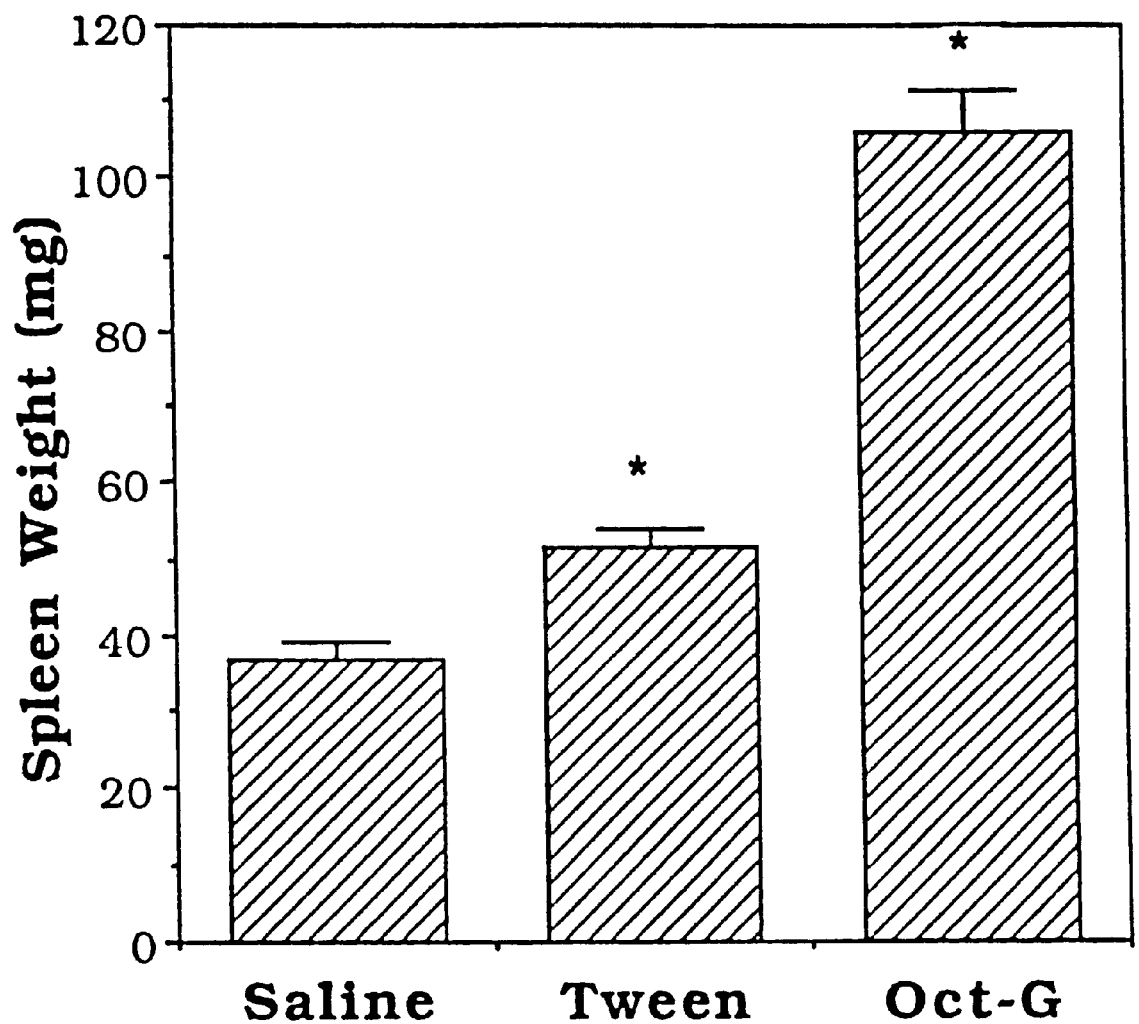
FIG. 26 is a graph comparing spleen weight of mice after treatment with saline, Tween-80 and octanoylguanosine as described in Example 46.

Treatment of these CP-compromised mice with Tween 80 resulted in some increase in the mean spleen weight, but treatment with octanoylguanosine at each of the three doses tested resulted in significantly larger spleens than in controls and larger than in Tween 80-treated mice (FIG. 23). Mice treated with the highest dose of octanoylguanosine (10 $\mu$moles) had the largest spleens (data not shown). More importantly, the total number of leukocytes and the total number of neutrophils was significantly increased above control values in a dose-dependent manner (FIGS. 24 and 25). The middle dose of octanoylguanosine (2.5 $\mu$moles) was, however, nearly as effective as the highest dose in accelerating the regeneration of hematopoiesis.

Example 46

Histological Examination of Spleens From Mice Treated with Octanoylguanosine after Cyclophosphamide

Cyclophosphamide (CP) (275 mg/kg, i.p.) was administered to 30 Balb/C female mice weighing approximately 20 grams each. Twenty-four hours later and each day thereafter for a total of 6 days, mice were given a 0.4 ml i.p. injection of either physiological saline (controls), Tween 80 (0.5%), or octanoylguanosine (5.0 $\mu$moles/mouse/day in 0.5% Tween 80). On day 7 following CP administration all 10 animals from each of the 3 groups were bled and then sacrificed by cervical dislocation. Spleens were removed, weighed, and fixed in 10% formalin for later histological examination. Complete blood cell counts were performed on the collected blood.

Treatment of mice with Tween 80 alone resulted in a modest increase in spleen weight compared to saline-treated controls. However, treatment with octanoylguanosine resulted in spleen weights significantly greater than those in either saline-treated controls or Tween 80-treated mice (FIG.

Figure 27:
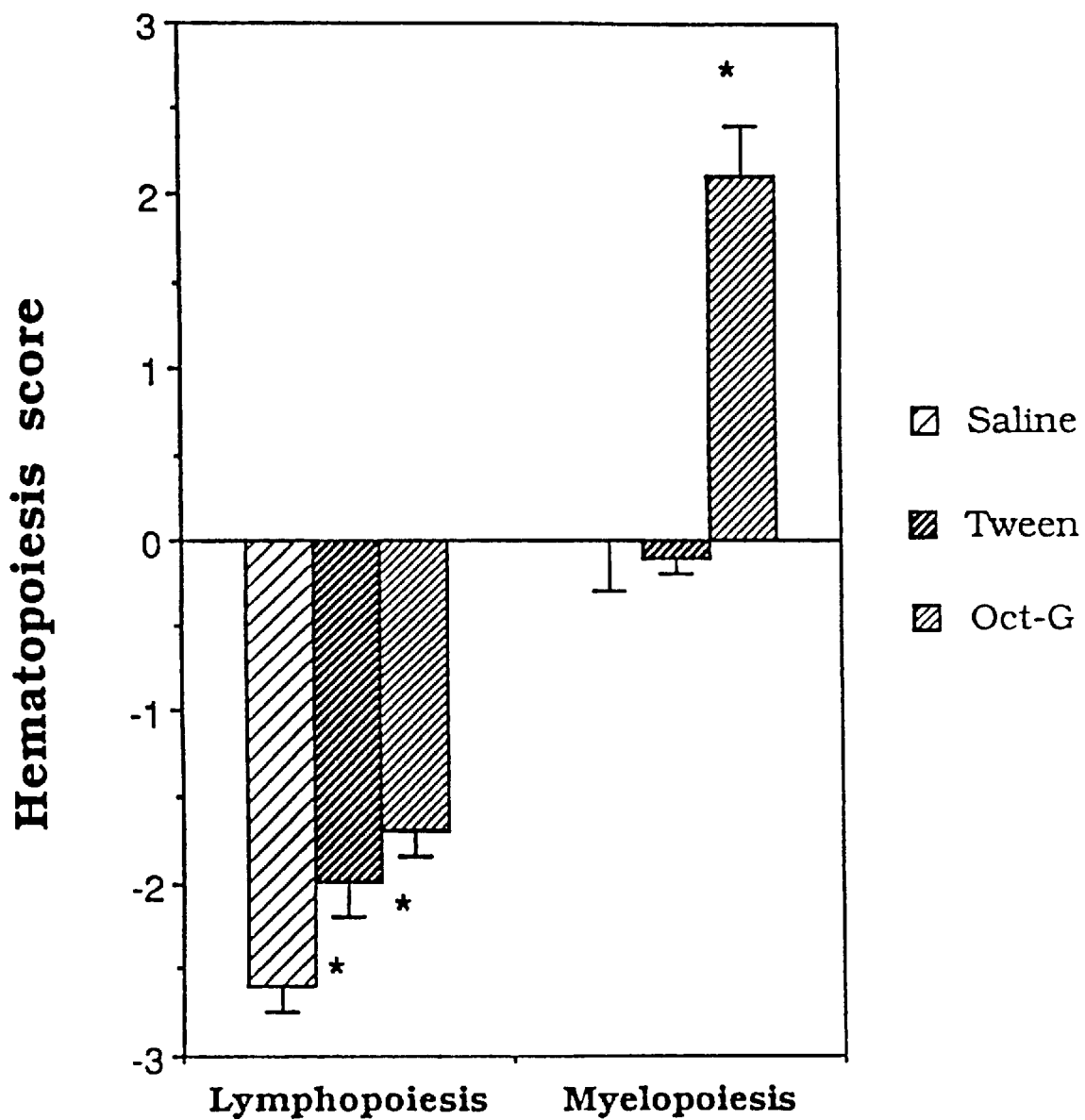
FIG. 27 is a graph showing the effect of saline, Tween-80 and octanoylguanosine in cyclophosphamide-treated mice on hematopoiesis score as described in Example 46.

26). Histological examination of the spleens revealed histologically normal tissue in all treatment groups and much greater lymphopoiesis (increased white pulp) and myelopoiesis (increased red pulp) in the spleens of the octanoylguanosine-treated mice compared to the saline-treated controls and those treated with Tween 80 (FIG. 27). These observations indicate that octanoylguanosine treatment of CP-compromised mice accelerates both myelopoiesis and lymphopoiesis, at least at the level of the spleen.

Figure 28:
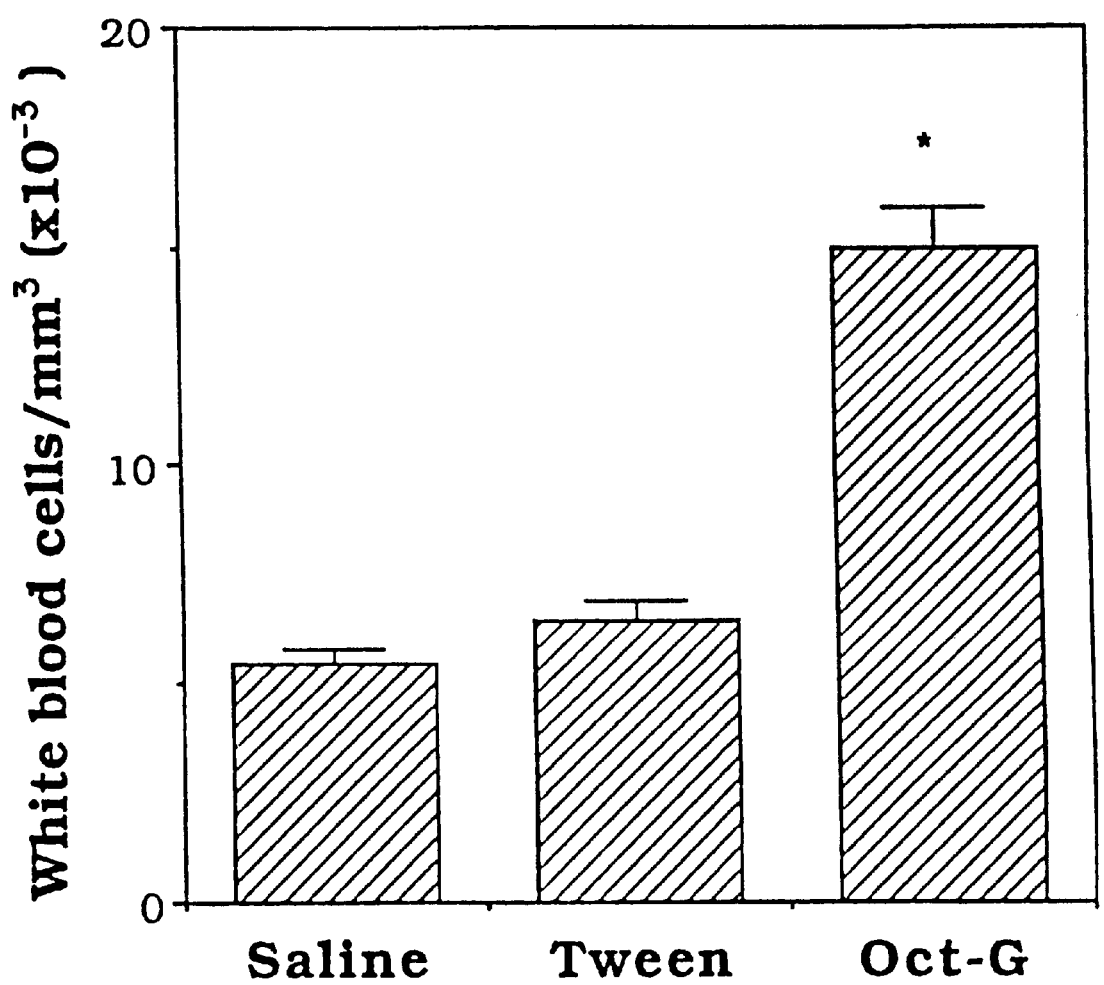
FIG. 28 is a graph comparing white blood cell count in mice after treatment with saline, Tween-80 and octanoylguanosine as described in Example 46.
Figure 29:
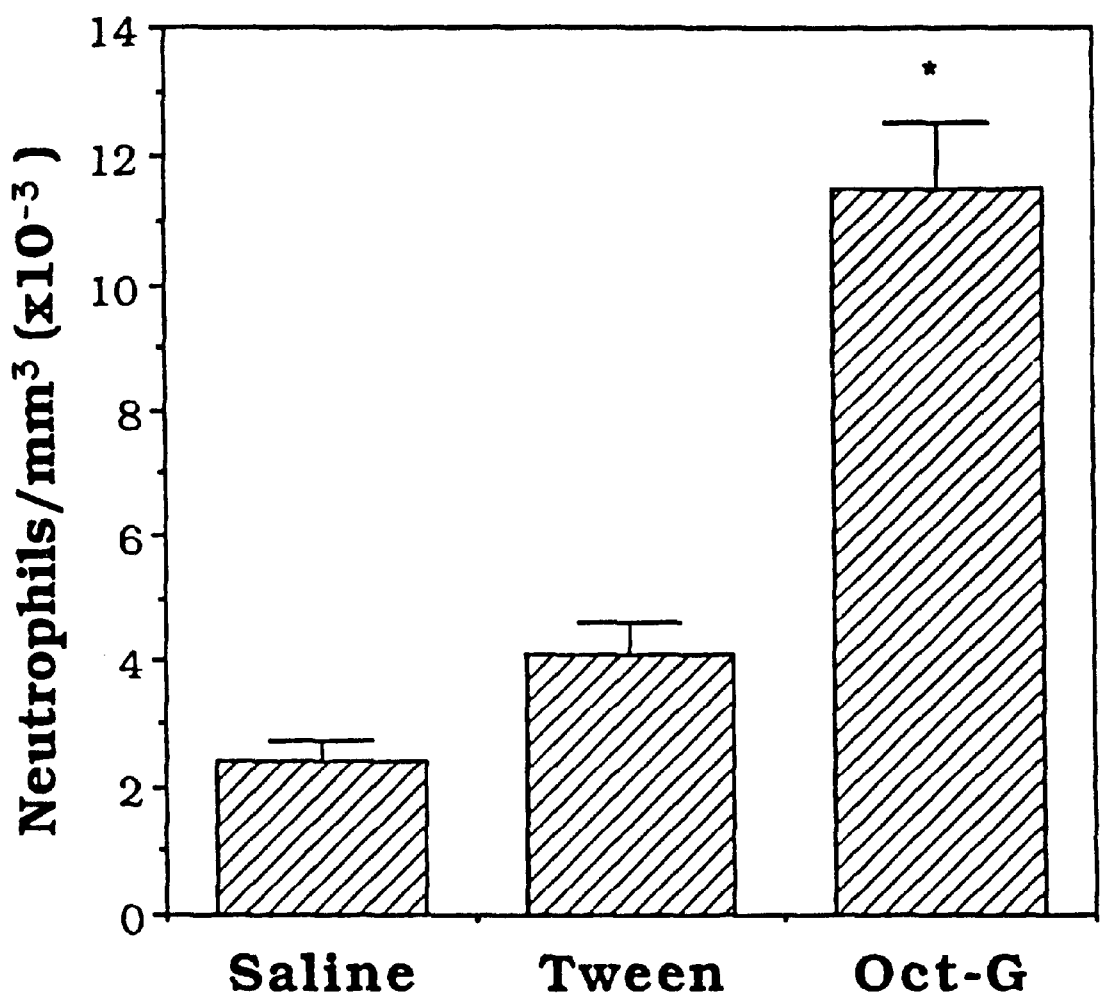
FIG. 29 is a graph comparing neutrophils in mice after treatment with saline, Tween-80 and octanoylguanosine as described in Example 46.

Treatment of mice with octanoylguanosine also clearly resulted in significantly greater numbers of peripheral white blood cells (WBC) and neutrophils than seen in either control or Tween 80-treated mice (FIGS. 28 and 29, respectively).

Example 47

Benzoylguanosine Improves Hematopoietic Recovery after Cyclophosphamide

Cyclophosphamide (CP) (275 mg/kg, i.p.) was administered to 48 Balb/C female mice weighing approximately 20 grams each. Twenty-four hours later and each day thereafter for a total of 6 days, mice were given a 0.4 ml i.p. injection of either physiological saline (controls), benzoylguanosine (2.5 μmoles/mouse/day in 0.2% Tween 80), or palmitoylguanosine (2.5 μmoles/mouse/day in 0.2% Tween 80). On days 7 and 10 following CP administration 8 animals from each of the 3 groups were bled and then were sacrificed by cervical dislocation. Spleens were removed and weighed, and complete blood cell counts performed.

Figure 30:
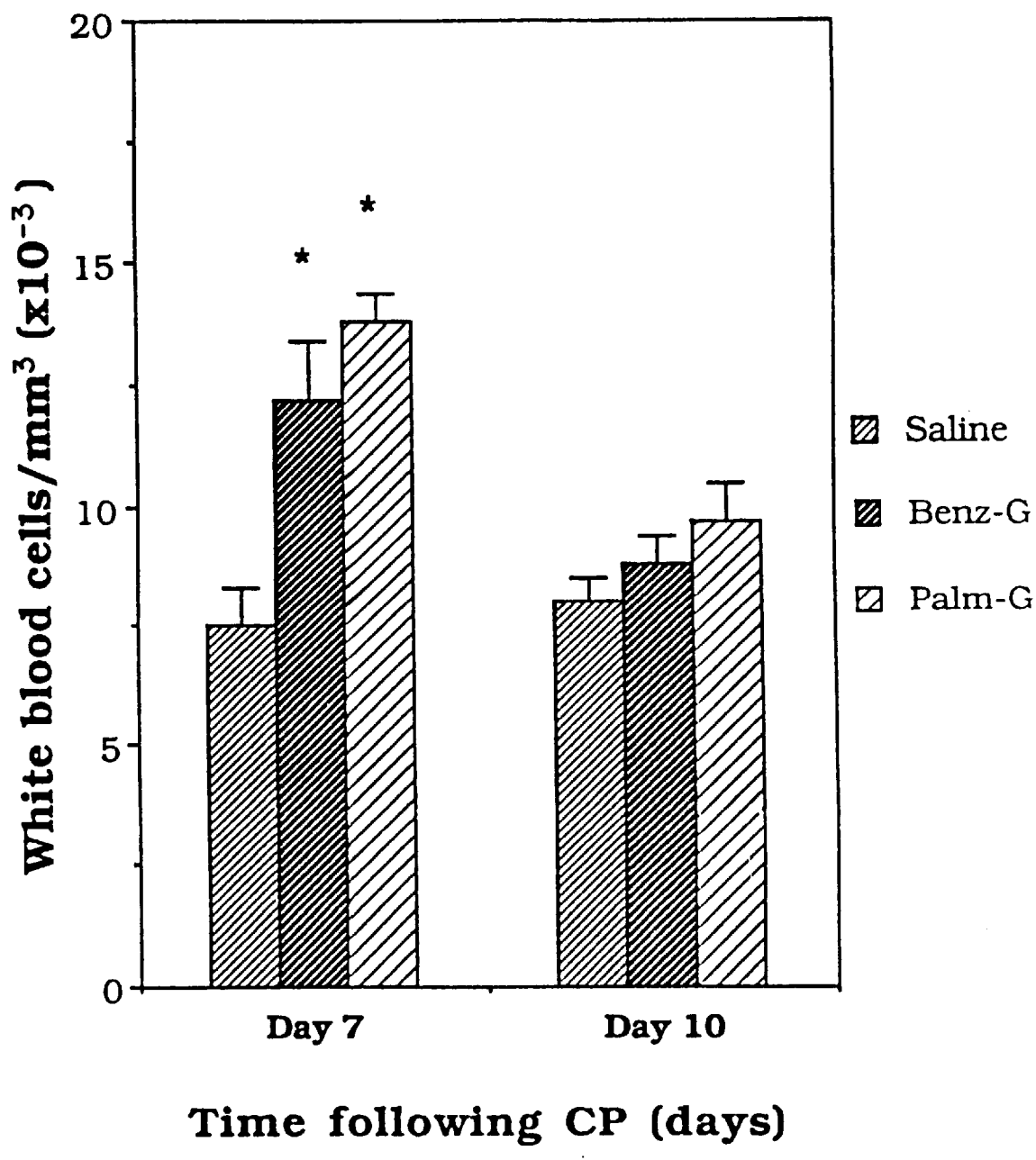
FIG. 30 is a graph comparing white blood cell count in mice after treatment with saline, benzoylguanosine and palmitoylguanosine as described in Example 47.
Figure 31:
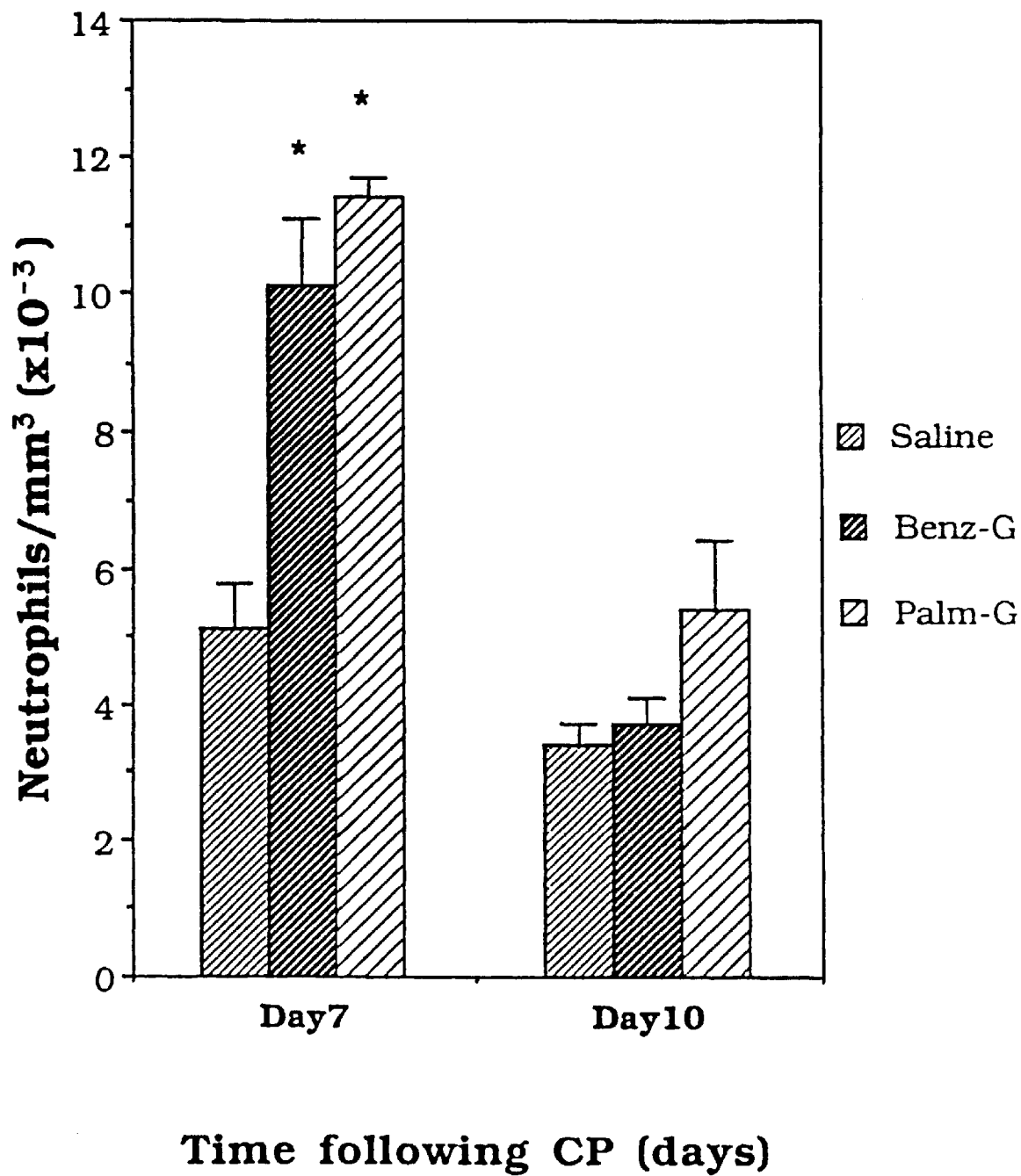
FIG. 31 is a graph comparing neutrophils in mice after treatment with saline, benzoylguanosine and palmitoylguanosine as described in Example 47.
Figure 32:
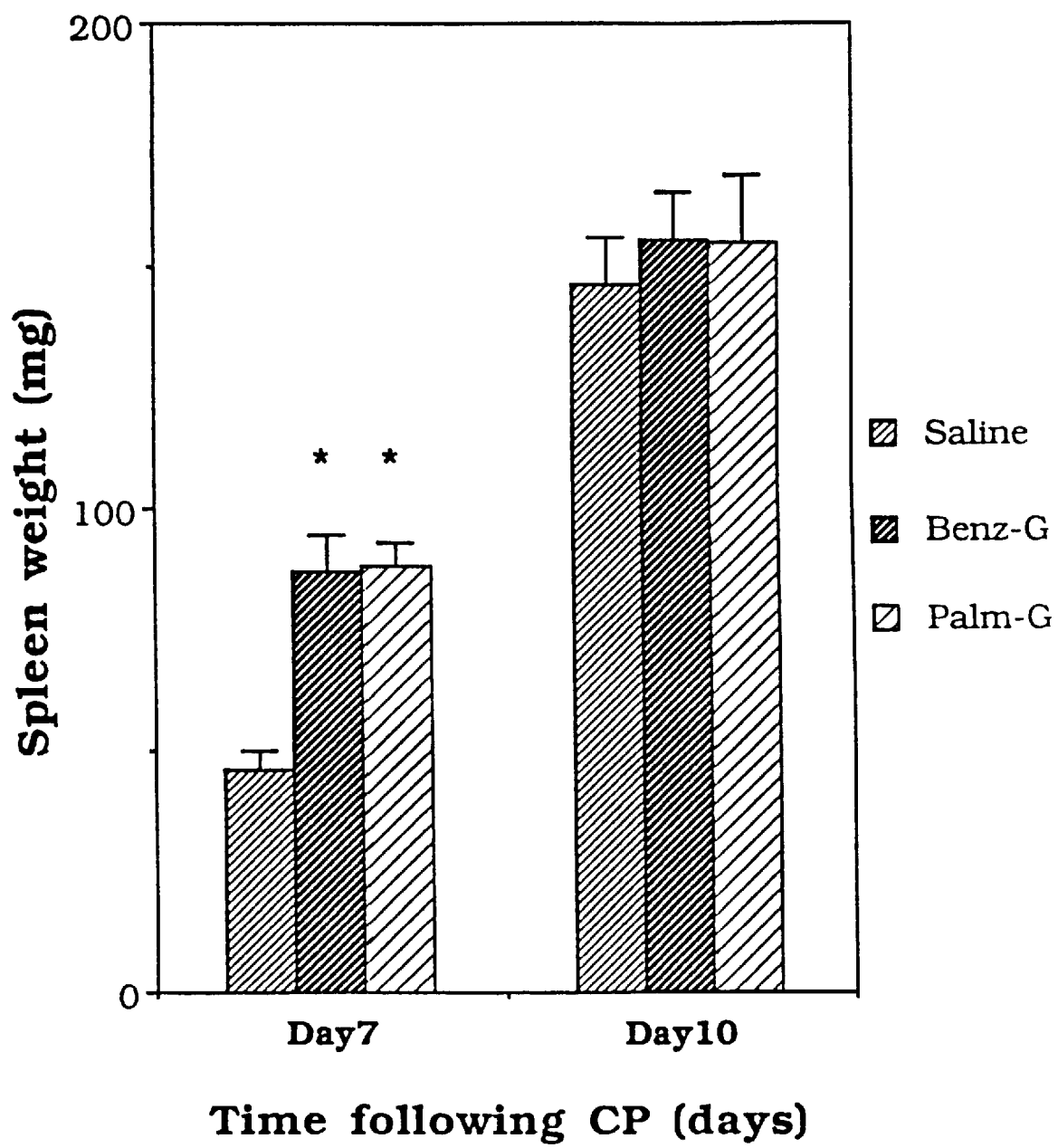
FIG. 32 is a graph comparing spleen weight of mice after treatment with saline, benzoylguanosine and palmitoylguanosine as described in Example 47.
Figure 33:
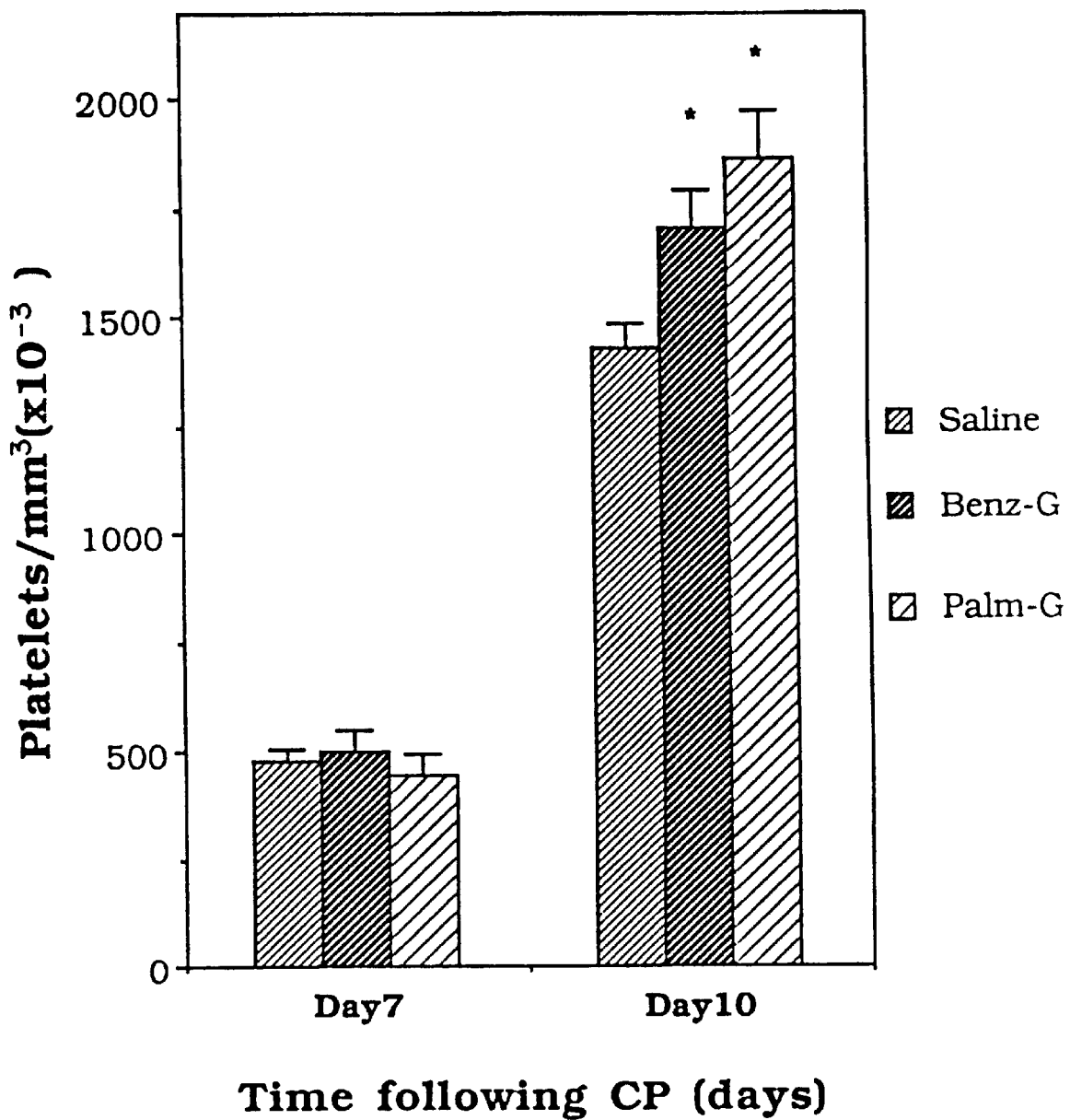
FIG. 33 is a graph comparing platelets in mice after treatment with saline, benzoylguanosine and palmitoylguanosine as described in Example 47.

On day 7 total white blood cells, neutrophils, and spleen weight were significantly elevated compared to controls in both the benzoylguanosine-treated and palmitoylguanosine-treated mice (FIGS. 30–32, respectively). There were no statistically significant differences between these two treatment groups. On day 10 platelet number in both of the acylated guanosine groups was significantly greater than in the control group (FIG. 33).

Example 48

Palmitoylxanthosine and Palmitoyldeoxyinosine Improve Hematopoietic Recovery after Cyclophosphamide Cyclophosphamide (CP) (275 mg/kg, i.p.) was administered to 36 Balb/C female mice weighing approximately 20 grams each. Twenty four hours later and each day thereafter for a total of 4 or 6 days, mice were given a 0.4 ml i.p. injection of either physiological saline (controls), palmitoyldeoxyinosine (2.5 μmoles/mouse), or palmitoylxanthosine (2.5 μmoles/mouse). On days 5 and 7 following CP administration 6 of the 12 animals in each of the 3 groups were bled and then sacrificed by cervical dislocation. Spleens were removed and weighed, and complete blood cell counts performed.

Figure 34:
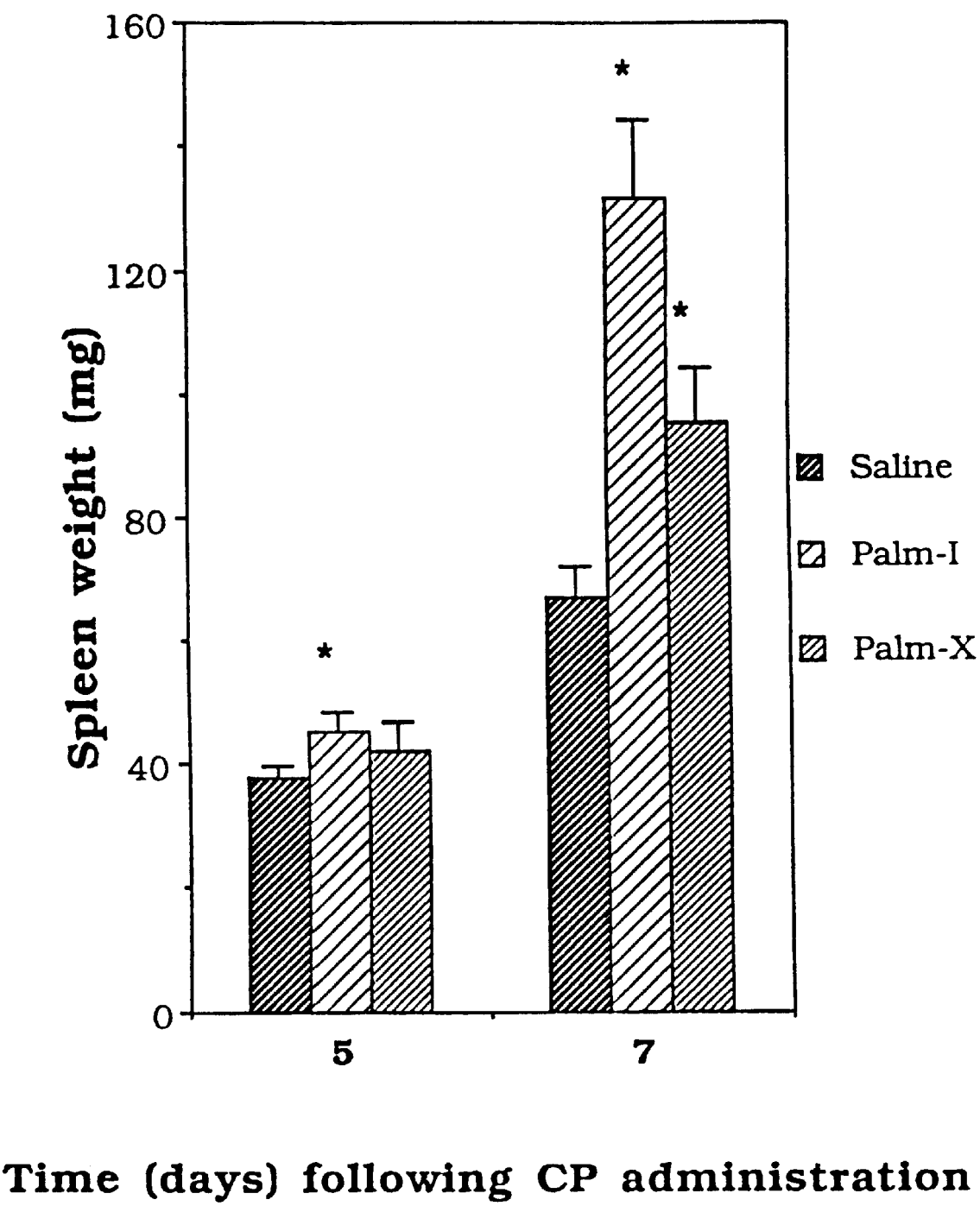
FIG. 34 is a graph comparing spleen weight of mice after treatment with saline, palmitoylinosine and palmitoylxanthosine as described in Example 48.
Figure 35:
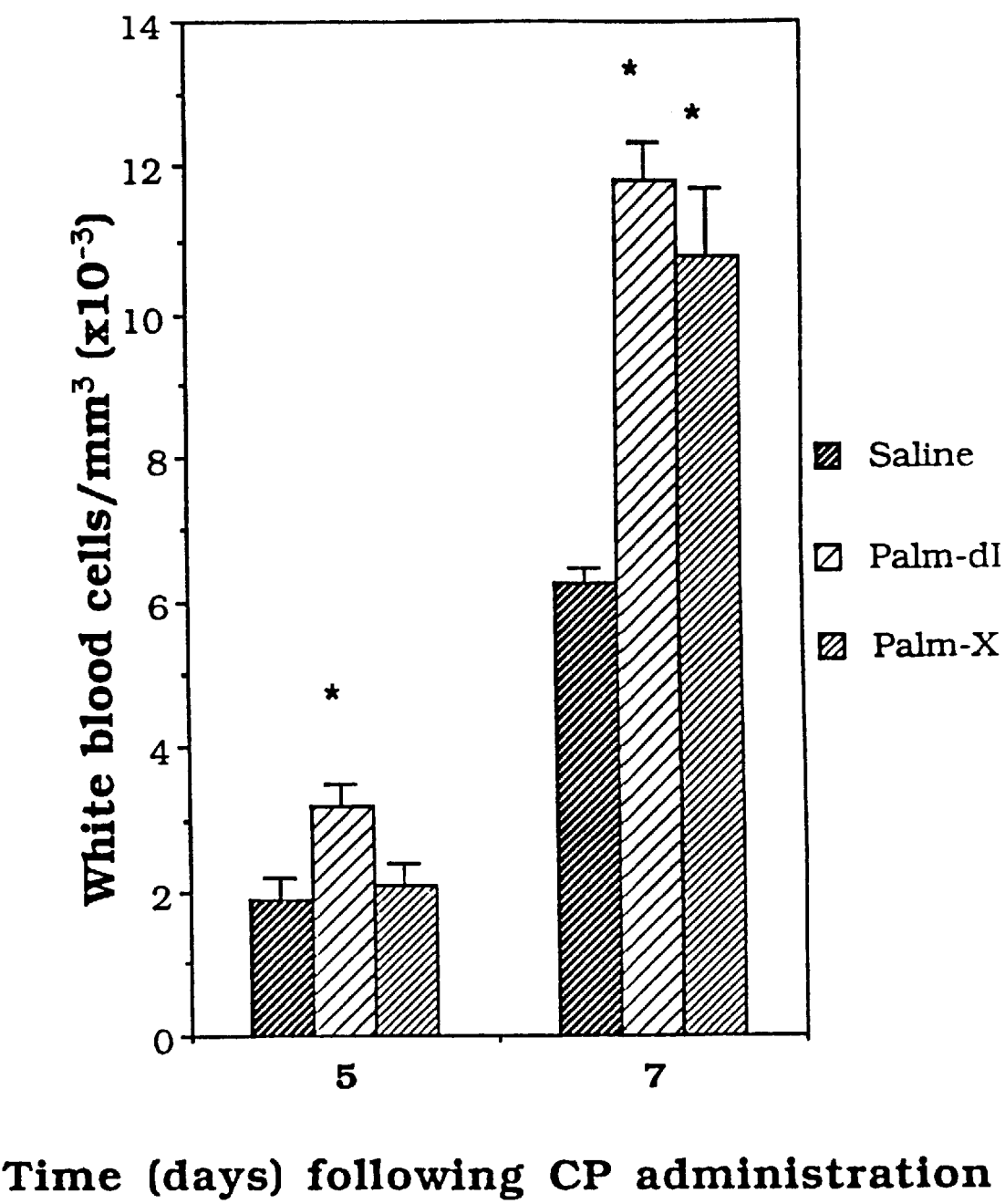
FIG. 35 is a graph comparing white blood cell count in mice after treatment with saline, palmitoyldeoxyinosine and palmitoylxanthosine as described in Example 48.
Figure 36:
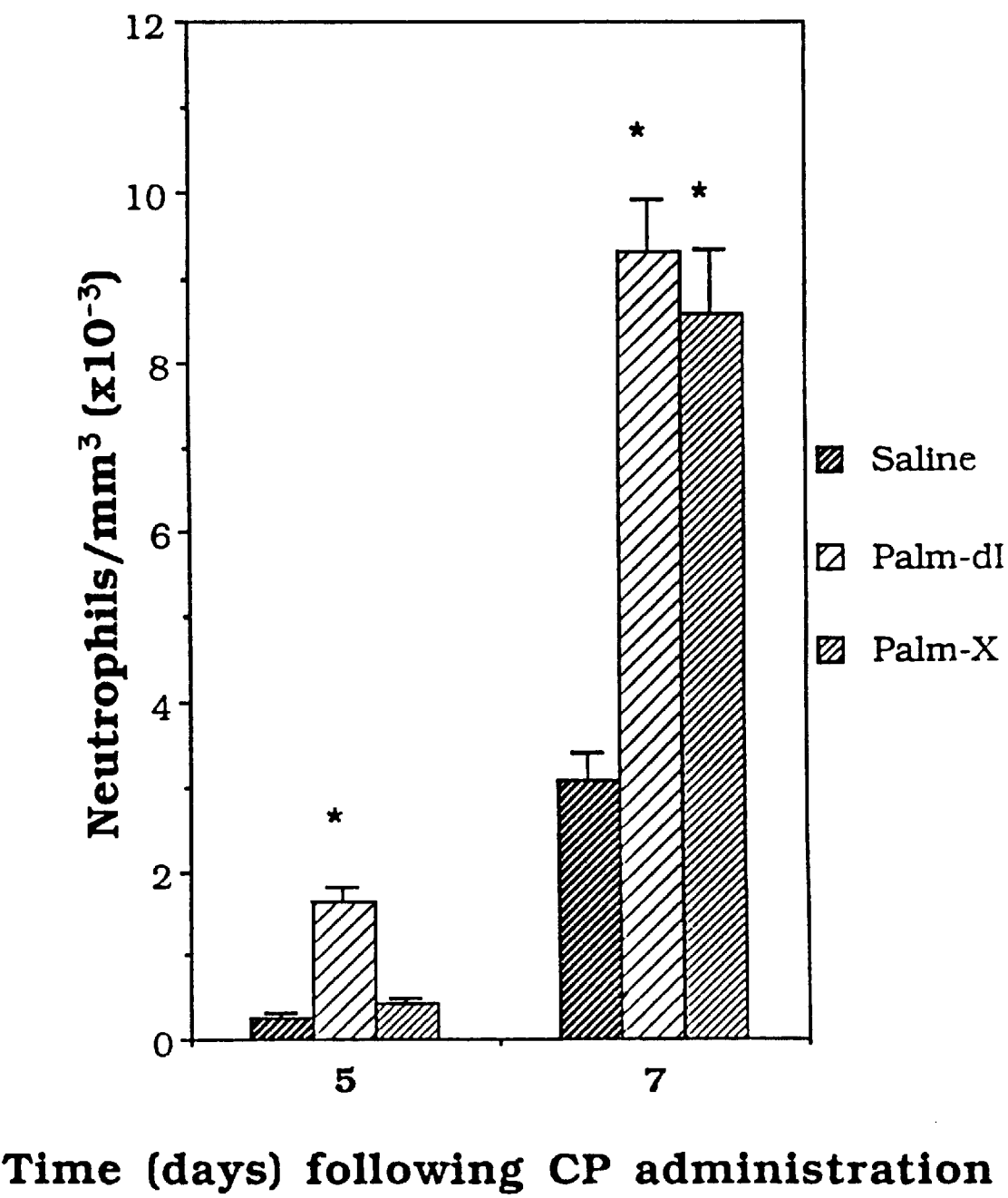
FIG. 36 is a graph comparing neutrophils in mice after treatment with saline, palmitoyldeoxyinosine and palmitoylxanthosine as described in Example 48.

Spleen weight, total leukocyte counts, and neutrophil counts were significantly elevated at day 5 in the group treated with palmitoyldeoxyinosine compared to controls (FIGS. 34, 35, and 36, respectively). Total leukocyte counts and neutrophil counts were significantly elevated compared to those in mice treated with palmitoylxanthosine as well at this time point.

On day 7 following CP administration spleen weight, total leukocytes, and neutrophils were significantly increased compared to controls in both the palmitoylxanthosine-treated and palmitoyldeoxyinosine-treated groups (FIGS. 34, 35, and 36).

Example 49

Palmitoylinosine Improves Hematopoietic Recovery after Cyclophosphamide

Cyclophosphamide (CP) (275 mg/kg, i.p.) was administered to 48 Balb/C female mice weighing approximately 20 grams each. Twenty-four hours later and each day thereafter for a total of 6 days, mice were given a 0.4 ml i.p. injection of either physiological saline (controls), octanoylguanosine (2.5 μmoles/mouse), lauroylguanosine (2.5 μmoles/mouse), palmitoylguanosine (2.5 μmoles/mouse), palmitoylinosine (2.5 μmoles/mouse), or palmitoylxanthosine (2.5 μmoles/mouse). On day 7 following CP administration the 8 animals in each of the 6 groups were bled and then sacrificed by cervical dislocation. Spleens were removed and weighed, and complete blood cell counts performed.

Figure 37:
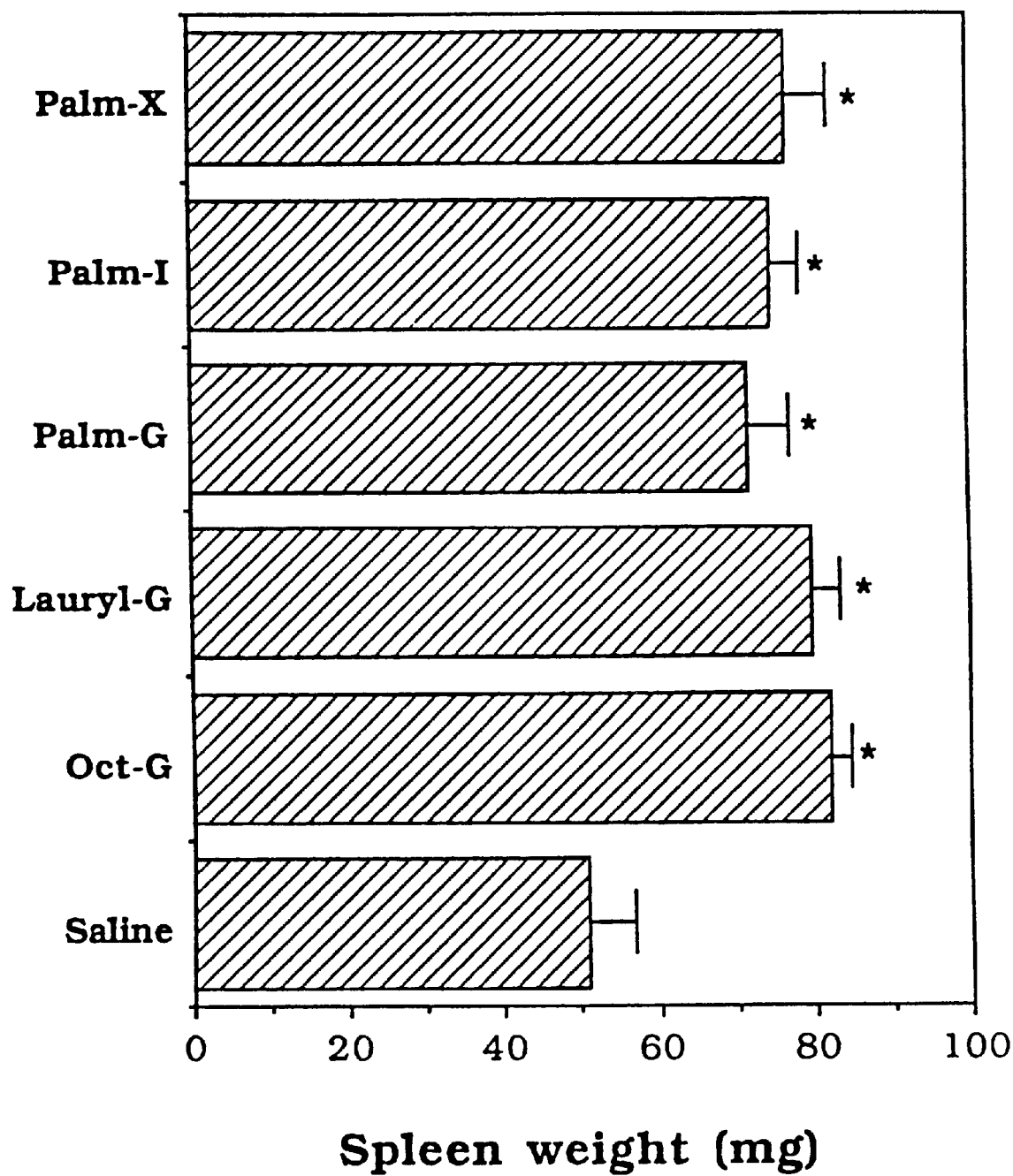
FIG. 37 is a graph comparing spleen weight of mice after treatment with saline, palmitoylxanthosine, palmitoylinosine, palmitoylguanosine, laurylguanosine and octanoylguanosine as described in Example 49.
Figure 38:
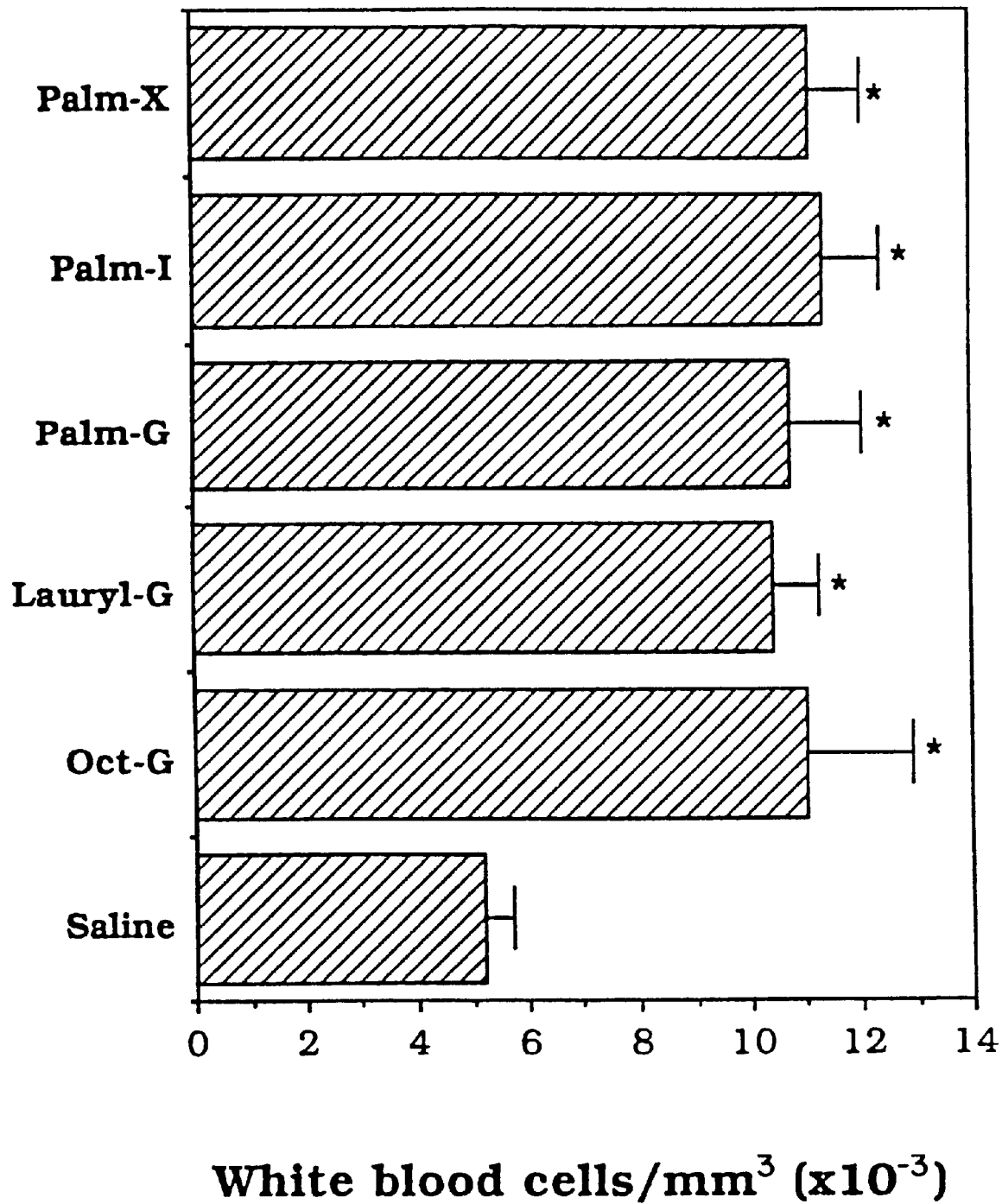
FIG. 38 is a graph comparing white blood cell count in mice after treatment with saline, palmitoylxanthosine, palmitoylinosine, palmitoylguanosine, laurylguanosine and octanoylguanosine as described in Example 49.
Figure 39:
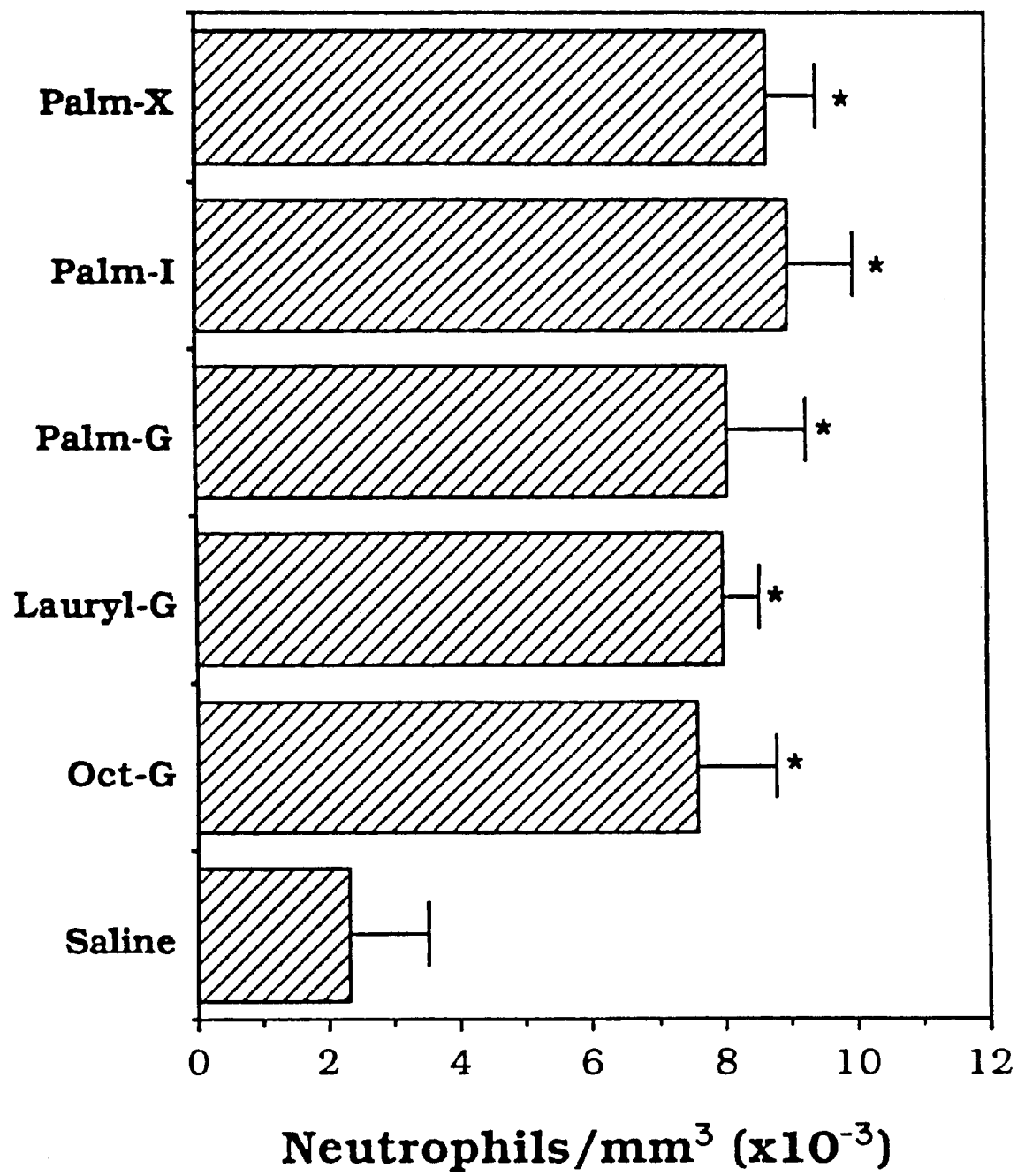
FIG. 39 is a graph comparing neutrophils in mice after treatment with saline, palmitoylxanthosine, palmitoylinosine, palmitoylguanosine, laurylguanosine and octanoylguanosine as described in Example 49.

Spleen weight, total leukocyte counts, and neutrophil counts were significantly elevated in each of the 5 treatment groups compared to controls (FIGS. 37, 38, and 39, respectively). No statistically significant differences were seen comparing the five treatment groups at this time point.

Example 50

Acyl Derivatives of Oxypurine Nucleoside Congeners Improve Hematopoietic Recovery after Cyclophosphamide Cyclophosphamide (CP) (275 mg/kg, i.p.) was administered to 96 Balb/C female mice weighing approximately 20 grams each. Twenty-four hours later and each day thereafter mice were given a 0.4 ml i.p. injection of either Tween-80 (0.2%) (controls), palmitoyldeoxyguanosine (2 μmoles/mouse), palmitoyldeoxyinosine (2 μmoles/mouse), palmitoylacyclovir (2 μmoles/mouse), palmitoylarabinosylguanine (2 μmoles/mouse), palmitoylarabinosylhypoxanthine (2 μmoles/mouse), monopalmitoylguanosine 2',3'-acyclic dialcohol (2 μmoles/mouse), and palmitoyl-8-thioguanosine (2 μmoles/mouse). On days 5 and 7 following CP administration 6 animals in each of the 8 groups were bled and then sacrificed by cervical dislocation. Spleens were removed and weighed, and complete blood cell counts performed.

Figure 40:
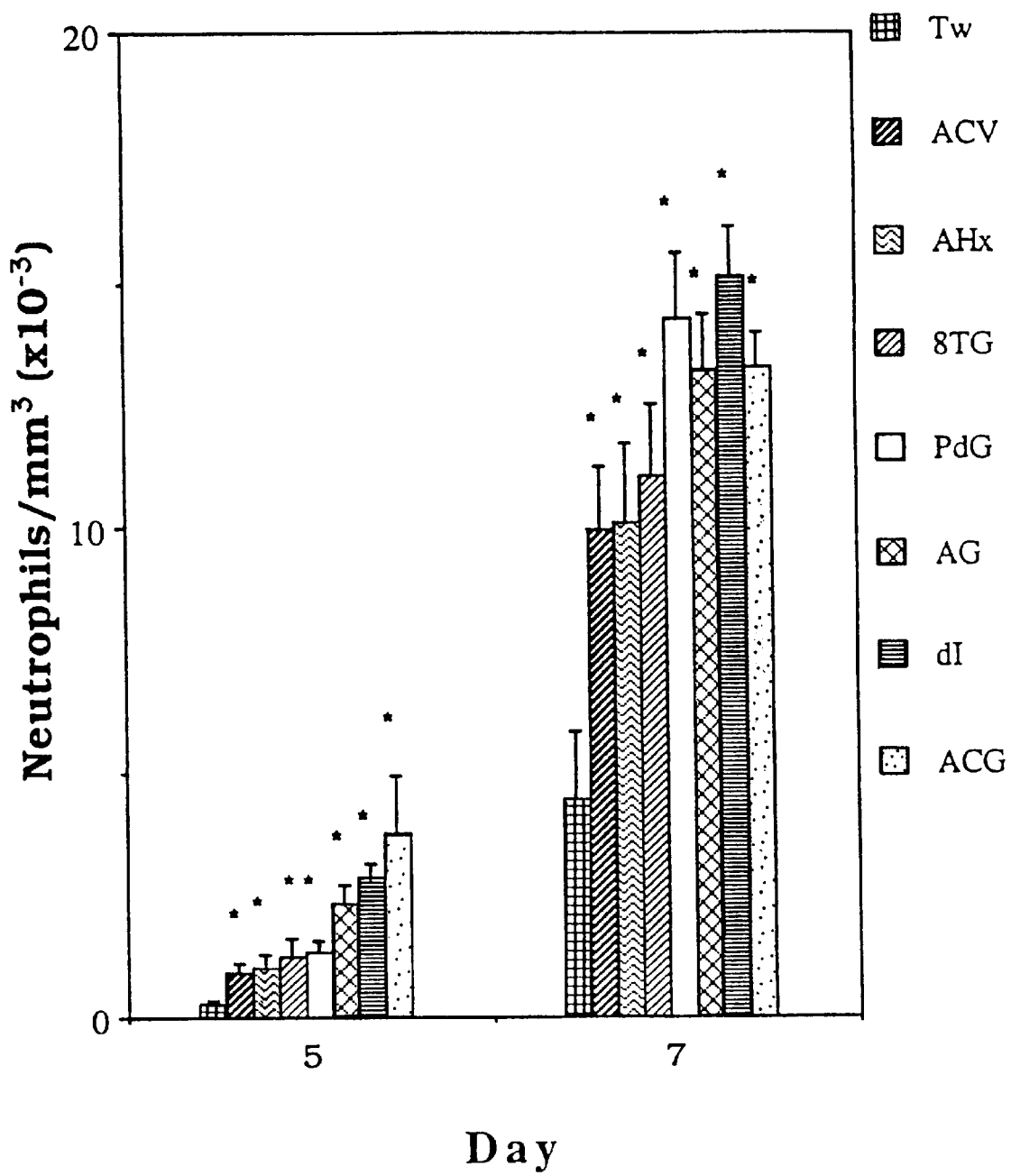
FIG. 40 is a graph comparing neutrophil counts in mice after treatment with Tween-80, palmitoylacyclovir, palmitoylarabinosylhypoxanthine, palmitoyl-8-thioguanosine palmitoyldeoxyguanosine, palmitoylarabinosylguanine, palmitoyldeoxyinosine, and monopalmitoylguanosine 2',3'-acyclic dialcohol as described in Example 50.

In all three FIGS. (40–42) associated with this example the following abbreviations are used:

Tw=Tween-80
ACV=palmitoylacyclovir
AHx=palmitoylarabinosylhypoxanthine
8TG=palmitoyl-8-thioguanosine
PdG=palmitoyldeoxyguanosine
AG=palmitoylarabinosylguanine
dI=palmitoyldeoxyinosine
ACG=monopalmitoylguanosine 2',3'-acyclic dialcohol The total neutrophil counts were significantly elevated compared to controls on days 5 and 7 in all 8 treatment groups (FIG. 40).

Figure 41:
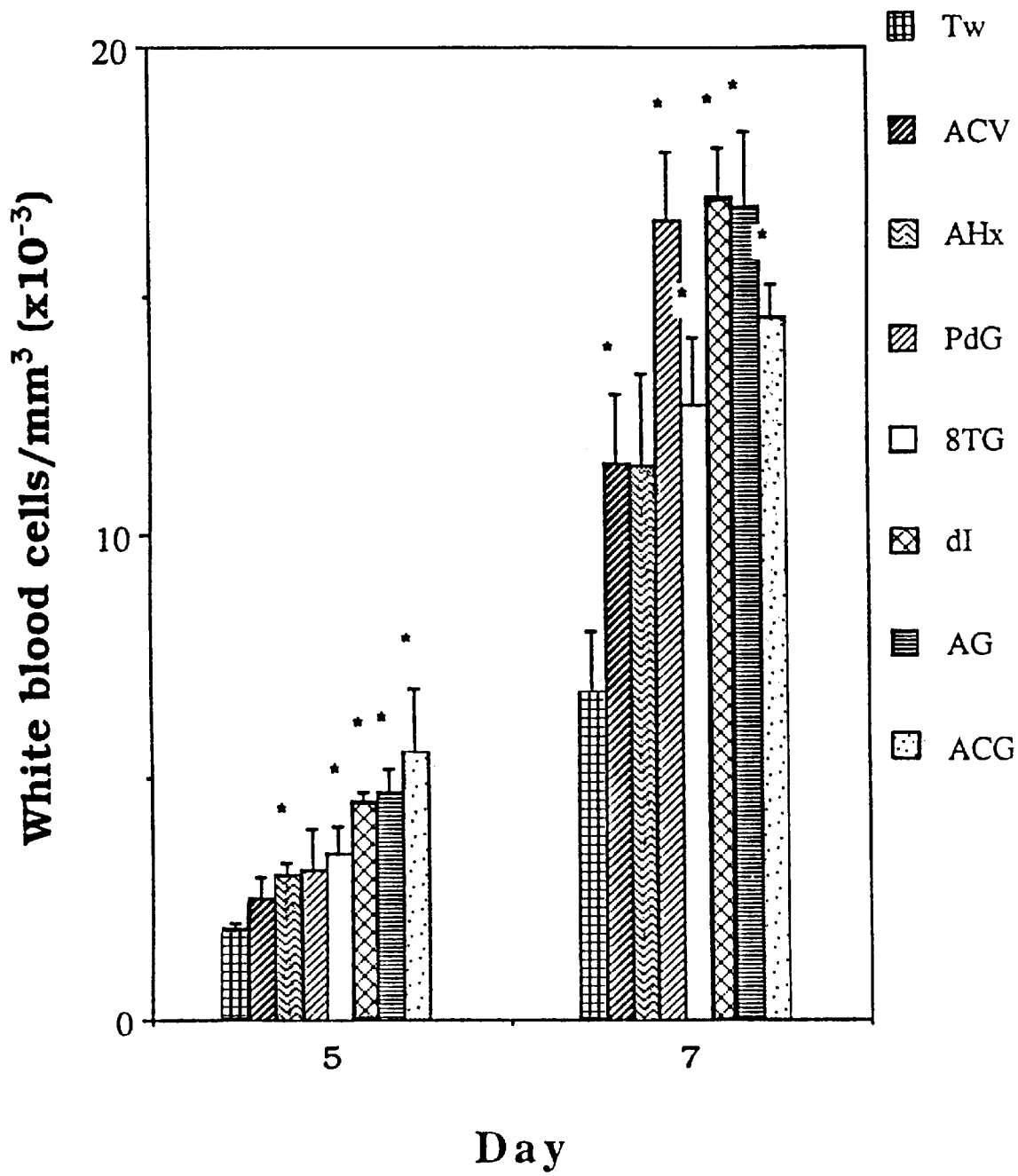
FIG. 41 is a graph comparing white blood cell counts in mice after treatment with Tween-80, palmitoylacyclovir, palmitoylarabinosylhypoxanthine, palmitoyl-8-thioguanosine palmitoyldeoxyguanosine, palmitoylarabinosylguanine, palmitoyldeoxyinosine, and monopalmitoylguanosine 2',3'-acyclic dialcohol as described in Example 50.

The white blood cell count was significantly elevated compared to controls in all but one treatment group (1-O-palmitoylacyclovir) on day 5 and in all 8 treatment groups on day 7 (FIG. 41).

Figure 42:
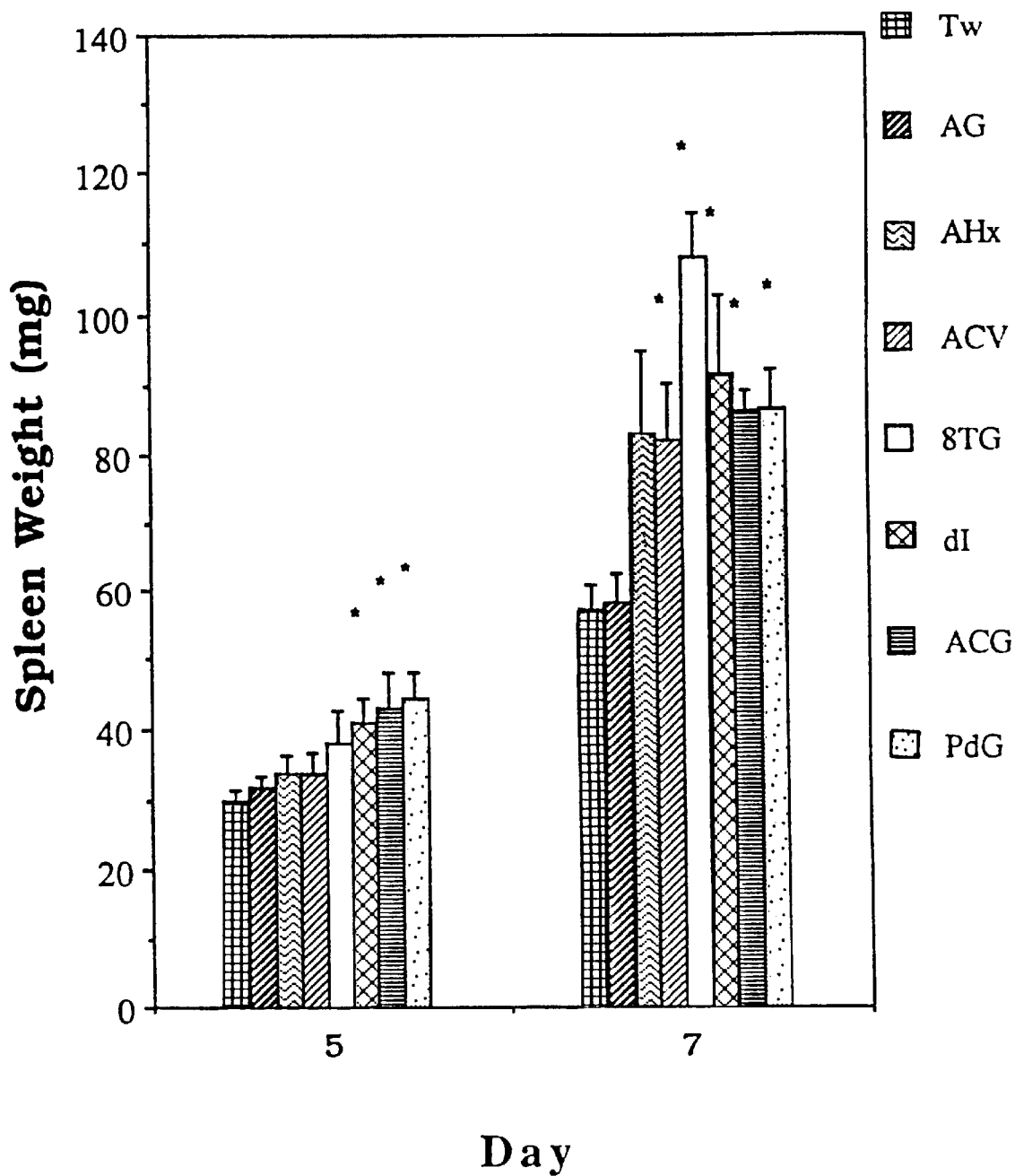
FIG. 42 is a graph comparing spleen weight in mice after treatment with Tween-80, palmitoylacyclovir, palmitoylarabinosylhypoxanthine, palmitoyl-8-thioguanosine palmitoyldeoxyguanosine, palmitoylarabinosylguanine, palmitoyldeoxyinosine, and monopalmitoylguanosine 2',3'-acyclic dialcohol as described in Example 50.

Spleen weight was significantly elevated compared to controls on day 5 in the following groups: monopalmitoylguanosine 2',3'-acyclic dialcohol, palmitoyldeoxyinosine, palmitoylguanosine. It was significantly elevated on day 7 in all treatment groups except palmitoylarabinosylguanine and palmitoylarabinosylhypoxanthine (FIG. 42).

Example 51

Acyl Derivatives of Deoxyguanosine Improve Hematopoietic Recovery after Cyclophosphamide Cyclophosphamide (CP) (275 mg/kg, i.p.) was administered to 88 Balb/C female mice weighing approximately 20 grams each. Twenty-four hours later and each day thereafter mice were given a 0.4 ml i.p. injection of either Tween-80 (0.2%) (controls), 3'-O-palmitoyldeoxyguanosine (2 μmoles/mouse), butyryldeoxyguanosine (2 μmoles/mouse), palmitoyl-N-isobutyryldeoxyguanosine (2 μmoles/mouse), lauryldeoxyguanosine (2 μmoles/mouse), octanoyldeoxyguanosine (2 μmoles/mouse), and palmitoyldeoxyguanosine (2 μmoles/mouse). On days 5 and 7 following CP administration 6 or 7 animals in each of the 7 groups were bled and then sacrificed by cervical dislocation. Spleens were removed and weighed, and complete blood cell counts performed.

Figure 43:
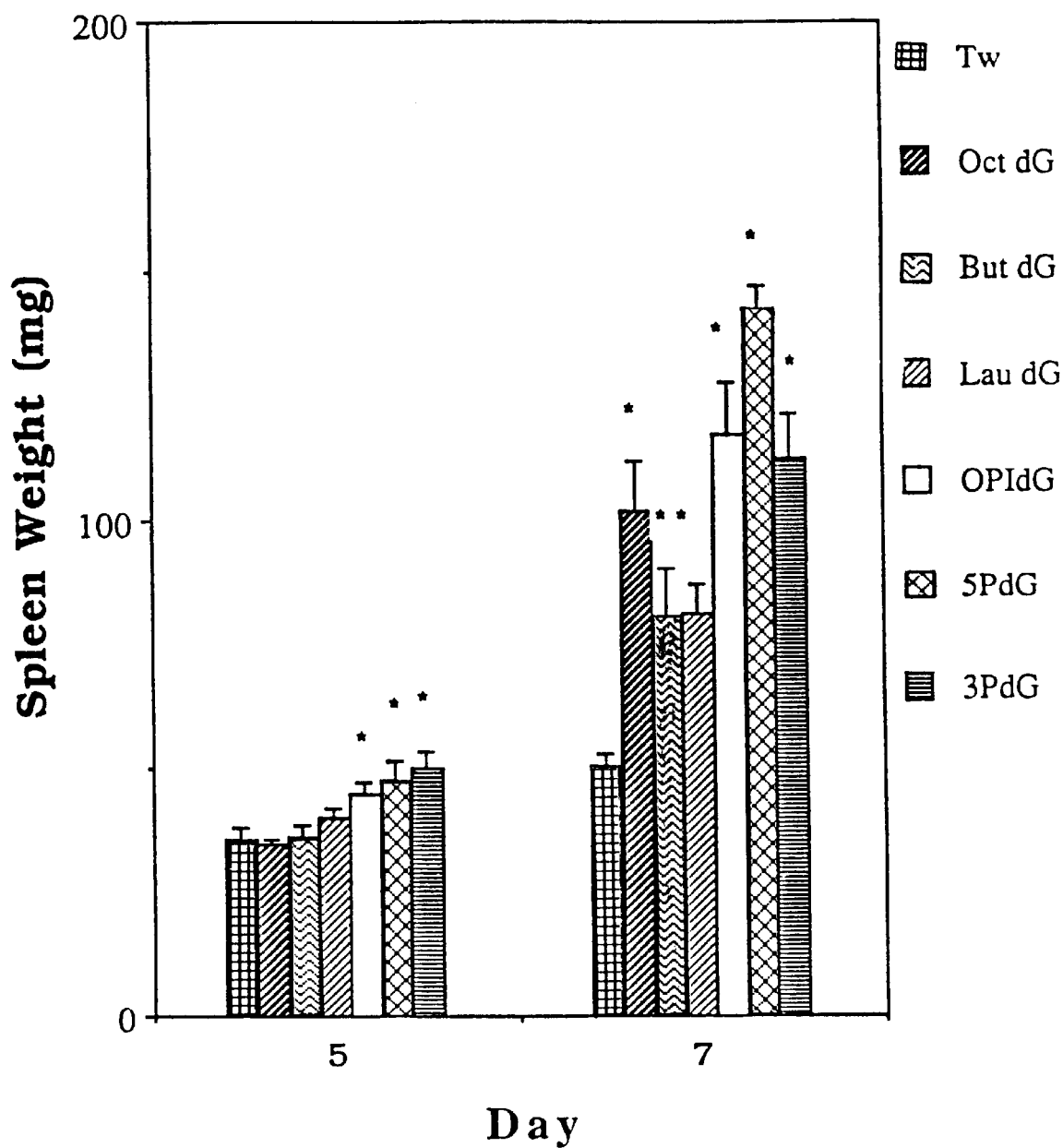
FIG. 43 is a graph comparing spleen weight in mice after treatment with Tween-80, 3'-O-palmitoyldeoxyguanosine, butyryldeoxyguanosine, palmitoyl-N-isobutyryldeoxyguanosine, lauryldeoxyguanosine, octanoyldeoxyguanosine, and palmitoyldeoxyguanosine as described in Example 51.
Figure 44:
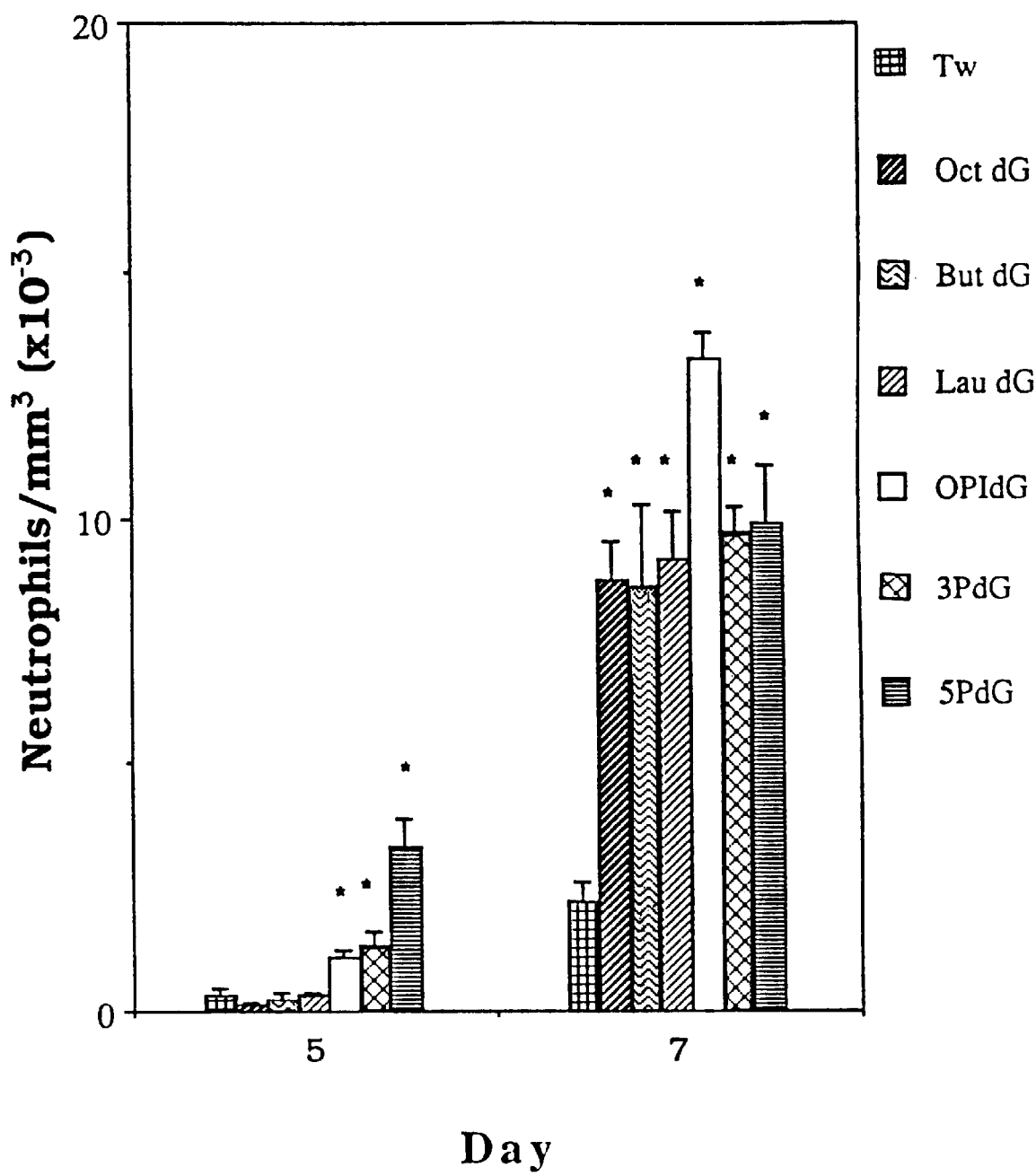
FIG. 44 is a graph comparing neutrophil counts in mice after treatment with Tween-80, 3'-O-palmitoyldeoxyguanosine, butyryldeoxyguanosine, palmitoyl-N-isobutyryldeoxyguanosine, lauryldeoxyguanosine, octanoyldeoxyguanosine, and palmitoyldeoxyguanosine as described in Example 51.

Spleen weight and total neutrophil counts were significantly elevated compared to controls on day 5 in the following groups: 3'-O-palmitoyldeoxyguanosine, palmitoyl-N-isobutyryldeoxyguanosine, and palmitoyldeoxyguanosine (FIGS. 43 and 44). On day 7 spleen weight and total neutrophil counts were significantly elevated relative to controls in all of the treatment groups.

Figure 45:
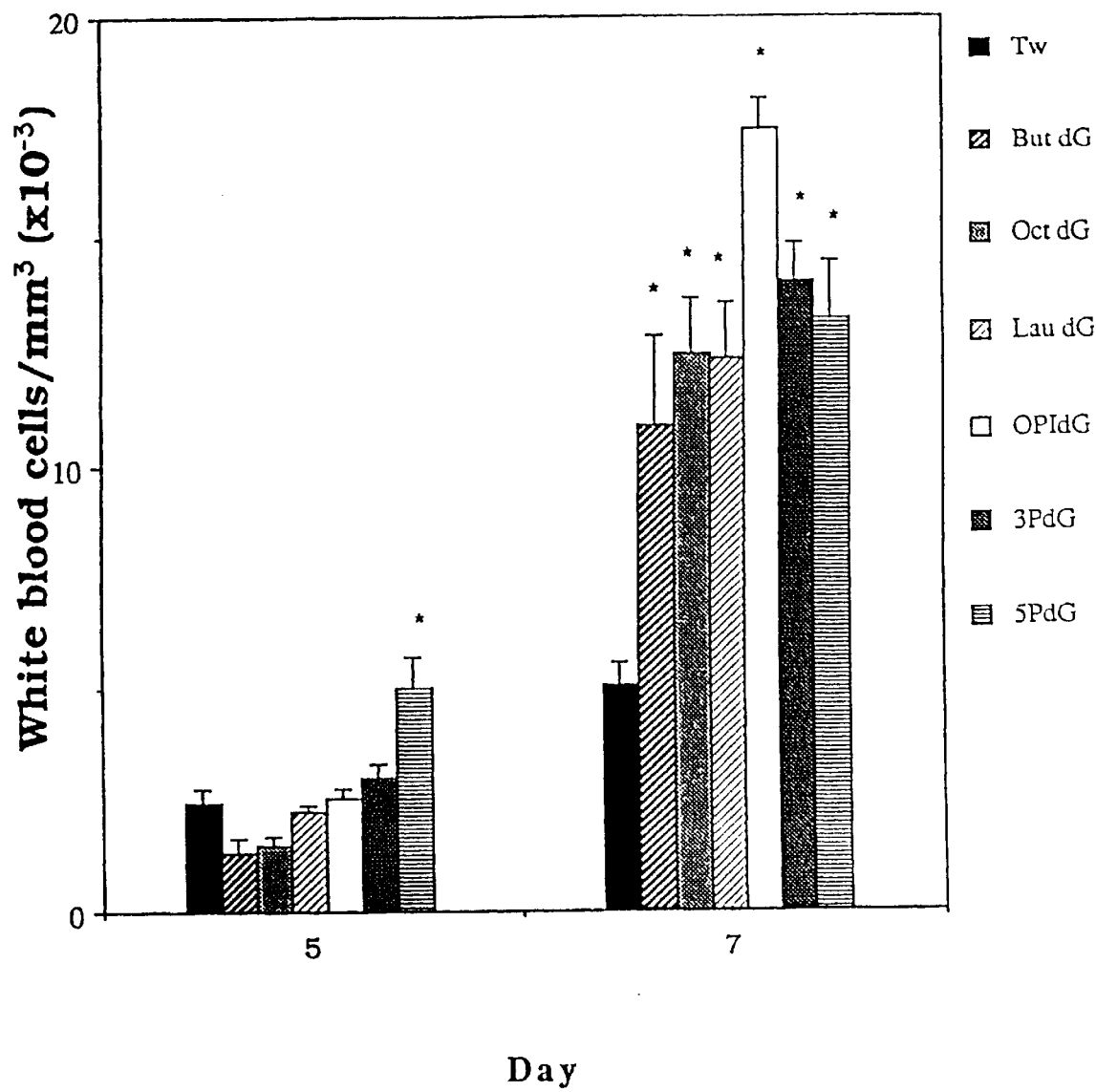
FIG. 45 is a graph comparing white blood cell counts in mice after treatment with Tween-80, 3'-O-palmitoyldeoxyguanosine, butyryldeoxyguanosine, palmitoyl-N-isobutyryldeoxyguanosine, lauryldeoxyguanosine, octanoyldeoxyguanosine, and palmitoyldeoxyguanosine as described in Example 51.

White blood cell counts were significantly elevated on day 5 in the palmitoyldeoxyguanosine groups. On day 7 white blood cell counts were significantly elevated compared to controls in all of the treatment groups (FIG. 45).

Example 52

Dose-response Characteristics of Palmitoyldeoxyguanosine in Improving Hematopoietic Recovery after Cyclophosphamide Cyclophosphamide (CP) (275 mg/kg, i.p.) was administered to 85 Balb/C female mice weighing approximately 20 grams each. Twenty-four hours later and each day thereafter mice were given a 0.4 ml i.p. injection of either physiological saline (controls), or palmitoyldeoxyguanosine at one of four different doses: 0.2, 0.4, 1.0 or 2.0 μmoles/mouse). On days 5 and 7 following CP administration 9 and 8 animals, respectively, in each of the 5 groups were bled and then sacrificed by cervical dislocation. Spleens were removed and weighed, and complete blood cell counts performed.

Figure 46:
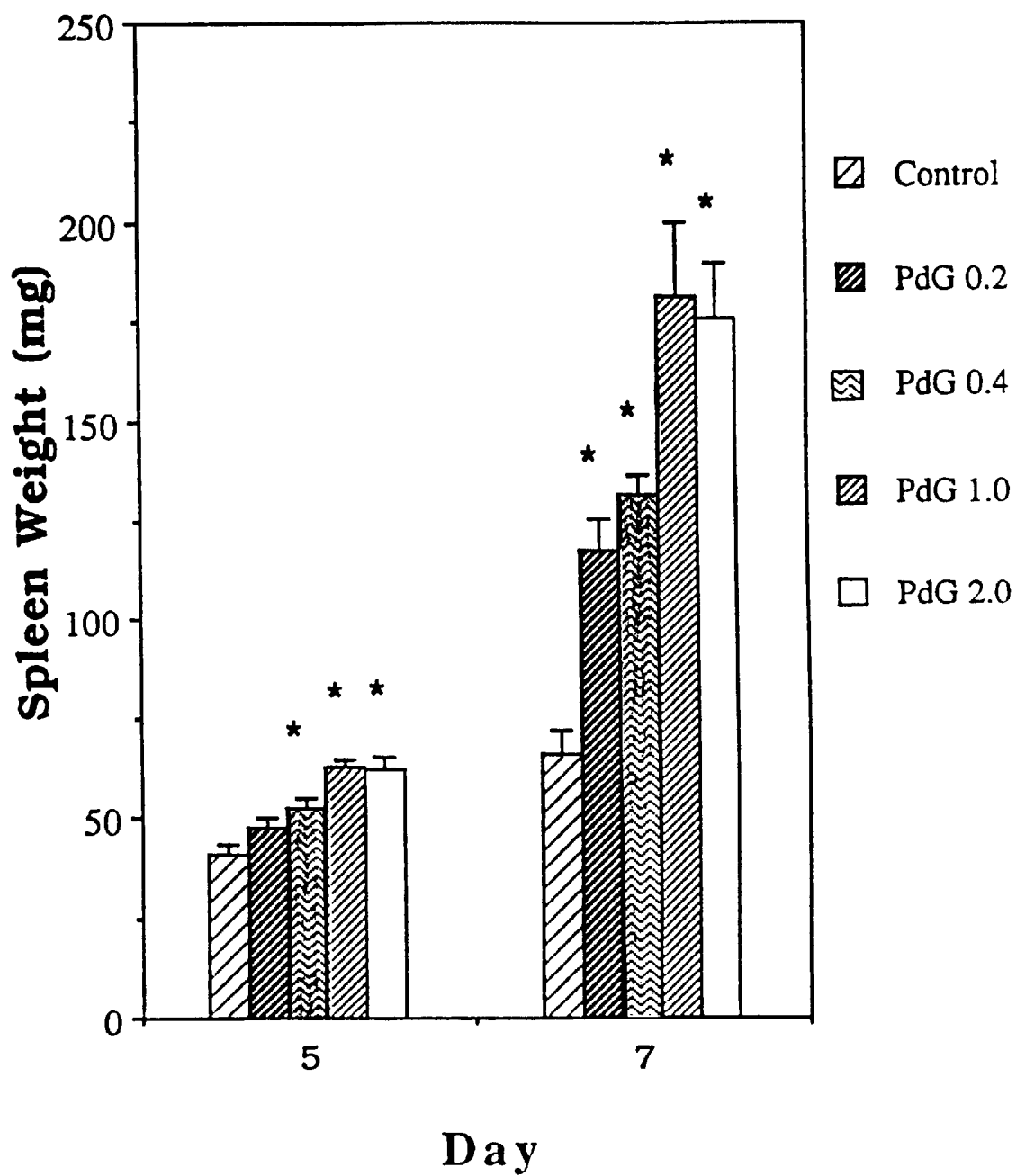
FIG. 46 is a graph comparing spleen weight in mice after treatment with physiological saline, and palmitoyldeoxyguanosine at four different doses: 0.2, 0.4, 1.0 and 2.0 µmoles/mouse as described in Example 52.
Figure 47:
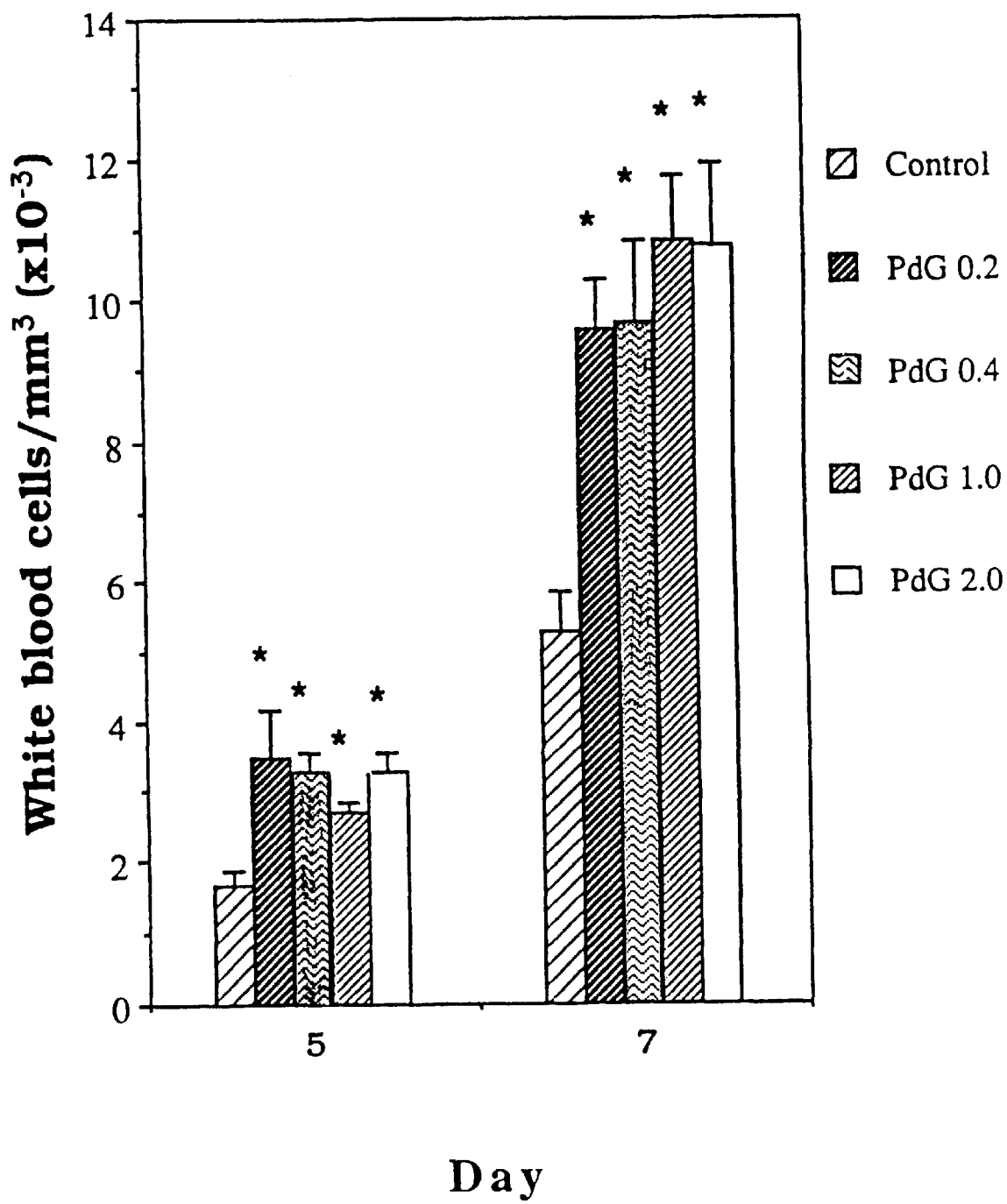
FIG. 47 is a graph comparing white blood cell counts in mice after treatment with physiological saline, and palmitoyldeoxyguanosine at four different doses: 0.2, 0.4, 1.0 and 2.0 µmoles/mouse as described in Example 52.
Figure 48:
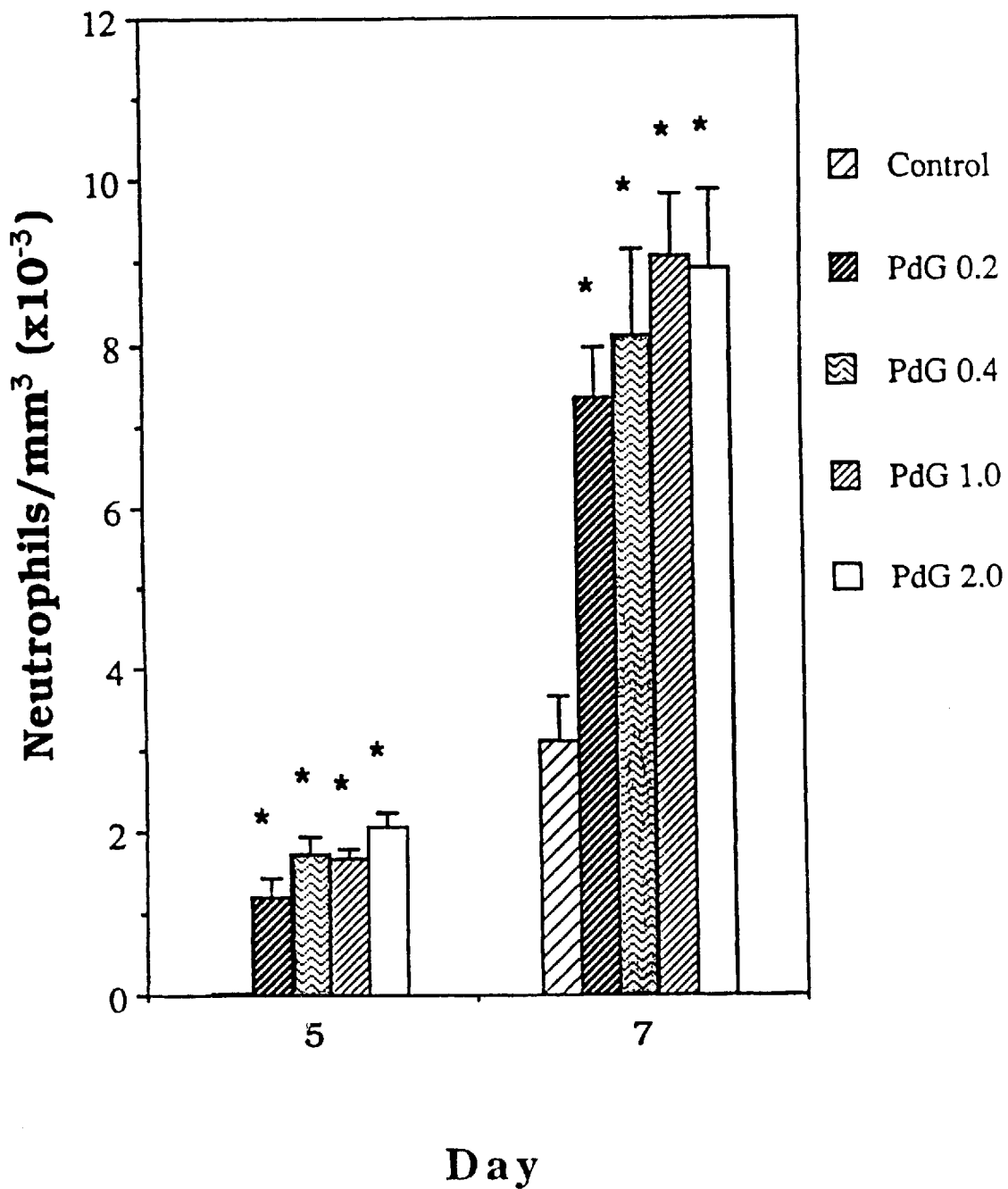
FIG. 48 is a graph comparing neutrophil counts in mice after treatment with physiological saline, and palmitoyldeoxyguanosine at four different doses: 0.2, 0.4, 1.0 and 2.0 µmoles/mouse as described in Example 52.

Spleen weight, white blood cell counts, and total neutrophil counts were significantly elevated compared to controls on day 5 and day 7 in all 4 of the treatment groups except at the lowest dose (0.2) of palmitoyldeoxyguanosine on day 5 (FIGS. 46, 47, and 48). A clear dose-response trend was seen, with increasing doses yielding heavier spleens and greater cell counts.

Example 53

Comparative Dose-response Characteristics of Palmitoyldeoxyguanosine and Palmitoylguanosine in Improving Hematopoietic Recovery after Cyclophosphamide Cyclophosphamide (CP) (275 mg/kg, i.p.) was administered to 96 Balb/C female mice weighing approximately 20 grams each. Twenty-four hours later and each day thereafter mice were given a 0.4 ml i.p. injection of either physiological saline (controls), palmitoylguanosine at one of four different doses: 0.2, 0.4, 1.0 or 2.0 μmoles/mouse), or palmitoyldeoxyguanosine at a dose of 1.0 μmoles/mouse.

On days 5 and 7 following CP administration 8 animals from each of the 6 groups were bled and then sacrificed by cervical dislocation. Spleens were removed and weighed, and complete blood cell counts performed.

Figure 49:
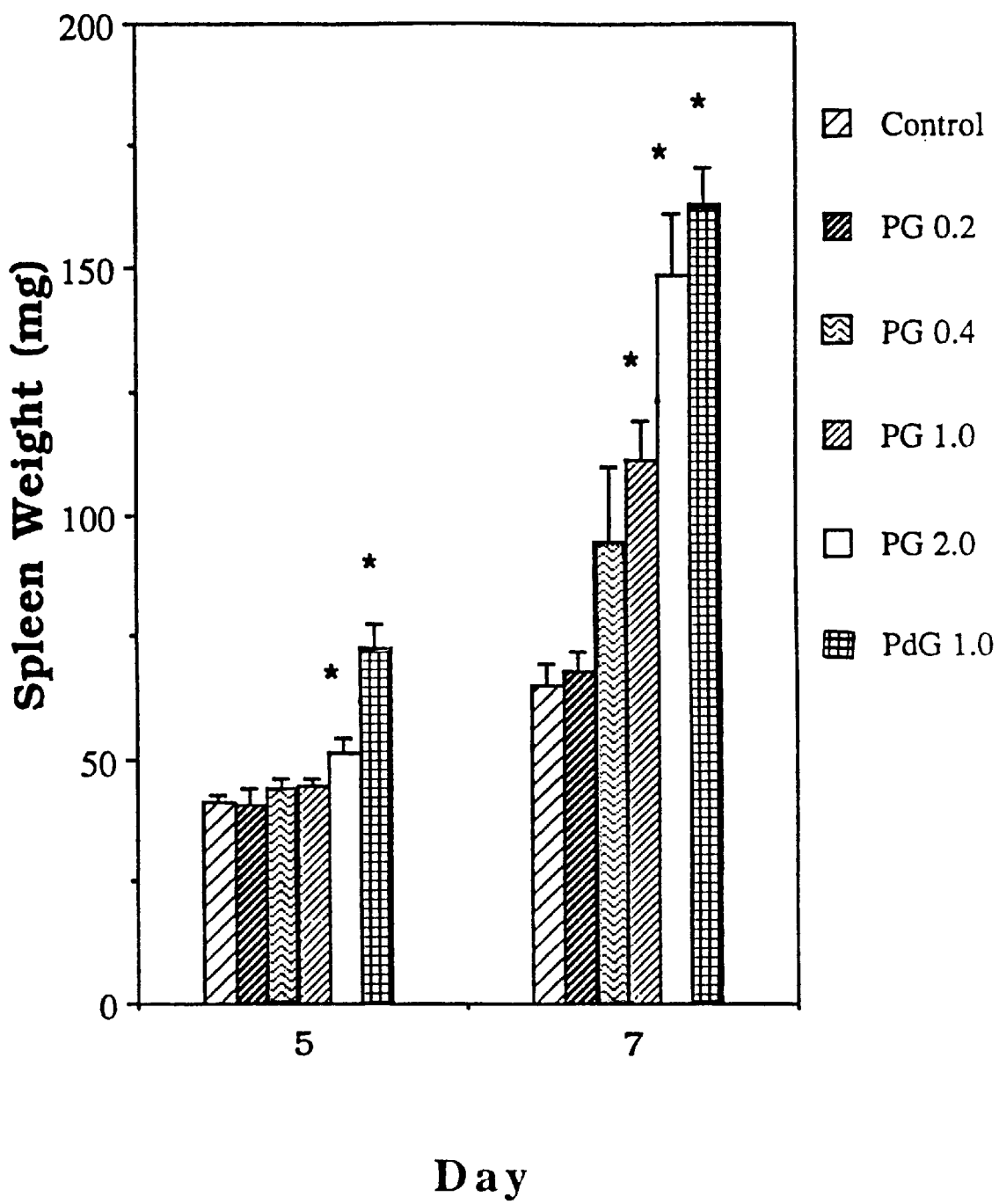
FIG. 49 is a graph comparing spleen weight in mice after treatment with physiological saline, palmitoyldeoxyguanosine, and palmitoylguanosine at four different doses: 0.2, 0.4, 1.0 and 2.0 µmoles/mouse as described in Example 53.
Figure 50:
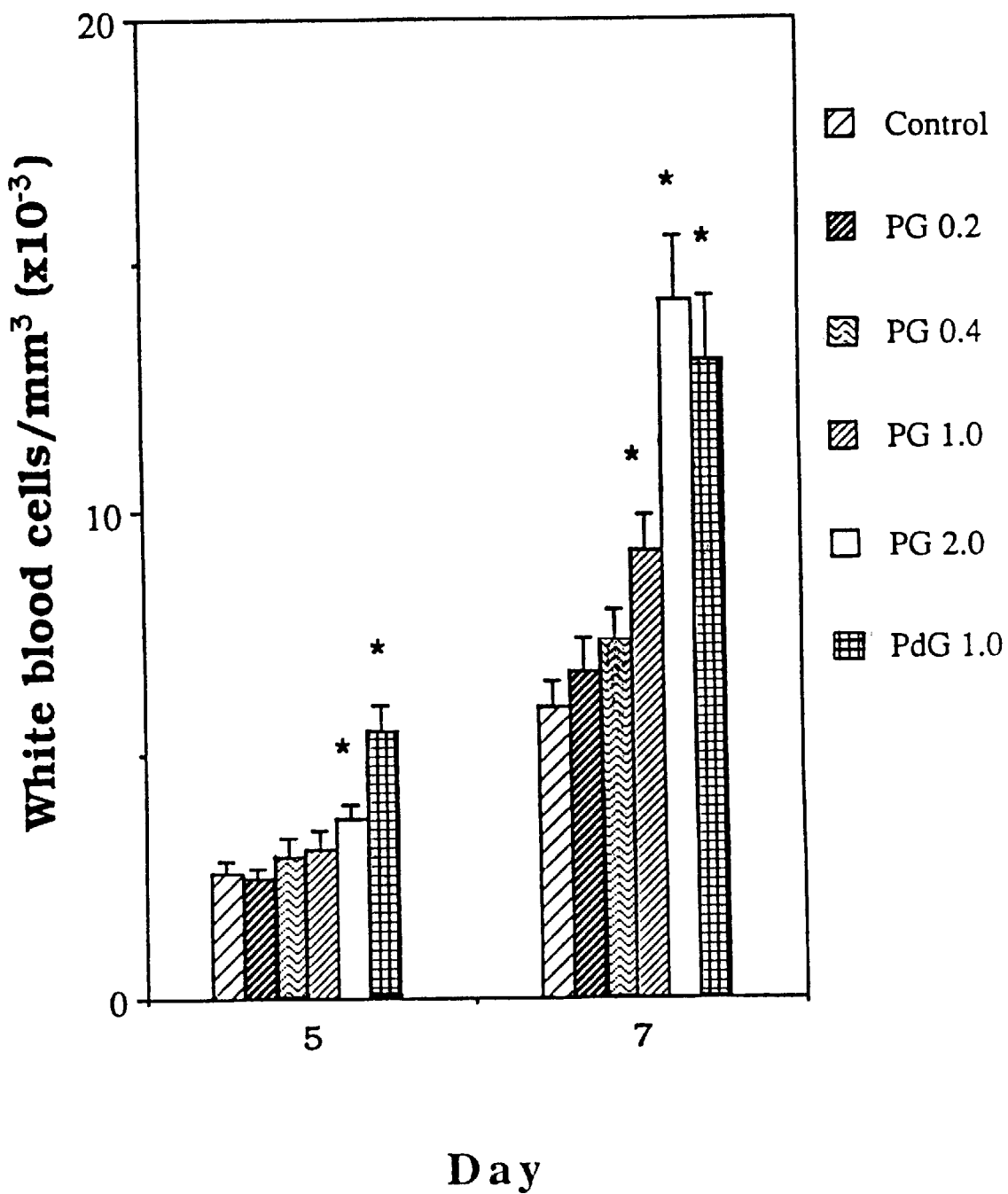
FIG. 50 is a graph comparing white blood cell counts in mice after treatment with physiological saline, palmitoyldeoxyguanosine, and palmitoylguanosine at four different doses: 0.2, 0.4, 1.0 and 2.0 µmoles/mouse as described in Example 53.
Figure 51:
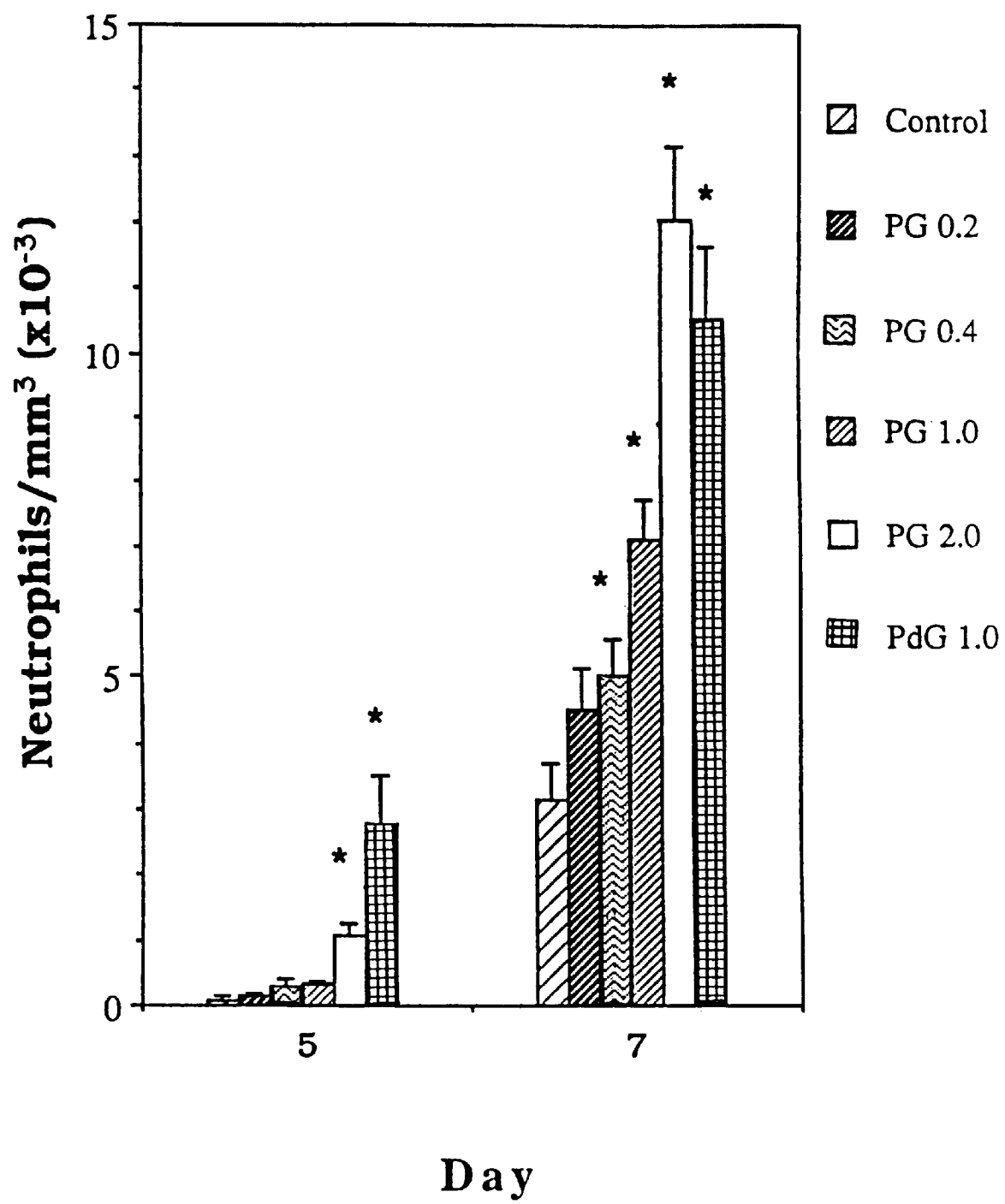
FIG. 51 is a graph comparing neutrophil counts in mice after treatment with physiological saline, palmitoyldeoxyguanosine, and palmitoylguanosine at four different doses: 0.2, 0.4, 1.0 and 2.0 µmoles/mouse as described in Example 53.

Spleen weight, white blood cell counts, and total neutrophil counts were significantly elevated compared to controls on day 5 at the highest tested dose (2.0 μmoles/mouse) of palmitoylguanosine and in the palmitoyldeoxyguanosine group (FIGS. 49, 50, and 51). Palmitoylguanosine at a dose of 1.0 μmoles/mouse also significantly increased total neutrophil counts on day 5. On day 7 spleen weight, white blood cell counts, and total neutrophil counts were significantly elevated compared to controls in the groups receiving 1.0 and 2.0 μmoles/mouse of palmitoylguanosine and in the palmitoyldeoxyguanosine group. A clear dose-response trend was seen, with increasing doses of palmitolyguanosine yielding heavier spleens and greater cell counts. Palmitoyldeoxyguanosine appeared to be more potent in elevating these parameters than the same or even a 2-fold greater dose of palmitoylguanosine.

Example 54

Dose-response Characteristics of Palmitoyldeoxyguanosine in Improving Hematopoietic Recovery after Cyclophosphamide Cyclophosphamide (CP) (275 mg/kg, i.p.) was administered to 112 Balb/C female mice weighing approximately 20 grams each. Twenty-four hours later and each day thereafter mice were given a 0.4 ml i.p. injection of either physiological saline (controls), or palmitoyldeoxyguanosine at one of six different doses: 0.04, 0.08, 0.2, 0.4, 0.6 or 0.8 μmoles/mouse. On days 5 and 7 following CP administration 8 animals from each of the 7 groups were bled and then sacrificed by cervical dislocation. Spleens were removed and weighed, and complete blood cell counts performed.

Figure 52:
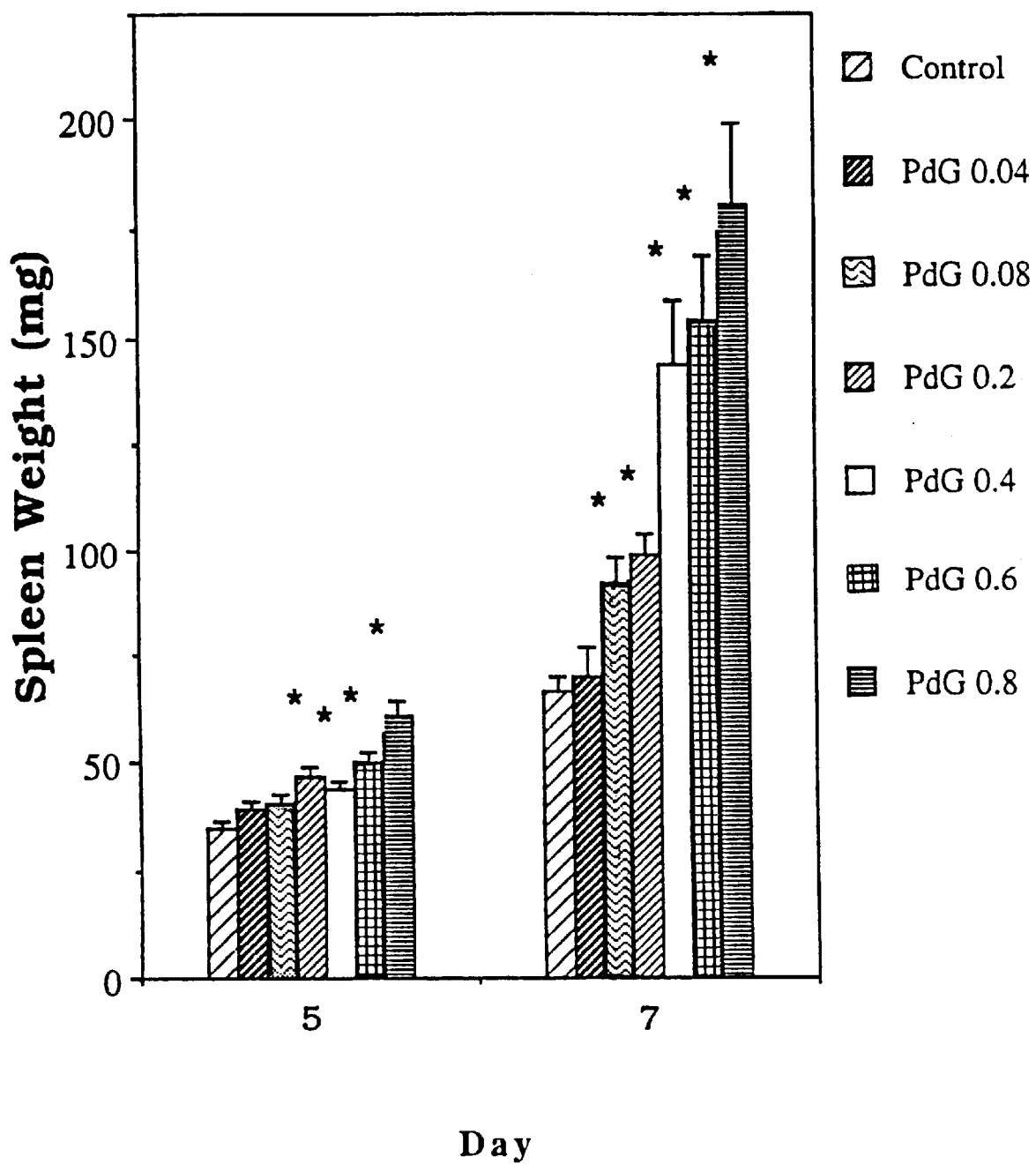
FIG. 52 is a graph comparing spleen weight in mice after treatment with physiological saline and palmitoyldeoxyguanosine at six different doses: 0.04, 0.08, 0.2, 0.4, 0.6 or 0.8 µmoles/mouse as described in Example 54.

Spleen weight was significantly elevated compared to controls on day 5 in all of the palmitoyldeoxyguanosine groups receiving doses of 0.2 μmoles/mouse or greater, and on day 7 in all of the groups except those receiving a dose of only 0.04 μmoles/mouse (FIG. 52).

Figure 53:
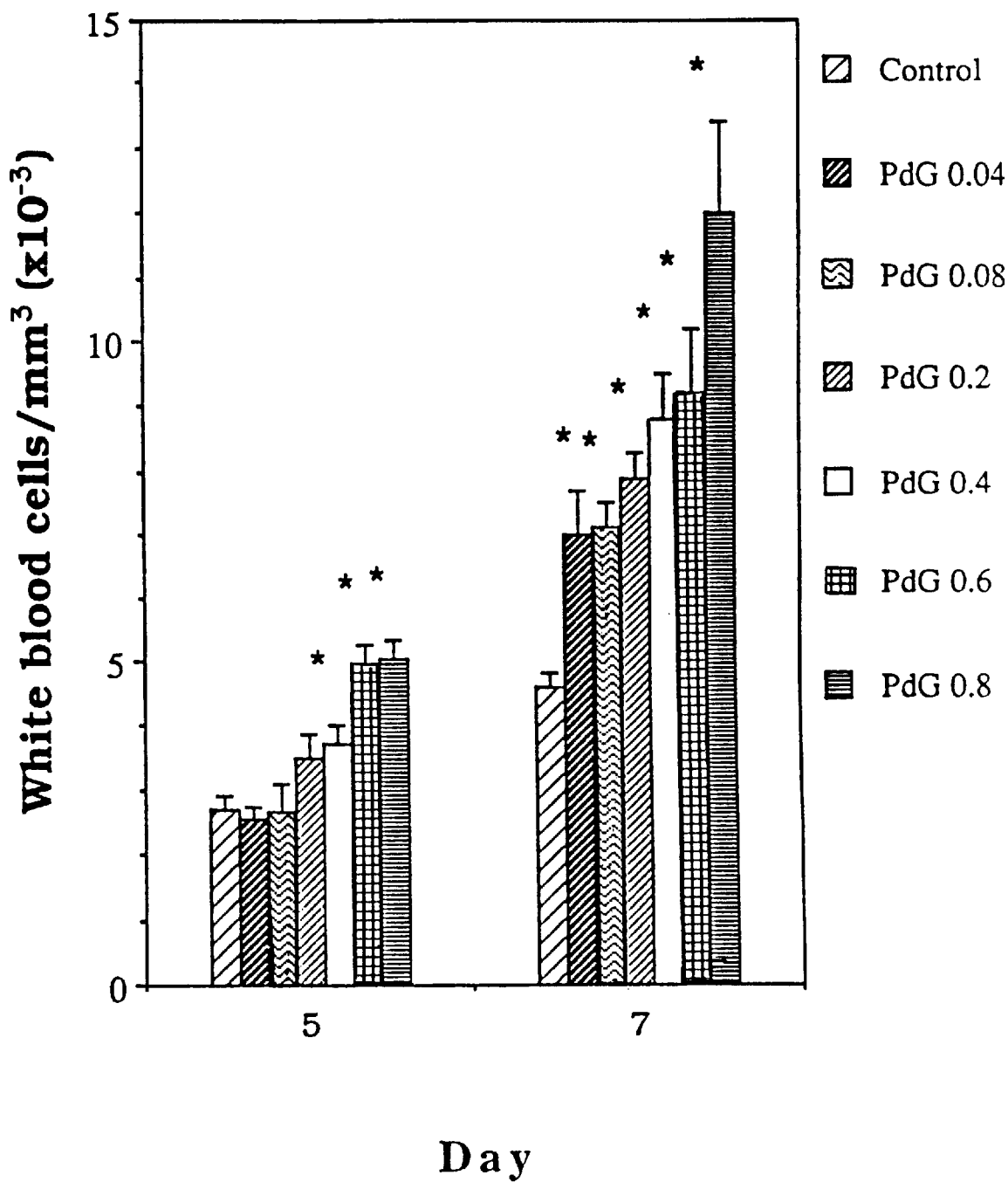
FIG. 53 is a graph comparing white blood cell counts in mice after treatment with physiological saline and palmitoyldeoxyguanosine at six different doses: 0.04, 0.08, 0.2, 0.4, 0.6 or 0.8 µmoles/mouse as described in Example 54.

White blood cell counts were significantly elevated compared to controls on day 5 in all of the palmitoyldeoxyguanosine groups receiving doses of 0.4 μmoles/mouse or greater (FIG. 53). On day 7 statistically significant differences were seen at all doses.

Figure 54:
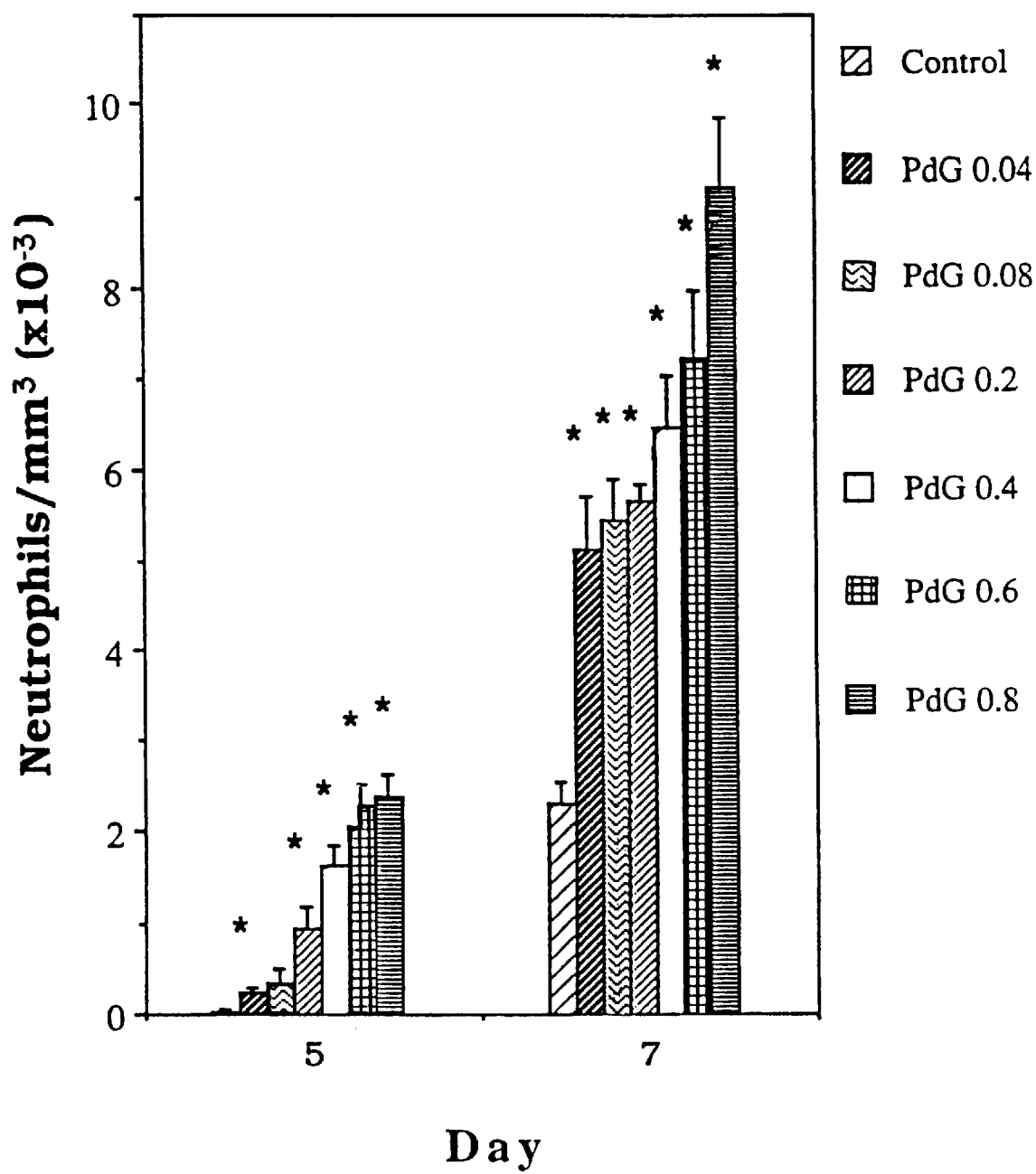
FIG. 54 is a graph comparing neutrophil counts in mice after treatment with physiological saline and palmitoyldeoxyguanosine at six different doses: 0.04, 0.08, 0.2, 0.4, 0.6 or 0.8 µmoles/mouse as described in Example 54.

Total neutrophil counts were significantly elevated relative to controls on both days 5 and 7 at all 6 doses tested (FIG. 54).

A clear dose-response relationship was seen, with increasing doses yielding heavier spleens and greater cell counts.

Example 55

Palmitoyldeoxyguanosine Improves Recovery of Neutrophil, Platelet, and Lymphocyte Counts in Rats after Cyclophosphamide Cyclophosphamide (CP) (40 mg/kg, i.p.) was administered to 16 F344 male rats weighing approximately 200 grams each. Twenty-four hours later and each day thereafter rats were given a 0.5 ml i.p. injection of either physiological saline (controls), or palmitoyldeoxyguanosine at a dose of 10 moles/rat. On days 5, 7 and 10 following CP administration all 8 animals from both groups were bled and complete blood cell counts performed. On day 10 all of the rats were sacrificed and their spleens removed and weighed.

Figure 55:
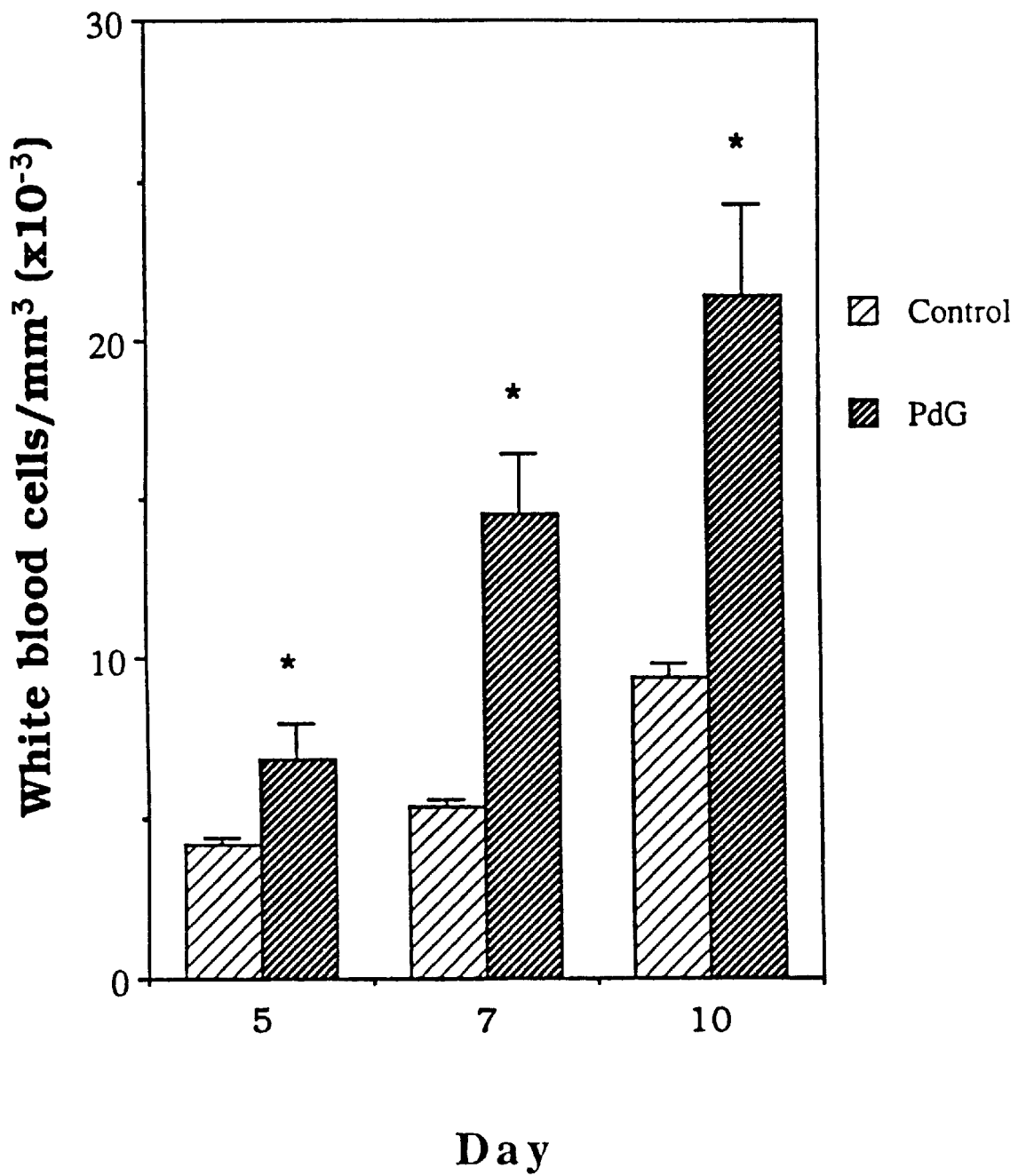
FIG. 55 is a graph comparing yhite blood cell counts in mice after treatment with physiological saline and palmitoyldeoxyguanosine as described in Example 55.
Figure 56:
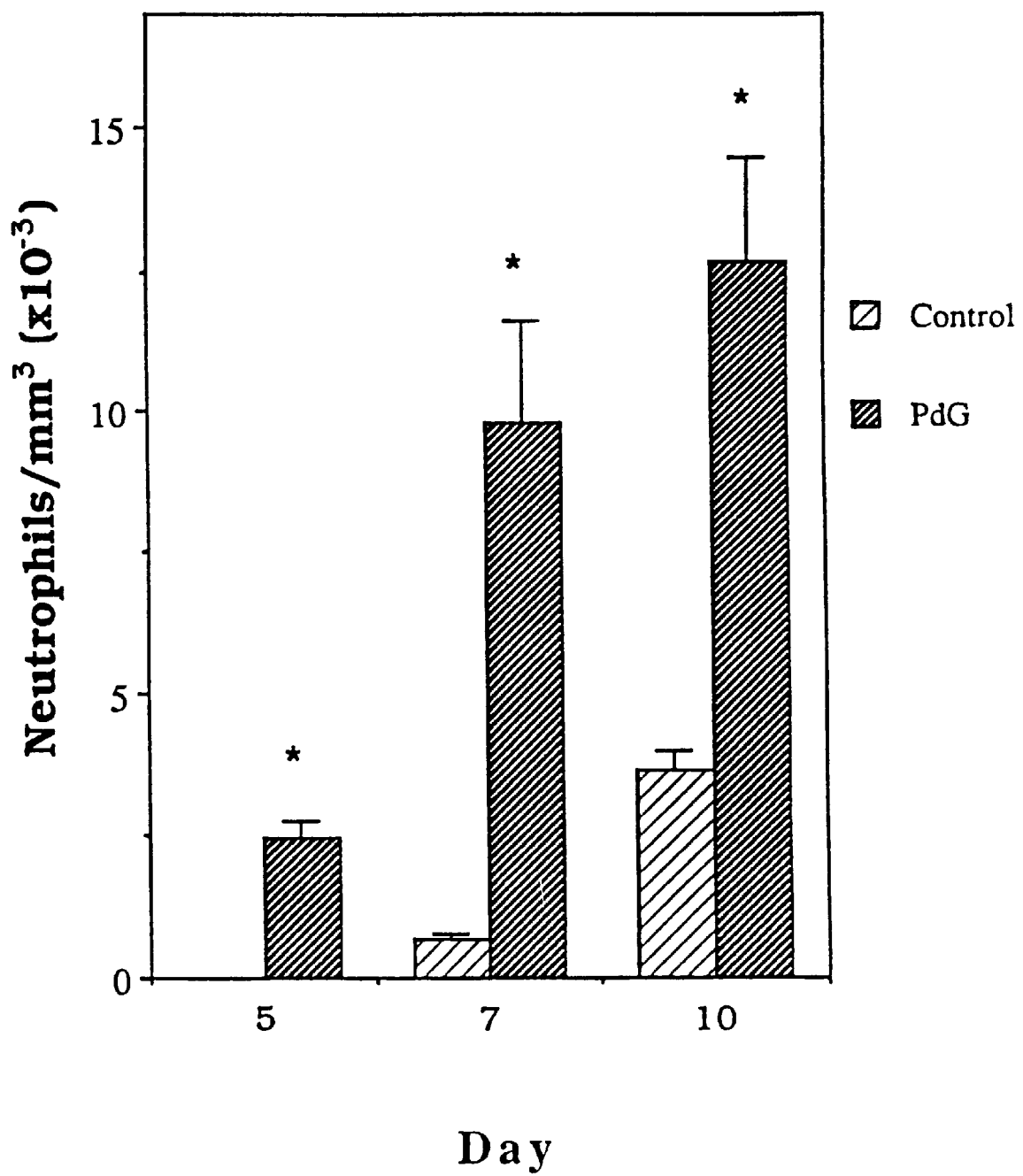
FIG. 56 is a graph comparing neutrophil counts in mice after treatment with physiological saline and palmitoyldeoxyguanosine as described in Example 55.
Figure 57:
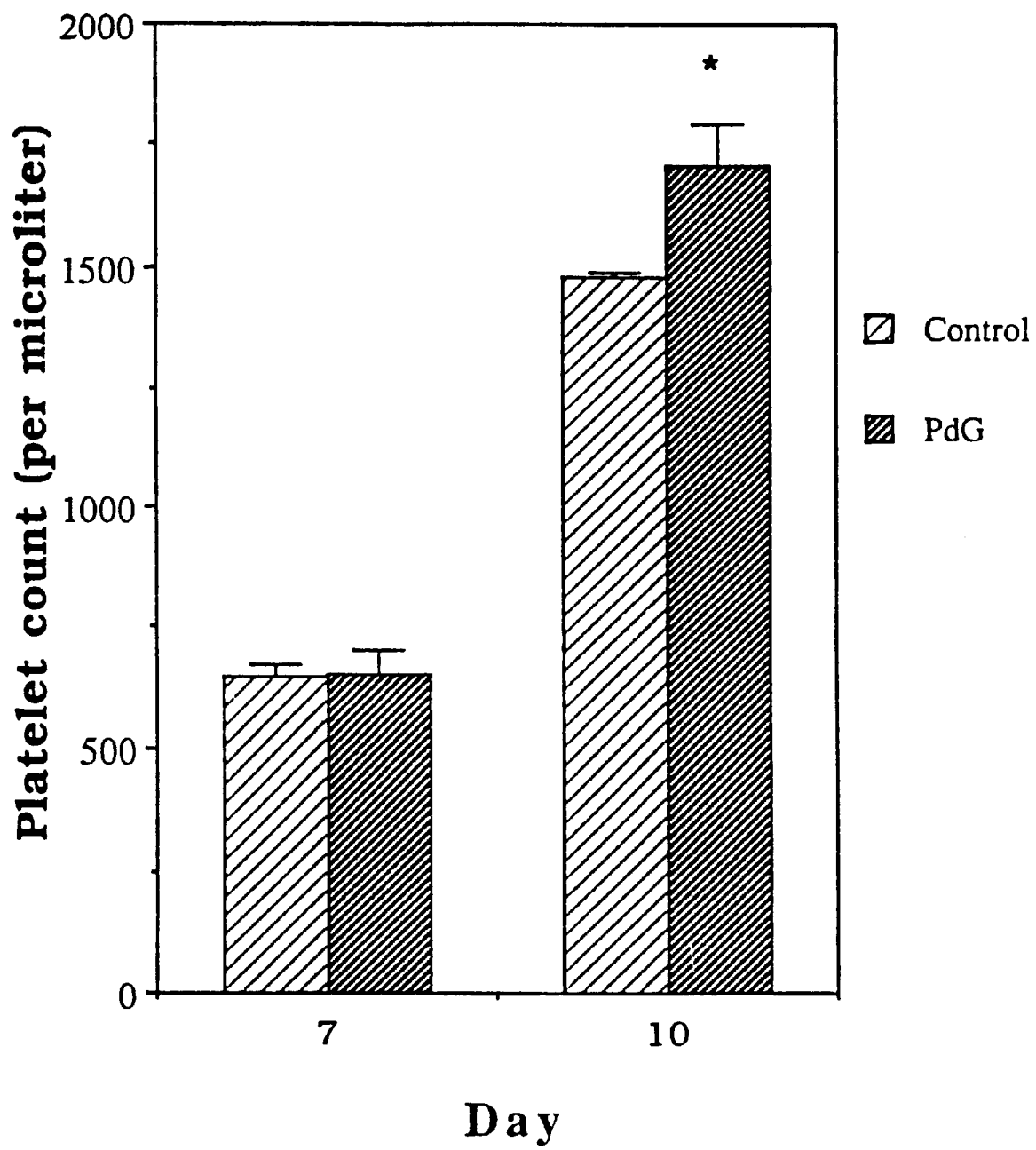
FIG. 57 is a graph comparing platelet counts in mice after treatment with physiological saline and palmitoyldeoxyguanosine as described in Example 55.
Figure 58:
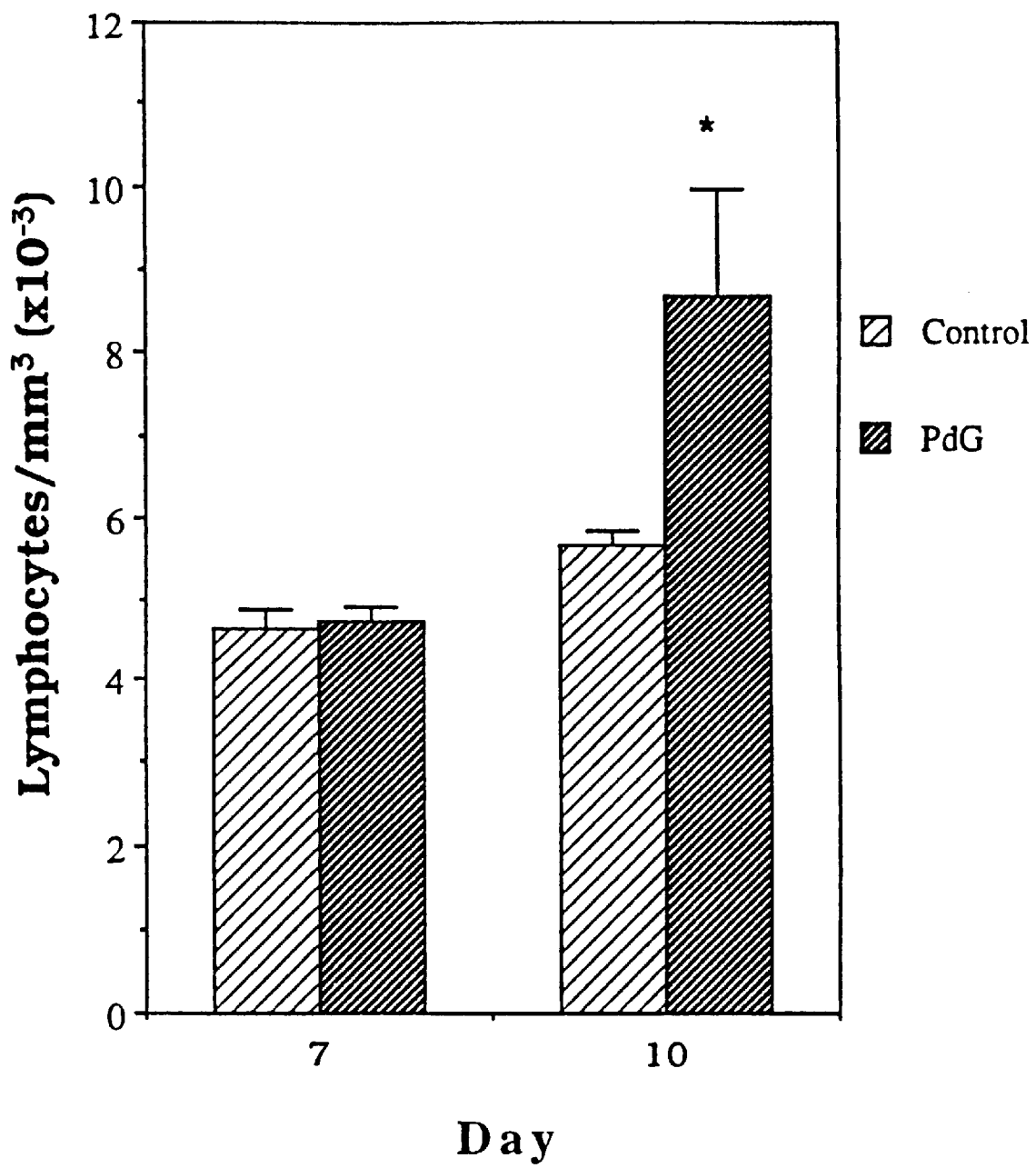
FIG. 58 is a graph comparing lymphocyte counts in mice after treatment with physiological saline and palmitoyldeoxyguanosine as described in Example 55.

White blood cell counts and total neutrophil counts were significantly elevated in the palmitoyldeoxyguanosine-treated rats compared to those in saline controls at all three time points (FIGS. 55 and 56). Platelets and lymphocytes were significantly elevated at day 10 in the palmitoyldeoxyguanosine treated group (FIGS. 57 and 58). Spleen weight of the treated rats was significantly elevated compared to controls.

These results in rats confirm and extend the above-noted findings in mice that acylated derivatives of the purine nucleosides dramatically improve hematopoietic recovery following chemical damage. Particularly notable in this experiment is the persistence of increased leukocyte counts after discontinuation of treatment with palmitoyldeoxyguanosine.

Example 56

Acyl Derivatives of Oxypurine Nucleoside Congeners Enhance Hematopoiesis in Normal Mice Normal Balb/C female mice weighing approximately 20 grams each were given a daily 0.4 ml i.p. injection of either physiological saline (controls), palmitoylguanosine (2.6 μmoles/mouse), palmitoyldeoxyguanosine (2.6 μmoles/mouse), monopalmitoylguanosine 2',3'-acyclic dialcohol (2.6 μmoles/mouse), and palmitoyl-8-bromoguanosine (2.6 μmoles/mouse) for 4 days. On the fifth day all 3 animals in each of the 5 groups were bled and then sacrificed by cervical dislocation. Spleens were removed and weighed, and complete blood cell counts performed. Femoral bone marrow from each mouse was collected and a differential cell count performed on marrow smears.

Figure 59:
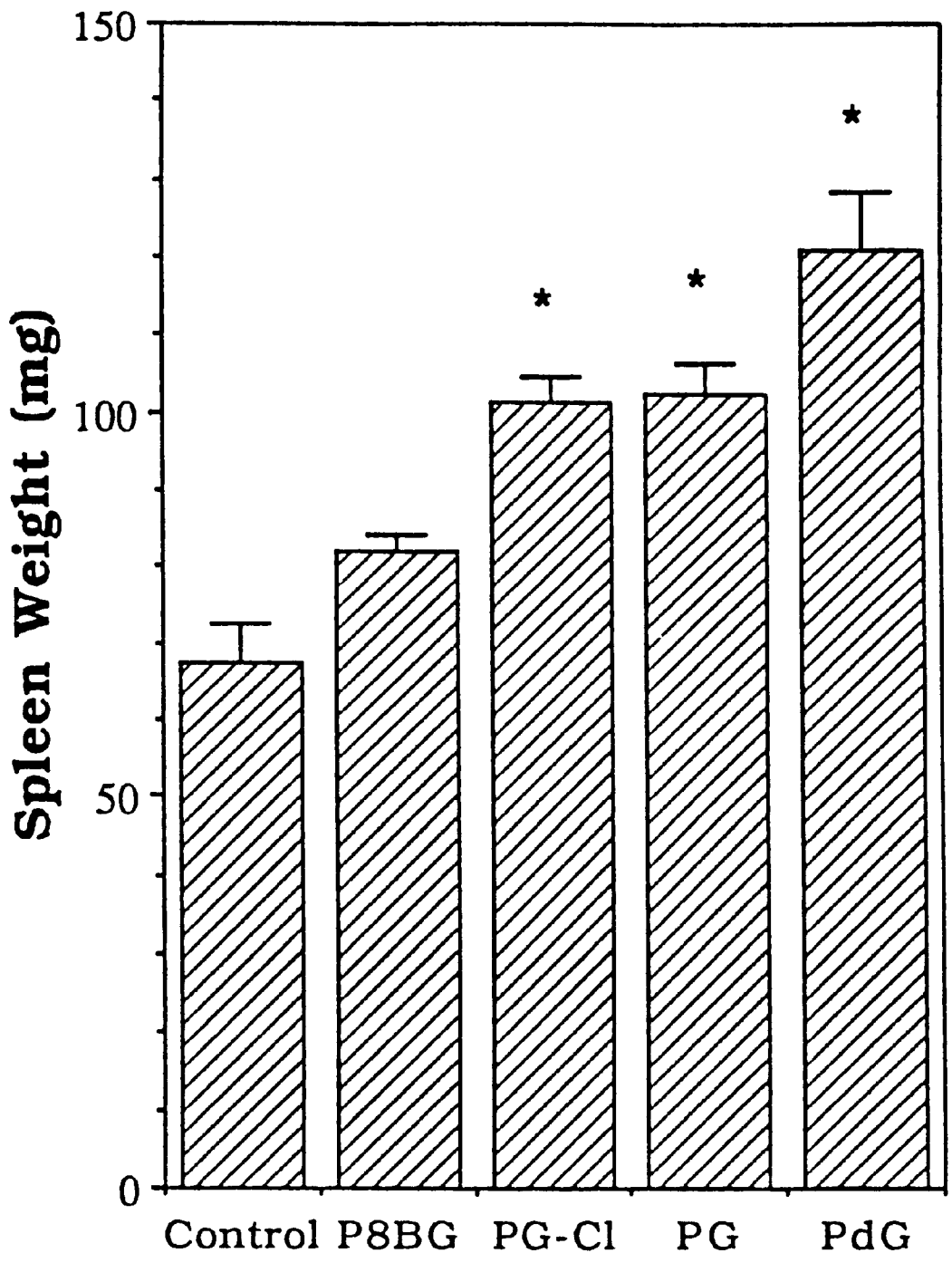
FIG. 59 is a graph comparing spleen weight in mice after treatment with physiological saline, palmitoyl-8-bromoguanosine, monopalmitoylguanosine 2',3'-acyclic dialcohol, palmitoylguanosine, and palmitoyldeoxyguanosine as described in Example 56.

In each of the figures associated with this example (59–61) the following abbreviations are used:

P8BG=palmitoyl-8-bromoguanosine
PG-Cl=monopalmitoylguanosine 2',3'-acyclic dialcohol
PG=palmitoylguanosine
PdG=palmitoyldeoxyguanosine Spleen weight was significantly elevated compared to controls in the following groups: palmitoylguanosine 2',3'-acyclic dialcohol, palmitoyldeoxyguanosine, and palmitoylguanosine (FIG. 59).

Figure 60:
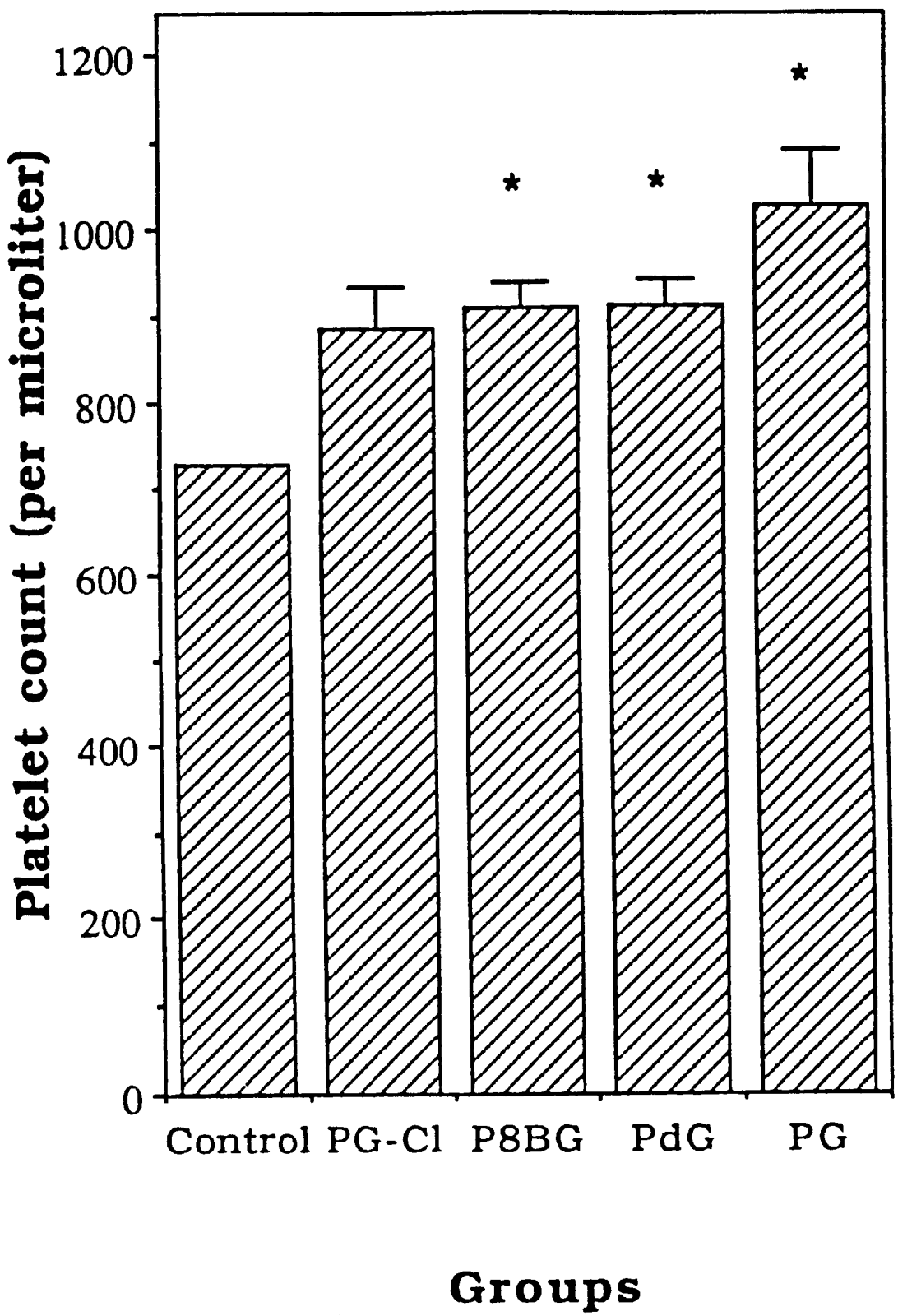
FIG. 60 is a graph comparing platelet counts in mice after treatment with physiological saline, palmitoyl-8-bromoguanosine, monopalmitoylguanosine 2',3'-acyclic dialcohol, palmitoylguanosine, and palmitoyldeoxyguanosine as described in Example 56.

Platelet counts were significantly elevated in the all of the treatment groups except palmitoylguanosine 2',3'-acyclic dialcohol (FIG. 60).

Figure 61:
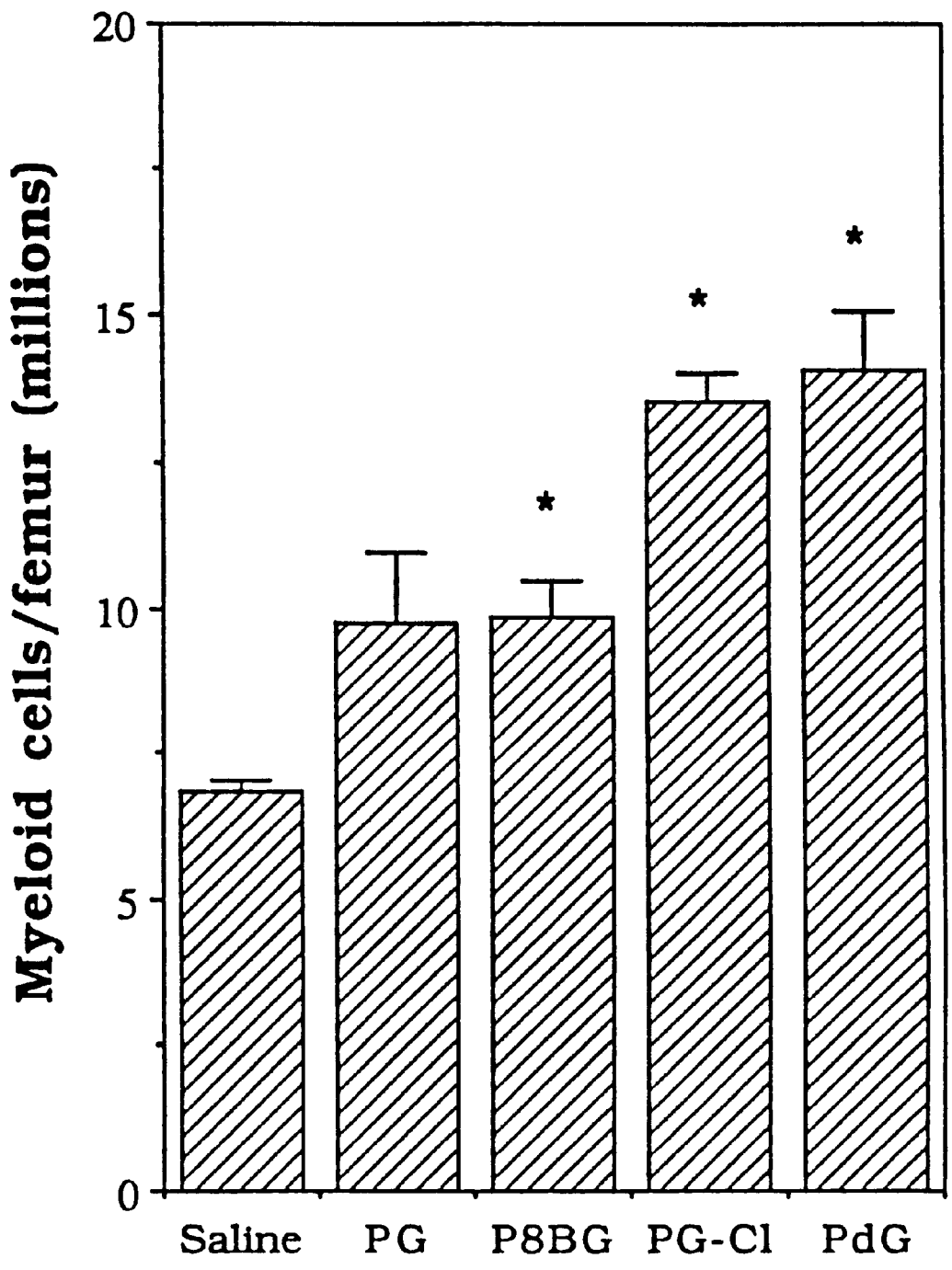
FIG. 61 is a graph comparing myeloid cell counts per femur in mice after treatment with physiological saline, palmitoyl-8-bromoguanosine, monopalmitoylguanosine 2',3'-acyclic dialcohol, palmitoylguanosine, and palmitoyldeoxyguanosine as described in Example 56.
Figure 62:
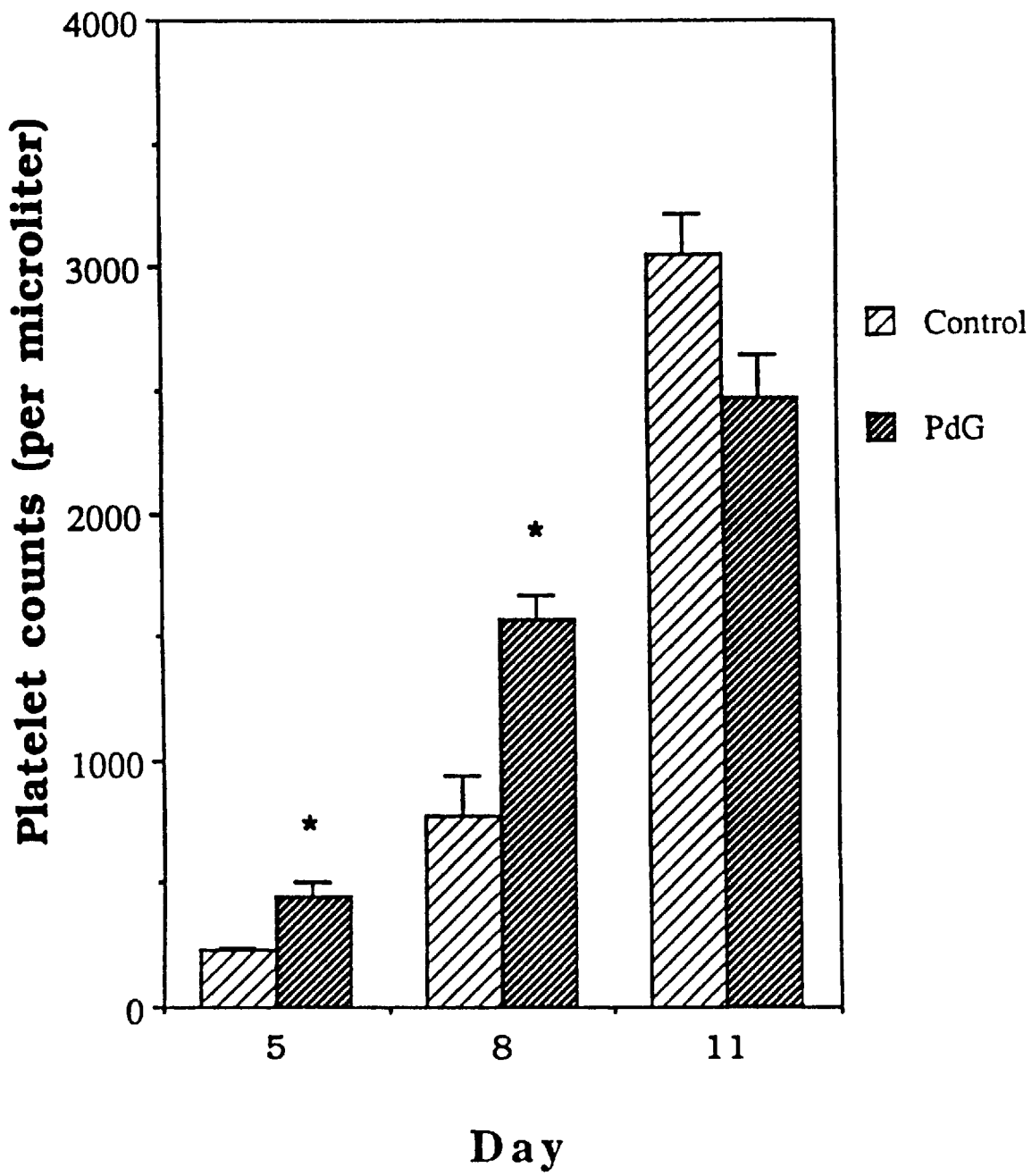
FIG. 62 is a graph comparing platelet counts in mice after treatment with physiological saline and palmitoyldeoxyguanosine as described in Example 57.
Figure 63:
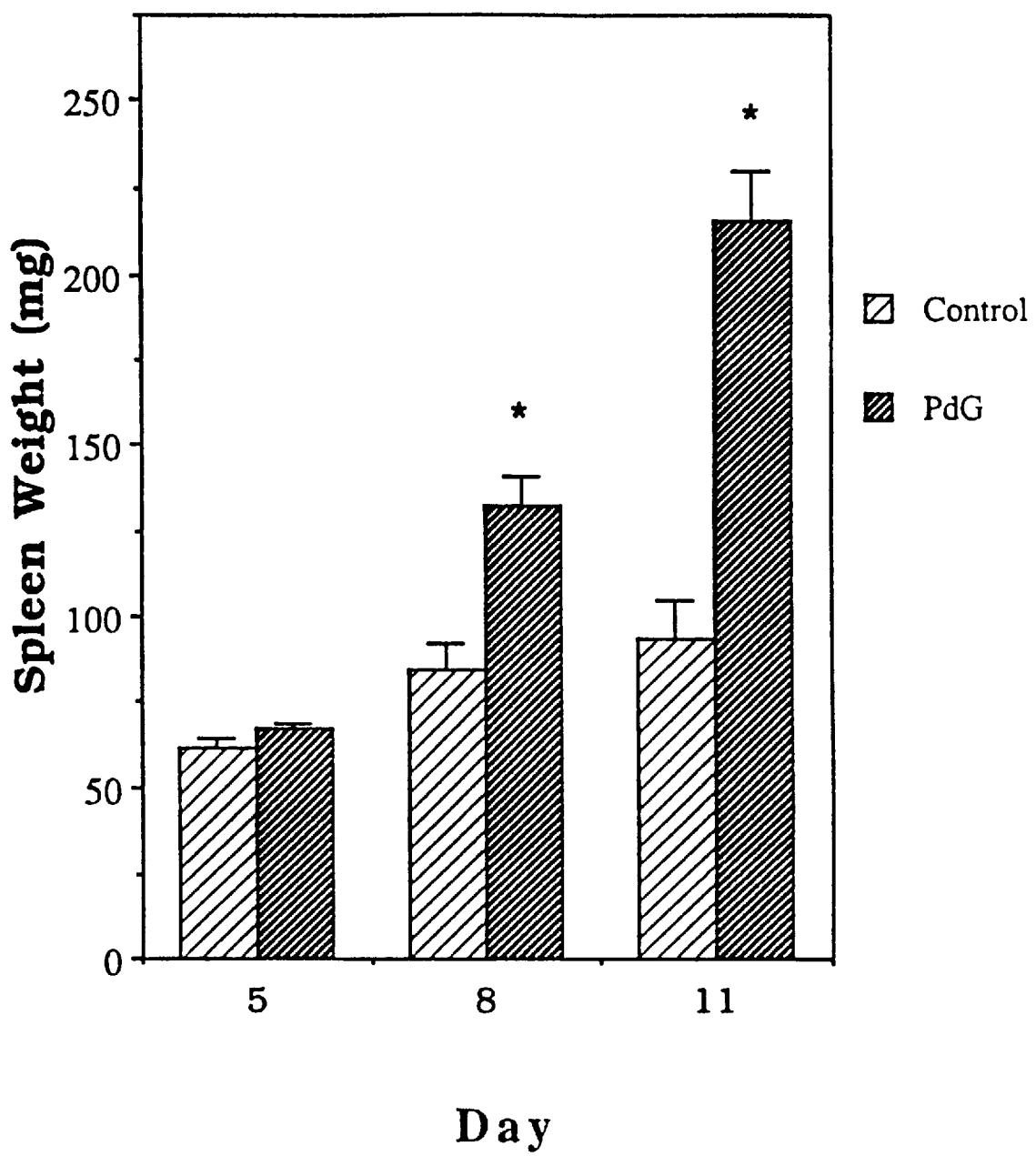
FIG. 63 is a graph comparing spleen weight in mice after treatment with physiological saline and palmitoyldeoxyguanosine as described in Example 57.
Figure 64:
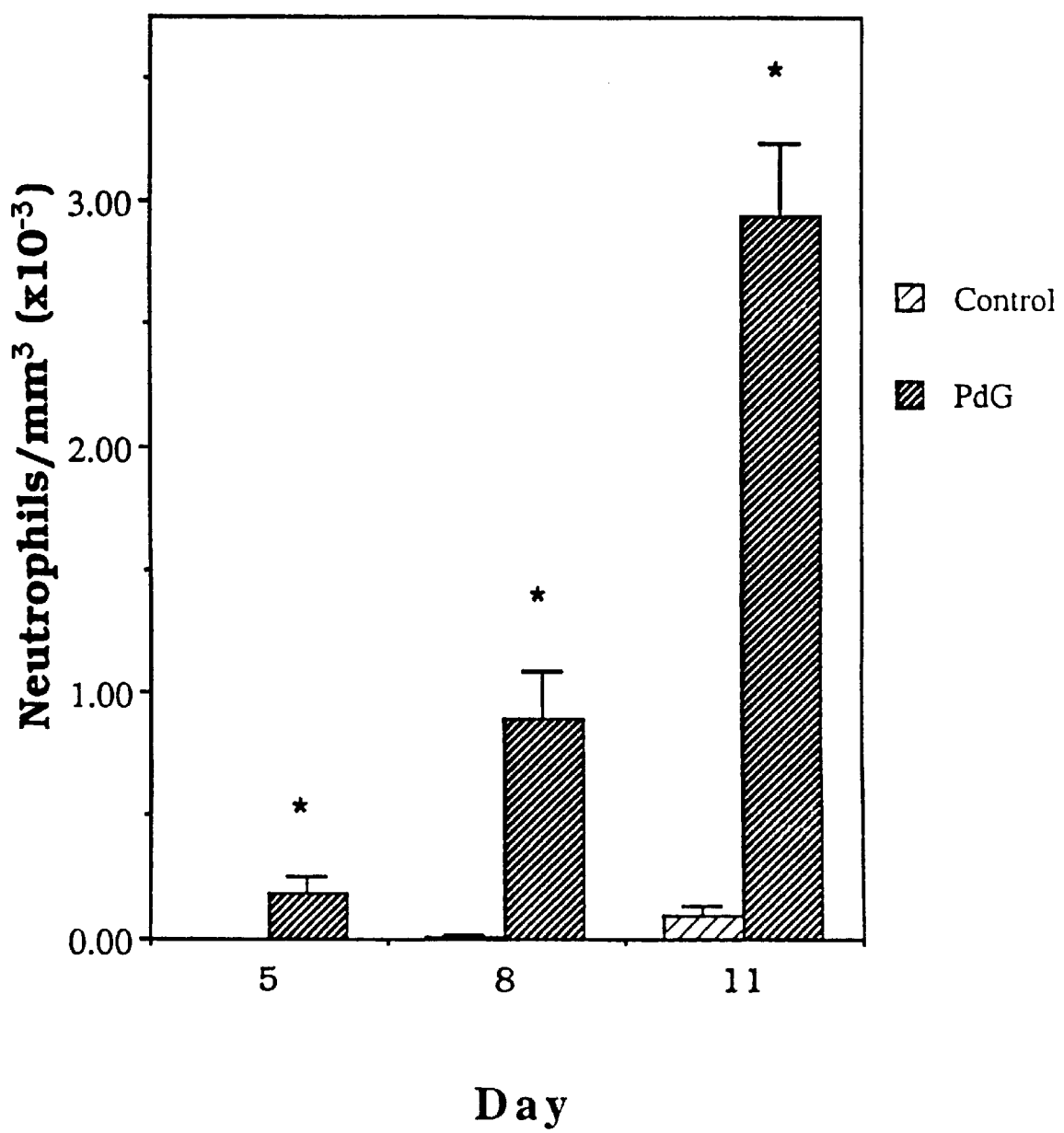
FIG. 64 is a graph comparing neutrophil counts in mice after treatment with physiological saline and palmitoyldeoxyguanosine as described in Example 57.
Figure 65:
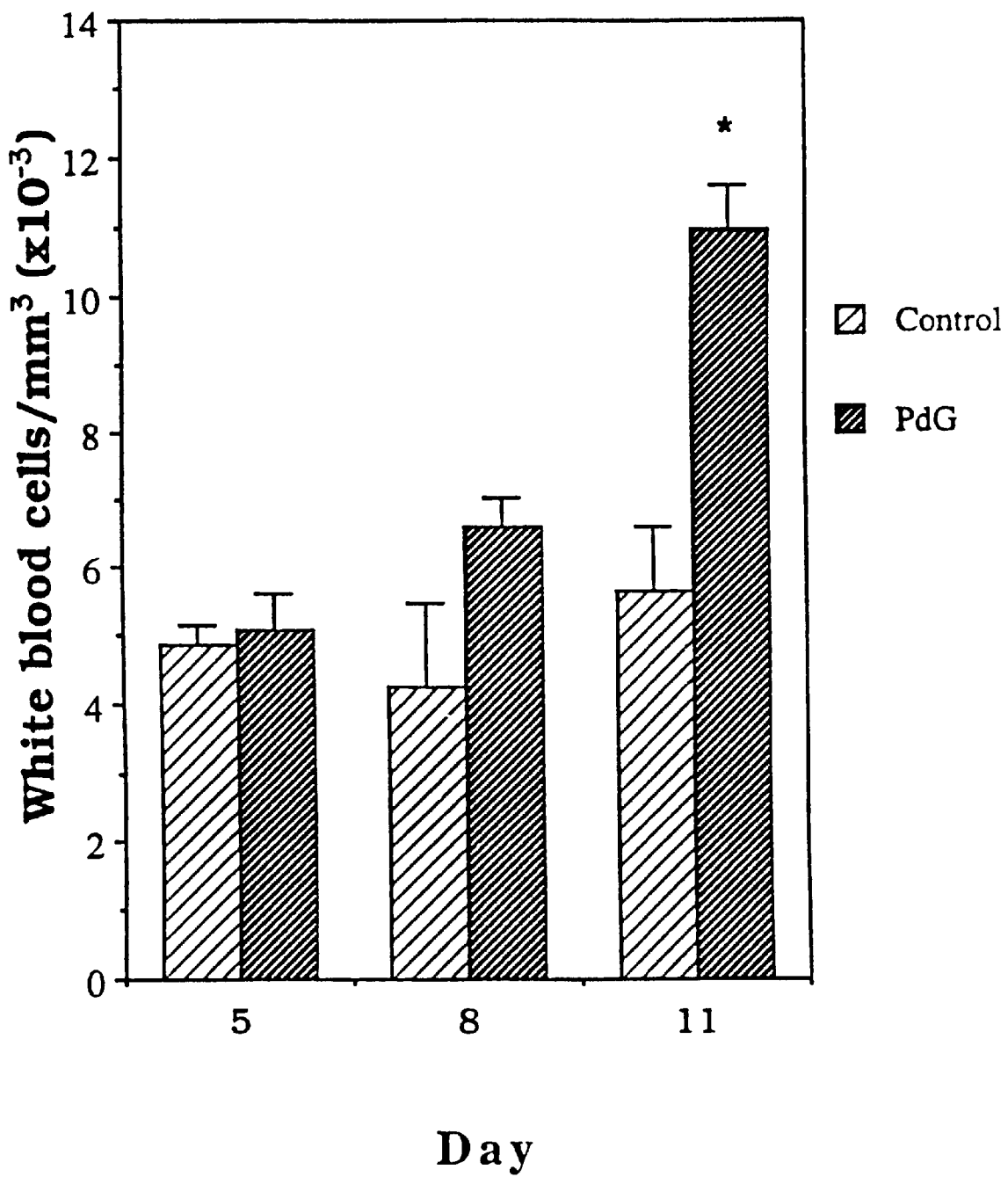
FIG. 65 is a graph comparing white blood cell counts in mice after treatment with physiological saline and palmitoyldeoxyguanosine as described in Example 57.

The number of myelocytes (obligatory neutrophil precursors) was also significantly greater than controls in the monopalmitoylguanosine 2',3'-acyclic dialcohol, palmitoyldeoxyguanosine, and palmitoyl-8-bromoguanosine groups (FIG. 61).

These results show the efficacy of several of the specified compounds in positively modifying hematopoiesis in normal animals. The evidence clearly shows that these compounds are effective at the level of the bone marrow.

Example 57

Pretreatment of Mice with Palmitoyldeoxyguanosine Improves Hematopoietic Recovery From Fluorouracil Twenty-eight female Balb/C mice weighing approximately 20 grams each received a 0.4 ml i.p. injection of either physiological saline (controls), or palmitoyldeoxyguanosine (1 μmole/mouse) daily for three days. On the fourth day 5-flourouracil (5-FU) (150 mg/kg, i.p.) was administered to all 28 of the animals. On days 5, 8 and 11 following 5-FU administration 4 (day 5) or 5 (days 8 and 11) animals from both groups were bled and then sacrificed by cervical dislocation. Spleens were removed and weighed, and complete blood cell counts performed.

On day 5 platelet counts were significantly elevated in the treated group compared to those in the control group. On day 8 spleen weight, platelet counts, and total neutrophil counts were significantly higher in the group pre-treated with palmitoyldeoxyguanosine. On day 11 those animals pre-treated with palmitoyldeoxyguanosine had significantly higher spleen weights, total white blood cell counts, platelet counts, total neutrophil counts and lymphocyte counts compared to the saline controls (FIGS. 62, 63, 64, and 65).

These results show that pretreatment of an animal with palmitoyldeoxyguanosine dramatically ameliorates the effects of 5-FU on the immune system and blood cell counts.

Example 58

Tween 80 Enhances Hematopoietic Recovery after Cyclophosphamide and Enhances Effect of Octanoylguanosine Cyclophosphamide (CP) (275 mg/kg, i.p.) was administered to 45 Balb/C female mice weighing approximately 20 grams each. Twenty-four hours later and each day thereafter for a total of 6 days, mice were divided into seven groups and given a 0.4 ml i.p. injection of either physiological saline (controls), Tween 80 at each of three concentrations (0.02%, 0.2% and 1%) or octanoylguanosine (50 mg/kg/dose) in three different concentrations of Tween 80 (0.02%, 0.2% and 1%). On day 7 following CP administration all 9 animals from each of the 5 groups were bled and then sacrificed by cervical dislocation. Spleens were removed and weighed, and complete blood cell counts performed.

Figure 66:
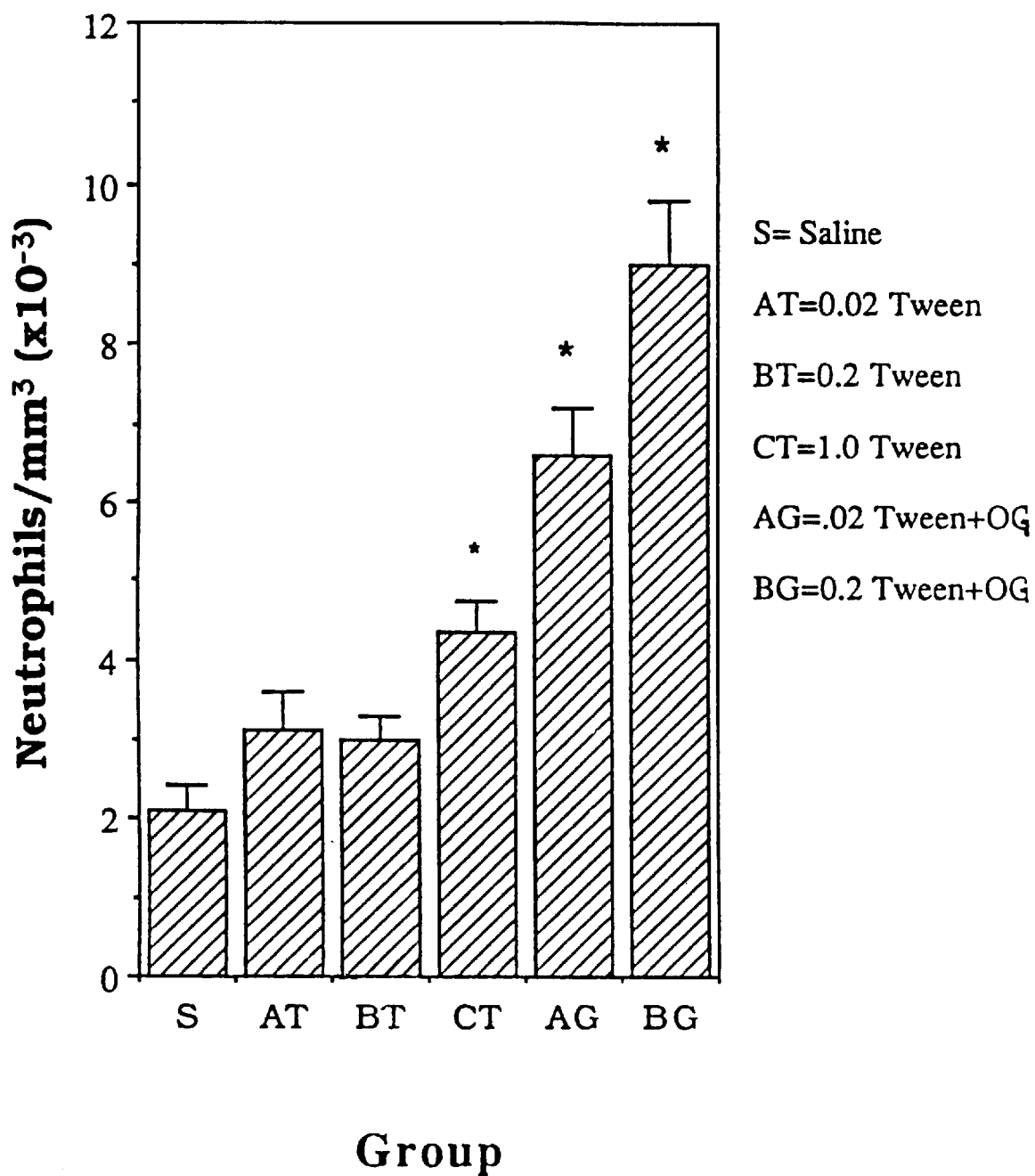
FIG. 66 is a graph comparing neutrophil counts in mice after treatment with Tween-80 at different concentrations with and without palmitoylguanosine as described in Example 58.

Seven days after administration of cyclophosphamide, neutrophil counts were elevated in all of the treatment groups compared to mice that received saline alone after cyclophosphamide, and were significantly different from controls in those mice treated with 1.0% Tween alone, and with octanoylguanosine in 0.02% and 0.2% Tween 80 (FIG. 66). Neutrophil counts in animals receiving 50 mg/kg octanoylguanosine in 0.2% Tween 80 were significantly higher than in animals receiving the same dose of octanoylguanosine in 0.02% Tween 80.

A variety of other nonionic surfactants, including Tween 20, Tween 40, Nonidet P-40, Brij 96, Triton X-100, also enhanced the recovery of blood cell counts in mice treated with cyclophosphamide.

Example 59

Palmitoyl-8-aminoguanosine Enhances Hematopoietic Recovery after Cyclophosphamide Cyclophosphamide (CP) (275 mg/kg, i.p.) was administered to 28 Balb/C female mice weighing approximately 20 grams each. Twenty-four hours later and each day for 4 days thereafter, mice were given a 0.4 ml i.p. injection of either physiological saline (controls) or palmitoyl-8-aminoguanosine (25 mg/kg/day in 0.2% Tween 80). On days 5 and 7 following CP administration 7 animals from each of the 2 groups were bled and then were sacrificed by cervical dislocation. Spleens were removed and weighed, and complete blood cell counts performed.

Figure 67:
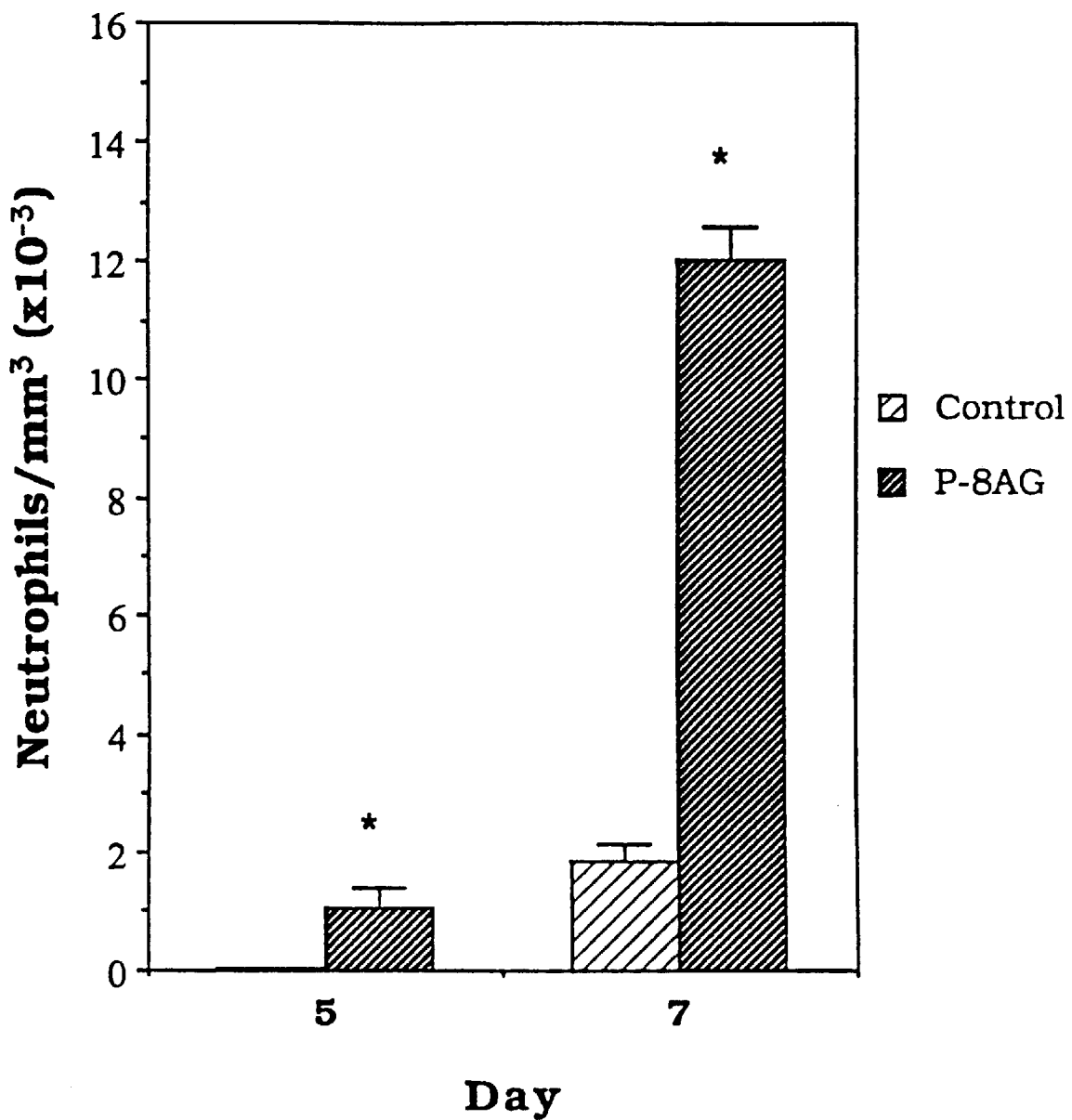
FIG. 67 is a graph comparing neutrophil counts in mice treated with saline and palmitoyl 8-aminoguanosine as described in Example 59.
Figure 68:
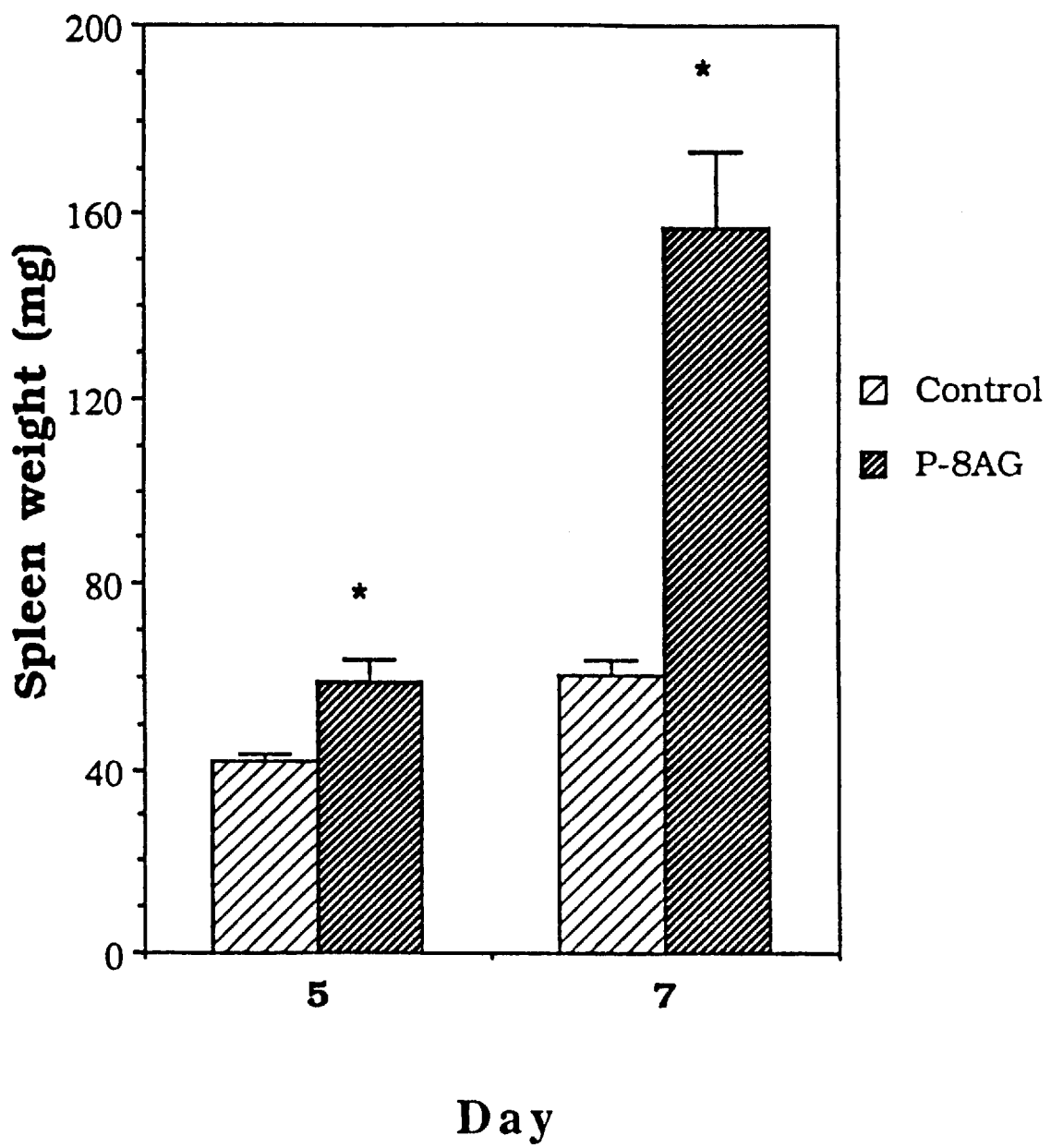
FIG. 68 is a graph comparing spleen weight in mice treated with saline and palmitoyl 8-aminoguanosine as described in Example 59.

On days 5 and 7, neutrophils, and spleen weight were significantly elevated compared to controls in the mice treated with palmitoyl-8-aminoguanosine (FIGS. 67–68, respectively).

Example 60

$N^2$-Palmitoylguanine Improves Spleen, Platelet and Leukocyte Recovery when Administered before 5-fluorouracil Twelve female Balb/C mice weighing approximately 20 grams each received a 0.4 ml i.p. injection of either N-palmitoylguanine (25 mg/kg/treatment) in a Tween-DMSO vehicle (0.2% Tween-80 and 7.5% DMSO in saline) or vehicle alone one time daily for three days. On the fourth day 5-fluorouracil (5-FU; 150 mg/kg, i.p.) was administered to all twelve animals. On day 7 following 5-FU administration all twelve of these animals were bled and then sacrificed by cervical dislocation. Six untreated mice were also bled and sacrificed to provide data on normal (basal) values. Spleens were removed and weighed, and complete blood cell counts performed.

Spleen weight, white blood cell counts, platelet counts, and lymphocyte counts were all significantly higher in those animals pretreated with N-palmitoylguanine than in those animals (controls) pretreated with vehicle alone (Table 3).

TABLE 3

Effect of $N^2$-Palmitoylguanine on blood cell counts 7 days after 5-FU

|  | Spleen | WBC | Lymphocytes | Platelets |
|---|---|---|---|---|
| Basal | 96 ± 4 mg | 6.1 ± .2 | 4.4 ± .4 | 834 ± 45 |
| 5FU (Control) | 64 ± 3 | 2.8 ± .3 | 2.8 ± .3 | 407 ± 52 |
| 5FU + NPG | 79 ± 3* | 4.6 ± .5* | 4.5 ± .5* | 787 ± 72* |

All blood cell count units are K/μl
* = greater than control (5FU alone) P < .01

Example 61

$N^2$-Palmitoylguanine Improves Spleen and Leukocyte Recovery when Administered after Cyclophosphamide Twelve female Balb/C mice weighing approximately 20 grams each received a 0.4 ml i.p. injection of either N-palmitoylguanine (25 mg/kg/treatment) in a Tween-DMSO vehicle (0.2% Tween-80 and 7.5% DMSO in saline) or vehicle alone one time daily for five days following a single injection of cyclophosphamide (CP) (250 mg/kg, i.p.). On day 7 following CP administration all twelve of these animals were bled and then sacrificed by cervical dislocation. Six untreated mice were also bled and sacrificed to provide data on normal (basal) values. Spleens were removed and weighed, and complete blood cell counts performed.

Spleen weight, white blood cell counts, and neutrophil counts were all significantly higher in those animals treated with N-palmitoylguanine than in mice treated with vehicle alone (controls). These data are presented in Table 4. Platelet counts in the N-palmitoylguanine-treated mice were also elevated compared to those in controls animals, but did not reach statistical significance largely due to variability in the control group.

TABLE 4

Effect of $N^2$-Palmitoylguanine on blood cell counts 7 days after Cyclophosphamide

|  | Spleen | WBC | Neutrophils | Platelets |
|---|---|---|---|---|
| Basal | 96 ± 4 mg | 6.1 ± .2 | 1.4 ± .1 | 834 ± 45 |
| CP (Control) | 50 ± 7 | 2.9 ± .6 | 1.4 ± .3 | 650 ± 100 |
| CP + NPG | 145 ± 13* | 7.3 ± .6* | 5.5 ± .5* | 774 ± 734 |

All blood cell count units are K/μl
* = greater than control (CP alone) P < .01

Example 62

Tripalmitoyl- and Dipalmitoyl-deoxyguanosine Improve Hematopoietic Recovery when Administered after Cyclophosphamide Thirty-six female Balb/C mice weighing approximately 20 grams each received a 0.4 ml i.p. injection of either 3',5'-O-$N^2$-tripalmitoyl-2'-deoxyguanosine (triPdG) at a dose of 25 mg/kg/treatment or 3',5'-O-dipalmitoyl-2'-deoxyguanosine (diPdG) at a dose that was the molar equivalent of 25 mg/kg tripalmitoylgdeoxyguanosine, in a Tween-DMSO vehicle (0.2% Tween-80 and 7.5% DMSO in saline) or vehicle alone one time daily for five days following a single injection of cyclophosphamide (CP) (250 mg/kg, i.p.). On days 5 and 7 following CP administration six animals from each of these three groups were bled and then sacrificed by cervical dislocation. Six untreated mice were also bled and sacrificed to provide data on normal. (basal) values. Spleens were removed and weighed, and complete blood cell counts performed.

Spleen weight and total neutrophil counts were significantly elevated in both treatment groups compared to those in the vehicle controls on day 5 (Table 5). Mice treated with triPdG also had significantly greater white blood cell counts than the controls at the same time point.

On day 7, spleen weight, white blood cell counts, and total neutrophil counts in both the diPdG- and triPdG-treated animals were significantly increased over those in the control mice (Table 6). Platelet counts were also significantly greater than control values at day 7 in mice receiving the triPdG treatment.

TABLE 5

Effect of Dipalmitoyldeoxyguanosine and Tripalmitoyldeoxyguanosine on blood cell counts 5 days after Cyclophosphamide

|  | Spleen | WBC | Neutrophils |
|---|---|---|---|
| Basal | 100 ± 4 mg | 6.1 ± .2 | 1.5 ± .2 |
| CP (Control) | 35 ± 2 | 1.4 ± .1 | .03 ± .02 |
| CP + TriPdG | 77 ± 7* | 4.1 ± .4* | 2.5 ± .3* |
| CP + DiPdG | 44 ± 1* | 1.5 ± .2 | 0.5 ± .1* |

All blood cell count units are K/μl
* = greater than control (CP alone) P < .01

TABLE 6

Effect of Dipalmitoyldeoxyguanosine and Tripalmitoyldeoxyguanosine on blood cell counts 7 days after Cyclophosphamide

|  | Spleen | WBC | Neutrophils | Platelets |
|---|---|---|---|---|
| Basal | 100 ± 4 mg | 7.6 ± .4 | 1.5 ± .2 | 784 ± 58 |
| CP (Control) | 55 ± 3 | 5.0 ± .3 | 2.3 ± .3 | 455 ± 22 |

TABLE 6-continued

Effect of Dipalmitoyldeoxyguanosine and Tripalmitoylde-
oxyguanosine on blood cell counts 7 days after Cyclophosphamide

|  | Spleen | WBC | Neutrophils | Platelets |
|---|---|---|---|---|
| CP + TriPdG | 156 ± 12* | 13.4 ± .4* | 9.9 ± .9* | 549 ± 25* |
| CP + DiPdG | 99 ± 7* | 8.4 ± .7* | 6.7 ± .7* | 432 ± 15 |

All blood cell count units are K/µl
* = greater than control (CP alone) P < .01

Example 63

Acylated Derivatives of Deoxyguanosine Improve Hematopoietic Recovery when Administered after Cyclophosphamide Fifty-eight female Balb-C mice weighing approximately 20 grams each received a single injection of cyclophosphamide (250 mg/kg, i.p.), and were then distributed into a vehicle control group (0.2% Tween-80+7.5% DMSO in saline; n=12) or one of five treatment groups:

| TriPdG-3',5'-O-N²-tripalmitoyl-2'-deoxyguanosine | n = 10 |
|---|---|
| TriOdG-3',5'-O-N²-trioleyl-2'-deoxyguanosine | n = 8 |
| TriSdG-3',5'-O-N²-tristearyl-2'-deoxyguanosine | n = 8 |
| DiPdG-5'-O-N²-dipalmitoyl-2'-deoxyguanosine | n = 10 |
| NIbuPdG-N²-isobutyryl-5'-O-palmitoyl-2'-deoxyguanosine | n = 10 |

Vehicle or treatment agents were administered to mice once daily for five days at a volume of 0.4 ml by i.p. injection. TriPdG was given at a dose of 25 mg/kg/treatment. The other four agents were given in doses that are the molar equivalent of 25 mg/kg/treatment of TriPdG. On days 5 and 7 following CP administration half of the animals from each of the six groups were bled and then sacrificed by cervical dislocation. Five untreated mice were also bled and sacrificed to provide data on normal (basal) values. Spleens were removed and weighed, and complete blood cell counts performed.

Spleen weight, white blood cell counts, platelet counts, and neutrophil counts were significantly greater in the mice treated with triPdG (3',5'-O-N²-tripalmitoyl-2'-deoxyguanosine) than in the vehicle control animals at the day 5 time point (Table 7). The spleen weight of animals treated with diPdG (5'-O-N²-dipalmitoyl-2'-deoxyguanosine) was also significantly greater than that of controls at day 5.

By day 7 following CP administration, each of the five treatment agents, when compared to control values, had significantly improved at least two parameters of hematopoietic recovery (Table 8). TriOdG (3',5'-O-N²-trioleyl-2'deoxyguanosine) increased both platelet and lymphocyte counts, while NIbuPdG (N²-isobutyryl- 5'-O-palmitoyl-2'-deoxyguanosine) significantly improved spleen weight and platelet counts. TriPdG, TriSdG (3',5'-O-N²-tristearyl-2'-deoxyguanosine), and DiPdG (5'-O-N²-dipalmitoyl-2'-deoxyguanosine) all significantly increased spleen weight, white blood cell counts and total neutrophil counts compared to control values. TriPdG also significantly increased platelet counts.

TABLE 7

Effect of acyl derivatives of deoxyguanosine on
blood cell counts 5 days after Cyclophosphamide

|  | Spleen | WBC | Neutrophils | Platelets |
|---|---|---|---|---|
| Basal | 117 ± 5 mg | 10.5 ± .5 | 1.8 ± .5 | 1041 ± 65 |
| CP (Control) | 33 ± 2 | 1.5 ± .3 | .002 ± .002 | 602 ± 19 |
| CP + TriPdG | 73 ± 3* | 3.6 ± .4* | 0.6 ± .1* | 330 ± 19 |
| CP + DiPdG | 39 ± 2* | 1.6 ± .2 | .46 ± .03* | 527 ± 15 |

All blood cell count units are K/µl
* = greater than control (CP alone) P < .01

TABLE 8

Effect of acyl derivatives of deoxyguanosine on
blood cell counts 7 days after Cyclophosphamide

|  | Spleen | WBC | Neutrophils | Platelets |
|---|---|---|---|---|
| Basal | 117 ± 5 mg | 10.5 ± .5 | 1.8 ± .5 | 1041 ± 65 |
| CP (Control) | 53 ± 4 | 4.2 ± .4 | 2.3 ± .25 | 562 ± 25 |
| CP + TriPdG | 198 ± 23* | 3.6 ± .4* | 7.3 ± .3* | 674 ± 37* |
| CP + DiPdG | 77 ± 5* | 7.6 ± .6* | 5.8 ± .6* | 562 ± 17 |
| CP + TriOdG | 59 ± 5 | 5.2 ± .4 | 2.7 ± .4 | 741 ± 54* |
| CP + TriSdG | 85 ± 9* | 7.6 ± .4* | 5.4 ± .5* | 498 ± 27 |
| CP + NibuPdG | 69 ± 6* | 4.4 ± .5 | 2.2 ± .5 | 649 ± 23* |

All blood cell count units are K/µl
* = greater than control (CP alone) P < .01

Example 64

N-isobutyryldeoxyguanosine Improves Hematopoietic Recovery when Administered after Cyclophosphamide Fourteen female Balb/C mice weighing approximately 20 grams each received a 0.4 ml i.p. injection of either N-isobutyryldeoxyguanosine (50 mg/kg/treatment) in a Tween vehicle (0.2% Tween-80 in saline) or vehicle alone one time daily for five days following a single injection of cyclophosphamide (CP) (250 mg/kg, i.p.). On day 7 following CP administration all fourteen animals were bled and then sacrificed by cervical dislocation. Spleens were removed and weighed, and complete blood cell counts performed.

N-isobutyryldeoxyguanosine significantly accelerated hematopoietic recovery from cyclophosphamide damage when compared to controls. Spleen weight (116.3±8.0 vs. 72.7±2.7, p<.001), white blood cell counts (8.9±0.5 vs. 4.6±0.5, p<.001), total neutrophil counts (6.6±0.5 vs. 3.3±0.4, p<.001), and lymphocyte counts (2.1±0.2 vs. 1.2±0.2, p<.02) were all significantly greater in animals treated with N-isobutyryldeoxyguanosine than in those mice receiving vehicle only.

Example 65

Tripalmitoyldeoxyguanosine Improves Hematopoietic Recovery in a Dose-dependent Manner when Administered before 5-fluorouracil Sixty female Balb/C mice weighing approximately 20 grams each were distributed into one of five treatment groups and treated once daily for three days by i.p. injection with 3',5'-O-N²-tripalmitoyl-2'-deoxyguanosine at a dose of either 1, 5, 10, 25, or 50 mg/kg/treatment in a Tween-DMSO vehicle (0.2% Tween-80 and 7.5% DMSO in physiological saline). Injection volume was 0.4 ml. An additional twelve animals (controls) received vehicle alone on those three days. On the fourth day all seventy-two animals received a single i.p. injection of 5-fluorouracil (5-FU) at a dose of 150 mg/kg. On days 7 and 10 following 5-FU administration six mice from each group were bled and then sacrificed by cervical dislocation. Six untreated mice were also bled and sacrificed to provide data on normal (basal) values. Spleens were removed and weighed, and complete blood cell counts performed.

On day 7, increasing doses of tripalmitoyldeoxyguanosine resulted in corresponding increases in spleen weight (Table 9). Statistically significant differences in spleen weight, when compared to control values, were achieved at a dose of 10 mg/kg and higher. Platelet counts also showed significant increases relative to controls at doses of 5 mg/kg and higher. The highest values, although not statistically significantly different compared to the higher dose levels, were in the 5 mg/kg treatment group.

On day 10, a clear dose-dependent trend was observed in spleen weight, white blood cell counts, total neutrophil counts, and lymphocyte counts (Table 10). Values for each and all of these parameters appeared to be maximal at the 25 mg/kg dose of tripalmitoyldeoxyguanosine, however.

TABLE 9

Effect of Tripalmitoyldeoxyguanosine on blood cell counts 7 days after 5-fluorouracil: Dose response

|  | Spleen | Platelets |
|---|---|---|
| Basal | 104 ± 5 mg | 820 ± 417 |
| 5FU (Control) | 68 ± 3 | 432 ± 15 |
| TriPDG 1 mg/kg | 74 ± 3 | 457 ± 36 |
| TriPDG 5 mg/kg | 78 ± 4 | 682 ± 66* |
| TriPDG 10 mg/kg | 83 ± 6* | 571 ± 41* |
| TriPDG 25 mg/kg | 93 ± 5* | 587 ± 19* |
| TriPDG 50 mg/kg | 102 ± 4* | 596 ± 43* |

All blood cell count units are K/µl
* = greater than control (5FU alone) $P < .01$

TABLE 10

Effect of Tripalmitoyldeoxyguanosine on blood cell counts 10 days after 5-fluorouracil: Dose response

|  | Spleen | WBC | Neutrophils | Lymphocytes |
|---|---|---|---|---|
| Basal | 104 ± 5 mg | 9.2 ± .7 | 2.0 ± .2 | 6.8 ± .6 |
| 5FU (Control) | 96 ± 9 | 6.1 ± .5 | 0.2 ± .03 | 5.8 ± .5 |
| TriPDG 1 mg/kg | 96 ± 13 | 6.2 ± .4 | 0.4 ± .2 | 5.7 ± .2 |
| TriPDG 5 mg/kg | 157 ± 13* | 8.2 ± .9 | 1.6 ± .4* | 6.3 ± .7 |
| TriPDG 10 mg/kg | 169 ± 24* | 7.7 ± .6 | 1.8 ± .4* | 5.7 ± .4 |
| TriPDG 25 mg/kg | 293 ± 17* | 11.4 ± .6* | 2.9 ± .4* | 8.3 ± .4* |
| TriPDG 50 mg/kg | 320 ± 39* | 10.8 ± 1.6* | 2.2 ± .5* | 8.3 ± 1.0* |

All blood cell count units are K/µl
* = greater than control (5FU alone) $P < .01$ Example 66

Pretreatment with Palmitoyldeoxyguanosine Protects Against Corticosteroid-induced Apoptosis in Mouse Thymus Thymic lymphocytes, or thymocytes, undergo a suicide process known as apoptosis or programmed cell death in response to various stimuli, including ionizing radiation, calcium ionophores, glucocorticoid hormones, and other agents. Apoptosis is also part of the normal physiological process of development and of lymphocyte (and other cell) selection. Using a well-known model of glucocorticoid-induced programmed cell death, the results below demonstrate that pretreatment with palmitoyldeoxyguanosine protects against corticosteroid-induced apoptosis in mouse thymus.

Eight male B6D2F1 mice weighing approximately twenty-five grams were given a single injection of either palmitoyldeoxyguanosine (25 mg/kg, i.p.) in a Tween-DMSO vehicle (0.02% Tween and 7.5% DMSO in physiological saline) or vehicle alone. Forty-eight hours later these mice were given an i.p. injection of a long-acting corticosteroid, methylprednisolone acetate (Depo-Medrol; 250 mg/kg). Forty-eight hours following administration of the corticosteroid, all eight of these animals and four additional untreated animals (basals) were sacrificed by cervical dislocation, the thymuses and spleens removed and weighed, and thymic cell number and viability measured by established methods. While thymus and spleen weight were dramatically reduced in both corticosteroid-treated groups, cell number per thymus and viability of thymic cells was significantly increased in those mice pretreated with palmitoyldeoxyguanosine (Table 11).

TABLE 11

Effect of palmitoyldeoxyguanosine on thymocyte apoptosis induced by corticosteroid treatment

|  | Spleen Wt. | Thymus Wt. | Cells/Thymus | % Viable |
|---|---|---|---|---|
| Basal | 78 ± 3 mg | 53 ± 5 mg | 2 ± 20 (x10$^6$) | 93 ± 3% |
| Depo-Nedrol (DM) | 51 ± 9 | 13 ± 1 | 27 ± 4 | 39 ± 6 |
| DM + PDG | 61 ± 11 | 16 ± 1 | 64 ± 12* | 87 ± 3* |

* = greater than control (Group 2; Depo-Medrol alone) $P < .01$

Example 67

Palmitoyldeoxyguanosine Prevents Apoptosis of IL-3-dependent Bone Marrow Cells in Vitro Withdrawal of interleukin-3 (IL-3) from cultures of IL-3-dependent cells leads to apoptosis, or programmed cell death. This experiment demonstrates that the addition of palmitoyldeoxyguanosine to cultures of IL-3 dependent cells deprived of IL-3 prevents programmed cell death.

Bone marrow cells were obtained by flushing the femurs of three male B6D2F1 mice. The cells were plated at 5.0×10$^5$/ml in MEM plus 10% fetal calf serum and 25 Units/ml of recombinant IL-3 for 24–48 hours. Non-adherent cells were then separated from adherent cells and maintained for an additional twelve days. IL-3 was washed from cells, and cells were plated in MEM plus 10% fetal calf serum in the presence or absence of IL-3 and with or without the addition of palmitoyldeoxyguanosine (10 micrograms per milliliter) or deoxyguanosine (10 micrograms per milliliter). Cells were counted using the trypan blue exclusion method, and the percent of dead cells (trypan blue positive) was determined at 24, 40, 60 and 84 hours following the wash. The mechanism of cell death was proven to be apoptosis by DNA fragmentation analysis.

The percent of dead cells in the cultures receiving IL-3 after the wash ranged from 7.5% at 24 hours to 13.0% at 84 hours. The percent of dead cells steadily and significantly increased in the cultures deprived of IL-3 from 18.5% at 24 hours to 75.3% at 84 hours (Table 12). The addition of palmitoyldeoxyguanosine to cultures deprived of IL-3 significantly reduced the percentage of dead cells, while addition of deoxyguanosine itself did nothing to prevent apoptotic cell death due to IL-3 deprivation.

These data demonstrate that the addition of palmitoyldeoxyguanosine to cultures of IL-3 dependent cells deprived of IL-3 prevents programmed cell death.

TABLE 12

Effect of palmitoyldeoxyguanosine on apoptosis of Interleukin-3 dependent bone marrow cells

| | Time (hr) | | | |
|---|---|---|---|---|
| Groups | 24 | 40 | 60 | 84 |
| | % Dead Cells | | | |
| −IL-3 | 18.5 ± 3.5 | 35.0 ± 1.0 | 47.7 ± 6.4 | 75.3 ± 5.5 |
| +IL-3 | 7.5 ± 12.5* | 6.5 ± 1.5* | 10.3 ± 1.9* | 13.0 ± 4.0* |
| −IL-3 + PdG | 11.0 ± 3.0 | 18.0 ± 3.0* | 16.0 ± 1.5* | 15.3 ± 5.5* |
| −IL-3 + dG | 15.5 ± 0.5 | 21.5 ± 3.5* | 46.3 ± 10.3 | 68.3 ± 6.0 |

* = less than control (Group 1; Minus IL-3) P <.01

Example 68

Palmitoyldeoxyguanosine Stimulates Proliferation of Bone Marrow Cells in Long-term Culture: Implications for Bone Marrow Transplantation Bone marrow transplantation is being used increasingly to treat various hematologic and oncologic diseases. The quality of the bone marrow transplant can be improved by short or long term incubation with factors that increase proliferation of normal hematopoietic cells and/or that stimulate production of colony-forming cells. This experiment demonstrate that the addition of palmitoyldeoxyguanosine to long-term cultures from normal mouse bone marrow cells dramatically increases the number of total cells and the proportion of colony-forming cells compared to control cultures.

Bone marrow cells from the femurs of B6D2F1 mice were used to establish long-term marrow cultures. After four weeks, when the stromal layer was confluent, the culture was treated with microphenolic acid in order to remove all cells from the stroma. New normal bone marrow cells ($1 \times 10^5$/ml) from the same source were then used to "recharge" the stromal layer. Palmitoyldeoxyguanosine was added to half of the cultures at a concentration of 10 micrograms per ml. Cells were counted on days 1, 3, 5, and 7 following addition of palmitoyldeoxyguanosine. On days 4 and 7 cells from the culture were removed, washed, and replated in methylcellulose. The number of granulomonocytic colonies was counted one week later.

Palmitoyldeoxyguanosine significantly increased the total number of cells and the proportion of colony-forming cells as indicated in Tables 13 and 14.

TABLE 13

Effect of palmitoyldeoxyguanosine on proliferation of bone marrow cells in vitro

| | Time (days) | | | |
|---|---|---|---|---|
| Groups | 1 | 3 | 5 | 7 |
| | Cells ($10^6$/flask) | | | |
| Control | 1.6 ± .13 | 2.4 ± .14 | 3.6 ± 5 | 2.4 ± .27 |
| TriPdG | 1.9 ± .13 | 2.9 ± .10 | 7.7 ± .2 | 4.3 ± .15 |

TABLE 14

Effect of palmitoyldeoxyguanosine on granulocyte/macrophage colony-forming units in vitro

| | Time (days) | |
|---|---|---|
| | 4 | 7 |
| Groups | CFU-GM/flask | |
| Control | 3297 ± 239 | 8417 ± 1361 |
| TriPdG | 5123 ± 561 | 33903 ± 9457 |

Example 69

Acyl Derivatives of Deoxyguanosine Inhibit Proliferation of Pluripotential Hematopoietic Cells in Vitro in a Dose-dependent Manner The $FDCP_{mix}$ cell line was used as a suitable in vitro model for predicting the effects of hematopoietic factors on pluripotential stem cells. These cells can be maintained in an-undifferentiated state in the presence of IL-3 or undergo multi-lineage development in the presence of specific hematopoietic growth factors.

$FDCP_{mix}$ cell proliferation in the presence of IL-3 with and without the addition of various test compounds was measured using the MTT (tetrazolium salt) colorimetric assay. Maximal proliferation of $FDCP_{mix}$ cells was measured 48 hours after adding an optimal dose of IL-3 to the cell culture. This level of proliferation (100%) served as the control value. Inhibition of proliferation by test compounds was represented as a percent of control.

$FDCP_{mix}$ cells were plated at a density of $5 \times 10^4$ cells per well in 96-well plates ($5 \times 10^5$/ml) using IMDM medium plus 10% fetal bovine serum. The optimal dose of IL-3 added to the cultures was 25 units/ml. Test compounds were added at a decreasing concentrations ranging from 10 micrograms/ml down to 1 nanogram/ml. The test compounds included: 3',5'-O-$N^2$-tripalmitoyl-2'-deoxyguanosine, 3',5'-di-O-palmitoyl-2'-deoxyguanosine, 3',5'-O-$N^2$-trioctanoyl-2'-deoxyguanosine, 3',5'-di-O-octanoyl-2'-deoxyguanosine, and 3',5'-O-$N^2$-trioleyl-2'-deoxyguanosine.

3',5'-O-$N^2$-tripalmitoyl-2'-deoxyguanosine and 3',5'-di-O-palmitoyl-2'-deoxyguanosine had significant dose-dependent inhibitory effects at doses from 10 micrograms per ml down to 100 nanograms per ml (Table 15). The other three compounds, 3',5'-O-$N^2$-trioctanoyl-2'-deoxyguanosine, 3',5'-di-O-octanoyl-2'-deoxyguanosine, and 3',5'-O-$N^2$-trioleyl-2'-deoxyguanosine, had little or no inhibitory effects at the doses tested.

Essentially the same results were also obtained with these five compounds in IL-3 enriched cell populations from normal mouse (B6D2F1) bone marrow using the MTT colorimetric assay system.

TABLE 15

Dose-dependent inhibition of proliferation of $FDCP_{mix}$ cells by acyl derivatives of deoxyguanosine

| | Dose: | | | | | |
|---|---|---|---|---|---|---|
| | 10 µg | 2.5 µg | 625 ng | 156 ng | 39 ng | 10 ng |
| Compound | Cell proliferation (% of Control) | | | | | |
| DiPdG | 38 ± .2 | 36 ± .1 | 40 ± .8 | 45 ± .9 | 52 ± .5 | 62 ± 2 |
| TriPdG | 51 ± .6 | 51 ± .7 | 60 ± 2 | 72 ± 3 | 76 ± 2 | 78 ± 1 |
| DiOctdG | 100 ± .3 | 78 ± 2 | 93 ± 1 | 84 ± 6 | 86 ± 1 | 84 ± 2 |

TABLE 15-continued

Dose-dependent inhibition of proliferation of
FDCP$_{mix}$ cells by acyl derivatives of deoxyguanosine

| Compound | Dose: | | | | | |
|---|---|---|---|---|---|---|
| | 10 μg | 2.5 μg | 625 ng | 156 ng | 39 ng | 10 ng |
| | Cell proliferation (% of Control) | | | | | |
| TriOctdG | 107 ± 1 | 96 ± .1 | 86 ± 2 | 89 ± 6 | 85 ± 2 | 87 ± 4 |
| TriOleyldG | 110 ± 3 | 80 ± 2 | 98 ± 6 | 92 ± 5 | 91 ± 5 | 92 ± 5 |

Example 70

Effect of $N^2$,3',5'-tripalmitoyldeoxyguanosine on Cisplatin-Induced Myelosuppression Cisplatin is an anti-neoplastic agent used in the treatment of testicular cancer, ovarian carcinoma, non-Hodgkins lymphoma, lung cancers and squamous-cell carcinoma of the head and neck. The dose-limiting toxicity with cisplatin use is generally nephrotoxicity, but the compound also causes a suppression of white blood cells, including lymphocytes and neutrophils, as well as platelets at high doses. Cisplatin has an unusually long half-life of approximately five days and is known to produce cumulative myelosuppression when multiple doses are given.

A study was conducted to assess the effects of $N^2$,3',5'-tripalmitoyldeoxyguanosine (PdG) in reducing the hematologic toxicity of cisplatin. Female Balb/C mice were divided into groups of five animals each per dose per time point. Half of the groups were given a series of three daily doses of PdG (25 mg/kg) by intraperitoneal injection and the other half were treated with the vehicle alone. Twenty-four hours later, the animals were given a single dose of cisplatin by intraperitoneal injection at one of four doses: 8, 11, 12 or 15 mg/kg. Blood samples were taken by retro-orbital eye bleed at four, seven and 11 days after administration of cisplatin. Blood cell counts four, seven and 11 days after administration of cisplatin were as listed in Tables 16, 17 and 18, respectively.

TABLE 16

Blood Cell Counts Four Days After Cisplatin Treatment

| Group | WBC (K/μL) | Neutrophils (K/μL) | Platelets (K/μL) | Lymphocytes (K/μL) |
|---|---|---|---|---|
| Basal: Day 4: | 10.0 | 2.0 | 1,000 | 9.0 |
| Cis-P (8 mg/kg) | 5.8 ± 1.1 | 0.65 ± 0.2 | 1,030 ± 24 | 5.15 ± 1.0 |
| Cis-P + PdG | 10.2 ± 1.4 | 1.77 ± 0.3 | 1,330 ± 57 | 8.0 ± 0.9 |
| Cis-P (11 mg/kg) | 5.6 ± 0.3 | 1.29 ± 0.2 | 1,110 ± 35 | 3.7 ± 0.1 |
| Cis-P + PdG | 7.2 ± 0.6 | 3.99 ± 0.7 | 1,408 ± 24 | 7.9 ± 1.1 |
| Cis-P (12 mg/kg) | 4.3 ± 6.5 | 0.83 ± 0.1 | 1,014 ± 39 | 2.41 ± 0.4 |
| Cis-P + PdG | 6.9 ± 0.9 | 1.59 ± 0.3 | 1,416 ± 56 | 5.14 ± 1.0 |
| Cis-P (15 mg/kg) | 5.6 ± 0.9 | — | 1,154 ± 57 | 2.10 ± 0.53 |
| Cis-P + PdG | 7.1 ± 1.0 | 2.69 ± 1.3 | 1,320 ± 43 | 4.37 ± 0.61 |

By day four, cisplatin had severely depressed total white blood cell counts, neutrophils and lymphocytes in animals not treated with PdG (relative to basal controls), even at the lowest cisplatin dose (8 mg/kg). In contrast, animals treated with PdG had no statistically-significant change in total white blood cell counts, neutrophils or lymphocytes relative to basal controls at the same cisplatin dose. Even though cisplatin did not reduce platelet counts at this time point, PdG-treated mice had platelet counts approximately 30% higher than those in vehicle-treated control animals. This pattern is similar to that seen in normal, non-compromised animals. The higher doses of cisplatin produced deficits in total white blood cells and lymphocytes even in mice receiving PdG. However, PdG pretreatment resulted in higher counts compared to controls. PdG pretreatment prevented neutrophil suppression at all doses, resulting in statistically- significant differences compared to controls. Platelets were elevated at all four doses of cisplatin in mice receiving PdG, even though cisplatin did not reduce platelet counts at this time point.

TABLE 17

Blood Cell Counts Seven Days After Cisplatin Treatment

| Group | WBC (K/μL) | Neutrophils (K/μL) | Platelets (K/μL) | Lymphocytes (K/μL) |
|---|---|---|---|---|
| Basal: Day 7: | 10.0 | 2.0 | 1,000 | 9.0 |
| Cis-P (8 mg/kg) | 7.6 ± 0.3 | 1.34 ± 0.38 | 974 ± 44 | 6.23 ± 0.46 |
| Cis-P + PdG | 8.3 ± 1.12 | 2.74 ± 0.50 | 910 ± 135 | 5.38 ± 0.71 |
| Cis-P (11 mg/kg) | 9.1 ± 0.45 | 3.64 ± 0.4 | 762 ± 91 | 4.78 ± 0.74 |
| Cis-P + PdG | 9.4 ± 0.83 | 4.58 ± 0.3 | 974 ± 49 | 5.44 ± 0.22 |
| Cis-P (12 mg/kg) | 5.5 ± 0.69 | 2.38 ± 0.5 | 866 ± 39 | 3.09 ± 0.57 |
| Cis-P + PdG | 8.5 ± 0.9 | 3.23 ± 0.7 | 1,030 ± 44 | 5.14 ± 0.91 |
| Cis-P (15 mg/kg) | 5.5 ± 0.59 | 4.22 ± 0.52 | 754 ± 54 | 1.21 ± 0.19 |
| Cis-P + PdG | 7.0 ± 0.38 | 4.06 ± 0.46 | 1,060 ± 40 | 2.80 ± 0.44 |

On day seven there was a neutrophil rebound in all groups at all doses. At the three higher doses, platelet suppression is obvious in the control groups, but PdG prevented the decline in platelets in the treatment groups.

On day 11 in the two lower cisplatin dose groups (8 and 11 mg/kg), total white blood cell counts, lymphocytes and platelets appeared to be in the normal range even in the control animals. However, at 12 mg/kg cisplatin, 60% of the controls had died by day 11. Meaningful statistics could not be done with only two mice remaining in this group. All of the PdG-treated animals survived. At the highest dose of cisplatin used, 15 mg/kg, all of the control animals were dead on day 11, while three of five mice survived in the group pretreated with PdG.

TABLE 18

Blood Cell Counts Eleven Days After Cisplatin Treatment

| Group | WBC (K/μL) | Neutrophils (K/μL) | Platelets (K/μL) | Lymphocytes (K/μL) |
|---|---|---|---|---|
| Basal: Day 11: | 10.0 | 2.0 | 1,000 | 9.0 |
| Cis-P (8 mg/kg) | 9.5 ± 0.5 | 0.64 ± 0.21 | 944 ± 58 | 8.8 ± 0.55 |
| Cis-P + PdG | 9.3 ± 0.3 | 1.33 ± 0.32 | 994 ± 29 | 7.9 ± 0.5 |
| Cis-P (11 mg/kg) | 9.6 ± 0.4 | 0.62 ± 0.25 | 936 ± 54 | 8.9 ± 0.47 |
| Cis-P + PdG | 8.7 ± 1.0 | 1.00 ± 0.37 | 968 ± 47 | 7.9 ± 1.23 |
| Cis-P (12 mg/kg) | (3/5 dead) | (3/5 dead) | (3/5 dead) | (3/5 dead) |
| Cis-P + PdG | 8.7 ± 0.6 | 3.26 ± 0.48 | 738 ± 35 | 5.34 ± 0.73 |
| Cis-P (15 mg/kg) | (5/5 dead) | (5/5 dead) | (5/5 dead) | (5/5 dead) |
| Cis-P + PdG | 9.7 ± 0.3 | 2.02 ± 0.68 | 657 ± 113 | 7.65 ± 0.49 |

There was no effect of cisplatin or PdG treatment on red blood cells at any time point. This experiment illustrates that PdG cisplatin protects mice from the immediate and more long-term hematopoietic toxicities of cisplatin. The effects on neutrophils and survival are particularly noteworthy.

Example 71

Effect of $N^2,3',5'$-tripalmitoyldeoxyguanosine on Doxorubicin-Induced Myelosuppression

Doxorubicin (Adriamycin) is a widely-used anticancer agent effective against breast carcinoma, sarcomas, small-cell lung cancer, ovarian cancer, thyroid cancer, Hodgkin's Disease and non-Hodgkins lymphoma. Its clinical application is limited by its cardiac and hematologic toxicities. A study was conducted to assess the effect of $N^2,3',5'$-tripalmitoyldeoxyguanosine (PdG) in reducing the hematologic toxicity of doxorubicin. Eighty male CDF8F1 mice were divided into three groups. One group received no treatment and served as basal control animals. Animals in the other two groups were each given a single dose of doxorubicin at a dose of 11 mg/kg by intraperitoneal injection. Beginning 24 hours later, animals in the two groups received three daily doses by intraperitoneal injection of either PdG or vehicle only. Blood samples were obtained by retro-orbital eye bleed just prior to administration of doxorubicin and then 4, 8, 11 and 14 days thereafter. Complete blood cell counts with differential were determined. Data are shown in Table 19. PdG, when given after doxorubicin, rapidly and effectively restored blood cell counts, spleen cellularity, and hematopoietic progenitor cells in the spleen.

TABLE 19

Effect of PdG on Blood Counts and Spleen Cellularity After Doxorubicin

| Group | WBC (K/μL) | Neutrophils (K/μL) | Lymphocytes (K/μL) | Spleen Cell # (×10⁷) | CFUc (Per 10⁵ Cells) |
|---|---|---|---|---|---|
| Day 4: | | | | | |
| Basal | 3.93 ± 0.13 | 1.37 ± 0.09 | 2.17 ± 0.1S | 23.2 | 0.33 |
| Dox | 1.87 ± 0.15 | 0.55 ± 0.13 | 1.17 ± 0.10 | 9.8 | 0.00 |
| Dox + PdG | 13.2 ± 1.59 | 4.35 ± 0.73 | 8.07 ± 1.21 | 15.7 | 0.61 |
| Day 8: | | | | | |
| Basal | 4.52 ± 0.36 | 1.48 ± 0.17 | 2.63 ± 0.33 | 19.2 | 0.45 |
| Dox | 2.95 ± 0.18 | 1.15 ± 0.13 | 1.58 ± 0.20 | 13.3 | 1.10 |
| Dox + PdG | 4.57 ± 0.35 | 2.47 ± 0.28 | 1.63 ± 0.13 | 28.3 | 21.60 |
| Day 11: | | | | | |
| Basal | 3.50 ± 0.23 | 1.40 ± 0.17 | 1.80 ± 0.13 | 20.7 | 0.28 |
| Dox | 3.20 ± 0.33 | 1.19 ± 0.12 | 1.70 ± 0.18 | 17.8 | 1.44 |
| Dox + PdG | 3.95 ± 0.42 | 1.80 ± 0.31 | 1.60 ± 0.33 | 27.0 | 3.72 |
| Day 14: | | | | | |
| Basal | 3.2 ± 0.31 | 1.0 ± 0.08 | 1.9 ± 0.29 | 21.0 | 0.17 |
| Dox | 4.4 ± 0.49 | 1.8 ± 0.35 | 1.9 ± 0.24 | 25.2 | 0.72 |
| Dox + PdG | 5.0 ± 0.39 | 2.3 ± 0.26 | 2.0 ± 0.15 | 30.2 | 1.11 |

Example 72

Therapeutic Activity of $N^2,3',5'$-tripalmitoyldeoxyguanosine (PdG) after Oral Administration

Effects of Intraperitoneal and Oral Administration of PdG on Neutrophil Recovery in Cyclophosphamide Model PdG was formulated in a preparation of mixed micelles comprising glycerol tricaprylate and the bile salt sodium cholate. Groups of 10 female Balb/C mice were given a single dose of cyclophosphamide (250 mg/kg) by intraperitoneal injection. Beginning 24 hours later, the animals received three daily doses of either PdG (25 mg/kg) by intraperitoneal injection, PdG (100 mg/kg) in the glycerol tricaprylate-sodium cholate-saline vehicle orally by gavage, or the glycerol tricaprylate-sodium cholatesaline vehicle alone by oral gavage. Blood samples were taken via the retro-orbital plexus five and seven days after administration of cyclophosphamide. Samples were also taken from a group of untreated animals, which served as basal controls. Neutrophil counts were as shown in Table 20. Oral delivery of PdG after cyclophosphamide produced a significant improvement in neutrophil recovery relative to control animals.

TABLE 20

Activity of PdG after oral administration

| Group | WBC (K/μL) | Neutrophils (K/μL) |
|---|---|---|
| Basal | 10.0 | 2.55 + 0.47 |
| Day 5: | | |
| CP + Vehicle (Oral) | 0.91 + 0.1 | 0.02 + 0.00 |
| CP + PdG (Oral) | 1.9 + 0.2 | 0.70 + 0.15 |
| CP + PdG (i.p.) | 4.0 + 0.1 | 1.80 + 0.06 |
| Day 7: | | |
| CP + Vehicle (Oral) | 5.2 + 0.5 | 2.05 + 0.39 |
| CP + PdG (Oral) | 7.5 + 0.2 | 5.64 + 0.35 |
| CP + PdG (i.p.) | 13.8 + 0.6 | 11.40 + 0.97 |

Example 73

$N^2,3',5'$-tripalmitoyldeoxyguanosine Improves Survival in Polymicrobial Infection

$N^2,3',5'$-tripalmitoyldeoxyguanosine (PdG) stimulates neutrophil production. Since neutrophils are important in defense against bacteria, PdG was tested for beneficial effects in bacterial sepsis. Bacterial infection as a consequence of the immunocompromising effects of radiotherapy or chemotherapy is an important cause of mortality in cancer patients. The potential utility of PdG was evaluated in the cecal ligation and puncture model (CLP), a model of polymicrobial sepsis in which the cecum of an animal is tied off without otherwise obstructing intestinal flow, and then punctured to allow fecal matter trapped in the cecum to leak into the peritoneal cavity (O'Reilly, et al. Journal of Trauma, 33:679–682). This release causes peritonitis as well as subsequent bacteremia, shock, and mortality. The CLP model is a particularly rigorous challenge because it creates a severe and complex polymicrobial sepsis due to both Gram-negative and Gram-positive bacteria. The CLP model is analogous to a ruptured appendix or punctured intestine in humans.

36 female Balb/C mice were employed. The mice were randomly assigned to one of three groups of twelve mice each. Two groups were treated once per day for three days prior to CLP by i.p. injection with either 25 mg/kg PdG or with vehicle alone. One group underwent the CLP procedure but received no other treatment. Survival was monitored for 60 days after CLP.

Shock was observed in both of the control groups (vehicle and no treatment) at 18–24 hours after CLP. Only one control animal survived beyond 72 hours, and none of the control animals survived past 100 hours. All of the PdG-treated mice were alive 72 hours after CLP. One animal died on day 3 and a second died on day 4. The remaining animals (10/12, or 83%) all survived through the 60 day observation period.

Example 74

N$^2$,3',5'-tripalmitoyldeoxyguanosine Improves Survival in Animals Treated with Bacterial Endotoxin Endotoxin is a lipopolysaccharide found in the cell wall of gram-negative bacteria. Endotoxin (LPS) is a potent inflammatory stimulus, the harmful effects of which are due to elicitation of synthesis and release of cytokines, leukotrienes and other inflammatory mediators. LPS contributes to disease not only in bacterial infections, but also in a variety of conditions in which bacterial infection is not necessarily present, since endotoxin can be translocated across the gut wall into the circulation. Endotoxin is in fact normally found in the portal vein leading from the gut to the liver, but translocation is enhanced in patients subjected to trauma, shock, intestinal ischemia, burns, and after ingestion of ethanol. Gut-derived LPS is implicated in a variety of liver disorders including viral and alcoholic hepatitis, complications of liver transplantation, and hepatic injury associated with total parenteral nutrition. The beneficial activity of PdG after LPS administration demonstrates anti-inflammatory activity of compounds of the invention.

In an experiment to test the effect of N$^2$,3',5'-tripalmitoyldeoxyguanosine (PdG) on animals challenged by endotoxin, 42 female Balb/C mice were divided into three groups of 14 animals each. Each group was given a single 100 µg dose (5 mg/kg) of salmonella typhimurium LPS. Two of the groups were treated once per day for three days prior to receiving the LPS by intraperitoneal injection with either 25 mg/kg PdG or with vehicle alone. The third group received no pretreatment. Survival of the animals was monitored for 21 days subsequent to the LPS dose.

In the group receiving only LPS (no pretreatment), 86% of the animals (12/14) had died by day three, but the remaining two animals (14%) survived to the end of the 21-day observation period. All of the animals receiving LPS plus the vehicle died by day three. All of the animals treated with PdG survived through the end of the observation period and appeared to have recovered completely.

This experiment demonstrates significant activity of PdG against toxic effects of bacterial endotoxin, and therefore indicates beneficial activity of PdG and other compounds of the invention in disease states associated with endotoxin, as well as inflammatory disease in general.

Example 75

N$^2$,3',5'-tripalmitoyldeoxyguanosine (PdG) Modulates Inflammatory Cytokine Activity Inflammatory cytokines including tumor necrosis factor alpha (TNF-alpha), interferon gamma (IFN-gamma) are involved in the onset and prolongation of a variety of inflammatory diseases. The capability to reduce the levels of these cytokines is beneficial in alleviating disease conditions. An agent with this capability is clinically useful in diseases such as rheumatoid arthritis, inflammatory bowel disease, and multiple sclerosis, and conditions associated with endotoxemia or exposure to other micropbial inflammatory stimuli.

Endotoxin (LPS), a component of gram negative bacterial cell walls, is an inflammatory stimulus which elicits dramatic increases in inflammatory cytokines like TNF-alpha and IFN-gamma. The effects of these endogenously released inflammatory agents can be extremely deleterious and contribute to LPS-induced tissue injury and mortality. These cytokines also mediate inflammatory responses initiated by other inflammatory stimuli.

Sixty-three female Balb/C mice were randomly assigned to one of three groups. The animals in one group received a single daily dose of N$^2$,3',5'-tripalmitoyldeoxyguanosine (PdG) (25 mg/kg, i.p.), while a second group received a single daily dose of the PdG treatment vehicle (control). The third group was left untreated. On the fourth day 100 µg salmonella typhimurium LPS was administered to all three groups. Serum samples were taken just prior to LPS administration (t=0) and at two, four, six, eight, ten, twelve, sixteen, and twenty hours after LPS administration. The samples were then frozen until the time of assay. Serum levels of TNF-alpha, and IFN-gamma were measured by ELISA.

PdG administration to animals exposed to LPS significantly attenuated increases in TNF-alpha levels compared to those in animals receiving vehicle and LPS and those receiving LPS only (Table 21). Peak levels in PdG treated animals were four-fold lower than those in the control groups. Attenuation of the IFN-gamma response was even more dramatic, with peak levels five- to seven-fold lower than control values (Table 22). The area under the curve (AUC) over the entire time course was significantly lower in animals treated with PdG. PdG also attenuated LPS-induced elevation of serum interleukin-l-alpha and interleukin-6.

In the tables below, units for cytokine concentrations are picograms per ml. A value of 0 indicates cytokine levels below the detection limit of the assay (50 to 100 pg/ml).

TABLE 21

PdG attenuates LPS-induced production of TNF-alpha

| Time after LPS | LPS | LPS + Vehicle | LPS + PdG |
|---|---|---|---|
| 0 hr | 0 | 0 | 0 |
| 2 hr | 5611 ± 424 | 5835 ± 232 | 1509 ± 86 |
| 4 hr | 1082 ± 175 | 1283 ± 130 | 529 ± 141 |
| 6 hr | 517 ± 40 | 599 ± 58 | 486 ± 63 |
| 8 hr | 195 ± 55 | 281 ± 62 | 73 ± 50 |

TABLE 22

PdG attenuates LPS-induced production of interferon-gamma

| Time after LPS | LPS | LPS + Vehicle | LPS + PdG |
|---|---|---|---|
| 0 hr | 0 | 0 | 0 |
| 2 hr | 0 | 128 ± 128 | 0 |
| 4 hr | 1375 ± 344 | 1779 ± 298 | 825 ± 248 |
| 8 hr | 9446 ± 2796 | 13029 ± 2857 | 2129 ± 454 |
| 10 hr | 5429 ± 1259 | 8375 ± 2785 | 911 ± 279 |
| 12 hr | 496 ± 236 | 1054 ± 232 | 0 |
| 16 hr | 107 ± 107 | 482 ± 241 | 0 |
| 20 hr | 0 | 0 | 0 |

Inflammatory cytokines are involved in numerous disease states; the attenuation of cytokine production demonstrated in this experiment supports utility of compounds of the invention in treating inflammatory diseases in which such cytokines or endotoxin contribute to pathogenesis.

Example 76

Effect of N$^2$,3',5'-tripalmitoyl-deoxyguanosine (PdG) on Stem Cell Nobilization Autologous bone marrow transplant (ABMT) has been used to speed recovery of hematopoietic function following high-dose chemotherapy. In this technique, the patient's own stem cells are removed by obtaining bone marrow aspirates and then retransplanted into the patient following chemotherapy. Recently, various cytokines have been shown to "mobilize" stem cells from the bone marrow to the peripheral circulation where they can be easily harvested; use of these stem cells results in enhanced engraftment of hematopoietic cells over that seen with ABMT. The ability of $N^2,3',5'$-tripalmitoyldeoxyguanosine (PdG) to promote such stem cell mobilization has been examined.

Figure 69:
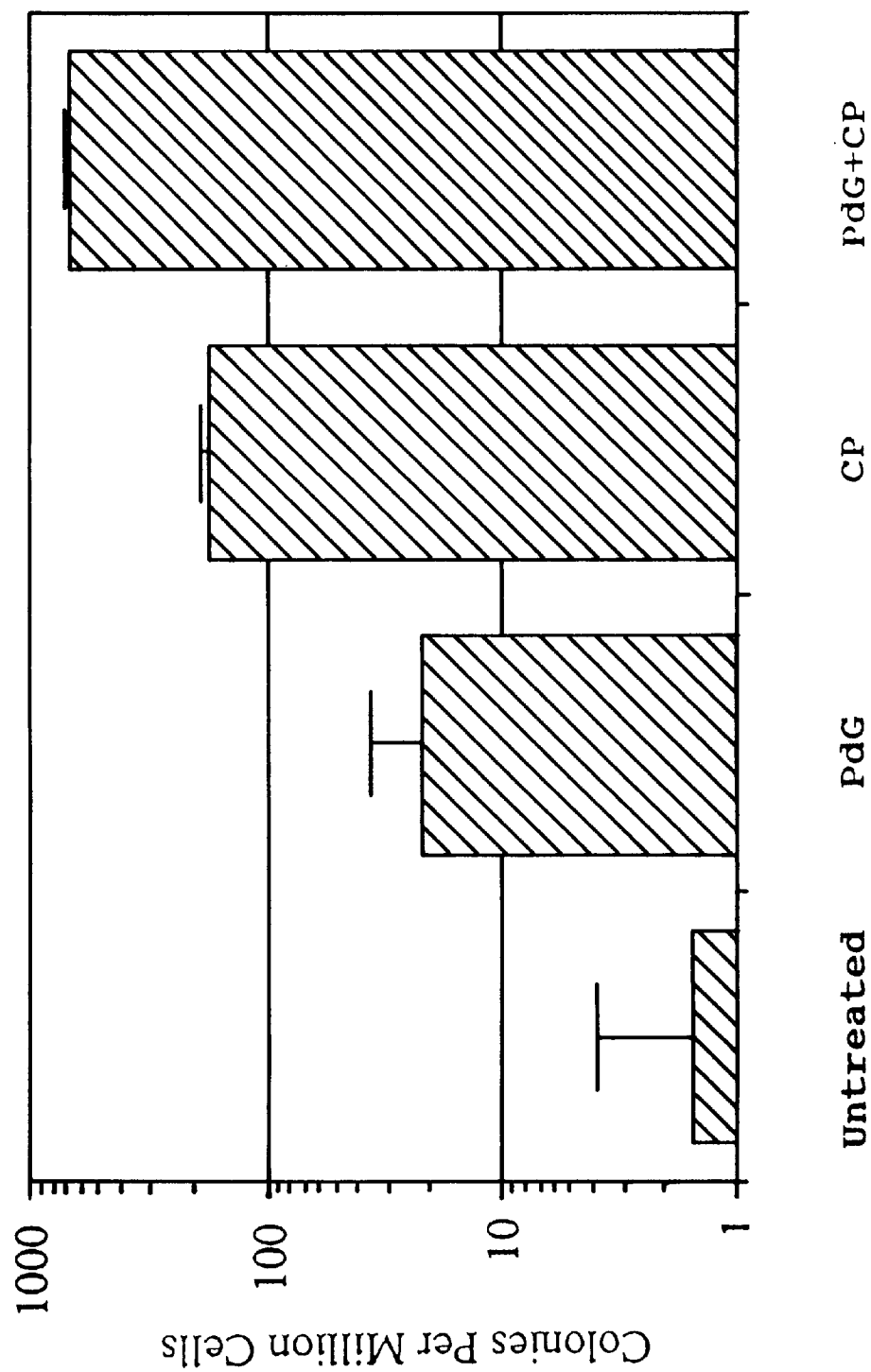
FIG. 69 shows that administration of PdG induces mobilizaton of stem cells.

As shown in FIG. 69, administration of PdG alone (25 mg/kg) can induce the mobilization of stem cells (note log scale). Its effect is also synergistic with that of cyclophosphamide, a chemotherapeutic agent which is currently being used clinically for stem cell mobilization, inducing a seven to eight-fold greater response to cyclophosphamide.

In order to demonstrate that PdG was causing mobilization from bone marrow stores and not from spleen (which can be a source of stem cells in the mouse, although not in humans, generally) the effect of splenectomy was studied. PdG was equally effective in mobilizing stem cells in both intact and splenectomized mice, with and without cyclophosphamide co-treatment. This indicates that the observed effect of PdG was in fact mobilization from bone marrow sites.

Compounds of the invention are therefore useful for mobilization of hematopoietic stem cells and other progenitor cells into peripheral blood for use as donor cells for bone marrow transplant, whether autologous or for transfer to an allogeneic recipient.

The foregoing is intended as illustrative of the present invention but not limiting. Numerous variations and modifications may be effected without departing from the true spirit and scope of the invention.

What is claimed is:
1. A compound having the formula

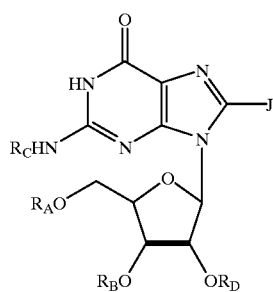

wherein $R_A$, $R_B$, and $R_D$ are the same, or different, and are hydrogen or
I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. a cycloalkyl carboxylic acid containing 4 to 22 carbon atoms,
  e. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
    ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
  a. an alkylphosphonic or alkylsulfonic acid, or
  b. an alkyl phosphate or alkyl sulfate,
provided that not all of $R_A$, $R_B$, and $R_D$ are hydrogen; and $R_C$ is hydrogen or
I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. a cycloalkyl carboxylic acid containing 4 to 22 carbon atoms,
  e. a nicotinic acid, or
  f. a substituted or unsubstituted aromatic carboxylic acid with 7 to 22 carbon atoms,
  g. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
    ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, and
J=H or NHR$_r$ where R$_r$ is H or an acyl or alkyl radical containing 1 to 10 carbon atoms;
or a pharmaceutically acceptable salt thereof.

2. A compound having the formula

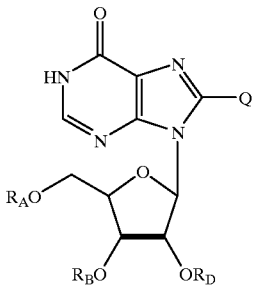

wherein $R_A$ is hydrogen or
I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
b. a dicarboxylic acid having 3–22 carbon atoms,
c. nicotinic acid or
d. a cycloalkyl carboxylic acid containing 4 to 22 carbon atoms; and
e. a carboxylic acid derived from
  i. a polymer of ethylene glycol with the structure HOOC—$(CH_2)_m$—$(CH_2CH_2O)_n$H or HOOC—$(CH_2)_m$—$(CH_2CH_2O)_n CH_3$, or
  ii. a polymer of vinyl alcohol with the structure HOOC—$(CH_2)_m$—$(CH_2CHOH)_n$H or HOOC—$(CH_2)_m$—$(CH_2CHOH)_n CH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
  a. an alkylphosphonic or alkylsulfonic acid, or
  b. an alkyl phosphate or alkyl sulfate,
wherein $R_B$ and/or $R_D$ are hydrogen or
I. an acyl group derived from
  a. an unbranched fatty acid with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n CH_3$, or
    ii. a polymer of vinyl alcohol with the structure HOOC—$(CH_2)_m$—$(CH_2CHOH)_n$H or HOOC—$(CH_2)_m$—$(CH_2CHOH)_n CH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
  a. an alkylphosphonic or alkylsulfonic acid, or
  b. an alkyl phosphate or alkyl sulfate,
provided that not all of $R_A$, $R_B$, and $R_D$ are hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

or a pharmaceutically acceptable salt thereof.

3. A compound having the formula wherein $R_A$, $R_B$, and $R_D$ are the same, or different, and are hydrogen or I. an acyl group derived from
  a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n CH_3$, or
    ii. a polymer of vinyl alcohol with the structure HOOC—$(CH_2)_m$—$(CH_2CHOH)_n$H or HOOC—$(CH_2)_m$—$(CH_2CHOH)_n CH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
  a. an alkylphosphonic or alkylsulfonic acid, or
  b. an alkyl phosphate or alkyl sulfate,
provided that not all of $R_A$, $R_B$, and $R_D$ are hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

or a pharmaceutically acceptable salt thereof.

4. A compound having the formula

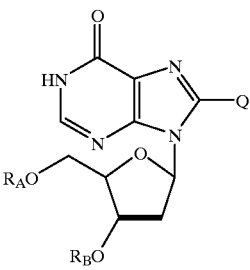

wherein $R_A$ and $R_B$ are the same, or different, and are hydrogen or

I. an acyl group derived from
   a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
   c. a dicarboxylic acid having 3–22 carbon atoms,
   d. nicotinic acid or
   e. a cycloalkyl carboxylic acid containing 4 to 22 carbon atoms,
   f. a carboxylic acid derived from
      i. a polymer of ethylene glycol with the structure HOOC—$(CH_2)_m$—$(CH_2CH_2O)_n$H or HOOC—$(CH_2)_m$—$(CH_2CH_2O)_n CH_3$, or
      ii. a polymer of vinyl alcohol with the structure HOOC—$(CH_2)_m$—$(CH_2CHOH)_n$H or HOOC—$(CH_2)_m$—$(CH_2CHOH)_n CH_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
   a. an alkylphosphonic or alkylsulfonic acid, or
   b. an alkyl phosphate or alkyl sulfate, provided that at least one of $R_A$ and $R_B$ is not hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms;

or a pharmaceutically acceptable salt thereof.

5. A compound having the formula:

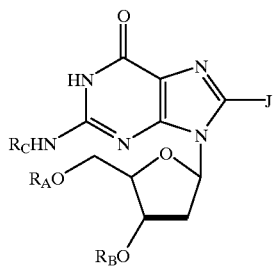

wherein $R_A$ and $R_B$ may be the same or different, and each is hydrogen or

I. an acyl group derived from
   a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, phenylalanine, and ornithine,
   c. a dicarboxylic acid having 3–22 carbon atoms,
   d. a cycloalkyl carboxylic acid containing 4 to 22 carbon atoms,
   e. nicotinic acid
   f. a carboxylic acid derived from
      i. a polymer of ethylene glycol with the structure HOOC—$(CH_2)_m$—$(CH_2CH_2O)_n$H or HOOC—$(CH_2)_m$—$(CH_2CH_2O)_n CH_3$, or
      ii. a polymer of vinyl alcohol with the structure HOOC—$(CH_2)_m$—$(CH_2CHOH)_n$H or HOOC—$(CH_2)_m$—$(CH_2CHOH)_n CH_3$, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
   a. an alkylphosphonic or alkylsulfonic acid, or
   b. an alkyl phosphate or alkyl sulfate,
provided that not both of $R_A$ and $R_B$ are hydrogen; and $R_C$ is hydrogen or
   I. an acyl group derived from
      a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
      b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
      c. a dicarboxylic acid having 3–22 carbon atoms,
      d. a cycloalkyl carboxylic acid containing 4 to 22 carbon atoms,
      e. a nicotinic acid, or
      f. a substituted or unsubstituted aromatic carboxylic acid with 7 to 22 carbon atoms,
      g. a carboxylic acid derived from
         i. a polymer of ethylene glycol with the structure HOOC—$(CH_2)_m$—$(CH_2CH_2O)_n$H or HOOC—$(CH_2)_m$—$(CH_2CH_2O)_n CH_3$, or ii. a polymer of vinyl alcohol with the structure HOOC—(CH$_2$)$_m$—(CH$_2$CHOH)$_n$H or HOOC—(CH$_2$)$_m$—(CH$_2$CHOH)$_n$CH$_3$, where m=0–3 and n=2–8, or II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, and where R$_C$ is not H, then R$_A$ and/or R$_B$ may also be acetyl, and J=NHR$_r$ where R$_r$ is H or an acyl or alkyl radical containing 1 to 10 carbon atoms;

or a pharmaceutically acceptable salt thereof.

6. A compound having the formula:

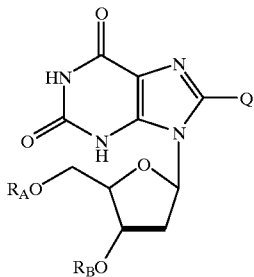

wherein R$_A$ and R$_B$ are the same, or different, and are hydrogen or

I. an acyl group derived from
 a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
 b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
 c. a dicarboxylic acid having 3–22 carbon atoms,
 d. nicotinic acid or
 e. a cycloalkyl carboxylic acid containing 4 to 22 carbon atoms,
 f. a carboxylic acid derived from
  i. a polymer of ethylene glycol with the structure HOOC—(CH$_2$)$_m$—(CH$_2$CH$_2$O)$_n$H or HOOC—(CH$_2$)$_m$—(CH$_2$CH$_2$O)$_n$CH$_3$, or
  ii. a polymer of vinyl alcohol with the structure HOOC—(CH$_2$)$_m$—(CH$_2$CHOH)$_n$H or HOOC—(CH$_2$)$_m$—(CH$_2$CHOH)$_n$CH$_3$, where m=0–3 and n=2–8, or II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, or III. an acyl group derived from
 a. an alkylphosphonic or alkylsulfonic acid, or
 b. an alkyl phosphate or alkyl sulfate, provided that at least one of R$_A$ and R$_B$ is not hydrogen, and Q=H, a halogen, NHR$_F$ where R$_F$ is H or an acyl or alkyl radical containing 1 to 10 carbon atoms, S divalently bound to the carbon in which case the adjacent carbon-nitrogen double bond is a single bond and an H is then attached to that nitrogen, SR$_G$ where R$_G$ is H or an acyl or alkyl radical containing 1 to 10 carbon atoms, O divalently bound to the carbon, in which case the adjacent carbon-nitrogen double bond is a single bond and an H is then attached to that nitrogen, or OR$_H$ where R$_H$ is H or an acyl or alkyl radical containing 1 to 10 carbon atoms;

or a pharmaceutically acceptable salt thereof.

7. A pharmaceutical compound selected from one of the groups of compounds having the formulae:

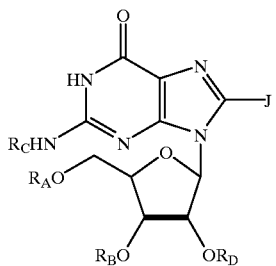

wherein R$_A$, R$_B$, and R$_D$ are the same, or different, and are hydrogen or

I. an acyl group derived from
 a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
 b. an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine and ornithine,
 c. a dicarboxylic acid having 3–22 carbon atoms,
 d. a cycloalkyl carboxylic acid containing 4 to 22 carbon atoms,
 e. a carboxylic acid derived from
  i. a polymer of ethylene glycol with the structure HOOC—(CH$_2$)$_m$—(CH$_2$CH$_2$O)$_n$H or HOOC—(CH$_2$)$_m$—(CH$_2$CH$_2$O)$_n$CH$_3$, or
  ii. a polymer of vinyl alcohol with the structure HOOC—(CH$_2$)$_m$—(CH$_2$CHOH)$_n$H or HOOC—(CH$_2$)$_m$—(CH$_2$CHOH)$_n$CH$_3$, where m=0–3 and n=2–8, or II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, or III. an acyl group derived from
 a. an alkylphosphonic or alkylsulfonic acid, or
 b. an alkyl phosphate or alkyl sulfate, provided that not all of R$_A$, R$_B$, and R$_D$ are hydrogen; and R$_C$ is hydrogen or
 I. an acyl group derived from
  a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. a cycloalkyl carboxylic acid containing 4 to 22 carbon atoms, e. a nicotinic acid, or
f. a substituted or unsubstituted aromatic carboxylic acid with 7 to 22 carbon atoms,
g. a carboxylic acid derived from
   i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
   ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, and
J=H or NHR$_I$ where R$_I$ is H or an acyl or alkyl radical containing 1 to 10 carbon atoms;
or a pharmaceutically acceptable salt thereof;

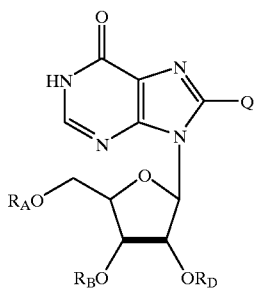

wherein R$_A$ is hydrogen or
I. an acyl group derived from
   a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. a dicarboxylic acid having 3–22 carbon atoms,
   c. nicotinic acid or
   d. a cycloalkyl carboxylic acid containing 4 to 22 carbon atoms; and
   e. a carboxylic acid derived from
      i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
      ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
III. an acyl group derived from
   a. an alkylphosphonic or alkylsulfonic acid, or
   b. an alkyl phosphate or alkyl sulfate,
wherein R$_B$ and/or R$_D$ are hydrogen or
I. an acyl group derived from
   a. an unbranched fatty acid with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
   c. a dicarboxylic acid having 3–22 carbon atoms,
   d. nicotinic acid or
   e. a cycloalkyl carboxylic acid containing 4 to 22 carbon atoms,
   f. a carboxylic acid derived from
      i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
      ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
   II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or
   III. an acyl group derived from
      a. an alkylphosphonic or alkylsulfonic acid, or
      b. an alkyl phosphate or alkyl sulfate,
provided that not all of R$_A$, R$_B$, and R$_D$ are hydrogen, and
Q=H, a halogen, NHR$_F$ where R$_F$ is H or an acyl or alkyl radical containing 1 to 10 carbon atoms, S divalently bound to the carbon in which case the adjacent carbon-nitrogen double bond is a single bond and an H is then attached to that nitrogen, SR$_G$ where R$_G$ is H or an acyl or alkyl radical containing 1 to 10 carbon atoms, O divalently bound to the carbon, in which case the adjacent carbon-nitrogen double bond is a single bond and an H is then attached to that nitrogen, or OR$_H$ where R$_H$ is H or an acyl or alkyl radical containing 1 to 10 carbon atoms,
or a pharmaceutically acceptable salt thereof;

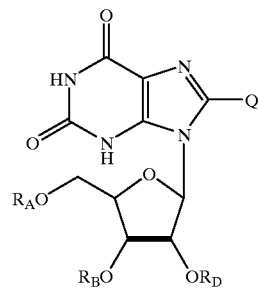

wherein R$_A$, R$_B$, and R$_D$ are the same, or different, and are hydrogen or
I. an acyl group derived from
   a. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
   b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
   c. a dicarboxylic acid having 3–22 carbon atoms,
   d. nicotinic acid or e. a cycloalkyl carboxylic acid containing 4 to 22 carbon atoms,
f. a carboxylic acid derived from
  i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
  ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, or
III. an acyl group derived from
  a. an alkylphosphonic or alkylsulfonic acid, or
  b. an alkyl phosphate or alkyl sulfate,
provided that not all of $R_A$, $R_B$, and $R_D$ are hydrogen, and
Q=H, a halogen, NHR$_F$ where R$_F$ is H or an acyl or alkyl radical containing 1 to 10 carbon atoms, S divalently bound to the carbon in which case the adjacent carbon-nitrogen double bond is a single bond and an H is then attached to that nitrogen, SR$_G$ where R$_G$ is H or an acyl or alkyl radical containing 1 to 10 carbon atoms, O divalently bound to the carbon, in which case the adjacent carbon-nitrogen double bond is a single bond and an H is then attached to that nitrogen, or OR$_H$ where R$_H$ is H or an acyl or alkyl radical containing 1 to 10 carbon atoms,
or a pharmaceutically acceptable salt thereof;

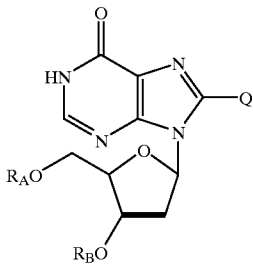

wherein $R_A$ and $R_B$ are the same, or different, and are hydrogen or
I. an acyl group derived from
  a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
  b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  c. a dicarboxylic acid having 3–22 carbon atoms,
  d. nicotinic acid or
  e. a cycloalkyl carboxylic acid containing 4 to 22 carbon atoms,
  f. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
    ii. a polymer of vinyl alcohol with the structure HOOC—$(CH_2)_m$—$(CH_2CHOH)_n$H or HOOC—$(CH_2)_m$—$(CH_2CHOH)_n$CH$_3$, where m=0–3 and n=2–8, or
II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, or
III. an acyl group derived from
  a. an alkylphosphonic or alkylsulfonic acid, or
  b. an alkyl phosphate or alkyl sulfate,
provided that at least one of $R_A$ and $R_B$ is not hydrogen, and
Q=H, a halogen, NHR$_F$ where R$_F$ is H or an acyl or alkyl radical containing 1 to 10 carbon atoms, S divalently bound to the carbon in which case the adjacent carbon-nitrogen double bond is a single bond and an H is then attached to that nitrogen, SR$_G$ where R$_G$ is H or an acyl or alkyl radical containing 1 to 10 carbon atoms, O divalently bound to the carbon, in which case the adjacent carbon-nitrogen double bond is a single bond and an H is then attached to that nitrogen, or OR$_H$ where R$_H$ is H or an acyl or alkyl radical containing 1 to 10 carbon atoms,
or a pharmaceutically acceptable salt thereof;

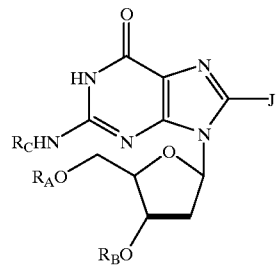

wherein $R_A$ and $R_B$ may be the same or different, and each is hydrogen or
I. an acyl group derived from
  a. an unbranched fatty acid with 6 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$,
  b. an amino acid selected from the group consisting of glycine, the L forms of alanine, valine, leucine, isoleucine, tyrosine, proline, hydroxyproline, serine, threonine, cysteine, aspartic acid, glutamic acid, arginine, lysine, histidine, phenylalanine, and ornithine,
  c. a dicarboxylic acid having 3–22 carbon atoms,
  d. a cycloalkyl carboxylic acid containing 4 to 22 carbon atoms,
  e. nicotinic acid
  f. a carboxylic acid derived from
    i. a polymer of ethylene glycol with the structure HOOC—$(CH_2)_m$—$(CH_2CH_2O)_n$H or HOOC—$(CH_2)_m$—$(CH_2CH_2O)_n$CH$_3$, or
    ii. a polymer of vinyl alcohol with the structure HOOC—$(CH_2)_m$—$(CH_2CHOH)_n$H or HOOC—$(CH_2)_m$—$(CH_2CHOH)_n$CH$_3$, or
II. an unbranched alkyl radical with 3 to 22 carbon atoms, optionally substituted at the terminal carbon with a hydrophilic moiety selected from the group consisting of NH$_2$, OH, OPO$_3^-$, PO$_3^-$, OSO$_3^-$, SO$_3^-$, or
III. an acyl group derived from
  a. an alkylphosphonic or alkylsulfonic acid, or
  b. an alkyl phosphate or alkyl sulfate, provided that not both of $R_A$ and $R_B$ are hydrogen; and $R_C$ is hydrogen or
- I. an acyl group derived from
  - a. an unbranched fatty acid with 6 to 22 carbon atoms, optionally substituted at the terminal carbon with a hydrophilic moiety selected from the group consisting of $NH_2$, $OH$, $OPO_3^-$, $PO_3^-$, $OSO_3^-$, $SO_3^-$,
  - b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  - c. a dicarboxylic acid having 3–22 carbon atoms,
  - d. a cycloalkyl carboxylic acid containing 4 to 22 carbon atoms,
  - e. a nicotinic acid, or
  - f. a substituted or unsubstituted aromatic carboxylic acid with 7 to 22 carbon atoms,
  - g. a carboxylic acid derived from
    - i. a polymer of ethylene glycol with the structure HOOC—$(CH_2)_m$—$(CH_2CH_2O)_nH$ or HOOC—$(CH_2)_m$—$(CH_2CH_2O)_nCH_3$, or
    - ii. a polymer of vinyl alcohol with the structure HOOC—$(CH_2)_m$—$(CH_2CHOH)_nH$ or HOOC—$(CH_2)_m$—$(CH_2CHOH)_nCH_3$, where m=0–3 and n=2–8, or
- II. an unbranched alkyl radical with 3 to 22 carbon atoms, optionally substituted at the terminal carbon with a hydrophilic moiety selected from the group consisting of $NH_2$, $OH$, $OPO_3^-$, $PO_3^-$, $OSO_3^-$, $SO_3^-$, and where $R_C$ is not H, then $R_A$ and/or $R_B$ may also be acetyl, and J=H or $NHR_r$ where $R_r$ is H or an acyl or alkyl radical containing 1 to 10 carbon atoms, or a pharmaceutically acceptable salt thereof;

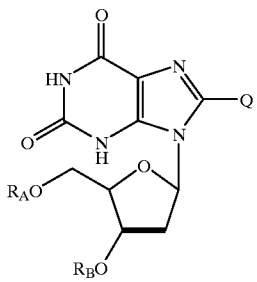

wherein $R_A$ and $R_B$ are the same, or different, and are hydrogen or
- I. an acyl group derived from
  - a. an unbranched fatty acid with 6 to 22 carbon atoms, optionally substituted at the terminal carbon with a hydrophilic moiety selected from the group consisting of $NH_2$, $OH$, $OPO_3^-$, $PO_3^-$, $OSO_3^-$, $SO_3^-$,
  - b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  - c. a dicarboxylic acid having 3–22 carbon atoms,
  - d. nicotinic acid or
  - e. a cycloalkyl carboxylic acid containing 4 to 22 carbon atoms,
  - f. a carboxylic acid derived from
    - i. a polymer of ethylene glycol with the structure HOOC—$(CH_2)_m$—$(CH_2CH_2O)_nH$ or HOOC—$(CH_2)_m$—$(CH_2CH_2O)_nCH_3$, or
    - ii. a polymer of vinyl alcohol with the structure HOOC—$(CH_2)_m$—$(CH_2CHOH)_nH$ or HOOC—$(CH_2)_m$—$(CH_2CHOH)_nCH_3$, where m=0–3 and n=2–8, or
- II. an unbranched alkyl radical with 3 to 22 carbon atoms, optionally substituted at the terminal carbon with a hydrophilic moiety selected from the group consisting of $NH_2$, $OH$, $OPO_3^-$, $PO_3^-$, $OSO_3^-$, $SO_3^-$, or
- III. an acyl group derived from
  - a. an alkylphosphonic or alkylsulfonic acid, or
  - b. an alkyl phosphate or alkyl sulfate, provided that at least one of $R_A$ and $R_B$ is not hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, or a pharmaceutically acceptable salt thereof;

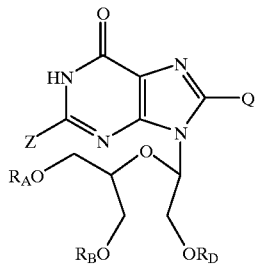

wherein $R_A$, $R_B$, and $R_D$ are the same, or different, and are hydrogen or
- I. an acyl group derived from
  - a. an unbranched fatty acid with 6 to 22 carbon atoms, optionally substituted at the terminal carbon with a hydrophilic moiety selected from the group consisting of $NH_2$, $OH$, $OPO_3^-$, $PO_3^-$, $OSO_3^-$, $SO_3^-$,
  - b. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
  - c. a dicarboxylic acid having 3–22 carbon atoms,
  - d. nicotinic acid or
  - e. a cycloalkyl carboxylic acid containing 4 to 22 carbon atoms,
  - f. a carboxylic acid derived from
    - i. a polymer of ethylene glycol with the structure HOOC—$(CH_2)_m$—$(CH_2CH_2O)_nH$ or HOOC—$(CH_2)_m$—$(CH_2CH_2O)_nCH_3$, or
    - ii. a polymer of vinyl alcohol with the structure HOOC—$(CH_2)_m$—$(CH_2CHOH)_nH$ or HOOC—$(CH_2)_m$—$(CH_2CHOH )_nCH_3$, where m=0–3 and n=2–8, or
- II. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, or III. an acyl group derived from
a. an alkylphosphonic or alkylsulfonic acid, or
b. an alkyl phosphate or alkyl sulfate, provided that not all of $R_A$, $R_B$, and $R_D$ are hydrogen, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, and Z is H, OH, =O, or $NHR_C$ where $R_C$=H or an acyl radical of a carboxylic acid with 2 to 30 carbon atoms or an alkyl radical with 2 to 30 carbon atoms, or a pharmaceutically acceptable salt thereof;

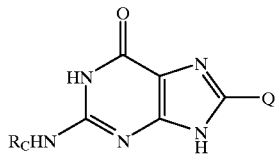

wherein $R_C$ is hydrogen or an acyl group derived from
i. an unbranched fatty acid with 6 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$,
ii. an amino acid selected from the group consisting of glycine, the L forms of phenylalanine, alanine, valine, leucine, isoleucine, tyrosine, proline, hydroxyproline, serine, threonine, cysteine, aspartic acid, glutamic acid, arginine, lysine, histidine and ornithine,
iii. a dicarboxylic acid having 3–22 carbon atoms,
iv. a cycloalkyl carboxylic acid containing 4 to 22 carbon atoms,
v. a nicotinic acid, or
vi. a substituted or unsubstituted aromatic carboxylic acid with 7 to 22 carbon atoms,
vii. a carboxylic acid derived from
1. a polymer of ethylene glycol with the structure $HOOC-(CH_2)_m-(CH_2CH_2O)_nH$ or $HOOC-(CH_2)_m-(CH_2CH_2O)_nCH_3$, or
2. a polymer of vinyl alcohol with the structure $HOOC-(CH_2)_m-(CH_2CHOH)_nH$ or $HOOC-(CH_2)_m-(CH_2CHOH)_nCH_3$, where m=0–3 and n=2–8, or
viii. an unbranched alkyl radical with 3 to 22 carbon atoms, optionally substituted at the terminal carbon with a hydrophilic moiety selected from the group consisting of $NH_2$, OH, $OPO_3^-$, $PO_3^-$, $OSO_3^-$, $SO_3^-$, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, or a pharmaceutically acceptable salt thereof.

8. A pharmaceutical composition comprising a compound as in claim 7 and a pharmaceutically acceptable carrier.

9. A pharmaceutical composition as in claim 8 in the form of a liquid, a suspension, an emulsion, a tablet, a dragee, an injectable solution, an injectable emulsion, a topical solution or a suppository.

10. A pharmaceutical composition as in claim 8 wherein said compound is present in from 0.1–99% by weight of said composition.

11. A pharmaceutical composition as in claim 8 in the form of a bioerodible matrix.

12. The pharmaceutical composition as recited in claim 11, wherein said bioerodible matrix comprises a polymer selected from the group consisting of polylactate and a lactate-glycolate copolymer.

13. A pharmaceutical composition comprising:
(a) one or more compounds having the formula

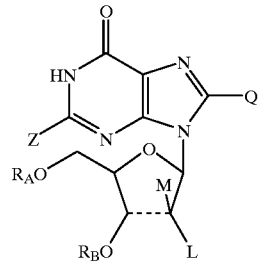

$R_A$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and $R_B$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and Z=H, OH, =O, or $NHR_C$ where $R_C$=H or an acyl radical of a carboxylic acid with 2 to 30 carbon atoms, or an alkyl radical with 2–30 carbon atoms, and L=H or $OR_D$, where $R_D$=H or an acyl radical of a carboxylic, alkylphosphonic, or alkylsulfonic acid, an acyl radical of an alkyl phosphate or alkyl sulfate, or an alkyl radical, with 2 to 30 carbon atoms, and M=H or $OR_E$, where $R_E$=H or an acyl radical of a carboxylic, alkylphosphonic, or alkylsulfonic acid, a radical of an alkyl phosphate or alkyl sulfate, or an alkyl radical, with 2 to 30 carbon atoms, with the proviso that at least one of L and M is H, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, and the C—C bond between the 2' and 3' positions of the aldose moiety is optionally present, or,

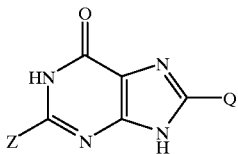

Z=NHR$_C$ where R$_C$=H or an acyl radical of a carboxylic acid with 2 to 30 carbon atoms, or an alkyl radical with 2–30 carbon atoms, and Q=H, a halogen, NHR$_F$ where R$_F$ is H or an acyl or alkyl radical containing 1 to 10 carbon atoms, S divalently bound to the carbon in which case the adjacent carbon-nitrogen double bond is a single bond and an H is then attached to that nitrogen, SR$_G$ where R$_G$ is H or an acyl or alkyl radical containing 1 to 10 carbon atoms, O divalently bound to the carbon, in which case the adjacent carbon-nitrogen double bond is a single bond and an H is then attached to that nitrogen, or OR$_H$ where R$_H$ is H or an acyl or alkyl radical containing 1 to 10 carbon atoms, or a pharmaceutically acceptable salt thereof, and (b) a pharmaceutically acceptable carrier.

14. A pharmaceutical composition as in claim 13 in the form of a liquid, a suspension, an emulsion, a tablet, a dragee, an injectable solution, an injectable emulsion, a topical solution or a suppository.

15. A pharmaceutical composition as in claim 13 wherein said compound is present in from 0.1–99% by weight of said composition.

16. A pharmaceutical composition as in claim 13 in the form of liposomes.

17. A pharmaceutical composition as in claim 13 in the form of a bioerodible matrix.

18. The pharmaceutical composition as recited in claim 17, wherein said bioerodible matrix comprises a polymer selected from the group consisting of polylactate and a lactate-glycolate copolymer.

19. A compound having the formula:

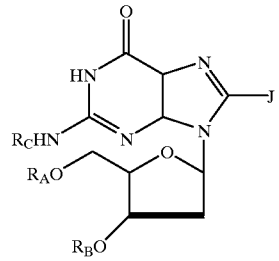

wherein R$_A$, R$_B$ and R$_C$ may be the same or different, and each is an acyl group derived from an unbranched fatty acid with 12 or 18 carbon atoms, optionally substituted at the terminal carbon with a hydrophilic moiety selected from the group consisting of NR$_2$, OH, OPO$_3^-$, OSO$_3^-$ and SO$_3^-$; and J=H or NHR$_I$ where R$_I$ is H or an acyl or alkyl radical containing 1 to 10 carbon atoms;

or a pharmaceutically acceptable salt thereof.

20. A compound according to claim 19 wherein J is H.

21. A compound according to claim 20 which is 3',5'-O-N$^2$-tripalmitoyl-2'-deoxyguanosine.

* * * * *

UNITED STATES PATENT AND TRADEMARK OFFICE
CERTIFICATE OF CORRECTION

PATENT NO. : 6,054,441
DATED : April 25, 2000
INVENTOR(S) : von Borstel et al.

It is certified that error appears in the above-identified patent and that said Letters Patent is hereby corrected as shown below:

Title page,
Item [60], please amend to read as follows -- Division of application No. 08/289,214, Aug. 12, 1994, which is a continuation-in-part of application No. 07/925,931, Aug. 7, 1992, abandoned, which is a continuation-in-part of application No. 07/653,882, Feb. 8, 1991, abandoned, which is a continuation-in-part of application No. 07/487,984, Feb. 5, 1990, abandoned, which is a 371 of PCT/US88/03824, Oct. 27, 1988, which is a continuation-in-part of application No. 07/115,923, Oct. 28, 1987, abandoned.

Column 1,
Line 10, insert -- which is a 371 of PCT/US88/03824, Oct. 27, 1988, -- after "abandoned;"

Column 9,
Lines 1 and 2, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 22, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 33 and 34, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 58, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 10,
Lines 19 and 20, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 36, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 46 and 47, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 11,
Lines 43 and 44, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 66, delete "$OPO_3^-$, $PO_3^-$, $OSO_3^-$, $SO_3^-$" and replace by -- $OPO_3^=$, $PO_3^=$, $OSO_3^=$, $SO_3^=$ --

UNITED STATES PATENT AND TRADEMARK OFFICE
CERTIFICATE OF CORRECTION

PATENT NO. : 6,054,441
DATED : April 25, 2000
INVENTOR(S) : von Borstel et al.

It is certified that error appears in the above-identified patent and that said Letters Patent is hereby corrected as shown below:

Column 12,
Lines 38 and 39, delete "$OPO_3^-, PO_3^-, OSO_3^-, SO_3^-$" and replace by -- $OPO_3^=, PO_3^=, OSO_3^=, SO_3^=$ --
Line 61, delete "$OPO_3^-, PO_3^-, OSO_3^-, SO_3^-$" and replace by -- $OPO_3^=, PO_3^=, OSO_3^=, SO_3^=$ --

Column 13,
Lines 35 and 36, delete "$OPO_3^-, PO_3^-, OSO_3^-, SO_3^-$" and replace by -- $OPO_3^=, PO_3^=, OSO_3^=, SO_3^=$ --
Line 57, delete "$OPO_3^-, PO_3^-, OSO_3^-, SO_3^-$" and replace by -- $OPO_3^=, PO_3^=, OSO_3^=, SO_3^=$ --

Column 14,
Lines 1 and 2, delete "$OPO_3^-, PO_3^-, OSO_3^-, SO_3^-$" and replace by -- $OPO_3^=, PO_3^=, OSO_3^=, SO_3^=$ --
Line 26, delete "$OPO_3^-, PO_3^-, OSO_3^-, SO_3^-$" and replace by -- $OPO_3^=, PO_3^=, OSO_3^=, SO_3^=$ --
Lines 52 and 53, delete "$OPO_3^-, PO_3^-, OSO_3^-, SO_3^-$" and replace by -- $OPO_3^=, PO_3^=, OSO_3^=, SO_3^=$ --

Column 15,
Line 8, delete "$OPO_3^-, PO_3^-, OSO_3^-, SO_3^-$" and replace by -- $OPO_3^=, PO_3^=, OSO_3^=, SO_3^=$ --
Lines 46 and 47, delete "$OPO_3^-, PO_3^-, OSO_3^-, SO_3^-$" and replace by -- $OPO_3^=, PO_3^=, OSO_3^=, SO_3^=$ --

Column 16,
Line 2, delete "$OPO_3^-, PO_3^-, OSO_3^-, SO_3^-$" and replace by -- $OPO_3^=, PO_3^=, OSO_3^=, SO_3^=$ --
Line 38, delete "$OPO_3^-, PO_3^-, OSO_3^-, SO_3^-$" and replace by -- $OPO_3^=, PO_3^=, OSO_3^=, SO_3^=$ --
Line 62, delete "$OPO_3^-, PO_3^-, OSO_3^-, SO_3^-$" and replace by -- $OPO_3^=, PO_3^=, OSO_3^=, SO_3^=$ --

UNITED STATES PATENT AND TRADEMARK OFFICE
CERTIFICATE OF CORRECTION

PATENT NO. : 6,054,441
DATED : April 25, 2000
INVENTOR(S) : von Borstel et al.

It is certified that error appears in the above-identified patent and that said Letters Patent is hereby corrected as shown below:

Column 23,
Lines 52 and 53, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 24,
Line 6, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 17 and 18, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 42, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 66 and 67, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 25,
Line 16, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 26 and 27, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 49, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 26,
Lines 23 and 24, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 46, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 27,
Lines 22 and 23, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 45, delete "$OPO_3^-$, $PO_3^-$, $OSO_3^-$, $SO_3^-$" and replace by -- $OPO_3^=$, $PO_3^=$, $OSO_3^=$, $SO_3^=$ --

UNITED STATES PATENT AND TRADEMARK OFFICE
CERTIFICATE OF CORRECTION

PATENT NO. : 6,054,441
DATED : April 25, 2000
INVENTOR(S) : von Borstel et al.

It is certified that error appears in the above-identified patent and that said Letters Patent is hereby corrected as shown below:

Column 28,
Lines 21 and 22, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 43, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 54, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 29,
Line 11, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 38 and 39, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 61, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 30,
Lines 34 and 35, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 57, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 31,
Line 26, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 50, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 75,
Line 58, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 76,
Line 11, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 21, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 45, delete "$OPO_3^-$, $PO_3^-$, $OSO_3^-$, $SO_3^-$" and replace by -- $OPO_3^=$, $PO_3^=$, $OSO_3^=$, $SO_3^=$ --

UNITED STATES PATENT AND TRADEMARK OFFICE
CERTIFICATE OF CORRECTION

PATENT NO. : 6,054,441
DATED : April 25, 2000
INVENTOR(S) : von Borstel et al.

It is certified that error appears in the above-identified patent and that said Letters Patent is hereby corrected as shown below:

Column 77,
Line 2, delete "$OPO_3^-, PO_3^-, OSO_3^-, SO_3^-$" and replace by -- $OPO_3^=, PO_3^=, OSO_3^=, SO_3^=$ --
Line 18, delete "$OPO_3^-, PO_3^-, OSO_3^-, SO_3^-$" and replace by -- $OPO_3^=, PO_3^=, OSO_3^=, SO_3^=$ --
Line 27, delete "$OPO_3^-, PO_3^-, OSO_3^-, SO_3^-$" and replace by -- $OPO_3^=, PO_3^=, OSO_3^=, SO_3^=$ --
Line 50, delete "$OPO_3^-, PO_3^-, OSO_3^-, SO_3^-$" and replace by -- $OPO_3^=, PO_3^=, OSO_3^=, SO_3^=$ --

Column 78,
Line 23, delete "$OPO_3^-, PO_3^-, OSO_3^-, SO_3^-$" and replace by -- $OPO_3^=, PO_3^=, OSO_3^=, SO_3^=$ --
Line 23, delete "$OPO_3^-, PO_3^-, OSO_3^-, SO_3^-$" and replace by -- $OPO_3^=, PO_3^=, OSO_3^=, SO_3^=$ --
Line 45, delete "$OPO_3^-, PO_3^-, OSO_3^-, SO_3^-$" and replace by -- $OPO_3^=, PO_3^=, OSO_3^=, SO_3^=$ --

Column 79,
Line 23, delete "$OPO_3^-, PO_3^-, OSO_3^-, SO_3^-$" and replace by -- $OPO_3^=, PO_3^=, OSO_3^=, SO_3^=$ --
Line 45, delete "$OPO_3^-, PO_3^-, OSO_3^-, SO_3^-$" and replace by -- $OPO_3^=, PO_3^=, OSO_3^=, SO_3^=$ --

Column 80,
Line 21, delete "$OPO_3^-, PO_3^-, OSO_3^-, SO_3^-$" and replace by -- $OPO_3^=, PO_3^=, OSO_3^=, SO_3^=$ --
Line 42, delete "$OPO_3^-, PO_3^-, OSO_3^-, SO_3^-$" and replace by -- $OPO_3^=, PO_3^=, OSO_3^=, SO_3^=$ --
Line 52, delete "$OPO_3^-, PO_3^-, OSO_3^-, SO_3^-$" and replace by -- $OPO_3^=, PO_3^=, OSO_3^=, SO_3^=$ --

Column 81,
Line 8, delete "$OPO_3^-, PO_3^-, OSO_3^-, SO_3^-$" and replace by -- $OPO_3^=, PO_3^=, OSO_3^=, SO_3^=$ --
Line 35, delete "$OPO_3^-, PO_3^-, OSO_3^-, SO_3^-$" and replace by -- $OPO_3^=, PO_3^=, OSO_3^=, SO_3^=$ --
Line 57, delete "$OPO_3^-, PO_3^-, OSO_3^-, SO_3^-$" and replace by -- $OPO_3^=, PO_3^=, OSO_3^=, SO_3^=$ --

UNITED STATES PATENT AND TRADEMARK OFFICE
CERTIFICATE OF CORRECTION

PATENT NO. : 6,054,441
DATED : April 25, 2000
INVENTOR(S) : von Borstel et al.

It is certified that error appears in the above-identified patent and that said Letters Patent is hereby corrected as shown below:

Column 82,
Line 28, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 48, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 58, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 83,
Line 15, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 37 and 38, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 54, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 64 and 65, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 84,
Line 20, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 58 and 59, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 85,
Line 14, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 50 and 51, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 86,
Line 6, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 43, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 64, delete "$OPO_3^-$, $PO_3^-$, $OSO_3^-$, $SO_3^-$" and replace by -- $OPO_3^=$, $PO_3^=$, $OSO_3^=$, $SO_3^=$ --

UNITED STATES PATENT AND TRADEMARK OFFICE
CERTIFICATE OF CORRECTION

PATENT NO. : 6,054,441
DATED : April 25, 2000
INVENTOR(S) : von Borstel et al.

It is certified that error appears in the above-identified patent and that said Letters Patent is hereby corrected as shown below:

Column 87,
Line 7, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 41, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 57, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 88,
Line 12, delete "$OPO_3^-$, $PO_3^-$, $OSO_3^-$, $SO_3^-$" and replace by -- $OPO_3^=$, $PO_3^=$, $OSO_3^=$, $SO_3^=$ --
Line 47, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 89,
Line 2, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 35 and 36, delete "$OPO_3^-$, $PO_3^-$, $OSO_3^-$, $SO_3^-$" and replace by -- $OPO_3^=$, $PO_3^=$, $OSO_3^=$, $SO_3^=$ --
Lines 60 and 61, delete "$OPO_3^-$, $PO_3^-$, $OSO_3^-$, $SO_3^-$" and replace by -- $OPO_3^=$, $PO_3^=$, $OSO_3^=$, $SO_3^=$ --

Column 92,
Line 26, delete "$OPO_3^-$, $PO_3^-$, $OSO_3^-$, $SO_3^-$" and replace by -- $OPO_3^=$, $PO_3^=$, $OSO_3^=$, $SO_3^=$ --

Signed and Sealed this

Eighteenth Day of December, 2001

Attest:

JAMES E. ROGAN
Attesting Officer
Director of the United States Patent and Trademark Office

UNITED STATES PATENT AND TRADEMARK OFFICE
CERTIFICATE OF CORRECTION

| | | |
|---|---|---|
| PATENT NO. | : 6,054,441 | Page 1 of 1 |
| APPLICATION NO. | : 08/463790 | |
| DATED | : April 25, 2000 | |
| INVENTOR(S) | : von Borstel et al. | |

It is certified that error appears in the above-identified patent and that said Letters Patent is hereby corrected as shown below:

Title page of the right hand column (56), "References Cited, Foreign Patent Documents", line 2 please delete "WO80/03838" and insert --WO89/03838--.

Signed and Sealed this

Seventh Day of November, 2006

JON W. DUDAS
*Director of the United States Patent and Trademark Office*